US010975129B2

(12) United States Patent
Flinspach et al.

(10) Patent No.: US 10,975,129 B2
(45) Date of Patent: *Apr. 13, 2021

(54) PROTOXIN-II VARIANTS AND METHODS OF USE

(71) Applicant: JANSSEN BIOTECH, INC., Horsham, PA (US)

(72) Inventors: Mack Flinspach, San Diego, CA (US); Alan Wickenden, San Diego, CA (US); Ross Fellows, San Diego, CA (US); Robert Neff, San Diego, CA (US); Yi Liu, San Diego, CA (US); Rebecca Hagan, San Diego, CA (US); Qinghao Xu, San Diego, CA (US)

(73) Assignee: JANSSEN BIOTECH, INC., Horsham, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/489,714

(22) Filed: Apr. 17, 2017

(65) Prior Publication Data

US 2020/0048316 A1    Feb. 13, 2020

Related U.S. Application Data

(63) Continuation of application No. 14/505,592, filed on Oct. 3, 2014, now Pat. No. 9,624,280.

(60) Provisional application No. 61/886,100, filed on Oct. 3, 2013.

(51) Int. Cl.
| C07K 14/47 | (2006.01) |
| C07K 14/435 | (2006.01) |
| A61P 25/02 | (2006.01) |
| C07K 14/765 | (2006.01) |
| C12N 15/11 | (2006.01) |
| A61K 38/00 | (2006.01) |

(52) U.S. Cl.
CPC .............. *C07K 14/47* (2013.01); *A61P 25/02* (2018.01); *C07K 14/43518* (2013.01); *C07K 14/765* (2013.01); *C12N 15/11* (2013.01); *A61K 38/00* (2013.01); *C07K 2319/31* (2013.01)

(58) Field of Classification Search
None
See application file for complete search history.

(56) References Cited

U.S. PATENT DOCUMENTS

| 4,309,989 A | 1/1982 | Fahim |
| 4,767,402 A | 8/1988 | Kost et al. |
| 6,103,495 A | 8/2000 | Mehta et al. |
| 6,521,427 B1 | 2/2003 | Evans |
| 6,670,127 B2 | 12/2003 | Evans |
| 6,881,725 B2 | 4/2005 | Yerxa et al. |
| 7,998,980 B2 | 8/2011 | Moran et al. |
| 9,102,751 B2 | 8/2015 | Chen et al. |
| 9,102,757 B2 | 8/2015 | Chen et al. |
| 9,624,280 B2 | 4/2017 | Flinspach et al. |
| 2003/0148273 A1 | 8/2003 | Dong et al. |
| 2007/0212685 A1 | 9/2007 | MacDonald et al. |
| 2011/0065647 A1 | 3/2011 | Meir et al. |
| 2011/0124711 A1 | 5/2011 | Sah et al. |
| 2012/0185956 A1 | 7/2012 | Gingras |
| 2013/0296247 A1 | 11/2013 | Park et al. |
| 2015/0087596 A1 | 3/2015 | Eckert et al. |
| 2015/0099705 A1 | 4/2015 | Flinspach et al. |
| 2016/0257726 A1 | 9/2016 | Flinspach et al. |
| 2016/0287666 A1 | 10/2016 | Flinspach et al. |

FOREIGN PATENT DOCUMENTS

| AU | 2013262630 A3 | 12/2014 |
| AU | 2014329454 B2 | 1/2019 |
| BR | 112016007062 A2 | 12/2017 |
| CA | 2873860 A1 | 11/2013 |
| CN | 101979411 A | 2/2011 |
| CN | 102859003 A | 1/2013 |
| CN | 103635593 A | 3/2014 |
| CN | 104768568 A | 7/2015 |
| CN | 2013825986 A | 7/2015 |
| CN | 105793277 A | 7/2016 |
| CN | 108220406 A | 6/2018 |
| EP | 2852397 A4 | 3/2016 |
| EP | 3052519 A1 | 8/2016 |
| JP | 2015518836 A | 7/2015 |
| JP | 2016519872 A | 7/2016 |
| JP | 2016-533710 A | 11/2016 |
| JP | 2018-512123 A | 5/2018 |
| WO | 9853847 A1 | 12/1998 |
| WO | 2006116156 A3 | 11/2006 |
| WO | 2007109324 A3 | 9/2007 |
| WO | 2008088422 A3 | 2/2009 |
| WO | 2010028089 A2 | 3/2010 |
| WO | 2010104115 A1 | 9/2010 |
| WO | 2012/004664 A2 | 1/2012 |
| WO | 2012004664 A2 | 1/2012 |
| WO | 2013/173706 A2 | 11/2013 |
| WO | 2014/016673 A1 | 1/2014 |

(Continued)

OTHER PUBLICATIONS

Communication pursuant to Article 94(3) EPC issued in European Application No. 14 790 422.1-1120 dated Sep. 10, 2018; 6 pages.
Examination report No. 2 issued in Australian Application No. 2014329454 dated Sep. 17, 2018; 2 pages.
English translation of Reexamination Decision No. 162864 issued by the Patent Reexamination Board of National Intellectual Property Administration, P.R. China in Chinese Application No. 201380025986.1 dated Oct. 23, 2018; 25 pages.

(Continued)

*Primary Examiner* — Adam Weidner
(74) *Attorney, Agent, or Firm* — Ditthavong, Steiner & Mlotkowski

(57) ABSTRACT

The present invention relates to Protoxin-II variants, polynucleotides encoding them, and methods of making and using the foregoing.

33 Claims, 17 Drawing Sheets
Specification includes a Sequence Listing.

(56) References Cited

FOREIGN PATENT DOCUMENTS

| WO | 2014165277 A2 | 10/2014 |
|---|---|---|
| WO | 2015/051216 A1 | 4/2015 |
| WO | 2016140859 A1 | 9/2016 |
| WO | 2016161100 A1 | 10/2016 |

OTHER PUBLICATIONS

English translation of Decision of Rejection issued in Japanese Application No. 2015-512885 dated Oct. 30, 2018; 16 pages.
Examination Report issued by the Government of Pakistan Intellectual Property Organization the Patent Office in Patent Application No. 189/2016 dated Nov. 9, 2018; 2 pages.
Whitney et al., "Fluorescent peptides highlight peripheral nerves during surgery in mice", nature biotechnology, vol. 29, No. 4, (2011), pp. 352-358.
Yang et al., "Mutations in SCN9A, encoding a sodium channel alpha subunit, in patients with primary erythermalgia", J Med Genet, (2004), 41, pp. 171-174.
Yogeeswari et al., "Ion Channels as Important Targets for Antiepileptic Drug Desgin", Current Drug Targets, (2004), 5, pp. 589-602.
Dib-Hajj et al., "The NaV1.7 sodium channel: from molecule to man" Nature Reviews Neuroscience, vol. 14, (2013), pp. 49-62.
Park et al., "Studies Examining the Relationship between the Chemical Structure of Protoxin II and Its Activity on Voltage Gated Sodium Channels", Journal of Medicinal Chemistry, 57, (2014), pp. 6623-6631.
International Search Report of International Application No. PCT/US2014/058972 dated Mar. 26, 2015.
Smith et al, "Molecular Interactions of the Gating Modifier Toxin, ProTx-II, with Nav1.5: implied existence of a novel toxin binding site coupled to activation", The American Society for Biochemistry and Molecular Biology, Inc. (2007) vol. 282, No. 17, pp. 12687-12697.
Yang et al., "Discovery of a selective NaV1.7 inhibitor from centipede venom with analgesic efficacy exceeding morphine in rodent pain models", Proceedings of the National Academy of Sciences (20013), vol. 110, No. 43, pp. 17534-17539.
International Application No. PCT/US2016/019549 filed Feb. 25, 2016.
International Application No. PCT/US2016/025247 filed Mar. 31, 2016.
U.S. Appl. No. 15/060,158, filed Mar. 3, 2016.
U.S. Appl. No. 15/090,328, filed Apr. 4, 2016.
Revel et al., "Potency optimization of Huwentoxin-IV onhNav1.7: A neurotoxin TTX-S sodium-channel antagonist from the venom of the Chinese bird-eating spider*Selenocosmia huwena*", Peptides, Elsevier, Amsterdam, NL, (2013), vol. 44, pp. 40-46, XP028551011.
Berjanskii et al., "Predictor: A Web Server for Predicting Protein Torsion Angle Restraints", Nucleic Acids Research, vol. 34, pp. W63-W69 (2006).
Cheung et al., "Dangle: A Bayesian Inferential Method for Predicting Protein Backbone Dihedral Angels and Secondary Structure", Journal of Magnetic Resonance, vol. 202, pp. 223-233 (2010).
Clare, et al., "Voltage-Gated Sodium Channels as Therapeutic Targets", Therapeutic Focus, vol. 15, No. 11, pp. 506-520 (2000).
Delaglio et al., "NMR Pipe: A Multidimensional Spectral Processing System Based on UNIX Pipes", Journal of Biomolecular NMR, vol. 6, pp. 277-291 (1995).
Genbank:ABY77745.1, "HWTX-IVb precursor [Haplopelma schmidti]", Protein—NCBI (2007).
Guntert, et al., "Torsion Angle Dynamics for NMR structure Calculation with the New Program Dyana", JMB, vol. 273, pp. 283-298 (1997).
Hubner, et al., "Ion Channel Diseases", Human Molecular Genetics, vol. 11, No. 20, pp. 2435-2445 (2002).
Humphrey, et al., "VMD: Visual Molecular Dynamics", Journal of Molecular Graphics, vol. 14, pp. 33-38 (1996).
Jeener, et al., Investigation of Exchange Processes by Two-Dimensional NMR Sectroscopy, J. Chem. Phys., vol. 71, No. 11, pp. 4546-4553 (1979).
Examination report No. 1 issued in Australian Patent Application No. 2014329454 dated Jan. 4, 2018.
Office Action issued in U.S. Appl. No. 14/399,088 dated Jun. 15, 2018.
Office Action issued in U.S. Appl. No. 15/090,328 dated Jun. 6, 2018.
Office Action issued in U.S. Appl. No. 15/583,793 dated May 18, 2018.
Examination Report issued by the Government of Pakistan Intellectual Property Organization the Patent Office in Patent Application No. 129/2016 dated Apr. 25, 2018.
Notice of Reexamination issued in Chinese Patent Application No. 201380025986.1 dated May 8, 2018.
Invitation pursuant to Rule 137(4) EPC and Article 94(3) EPC issued in European Application No. 14790422.1-1120 dated May 17, 2018.
Communication pursuant to Article 94(3) EPC issued in European Application No. 13791454.5-1120 dated May 17, 2018.
International Preliminary Report on Patentability; PCT/US2016/025247; dated Apr. 4, 2017.
International Preliminary Report on Patentability; PCT/US2016/019549; dated Sep. 5, 2017.
Notice of Allowance issued in U.S. Appl. No. 14/505,592, dated Aug. 9, 2016.
Notice of Allowance issued in U.S. Appl. No. 13/833,555, dated Feb. 27, 2015.
Gingras et al., Global Nav1.7 KO mice recapitulate phenotype of congenital indifference to pain reported in humans; American Pain Society Meeting, The Journal of Pain, Abstract 2013.
Remington's Pharmaceutical Sciences, 15th Edition. Edited under the direction of Arthur Osol and John E. Hoover. Mack Publishing Co., Easton, PA 18042, 1975.
Minassian et al., "Functional Studies of the Interaction Between Huwentoxin-IV and the Voltage-Gated Sodium Channel Nav1.7", Janssen—Pharmaceutical Companies of Johnson and Johnson, Janssen Research and Development, San Diego, CA, Poster.
Office Action issued in U.S. Appl. No. 15/583,793 dated Dec. 14, 2017.
Office Action issued in U.S. Appl. No. 13/833,555 dated Sep. 23, 2011.
Office Action issued in U.S. Appl. No. 13/833,555 dated Jan. 8, 2014.
Office Action issued in U.S. Appl. No. 13/833,555 dated Jul. 17, 2014.
Office Action issued in U.S. Appl. No. 13/833,555 dated Nov. 3, 2014.
Notice of Allowance issued in U.S. Appl. No. 14/505,592, dated Dec. 23, 2016.
Chen et al., "Synthesis, Folding and Bioactivity Analysis of K27A-HWTX-IV: A mutant of the TTX-sensitive Sodium Channel Inhibitor, Huwentoxin-IV", Jour Nat Scie Hunan Naun Univ, Sep. 2003, vol. 26, No. 3, pp. 2-7, English Abstract.
Dib-Hajj et al., "Sodium Channels in Normal and Pathological Pain", Annual Review Neuroscience, (2010), vol. 33, pp. 325-347.
U.S. Appl. No. 13/833,555, filed Mar. 15, 2013.
European Communication pursuant to Article 94(3) EPC issued in corresponding EP Application No. 14 790 422.1-1410 dated May 4, 2017.
European Communication pursuant to Article 94(3) EPC, issued in European Patent Application No. 14 790 422.1-410 dated Nov. 16, 2017.
Patent Examination Report No. 1 issued in corresponding Australian Patent Application No. 2013262630 dated Nov. 2, 2016.
English translation of First Office Action issued in corresponding Chinese Patent Application No. 201380025986.1 dated Jan. 27, 2016.
English translation of Second Office Action issued in corresponding Chinese Patent Application No. 201380025986.1 dated Sep. 26, 2016.

(56) References Cited

OTHER PUBLICATIONS

European Communication pursuant to Article 94(3) EPC; EP Application No. 13 791 454.5-1402; dated Jul. 11, 2017.
English translation of Notice of Reasons for Rejection issued in corresponding Japanese Patent Application No. 2015-512885 dated Mar. 14, 2017.
English translation of Notice of Reasons for Rejection issued in corresponding Japanese Patent Application No. 2015-512885 dated Dec. 12, 2017.
Deng et al., Life Science Research,vol. 17, No. 2 (Apr. 2013) pp. 111-115. (English Abstract Only).
Cavanagh et al., Protein NMR Spectroscopy: Principles and Practice, 2nd Edition, 2006 Academic Press. (Description Only).
Bax et al., MLEV-17 Based Two-Dimensional Homonuclear Magnetization Transfer Spectroscopy. Journal of Magnetic Resonance, vol. 65, (1985) pp. 355-360.
Minett et al., "Pain without Nociceptors? Nav1.7-Independent Pain Mechanisms", Cell Reports, (2014), vol. 6, No. 2301-302.
Wang et al., "Expression and characterization of Huwentoxin-XI (HWTX-XI) and its mutants", Chinese Journal of Biotechnology, (2011), vol. 27, No. 2, pp. 262-268, English Abstract.
Xiao et al., "The Tarantula Toxins ProTx-II and Huwentoxin-IV Differentially Interact with Human Nav1.7 Voltage Sensors to Inhibit Channel Activation and Inactivation", Molecular Pharmacology, (2010), vol. 78, No. 6, pp. 1124-1134.
Office Action issued in U.S. Appl. No. 14/505,592 dated Mar. 16, 2016.
Office Action issued in U.S. Appl. No. 14/505,592 dated Nov. 3, 2015.
Office Action issued in U.S. Appl. No. 14/399,088 dated Mar. 13, 2017.
Office Action issued in U.S. Appl. No. 15/090,328 dated Jun. 23, 2017.
Office Action issued in U.S. Appl. No. 15/090,328 dated Oct. 13, 2017.
Australian Office Action issued in Application No. 2016226443 dated Oct. 25, 2019, 3 pages.
International Search Report and Written Opinion of related International Application No. PCT/US2013/041572 dated Dec. 13, 2013.
International Preliminary Report on Patentability of related International Application No. PCT/US2013/041572 dated Nov. 1, 2014.
International Search Report and Written Opinion of International Application No. PCT/US2016/025247 dated Jul. 12, 2016.
International Search Report and Written Opinion of related International Application No. PCT/US2014/058972 dated Mar. 26, 2015.
International Preliminary Report on Patentability of related International Application No. PCT/US2014/058972 dated Apr. 5, 2016.
International Search Report and Written Opinion of International Application No. PCT/US2016/019549 dated Aug. 30, 2016.
Office Action dated Dec. 24, 2015 from U.S. Appl. No. 14/399,088.
Office Action dated Oct. 7, 2016 from U.S. Appl. No. 14/399,088.
U.S. Appl. No. 61/648,871, filed May 18, 2012.
U.S. Appl. No. 61/702,538, filed Sep. 18, 2012.
U.S. Appl. No. 61/781,276, filed Mar. 14, 2013.
Extended European Search Report issued in European Application No. 16774187.5 dated Nov. 15, 2018.
Communication pursuant to Rules 70(2) and 70a(2) EPC issued in European Application No. 16774187.5 dated Dec. 4, 2018.
Notice of Allowance issued in U.S. Appl. No. 15/090,328 dated Dec. 26, 2018.
Office Action issued in U.S. Appl. No. 15/583,793 dated Jan. 4, 2019.
Notice of Allowance issued in U.S. Appl. No. 14/399,088 dated Nov. 21, 2018.
English translation of Examination Report issued by the Patent Office of the Cooperation Council for the Arab States of the Gulf in Application No. GC 2016-30933 dated Jan. 10, 2019.
Frank Bosmans et al., "Four Novel Tarantula Toxins as Selective Modulators of Voltage-Gated Sodium Channel Subtypes", Molecular Pharmacology, vol. 62, No. 2, (2006), pp. 419-429.
Stephen C. Cannon et al., "Sodium channels gone wild: resurgent current from neuronal and muscle channelopathies", The Journal of Clinical Investigation, vol. 120, No. 1, (2010), pp. 80-84.
James J. Cox et al., "An SCN9A channelopathy causes congenital inability to experience pain", Nature PublishingGroup, vol. 444, (2006), pp. 894-898.
Roman Gregg et al., "Pain channelopathies", The Journal of Physiology, vol. 588, No. 11, (2010), pp. 1897-1904.
David M. Dirig et al., "Characterization of variables defining hindpaw withdrawal latency evoked by radiant thermal stimuli", Journal of Neuroscience Methods, No. 76, (1997), pp. 183-191.
Mark Estacion et al., "A Sodium Channel Gene SCN9A Polymorphism That Increases Nociceptor Excitability", Annals of Neurology, vol. 66, No. 6, (2009), pp. 862-866.
Sultan Ahmad et al., "A stop codon mutation in SCN9A causes lack of pain sensation", Human Molecular Genetics, vol. 16, No. 17, (2007), pp. 2114-2121.
Caroline R. Fertleman et al., "SCN9A Mutations in Paroxysmal Clinical Study Extreme Pain Disorder: Allelic Variants Underlie Distinct Channel Defects and Phenotypes", Neuron 52, (2006), pp. 767-774.
Goldberg YP et al., "Loss-of-function mutations in the Nav1.7 gene underlie congenital indifference to pain in multiple human populations", Clinical Genetics, (2007), pp. 311-319.
Dagmar Hackel et al.,"Transient opening of the perineurial barrier for analgesic drug delivery", PNAS, (2012) pp. 2018-2027.
K. Hargreaves et al., "A new and sensitive method for measuring thermal nociception in cutaneous hyperalgesia", Elsevier, (1998), pp. 77-88.
Christian A. Hubner, "Ion channel diseases", Human Molecular Genetics, vol. 11, No. 2, (2002), pp. 2435-2445.
Julie K. Klint et al., "Spider-venom peptides that target voltage-gated sodium channels: Pharmacological tools and potential therapeutic leads", Toxicon, 60, (2012), pp. 478-491.
E. Legroux-Crespel et al., "Traitement de l'erythermalgie familiale par I;association lidocaine-mexiletine", Articles Scientifiques, (2003), vol. 130, pp. 429-433.
Richard E. Middleton et al., "Two Tarantula Peptides Inhibit Activation of Multiple Sodium Channels", Biochemistry, (2002), pp. 14734-14747.
Michael S. Minett et al., "Distinct Nav1.7-dependent pain sensations require different sets of sensory and sympathetic neurons", Nature communications, (2012), pp. 1-9.
Yukiko Muroi et al.,"Selective silencing of NaV1.7 decreases excitability and conduction in vagal sensory neurons", The Journal of Physiology, 589/3, (2011), pp. 5663-5676.
Niassar et al., "Nociceptor-specific gene deletion reveals a major role for Nav1.7 (PN1) in acute and inflammatory pain", PNAS, vol. 101, No. 34, (2004), pp. 12706-12711.
Oi et al., "Isolation of specific peptides that home to dorsal root ganglion neurons in mice", Neuroscience Letters, 434, (2008), pp. 266-272.
Peng et al., "Function and Solution Structure of Huwentoxin-IV, a Potent Neuronal Tetrodotoxin (TTX)-sensitive Sodium Channel Antagonist from Chinese Bird Spider *Selenocosmia huwena*", The Journal of Biological Chemistry, vol. 277, No. 49, Issue of Dec. 2002, pp. 47564-47671.
Reimann et al., "Pain perception is altered by a nucleotide polymorphism in SCN9A", PNAS, vol. 107, No. 11, (2010), pp. 5148-5153.
Schmalhofer et al., "ProTx-II, a Selective Inhibitor of NaV1.7 Sodium Channels, Blocks Action Potential Propagation in Nociceptors", Molecular Pharmacology, vol. 74, No. 6, (2008), pp. 1476-1484.
Sockolosky et al., "Engineering neonatal Fc receptor-mediated recycling and transcytosis in recombinant proteins by short terminal peptide extensions", PNAS, vol. 109, No. 40, (2012), pp. 16095-16100.
Tfelt-Hansen et al., "Inherited Cardiac Diseases Caused by Mutations in the Nav1.5 Sodium Channel", Journal of Cardiovascular Electrophysiology, vol. 21, No. 1, (2010), pp. 107-115.

(56) References Cited

OTHER PUBLICATIONS

Hagman, "Sterilization", Pharmaceutical Manufacturing, Lippincott Williams & Wilkins, Baltimore, MD (2005) Chapters 40, pp. 776-801.
Vargas-Alarcon et al., "A SCN9A gene-encoded dorsal root ganglia sodium channel polymorphism associated with severe fibromyalgia", BMC Musculoskeletal Disorders, (2012),13:23, pp. 5 pages.
Chinese Search Report of Chinese Application No. 201380025986.1 dated Jan. 19, 2016.
European Search Report of European Application No. 13791454.5, dated Jan. 27, 2016.
Minassian et al., "Functional Studies of the Interaction Between Huwentoxin-IV and the Voltage-Gated Sodium Chanel NAv 1.7", Johnson & Johnson Pharmaceutical Research & Development, San Diego, CA (2011).
Minassian, N., et al., "Analysis of the Structural and Molecular Basis of Voltage-Sensitive Sodium Channel Inhibition by the spider Toxin, Huwentoxin-IV (μ-TRTX-Hh2a)", The Journal of Biological Chemistry, online Jun. 12, 2013.
Jiang et al., "Molecular diversification based on analysis of expressed sequence tags from the venom glands of the Chinese bird spider *Ornithoctonus huwena*" Toxicon, 2008, vol. 51, pp. 1479-1489.
Liu et al., "Isolation and Characterization of Hainantoxin-IV, a Novel Antagonist of Tetrodotoxin-Sensitive Sodium Channels From the Chinese Bird Spider *Selenocosmia hainana*", Cellular and Molecular Life Sciences, vol. 60 (5), 2003, pp. 972-978.
Mackerell et al., "Extending the Treatment of Backbone Energetics in Protein Force Fiels: Limitations of Gas-Phase Quantum Mechanics in Reproducing Protein Conformational Distributions in Molecular Dynamics Simulations" Improved Force Fields for Proteins, 2004, pp. 1401-1415.
Liu, "Screening of peptide-based modulators of voltage-gated sodium channels using QPatch", Janssen Research and Development, 2012, pp. 1-22.
Xiao et al., "Common Molecular Determinants of Tarantula Huwentoxin-IV Inhibition of NA Channel Voltage Sensors on Domains II and IV", Journal of Biological Chemistry, 2011, pp. 27301-27334.
Xiao et al., "Tarantula Huwentoxin-IV Inhibits Neuronal Sodium Channels by Binding to Receptor Site 4 and Trapping the Domain II Voltage Sensor in the Closed Configuration", Journal of Biological Chemistry, 2008, pp. 27300-27313.
Spassov et al., "Introducing and Implicit Membrane in Generalized Born/Solvent Accessibility Continuum Solvent Models", J. Phys. Chem, 2002, vol. 106, pp. 8726-8738.
Shih et al., "Functional Studies of the interaction between Huwentoxin-IV and the Voltage-gated sodium channel Na 1.7", Janssen, pp. 1. (2012).
Phillips et al., "Scalable Molecular Dynamics with NAMD", Journal of Computational Chemistry, 2005, vol. 26, pp. 1781-1802.
Xuan "A Study of the Interactive Mechanism between Huwentoxin-IV and Sodium Channel", Chinese Master's Theses Full Test Database, Medicine and Health Sciences, No. S1, pp. E079-E241, Dec. 15, 2011.
Bodenhausen, G., et al., Natural Abundance Nitrogen-15 NMR by Enhanced Heteronuclear Spectroscopy:, vol. 69, No. 1, Jan. 1980 pp. 185-189.
Zhang, M., et al., "Structure/Function Characterization of μ-Conotoxin KIIIA, an Analgesic, Nearly Irreversible Blocker of Mammalian Neuronal Sodium Channels", Journal of Biological Chemistry, vol. 282, No. 42, pp. 30699-30706 (2007).
Kumer et al., "A Two-Dimensional Nuclear Overhauser Enhancement (2D NOE) Experiment for the Elucidation of Complete Proton-Proton Cross-Relaxation Networks in Biological Macromolecules", Biochemical and Biophysical Research Communications, vol. 95, No. 1, Jul. 16, 1980, pp. 1-6.
Muroi et al., "Selective Inhibition of Vagal Afferent Nerve Pathways Regulating Cough using Na 1.7 shrnA Silencing in Guinea Pig Nodose Ganglia", Am. J. Physiol regul Integr Comp Physiol, vol. 304, pp. R1017-R1023 (2013).

M. Flinspach et al., "Insensitivity to pain induced by a potent selective closed-state Nav1.7 inhibitor", Scientific Reports, Jan. 3, 2017, pp. 1-16, vol. 7.
Justin K. Murray et al., "Engineering Potent and Selective Analogues of GpTx-1, a Tarantula Venom Peptide Antagonist of the Nav1.7 Sodium Channel", Journal of Medicinal Chemistry, 2015, pp. 2299-2314, vol. 58, American Chemical Society, ACS Publications.
Extended European Search Report issued in European Patent Application No. 16759288.0 dated Jul. 20, 2018.
Communication pursuant to Rules 70(2) and 70a(2) EPC issued in European Patent Application No. 16759288.0 dated Aug. 7, 2018.
English Translation of Notice of Reasons for Rejection issued in Japanese Patent Application No. 2016-519872, dated Aug. 28, 2018.
Office Action issued in U.S. Appl. No. 15/090,328 dated Sep. 11, 2018.
Translation of Notification of Defects for related Israeli Patent Application No. 254599, dated Dec. 17, 2019, 3 pages.
Translation of Notification of Defects for related Israeli Patent Application No. 254273, dated Dec. 18, 2019, 3 pages.
Office Action for related U.S. Appl. No. 16/673,750, dated Mar. 19, 2020, 36 pages.
Office Action for related Chinese Patent Application No. 201480066344.0, dated Jan. 22, 2020, 11 pages.
Office Action for related European Patent Application No. 16744187.5-1111, dated Mar. 2, 2020, 4 pages.
Notice of Reasons for Rejection for related Japanese Patent Application No. 2017-551164, dated Feb. 19, 2020, 14 pages.
Annex to EPO Form 2004, Communication pursuant to Rule 71(3) EPC; Communication under Rule 71(3) EPC for related European Patent Application No. 14 790 422.1-1118, dated Apr. 24, 2020, 906 pages.
Office Action for related Canadian Patent Application No. 2,882,123, dated Mar. 13, 2020, 3 pages.
Notice of Reasons for Rejection for related Japanese Patent Application No. 2019-036383, dated Dec. 24, 2019, 4 pages.
Schmalhofer, et al., "ProTx-II, a Selective Inhibitor of NaV1.7 Sodium Channels,Blocks Action Potential Propagation in Nociceptors" Molecular Pharmacology, 74:1476-1484, 2008.
Murray et al., "Engineering Potent and Selective Analogues of GpTx-1, a Tarantula Venom Peptide Antagonist of the NaV1.7 Sodium Channel" J. Med. Chem. 2015, 58, pp. 2299-2314.
Minassian et al., "Analysis of the Structural and Molecular Basis of Voltage-sensitive Sodium Channel Inhibition by the Spider Toxin Huwentoxin-IV (_-TRTXHh2a)" The Journal of Biological Chemistry vol. 288, No. 31, dated Aug. 2, 2013, pp. 22707-22720.
Office Action for the Taiwanese Patent Application No. 105110361, dated May 14, 2020, 16 pages.
Office Action for the Taiwanese Patent Application No. 105106183, dated May 14, 2020, 16 pages.
Japanese Office Action for related Japanese Patent Application No. 2015-512885 dated Apr. 7, 2020, 6 Pages.
Canadian Office Action for related Canadian Patent Application No. 2873860 dated Apr. 27, 2020, 3 Pages.
European Office Action for related European Patent Application No. 16759288.0-1118 dated May 12, 2020, 6 Pages.
Office Action for the related Argentina Patent Application No. 20160100893, dated Jul. 23, 2020, 6 pages.
Office Action for the related European Patent Application No. 13791454.5-1118, dated Jul. 28, 2020, 3 pages.
Office Action for the related Argentina Patent Application No. 20160100558 dated Jul. 7, 2020, 15 pages.
Flinspach et al., "Insensitivity to pain induced by a potent selective closed-state Nav1. 7 inhibitor. Scientific reports, 2017, vol. 7, No. 1, pp. 1-16."
Office Action for the related Chinese Patent Application No. 201680026028.X, dated Jul. 17, 2020, 27 pages.
Office Action for the related Japanese Patent Application No. 2017-551164, dated Sep. 29, 2020, 7 pages.
Preliminary Office Action for the related Brazilian Patent Application No. BR112017018834-1, dated Oct. 8, 2020, 5 pages.
Preliminary Office Action for the related Brazilian Patent Application No. BR112017020896-2, dated Sep. 14, 2020, 5 pages.

(56) References Cited

OTHER PUBLICATIONS

Office Action for the related European Patent Application No. 16774187.5-1111, dated Sep. 14, 2020, 4 pages.
Office Action for the related Japanese Patent Application No. 2019-036383, dated Nov. 4, 2020, 16 pages.
Chen et al., Synthesis, folding and bioactivity analysis of K27A-HWTX-IV: a mutant of the TTX-sensitive sodium channel inhibitor, Hu wentoxin-IV., Hunan Shifan Daxue Ziran Kexue Xuebao, 26(3) (2003), pp. 67-72, 6 pages.
Office Action for the related Pakistan Patent Application No. 18912016, dated Nov. 5, 2020, 2 pages.
Office Action for the related Canadian Patent Application No. 2926052, dated Oct. 6, 2020, 5 pages.
Office Action for the related U.S. Appl. No. 15/583,793, dated Sep. 10, 2020, 81 pages.
Office Action for the related U.S. Appl. No. 16/673,750, dated Sep. 15, 2020, 38 pages.
Office Action for the related Chinese Patent Application No. 20201109011278310, dated Nov. 12, 2020, 12 pages.
Office Action for the related U.S. Appl. No. 16/673,750, dated Jan. 8, 2021, 37 pages.
Office Action for the related Japanese Patent Application No. 2017-546100, dated Jan. 12, 2021, 14 pages.
Office Action for the related Japanese Patent Application No. 2020-013560, dated Jan. 26, 2021, 7 pages.
Office Action for the related Taiwanese Patent Application No. 105106183, dated Jan. 12, 2021, 14 pages.
Office Action for the related Taiwanese Patent Application No. 105110361, dated Jan. 12, 2021, 15 pagges.

Figure 1.

| Residue numbering | -2 | -1 | 1 | 2 | 3 | 4 | 5 | 6 | 7 | 8 | 9 | 10 |
|---|---|---|---|---|---|---|---|---|---|---|---|---|
| Genus | X1 | X2 | X3 | C | X4 | X5 | W | X6 | Q | X7 | C | X8 |
| Diversity | (GAP) | (PA) | (SQARY) | C | (QRKAS) | (KSQR) | W | (MF) | Q | (TSRKQ) | C | (DT) |

| Residue numbering | 11 | 12 | 13 | 14 | 15 | 16 | 17 | 18 | 19 | 20 |
|---|---|---|---|---|---|---|---|---|---|---|
| Genus | X9 | X10 | X11 | X12 | C | C | X13 | X14 | F | X15 |
| Diversity | (SAR) | (ERNKTQ) | (RK) | (KQSA) | C | C | (EQD) | (GQ) | F | (VS) |

| Residue numbering | 21 | 22 | 23 | 24 | 25 | 26 | 27 | 28 | 29 | 30 |
|---|---|---|---|---|---|---|---|---|---|---|
| Genus | C | X16 | L | W | C | X17 | K | K | L | W |
| Diversity | C | (RT) | L | W | C | (KR) | K | K | L | W |

Figure 2.

| Protein name | Protoxin-II variant name | Protein SEQ ID NO: | Selectivity * | Nav1.6 | | Nav1.7 | |
|---|---|---|---|---|---|---|---|
| | | | | $IC_{50}$ (nM) | SE** | $IC_{50}$ (nM) | SE** |
| NV1D12_5 | wild type | 2 | 28 | 2.2 | 3.8 | 62 | 1.3 |
| NV1G1153-NH-butyl | NV1D3034-NH-butyl | 118 | 509.6 | 501.9 | 826.2 | 1.0 | 0.8 |
| NV1G1153-NH-methyl | NV1D3034-NH-methyl | 119 | 467.1 | 563.3 | 408.9 | 1.2 | 1.3 |
| NV1G1818 | NV1D3368 | 122 | 257.4 | 1466.7 | 789.0 | 5.7 | 2.9 |
| NV1G1818-NH2 | NV1D3368-NH2 | 123 | 201.6 | 862.0 | 330.9 | 4.3 | 1.9 |
| NV1G1153 | NV1D3034 | 78 | 128.7 | 568.6 | 352.6 | 4.4 | 4.3 |
| NV1G1781 | NV1D3388 | 217 | 105.9 | 1196.2 | 977.0 | 11.3 | 11.2 |
| NV1G1137 | NV1D2974 | 129 | 87.9 | 617.9 | 528.1 | 7.0 | 6.1 |
| NV1G1750 | NV1D3586 | 324 | 73.3 | 894.606 | 429.0 | 12.2 | 9.4 |
| (-GP) N-Ac-NV1G1153-NH2 | (-GP) N-Ac-NV1D3034-NH2 | 121 | 67.1 | 164.6 | 130.5 | 2.5 | 1.3 |
| NV1G1267 | NV1D3044 | 150 | 66.7 | 308.4 | 264.7 | 4.6 | 2.8 |
| NV1G1750-NH2 | NV1D3586-NH2 | 325 | 66.4 | 98.5 | 107.4 | 1.5 | 0.2 |
| NV1G1728 | NV1D3541 | 281 | 65.0 | 1746.5 | 372.0 | 26.9 | 105.6 |
| NV1G1007 | NV1D2775 | 56 | 59.0 | 236.4 | 108.1 | 4.0 | 8.9 |
| NV1G1007-NH2 | NV1D2775-NH2 | 111 | 52.0 | 61.4 | 38.5 | 1.2 | 0.8 |
| NV1G1137-NH2 | NV1D2974-NH2 | 130 | 50.8 | 218.9 | 185.2 | 4.3 | 2.5 |
| Protein name | Protoxin-II variant name | Protein SEQ ID NO: | Selectivity * | Nav1.6 | | Nav1.7 | |
| | | | | $IC_{50}$ (nM) | se** | $IC_{50}$ (nM) | se** |
| (-GP) N-Ac-NV1G1137-NH2 | (-GP) N-Ac-NV1D2974-NH2 | 114 | 46.4 | 476.1 | 139.2 | 10.3 | 5.9 |
| NV1G1001 | NV1D2773 | 65 | 45.9 | 197.3 | 44.4 | 4.3 | 3.3 |
| NV1G1153-NH2 | NV1D3034-NH2 | 117 | 43.5 | 160.3 | 107.3 | 3.7 | 2.7 |
| NV1G1005 | NV1D2772 | 59 | 39.2 | 241.8 | 82.6 | 6.2 | 3.2 |
| NV1G1519 | NV1D3006 | 133 | 37.9 | 123.6 | 34.3 | 3.3 | 3.1 |
| NV1G1749 | NV1D3587 | 326 | 34.1 | 433.9 | 483.8 | 12.7 | 8.2 |
| NV1G1836 | NV1D3359 | 190 | 31.5 | 485.9 | 277.4 | 15.4 | 10.6 |

*IC50(Nav1.6)/IC50(Nav1.7)

**standard error

Figure 3.

| Protein name | Protoxin-II variant name | SEQ ID NO: | Residue numbering (according to SEQ ID NO: 1) | | | | | | | | | | | |
|---|---|---|---|---|---|---|---|---|---|---|---|---|---|---|
| | | | -2 | -1 | 1 | 2 | 3 | 4 | 5 | 6 | 7 | 8 | 9 | 10 |
| | wild type | 2 | G | P | Y | C | Q | K | W | M | W | T | C | D |
| NV1G1153-NH-butyl | NV1D3034-NH-butyl | 118 | G | P | Q | C | Q | K | W | M | Q | T | C | D |
| NV1G1153-NH-methyl | NV1D3034-NH-methyl | 119 | G | P | Q | C | Q | K | W | M | Q | T | C | D |
| NV1G1818 | NV1D3368 | 122 | G | P | Q | C | Q | K | W | M | Q | T | C | D |
| NV1G1818-NH2 | NV1D3368-NH2 | 123 | G | P | Q | C | Q | K | W | M | Q | T | C | D |
| NV1G1153 | NV1D3034 | 78 | G | P | Q | C | Q | K | W | M | Q | T | C | D |
| NV1G1781 | NV1D3388 | 217 | G | P | Q | C | Q | K | W | M | Q | T | C | D |
| NV1G1137 | NV1D2974 | 129 | G | P | Q | C | Q | K | W | M | Q | T | C | D |
| NV1G1750 | NV1D3586 | 324 | G | P | Y | C | Q | K | W | M | Q | T | C | D |
| (-GP) N-Ac-NV1G1153-NH2 | (-GP) N-Ac-NV1D3034-NH2 | 121 | | | Q | C | Q | K | W | M | Q | T | C | D |
| NV1G1267 | NV1D3044 | 150 | G | P | Q | C | Q | K | W | M | Q | T | C | D |
| NV1G1750-NH2 | NV1D3586-NH2 | 325 | G | P | Y | C | Q | K | W | M | Q | T | C | D |
| NV1G1728 | NV1D3541 | 281 | G | P | A | C | Q | K | W | M | Q | T | C | D |
| NV1G1007 | NV1D2775 | 56 | G | P | Q | C | Q | K | W | M | Q | T | C | D |
| NV1G1007-NH2 | NV1D2775-NH2 | 111 | G | P | Q | C | Q | K | W | M | Q | T | C | D |
| NV1G1137-NH2 | NV1D2974 | 130 | G | P | Q | C | Q | K | W | M | Q | T | C | D |
| (-GP) N-Ac-NV1G1137-NH2 | (-GP) N-Ac-NV1D2974-NH2 | 114 | G | P | Q | C | Q | K | W | M | Q | T | C | D |
| NV1G1001 | NV1D2773 | 65 | G | P | S | C | Q | K | W | M | Q | T | C | D |
| NV1G1153-NH2 | NV1D3034-NH2 | 117 | G | P | Q | C | Q | K | W | M | Q | T | C | D |
| NV1G1005 | NV1D2772 | 59 | G | P | R | C | Q | K | W | M | Q | T | C | D |
| NV1G1519 | NV1D3006 | 133 | G | P | Q | C | Q | K | W | M | Q | T | C | D |
| NV1G1749 | NV1D3587 | 326 | G | P | A | C | Q | K | W | M | Q | T | C | D |
| NV1G1836 | NV1D3359 | 190 | G | P | Q | C | Q | K | W | M | Q | S | C | D |
| Diversity | | | G | P | (YQASR) | C | Q | K | W | M | Q | (TS) | C | D |
| Genus sequence | | 405 | G | P | X1 | C | Q | K | W | M | Q | X2 | C | D |

Figure 3 (continued)

| Protein name | Protoxin-II variant name | SEQ ID NO: | 11 | 12 | 13 | 14 | 15 | 16 | 17 | 18 | 19 | 20 |
|---|---|---|---|---|---|---|---|---|---|---|---|---|
| | wild type | 2 | S | E | R | K | C | C | E | G | M | V |
| NV1G1153-NH-butyl | NV1D3034-NH-butyl | 118 | R | E | R | K | C | C | E | G | F | V |
| NV1G1153-NH-methyl | NV1D3034-NH-methyl | 119 | R | E | R | K | C | C | E | G | F | V |
| NV1G1818 | NV1D3368 | 122 | R | T | R | K | C | C | E | G | F | V |
| NV1G1818-NH2 | NV1D3368-NH2 | 123 | R | T | R | K | C | C | E | G | F | V |
| NV1G1153 | NV1D3034 | 78 | R | E | R | K | C | C | E | G | F | V |
| NV1G1781 | NV1D3388 | 217 | R | E | R | K | C | C | Q | G | F | V |
| NV1G1137 | NV1D2974 | 129 | A | N | R | K | C | C | E | G | F | S |
| NV1G1750 | NV1D3586 | 324 | A | E | R | K | C | C | E | G | F | S |
| (-GP) M-Ac-NV1G1153-NH2 | (-GP) M-Ac-NV1D3034-NH2 | 121 | R | E | R | K | C | C | E | G | F | V |
| NV1G1267 | NV1D3044 | 150 | R | N | R | K | C | C | E | G | F | V |
| NV1G1750-NH2 | NV1D3586-NH2 | 325 | A | N | R | K | C | C | E | G | F | S |
| NV1G1728 | NV1D3541 | 281 | R | N | R | K | C | C | E | G | F | V |
| NV1G1007 | NV1D2775 | 56 | A | E | R | K | C | C | E | G | F | V |
| NV1G1007-NH2 | NV1D2775-NH2 | 111 | A | E | R | K | C | C | E | G | F | V |
| NV1G1137-NH2 | NV1D2974-NH2 | 130 | A | E | R | K | C | C | E | G | F | S |
| (-GP) M-Ac-NV1G1137-NH2 | (-GP) M-Ac-NV1D2974-NH2 | 114 | A | E | R | K | C | C | E | G | F | S |
| NV1G1001 | NV1D2773 | 65 | R | E | R | K | C | C | E | G | F | V |
| NV1G1153-NH2 | NV1D3034-NH2 | 117 | A | E | R | K | C | C | E | G | F | V |
| NV1G1005 | NV1D2772 | 59 | A | R | R | K | C | C | E | G | F | V |
| NV1G1519 | NV1D3006 | 133 | A | R | R | K | C | C | E | G | F | V |
| NV1G1749 | NV1D3587 | 326 | A | N | R | K | C | C | E | G | F | S |
| NV1G1836 | NV1D3359 | 190 | R | E | R | K | C | C | E | G | F | V |
| Diversity | | | (SRA) | (ETN) | R | K | C | C | (EQ) | G | F | (VS) |
| Genus sequence | | 405 | X3 | X4 | R | K | C | C | X5 | G | F | X6 |

Figure 3 (continued)

| Protein name | Protoxin-II variant name | SEQ ID NO: | Residue numbering (according to SEQ ID NO: 1) | | | | | | | | | |
|---|---|---|---|---|---|---|---|---|---|---|---|---|
| | | | 21 | 22 | 23 | 24 | 25 | 26 | 27 | 28 | 29 | 30 |
| | wild type | 2 | C | R | L | W | C | K | K | K | L | W |
| NV1G1153-NH-butyl | NV1D3034-NH-butyl | 118 | C | T | L | W | C | R | K | K | L | W |
| NV1G1153-NH-methyl | NV1D3034-NH-methyl | 119 | C | T | L | W | C | R | K | K | L | W |
| NV1G1818 | NV1D3368 | 122 | C | T | L | W | C | R | K | K | L | W |
| NV1G1818-NH2 | NV1D3368-NH2 | 123 | C | T | L | W | C | R | K | K | L | W |
| NV1G1153 | NV1D3034 | 78 | C | T | L | W | C | R | K | K | L | W |
| NV1G1781 | NV1D3388 | 217 | C | T | L | W | C | R | K | K | L | W |
| NV1G1137 | NV1D2974 | 129 | C | T | L | W | C | K | K | K | L | W |
| NV1G1750 | NV1D3586 | 324 | C | R | L | W | C | K | K | K | L | W |
| (-GP) N-Ac-NV1G1153-NH2 | (-GP) N-Ac-NV1D3034-NH2 | 121 | C | T | L | W | C | R | K | K | L | W |
| NV1G1267 | NV1D3044 | 150 | C | T | L | W | C | R | K | K | L | W |
| NV1G1750-NH2 | NV1D3586-NH2 | 325 | C | R | L | W | C | K | K | K | L | W |
| NV1G1728 | NV1D3541 | 281 | C | T | L | W | C | R | K | K | L | W |
| NV1G1007 | NV1D2775 | 56 | C | R | L | W | C | K | K | K | L | W |
| NV1G1007-NH2 | NV1D2775-NH2 | 111 | C | R | L | W | C | K | K | K | L | W |
| NV1G1137-NH2 | NV1D2974-NH2 | 130 | C | T | L | W | C | K | K | K | L | W |
| (-GP) N-Ac-NV1G1137-NH2 | (-GP) N-Ac-NV1D2974-NH2 | 114 | C | T | L | W | C | K | K | K | L | W |
| NV1G1001 | NV1D2773 | 65 | C | R | L | W | C | K | K | K | L | W |
| NV1G1153-NH2 | NV1D3034-NH2 | 117 | C | T | L | W | C | R | K | K | L | W |
| NV1G1005 | NV1D2772 | 59 | C | R | L | W | C | K | K | K | L | W |
| NV1G1519 | NV1D3006 | 133 | C | R | L | W | C | K | K | K | L | W |
| NV1G1749 | NV1D3587 | 326 | C | R | L | W | C | K | K | K | L | W |
| NV1G1836 | NV1D3359 | 190 | C | T | L | W | C | R | K | K | L | W |
| Diversity | | | C | (RT) | L | W | C | (KR) | K | K | L | W |
| Genus sequence | | 405 | C | X7 | L | W | C | X8 | K | K | L | W |

SEQUENCE LISTING

<160> NUMBER OF SEQ ID NOS: 407

<210> SEQ ID NO 1
<211> LENGTH: 30
<212> TYPE: PRT

```
<213> ORGANISM: Thrixopelma pruriens
<220> FEATURE:
<221> NAME/KEY: MOD_RES
<222> LOCATION: (30)..(30)
<223> OTHER INFORMATION: COOH

<400> SEQUENCE: 1

Tyr Cys Gln Lys Trp Met Trp Thr Cys Asp Ser Glu Arg Lys Cys Cys
1               5                   10                  15

Glu Gly Met Val Cys Arg Leu Trp Cys Lys Lys Lys Leu Trp
            20                  25                  30

<210> SEQ ID NO 2
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D12 polypeptide
<220> FEATURE:
<221> NAME/KEY: MOD_RES
<222> LOCATION: (32)..(32)
<223> OTHER INFORMATION: COOH

<400> SEQUENCE: 2

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 3
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D748 polypeptide
<220> FEATURE:
<221> NAME/KEY: MOD_RES
<222> LOCATION: (32)..(32)
<223> OTHER INFORMATION: COOH

<400> SEQUENCE: 3

Gly Pro Ala Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 4
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D751 polypeptide
<220> FEATURE:
<221> NAME/KEY: MOD_RES
<222> LOCATION: (32)..(32)
<223> OTHER INFORMATION: COOH

<400> SEQUENCE: 4

Gly Pro Gln Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 5
```

```
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2292 polypeptide
<220> FEATURE:
<221> NAME/KEY: MOD_RES
<222> LOCATION: (32)..(32)
<223> OTHER INFORMATION: COOH

<400> SEQUENCE: 5

Gly Pro Arg Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 6
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D750 polypeptide
<220> FEATURE:
<221> NAME/KEY: MOD_RES
<222> LOCATION: (32)..(32)
<223> OTHER INFORMATION: COOH

<400> SEQUENCE: 6

Gly Pro Ser Cys Gln Lys Trp Met Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 7
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D1328 polypeptide
<220> FEATURE:
<221> NAME/KEY: MOD_RES
<222> LOCATION: (32)..(32)
<223> OTHER INFORMATION: COOH

<400> SEQUENCE: 7

Gly Pro Tyr Cys Gln Lys Trp Phe Trp Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 8
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D774 polypeptide
<220> FEATURE:
<221> NAME/KEY: MOD_RES
<222> LOCATION: (32)..(32)
<223> OTHER INFORMATION: COOH

<400> SEQUENCE: 8

Gly Pro Tyr Cys Gln Lys Trp Met Gln Thr Cys Asp Ser Glu Arg Lys
1               5                   10                  15
```

Cys Cys Glu Gly Met Val Cys Arg Leu Trp Cys Lys Lys Lys Leu Trp
            20                  25                  30

<210> SEQ ID NO 9
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D786 polypeptide
<220> FEATURE:
<221> NAME/KEY: MOD_RES
<222> LOCATION: (32)..(32)
<223> OTHER INFORMATION: COOH

<400> SEQUENCE: 9

Gly Pro Tyr Cys Gln Lys Trp Met Trp Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 10
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2300 polypeptide
<220> FEATURE:
<221> NAME/KEY: MOD_RES
<222> LOCATION: (32)..(32)
<223> OTHER INFORMATION: COOH

<400> SEQUENCE: 10

Gly Pro Tyr Cys Gln Lys Trp Met Trp Thr Cys Asp Arg Glu Arg Lys
1               5                   10                  15

Cys Cys Glu Gly Met Val Cys Arg Leu Trp Cys Lys Lys Lys Leu Trp
            20                  25                  30

<210> SEQ ID NO 11
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D791 polypeptide
<220> FEATURE:
<221> NAME/KEY: MOD_RES
<222> LOCATION: (32)..(32)
<223> OTHER INFORMATION: COOH

<400> SEQUENCE: 11

Gly Pro Tyr Cys Gln Lys Trp Met Trp Thr Cys Asp Ser Lys Arg Lys
1               5                   10                  15

Cys Cys Glu Gly Met Val Cys Arg Leu Trp Cys Lys Lys Lys Leu Trp
            20                  25                  30

<210> SEQ ID NO 12
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D1332 polypeptide
<220> FEATURE:
<221> NAME/KEY: MOD_RES
<222> LOCATION: (32)..(32)
<223> OTHER INFORMATION: COOH

```
<400> SEQUENCE: 12

Gly Pro Tyr Cys Gln Lys Trp Met Trp Thr Cys Asp Ser Asn Arg Lys
1               5                   10                  15

Cys Cys Glu Gly Met Val Cys Arg Leu Trp Cys Lys Lys Lys Leu Trp
            20                  25                  30

<210> SEQ ID NO 13
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2512 polypeptide
<220> FEATURE:
<221> NAME/KEY: MOD_RES
<222> LOCATION: (32)..(32)
<223> OTHER INFORMATION: COOH

<400> SEQUENCE: 13

Gly Pro Tyr Cys Gln Lys Trp Met Trp Thr Cys Asp Ser Glu Arg Lys
1               5                   10                  15

Cys Cys Glu Gly Phe Val Cys Arg Leu Trp Cys Lys Lys Lys Leu Trp
            20                  25                  30

<210> SEQ ID NO 14
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D1336 polypeptide
<220> FEATURE:
<221> NAME/KEY: MOD_RES
<222> LOCATION: (32)..(32)
<223> OTHER INFORMATION: COOH

<400> SEQUENCE: 14

Gly Pro Tyr Cys Gln Lys Trp Met Trp Thr Cys Asp Ser Glu Arg Lys
1               5                   10                  15

Cys Cys Glu Gly Leu Val Cys Arg Leu Trp Cys Lys Lys Lys Leu Trp
            20                  25                  30

<210> SEQ ID NO 15
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D1337 polypeptide
<220> FEATURE:
<221> NAME/KEY: MOD_RES
<222> LOCATION: (32)..(32)
<223> OTHER INFORMATION: COOH

<400> SEQUENCE: 15

Gly Pro Tyr Cys Gln Lys Trp Met Trp Thr Cys Asp Ser Glu Arg Lys
1               5                   10                  15

Cys Cys Glu Gly Met Val Cys Thr Leu Trp Cys Lys Lys Lys Leu Trp
            20                  25                  30

<210> SEQ ID NO 16
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2308 polypeptide
```

```
<220> FEATURE:
<221> NAME/KEY: MOD_RES
<222> LOCATION: (32)..(32)
<223> OTHER INFORMATION: COOH

<400> SEQUENCE: 16

Gly Pro Tyr Cys Gln Lys Trp Met Trp Thr Cys Asp Ser Glu Arg Lys
1               5                   10                  15

Cys Cys Glu Gly Met Val Cys Arg Leu Trp Cys Arg Lys Lys Leu Trp
            20                  25                  30

<210> SEQ ID NO 17
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2670 polypeptide
<220> FEATURE:
<221> NAME/KEY: MOD_RES
<222> LOCATION: (32)..(32)
<223> OTHER INFORMATION: COOH

<400> SEQUENCE: 17

Gly Pro Ala Cys Gln Lys Trp Met Gln Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 18
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2674 polypeptide
<220> FEATURE:
<221> NAME/KEY: MOD_RES
<222> LOCATION: (32)..(32)
<223> OTHER INFORMATION: COOH

<400> SEQUENCE: 18

Gly Pro Ala Cys Gln Lys Trp Met Trp Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 19
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2664 polypeptide
<220> FEATURE:
<221> NAME/KEY: MOD_RES
<222> LOCATION: (32)..(32)
<223> OTHER INFORMATION: COOH

<400> SEQUENCE: 19

Gly Pro Ala Cys Gln Lys Trp Met Trp Thr Cys Asp Ser Glu Arg Lys
1               5                   10                  15

Cys Cys Glu Gly Phe Val Cys Arg Leu Trp Cys Lys Lys Lys Leu Trp
            20                  25                  30

<210> SEQ ID NO 20
<211> LENGTH: 32
```

-continued

```
<212> TYPE: PRT
<213> ORGANISM: Artificial Sequence
<220> FEATURE:
<223> OTHER INFORMATION: Description of Artificial Sequence: Synthetic
      NV1D2671 polypeptide
<220> FEATURE:
<221> NAME/KEY: MOD_RES
<222> LOCATION: (32)..(32)
<223> OTHER INFORMATION: COOH

<400> SEQUENCE: 20

Gly Pro Gln Cys Gln Lys Trp Met Gln Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 21
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2675 polypeptide
<220> FEATURE:
<221> NAME/KEY: MOD_RES
<222> LOCATION: (32)..(32)
<223> OTHER INFORMATION: COOH

<400> SEQUENCE: 21

Gly Pro Gln Cys Gln Lys Trp Met Trp Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 22
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2665 polypeptide
<220> FEATURE:
<221> NAME/KEY: MOD_RES
<222> LOCATION: (32)..(32)
<223> OTHER INFORMATION: COOH

<400> SEQUENCE: 22

Gly Pro Gln Cys Gln Lys Trp Met Trp Thr Cys Asp Ser Glu Arg Lys
1               5                   10                  15

Cys Cys Glu Gly Phe Val Cys Arg Leu Trp Cys Lys Lys Lys Leu Trp
            20                  25                  30

<210> SEQ ID NO 23
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2668 polypeptide
<220> FEATURE:
<221> NAME/KEY: MOD_RES
<222> LOCATION: (32)..(32)
<223> OTHER INFORMATION: COOH

<400> SEQUENCE: 23

Gly Pro Arg Cys Gln Lys Trp Met Gln Thr Cys Asp Ser Glu Arg Lys
1               5                   10                  15

Cys Cys Glu Gly Met Val Cys Arg Leu Trp Cys Lys Lys Lys Leu Trp
```

-continued

```
            20                  25                  30
```

<210> SEQ ID NO 24
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2672 polypeptide
<220> FEATURE:
<221> NAME/KEY: MOD_RES
<222> LOCATION: (32)..(32)
<223> OTHER INFORMATION: COOH

<400> SEQUENCE: 24

```
Gly Pro Arg Cys Gln Lys Trp Met Trp Thr Cys Asp Ala Glu Arg Lys
1               5                   10                  15

Cys Cys Glu Gly Met Val Cys Arg Leu Trp Cys Lys Lys Lys Leu Trp
            20                  25                  30
```

<210> SEQ ID NO 25
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2662 polypeptide
<220> FEATURE:
<221> NAME/KEY: MOD_RES
<222> LOCATION: (32)..(32)
<223> OTHER INFORMATION: COOH

<400> SEQUENCE: 25

```
Gly Pro Arg Cys Gln Lys Trp Met Trp Thr Cys Asp Ser Glu Arg Lys
1               5                   10                  15

Cys Cys Glu Gly Phe Val Cys Arg Leu Trp Cys Lys Lys Lys Leu Trp
            20                  25                  30
```

<210> SEQ ID NO 26
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2669 polypeptide
<220> FEATURE:
<221> NAME/KEY: MOD_RES
<222> LOCATION: (32)..(32)
<223> OTHER INFORMATION: COOH

<400> SEQUENCE: 26

```
Gly Pro Ser Cys Gln Lys Trp Met Gln Thr Cys Asp Ser Glu Arg Lys
1               5                   10                  15

Cys Cys Glu Gly Met Val Cys Arg Leu Trp Cys Lys Lys Lys Leu Trp
            20                  25                  30
```

<210> SEQ ID NO 27
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2673 polypeptide
<220> FEATURE:
<221> NAME/KEY: MOD_RES
<222> LOCATION: (32)..(32)
<223> OTHER INFORMATION: COOH

<400> SEQUENCE: 27

-continued

```
Gly Pro Ser Cys Gln Lys Trp Met Trp Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 28
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2663 polypeptide
<220> FEATURE:
<221> NAME/KEY: MOD_RES
<222> LOCATION: (32)..(32)
<223> OTHER INFORMATION: COOH

<400> SEQUENCE: 28

Gly Pro Ser Cys Gln Lys Trp Met Trp Thr Cys Asp Ser Glu Arg Lys
1               5                   10                  15

Cys Cys Glu Gly Phe Val Cys Arg Leu Trp Cys Lys Lys Lys Leu Trp
            20                  25                  30

<210> SEQ ID NO 29
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2676 polypeptide
<220> FEATURE:
<221> NAME/KEY: MOD_RES
<222> LOCATION: (32)..(32)
<223> OTHER INFORMATION: COOH

<400> SEQUENCE: 29

Gly Pro Tyr Cys Gln Lys Trp Met Gln Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 30
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2666 polypeptide
<220> FEATURE:
<221> NAME/KEY: MOD_RES
<222> LOCATION: (32)..(32)
<223> OTHER INFORMATION: COOH

<400> SEQUENCE: 30

Gly Pro Tyr Cys Gln Lys Trp Met Gln Thr Cys Asp Ser Glu Arg Lys
1               5                   10                  15

Cys Cys Glu Gly Phe Val Cys Arg Leu Trp Cys Lys Lys Lys Leu Trp
            20                  25                  30

<210> SEQ ID NO 31
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2816 polypeptide
<220> FEATURE:
```

```
<221> NAME/KEY: MOD_RES
<222> LOCATION: (32)..(32)
<223> OTHER INFORMATION: COOH

<400> SEQUENCE: 31

Gly Pro Ala Cys Gln Lys Trp Phe Gln Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 32
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2735 polypeptide
<220> FEATURE:
<221> NAME/KEY: MOD_RES
<222> LOCATION: (32)..(32)
<223> OTHER INFORMATION: COOH

<400> SEQUENCE: 32

Gly Pro Ala Cys Gln Lys Trp Met Gln Thr Cys Asp Ser Glu Arg Lys
1               5                   10                  15

Cys Cys Glu Gly Phe Val Cys Arg Leu Trp Cys Lys Lys Lys Leu Trp
            20                  25                  30

<210> SEQ ID NO 33
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2739 polypeptide
<220> FEATURE:
<221> NAME/KEY: MOD_RES
<222> LOCATION: (32)..(32)
<223> OTHER INFORMATION: COOH

<400> SEQUENCE: 33

Gly Pro Ala Cys Gln Lys Trp Met Trp Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 34
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2731 polypeptide
<220> FEATURE:
<221> NAME/KEY: MOD_RES
<222> LOCATION: (32)..(32)
<223> OTHER INFORMATION: COOH

<400> SEQUENCE: 34

Gly Pro Ala Cys Gln Lys Trp Met Gln Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 35
<211> LENGTH: 32
<212> TYPE: PRT
```

<213> ORGANISM: Artificial Sequence
<220> FEATURE:
<223> OTHER INFORMATION: Description of Artificial Sequence: Synthetic
      NV1D2810 polypeptide
<220> FEATURE:
<221> NAME/KEY: MOD_RES
<222> LOCATION: (32)..(32)
<223> OTHER INFORMATION: COOH

<400> SEQUENCE: 35

Gly Pro Gln Cys Gln Lys Trp Phe Gln Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 36
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2732 polypeptide
<220> FEATURE:
<221> NAME/KEY: MOD_RES
<222> LOCATION: (32)..(32)
<223> OTHER INFORMATION: COOH

<400> SEQUENCE: 36

Gly Pro Gln Cys Gln Lys Trp Met Gln Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 37
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2740 polypeptide
<220> FEATURE:
<221> NAME/KEY: MOD_RES
<222> LOCATION: (32)..(32)
<223> OTHER INFORMATION: COOH

<400> SEQUENCE: 37

Gly Pro Gln Cys Gln Lys Trp Met Trp Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 38
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2819 polypeptide
<220> FEATURE:
<221> NAME/KEY: MOD_RES
<222> LOCATION: (32)..(32)
<223> OTHER INFORMATION: COOH

<400> SEQUENCE: 38

Gly Pro Arg Cys Gln Lys Trp Phe Trp Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 39
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2729 polypeptide
<220> FEATURE:
<221> NAME/KEY: MOD_RES
<222> LOCATION: (32)..(32)
<223> OTHER INFORMATION: COOH

<400> SEQUENCE: 39

Gly Pro Arg Cys Gln Lys Trp Met Gln Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 40
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2733 polypeptide
<220> FEATURE:
<221> NAME/KEY: MOD_RES
<222> LOCATION: (32)..(32)
<223> OTHER INFORMATION: COOH

<400> SEQUENCE: 40

Gly Pro Arg Cys Gln Lys Trp Met Gln Thr Cys Asp Ser Glu Arg Lys
1               5                   10                  15

Cys Cys Glu Gly Phe Val Cys Arg Leu Trp Cys Lys Lys Lys Leu Trp
            20                  25                  30

<210> SEQ ID NO 41
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2814 polypeptide
<220> FEATURE:
<221> NAME/KEY: MOD_RES
<222> LOCATION: (32)..(32)
<223> OTHER INFORMATION: COOH

<400> SEQUENCE: 41

Gly Pro Ser Cys Gln Lys Trp Phe Gln Thr Cys Asp Ser Glu Arg Lys
1               5                   10                  15

Cys Cys Glu Gly Met Val Cys Arg Leu Trp Cys Lys Lys Lys Leu Trp
            20                  25                  30

<210> SEQ ID NO 42
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2820 polypeptide
<220> FEATURE:
<221> NAME/KEY: MOD_RES
<222> LOCATION: (32)..(32)
<223> OTHER INFORMATION: COOH

<400> SEQUENCE: 42

Gly Pro Ser Cys Gln Lys Trp Phe Trp Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 43
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2730 polypeptide
<220> FEATURE:
<221> NAME/KEY: MOD_RES
<222> LOCATION: (32)..(32)
<223> OTHER INFORMATION: COOH

<400> SEQUENCE: 43

Gly Pro Ser Cys Gln Lys Trp Met Gln Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 44
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2734 polypeptide
<220> FEATURE:
<221> NAME/KEY: MOD_RES
<222> LOCATION: (32)..(32)
<223> OTHER INFORMATION: COOH

<400> SEQUENCE: 44

Gly Pro Ser Cys Gln Lys Trp Met Gln Thr Cys Asp Ser Glu Arg Lys
1               5                   10                  15

Cys Cys Glu Gly Phe Val Cys Arg Leu Trp Cys Lys Lys Lys Leu Trp
            20                  25                  30

<210> SEQ ID NO 45
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2738 polypeptide
<220> FEATURE:
<221> NAME/KEY: MOD_RES
<222> LOCATION: (32)..(32)
<223> OTHER INFORMATION: COOH

<400> SEQUENCE: 45

Gly Pro Ser Cys Gln Lys Trp Met Trp Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 46
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2851 polypeptide
<220> FEATURE:
<221> NAME/KEY: MOD_RES -continued

```
<222> LOCATION: (32)..(32)
<223> OTHER INFORMATION: COOH

<400> SEQUENCE: 46

Gly Pro Tyr Cys Gln Lys Trp Phe Lys Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 47
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2850 polypeptide
<220> FEATURE:
<221> NAME/KEY: MOD_RES
<222> LOCATION: (32)..(32)
<223> OTHER INFORMATION: COOH

<400> SEQUENCE: 47

Gly Pro Tyr Cys Gln Lys Trp Phe Gln Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 48
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2667 polypeptide
<220> FEATURE:
<221> NAME/KEY: MOD_RES
<222> LOCATION: (32)..(32)
<223> OTHER INFORMATION: COOH

<400> SEQUENCE: 48

Gly Pro Tyr Cys Gln Lys Trp Met Trp Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 49
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2867 polypeptide
<220> FEATURE:
<221> NAME/KEY: MOD_RES
<222> LOCATION: (32)..(32)
<223> OTHER INFORMATION: COOH

<400> SEQUENCE: 49

Gly Pro Ala Cys Gln Lys Trp Phe Gln Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 50
<211> LENGTH: 32
<212> TYPE: PRT
<213> ORGANISM: Artificial Sequence
```

```
<220> FEATURE:
<223> OTHER INFORMATION: Description of Artificial Sequence: Synthetic
      NV1D2881 polypeptide
<220> FEATURE:
<221> NAME/KEY: MOD_RES
<222> LOCATION: (32)..(32)
<223> OTHER INFORMATION: COOH

<400> SEQUENCE: 50

Gly Pro Ala Cys Gln Lys Trp Phe Gln Thr Cys Asp Ser Glu Arg Lys
1               5                   10                  15

Cys Cys Glu Gly Phe Val Cys Arg Leu Trp Cys Lys Lys Lys Leu Trp
            20                  25                  30

<210> SEQ ID NO 51
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2882 polypeptide
<220> FEATURE:
<221> NAME/KEY: MOD_RES
<222> LOCATION: (32)..(32)
<223> OTHER INFORMATION: COOH

<400> SEQUENCE: 51

Gly Pro Ala Cys Gln Lys Trp Phe Gln Thr Cys Asp Ser Glu Arg Lys
1               5                   10                  15

Cys Cys Glu Gly Leu Val Cys Arg Leu Trp Cys Lys Lys Lys Leu Trp
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2774 polypeptide
<220> FEATURE:
<221> NAME/KEY: MOD_RES
<222> LOCATION: (32)..(32)
<223> OTHER INFORMATION: COOH

<400> SEQUENCE: 52

Gly Pro Ala Cys Gln Lys Trp Met Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 53
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2902 polypeptide
<220> FEATURE:
<221> NAME/KEY: MOD_RES
<222> LOCATION: (32)..(32)
<223> OTHER INFORMATION: COOH

<400> SEQUENCE: 53

Gly Pro Ala Cys Gln Lys Trp Met Gln Thr Cys Asp Ala Glu Arg Lys
1               5                   10                  15

Cys Cys Glu Gly Leu Val Cys Arg Leu Trp Cys Lys Lys Lys Leu Trp
            20                  25                  30
```

```
<210> SEQ ID NO 54
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2861 polypeptide
<220> FEATURE:
<221> NAME/KEY: MOD_RES
<222> LOCATION: (32)..(32)
<223> OTHER INFORMATION: COOH

<400> SEQUENCE: 54

Gly Pro Gln Cys Gln Lys Trp Phe Gln Thr Cys Asp Ala Glu Arg Lys
1               5                   10                  15

Cys Cys Glu Gly Met Val Cys Arg Leu Trp Cys Lys Lys Lys Leu Trp
            20                  25                  30

<210> SEQ ID NO 55
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2870 polypeptide
<220> FEATURE:
<221> NAME/KEY: MOD_RES
<222> LOCATION: (32)..(32)
<223> OTHER INFORMATION: COOH

<400> SEQUENCE: 55

Gly Pro Gln Cys Gln Lys Trp Phe Gln Thr Cys Asp Ser Glu Arg Lys
1               5                   10                  15

Cys Cys Glu Gly Leu Val Cys Arg Leu Trp Cys Lys Lys Lys Leu Trp
            20                  25                  30

<210> SEQ ID NO 56
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2775 polypeptide
<220> FEATURE:
<221> NAME/KEY: MOD_RES
<222> LOCATION: (32)..(32)
<223> OTHER INFORMATION: COOH

<400> SEQUENCE: 56

Gly Pro Gln Cys Gln Lys Trp Met Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 57
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2893 polypeptide
<220> FEATURE:
<221> NAME/KEY: MOD_RES
<222> LOCATION: (32)..(32)
<223> OTHER INFORMATION: COOH

<400> SEQUENCE: 57

Gly Pro Gln Cys Gln Lys Trp Met Gln Thr Cys Asp Ala Glu Arg Lys
```

```
                1               5                   10                  15
Cys Cys Glu Gly Leu Val Cys Arg Leu Trp Cys Lys Lys Lys Leu Trp
            20                  25                  30
```

<210> SEQ ID NO 58
<211> LENGTH: 32
<212> TYPE: PRT
<213> ORGANISM: Artificial Sequence
<220> FEATURE:
<223> OTHER INFORMATION: Description of Artificial Sequence: Synthetic
       NV1D2887 polypeptide
<220> FEATURE:
<221> NAME/KEY: MOD_RES
<222> LOCATION: (32)..(32)
<223> OTHER INFORMATION: COOH

<400> SEQUENCE: 58

```
Gly Pro Arg Cys Gln Lys Trp Phe Trp Thr Cys Asp Ala Glu Arg Lys
1               5                   10                  15
Cys Cys Glu Gly Phe Val Cys Arg Leu Trp Cys Lys Lys Lys Leu Trp
            20                  25                  30
```

<210> SEQ ID NO 59
<211> LENGTH: 32
<212> TYPE: PRT
<213> ORGANISM: Artificial Sequence
<220> FEATURE:
<223> OTHER INFORMATION: Description of Artificial Sequence: Synthetic
       NV1D2772 polypeptide
<220> FEATURE:
<221> NAME/KEY: MOD_RES
<222> LOCATION: (32)..(32)
<223> OTHER INFORMATION: COOH

<400> SEQUENCE: 59

```
Gly Pro Arg Cys Gln Lys Trp Met Gln Thr Cys Asp Ala Glu Arg Lys
1               5                   10                  15
Cys Cys Glu Gly Phe Val Cys Arg Leu Trp Cys Lys Lys Lys Leu Trp
            20                  25                  30
```

<210> SEQ ID NO 60
<211> LENGTH: 32
<212> TYPE: PRT
<213> ORGANISM: Artificial Sequence
<220> FEATURE:
<223> OTHER INFORMATION: Description of Artificial Sequence: Synthetic
       NV1D2896 polypeptide
<220> FEATURE:
<221> NAME/KEY: MOD_RES
<222> LOCATION: (32)..(32)
<223> OTHER INFORMATION: COOH

<400> SEQUENCE: 60

```
Gly Pro Arg Cys Gln Lys Trp Met Gln Thr Cys Asp Ala Glu Arg Lys
1               5                   10                  15
Cys Cys Glu Gly Leu Val Cys Arg Leu Trp Cys Lys Lys Lys Leu Trp
            20                  25                  30
```

<210> SEQ ID NO 61
<211> LENGTH: 32
<212> TYPE: PRT
<213> ORGANISM: Artificial Sequence
<220> FEATURE:
<223> OTHER INFORMATION: Description of Artificial Sequence: Synthetic
       NV1D2877 polypeptide
<220> FEATURE:
<221> NAME/KEY: MOD_RES
<222> LOCATION: (32)..(32)

<223> OTHER INFORMATION: COOH

<400> SEQUENCE: 61

Gly Pro Ser Cys Gln Lys Trp Phe Gln Thr Cys Asp Ser Glu Arg Lys
1               5                   10                  15

Cys Cys Glu Gly Phe Val Cys Arg Leu Trp Cys Lys Lys Lys Leu Trp
            20                  25                  30

<210> SEQ ID NO 62
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2878 polypeptide
<220> FEATURE:
<221> NAME/KEY: MOD_RES
<222> LOCATION: (32)..(32)
<223> OTHER INFORMATION: COOH

<400> SEQUENCE: 62

Gly Pro Ser Cys Gln Lys Trp Phe Gln Thr Cys Asp Ser Glu Arg Lys
1               5                   10                  15

Cys Cys Glu Gly Leu Val Cys Arg Leu Trp Cys Lys Lys Lys Leu Trp
            20                  25                  30

<210> SEQ ID NO 63
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2889 polypeptide
<220> FEATURE:
<221> NAME/KEY: MOD_RES
<222> LOCATION: (32)..(32)
<223> OTHER INFORMATION: COOH

<400> SEQUENCE: 63

Gly Pro Ser Cys Gln Lys Trp Phe Trp Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 64
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2889 polypeptide
<220> FEATURE:
<221> NAME/KEY: MOD_RES
<222> LOCATION: (32)..(32)
<223> OTHER INFORMATION: COOH

<400> SEQUENCE: 64

Gly Pro Ser Cys Gln Lys Trp Phe Trp Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 65
<211> LENGTH: 32
<212> TYPE: PRT
<213> ORGANISM: Artificial Sequence
<220> FEATURE:

```
<223> OTHER INFORMATION: Description of Artificial Sequence: Synthetic
      NV1D2773 polypeptide
<220> FEATURE:
<221> NAME/KEY: MOD_RES
<222> LOCATION: (32)..(32)
<223> OTHER INFORMATION: COOH

<400> SEQUENCE: 65

Gly Pro Ser Cys Gln Lys Trp Met Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 66
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2890 polypeptide
<220> FEATURE:
<221> NAME/KEY: MOD_RES
<222> LOCATION: (32)..(32)
<223> OTHER INFORMATION: COOH

<400> SEQUENCE: 66

Gly Pro Ser Cys Gln Lys Trp Phe Trp Thr Cys Asp Ala Glu Arg Lys
1               5                   10                  15

Cys Cys Glu Gly Leu Val Cys Arg Leu Trp Cys Lys Lys Lys Leu Trp
            20                  25                  30

<210> SEQ ID NO 67
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2899 polypeptide
<220> FEATURE:
<221> NAME/KEY: MOD_RES
<222> LOCATION: (32)..(32)
<223> OTHER INFORMATION: COOH

<400> SEQUENCE: 67

Gly Pro Ser Cys Gln Lys Trp Met Gln Thr Cys Asp Ala Glu Arg Lys
1               5                   10                  15

Cys Cys Glu Gly Leu Val Cys Arg Leu Trp Cys Lys Lys Lys Leu Trp
            20                  25                  30

<210> SEQ ID NO 68
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2905 polypeptide
<220> FEATURE:
<221> NAME/KEY: MOD_RES
<222> LOCATION: (32)..(32)
<223> OTHER INFORMATION: COOH

<400> SEQUENCE: 68

Gly Pro Tyr Cys Gln Lys Trp Phe Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30
```

```
<210> SEQ ID NO 69
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2906 polypeptide
<220> FEATURE:
<221> NAME/KEY: MOD_RES
<222> LOCATION: (32)..(32)
<223> OTHER INFORMATION: COOH

<400> SEQUENCE: 69

Gly Pro Tyr Cys Gln Lys Trp Phe Gln Thr Cys Asp Ala Glu Arg Lys
1               5                   10                  15

Cys Cys Glu Gly Leu Val Cys Arg Leu Trp Cys Lys Lys Lys Leu Trp
            20                  25                  30

<210> SEQ ID NO 70
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2921 polypeptide
<220> FEATURE:
<221> NAME/KEY: MOD_RES
<222> LOCATION: (32)..(32)
<223> OTHER INFORMATION: COOH

<400> SEQUENCE: 70

Gly Pro Ala Cys Gln Lys Trp Phe Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 71
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2922 polypeptide
<220> FEATURE:
<221> NAME/KEY: MOD_RES
<222> LOCATION: (32)..(32)
<223> OTHER INFORMATION: COOH

<400> SEQUENCE: 71

Gly Pro Ala Cys Gln Lys Trp Phe Gln Thr Cys Asp Ala Glu Arg Lys
1               5                   10                  15

Cys Cys Glu Gly Leu Val Cys Arg Leu Trp Cys Lys Lys Lys Leu Trp
            20                  25                  30

<210> SEQ ID NO 72
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2909 polypeptide
<220> FEATURE:
<221> NAME/KEY: MOD_RES
<222> LOCATION: (32)..(32)
<223> OTHER INFORMATION: COOH

<400> SEQUENCE: 72

Gly Pro Gln Cys Gln Lys Trp Phe Gln Thr Cys Asp Ala Glu Arg Lys
1               5                   10                  15
```

Cys Cys Glu Gly Phe Val Cys Arg Leu Trp Cys Lys Lys Lys Leu Trp
            20                  25                  30

<210> SEQ ID NO 73
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2910 polypeptide
<220> FEATURE:
<221> NAME/KEY: MOD_RES
<222> LOCATION: (32)..(32)
<223> OTHER INFORMATION: COOH

<400> SEQUENCE: 73

Gly Pro Gln Cys Gln Lys Trp Phe Gln Thr Cys Asp Ala Glu Arg Lys
1               5                   10                  15

Cys Cys Glu Gly Leu Val Cys Arg Leu Trp Cys Lys Lys Lys Leu Trp
            20                  25                  30

<210> SEQ ID NO 74
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2913 polypeptide
<220> FEATURE:
<221> NAME/KEY: MOD_RES
<222> LOCATION: (32)..(32)
<223> OTHER INFORMATION: COOH

<400> SEQUENCE: 74

Gly Pro Arg Cys Gln Lys Trp Phe Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 75
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2914 polypeptide
<220> FEATURE:
<221> NAME/KEY: MOD_RES
<222> LOCATION: (32)..(32)
<223> OTHER INFORMATION: COOH

<400> SEQUENCE: 75

Gly Pro Arg Cys Gln Lys Trp Phe Gln Thr Cys Asp Ala Glu Arg Lys
1               5                   10                  15

Cys Cys Glu Gly Leu Val Cys Arg Leu Trp Cys Lys Lys Lys Leu Trp
            20                  25                  30

<210> SEQ ID NO 76
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2917 polypeptide
<220> FEATURE:
<221> NAME/KEY: MOD_RES
<222> LOCATION: (32)..(32)
<223> OTHER INFORMATION: COOH

<400> SEQUENCE: 76

Gly Pro Ser Cys Gln Lys Trp Phe Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

<210> SEQ ID NO 77
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D2918 polypeptide
<220> FEATURE:
<221> NAME/KEY: MOD_RES
<222> LOCATION: (32)..(32)
<223> OTHER INFORMATION: COOH

<400> SEQUENCE: 77

Gly Pro Ser Cys Gln Lys Trp Phe Gln Thr Cys Asp Ala Glu Arg Lys
1               5                   10                  15

Cys Cys Glu Gly Leu Val Cys Arg Leu Trp Cys Lys Lys Lys Leu Trp
            20                  25                  30

<210> SEQ ID NO 78
<211> LENGTH: 32
<212> TYPE: PRT
<213> ORGANISM: Artificial Sequence
<220> FEATURE:
<223> OTHER INFORMATION: Description of Artificial Sequence: Synthetic
      NV1D3034 polypeptide
<220> FEATURE:
<221> NAME/KEY: MOD_RES
<222> LOCATION: (32)..(32)
<223> OTHER INFORMATION: COOH

<400> SEQUENCE: 78

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 79
<211> LENGTH: 1977
<212> TYPE: PRT
<213> ORGANISM: Homo Sapiens

<400> SEQUENCE: 79

Met Ala Met Leu Pro Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
            20                  25                  30

Lys Glu Pro Lys Glu Glu Lys Lys Asp Asp Asp Glu Glu Ala Pro Lys
        35                  40                  45

Pro Ser Ser Asp Leu Glu Ala Gly Lys Gln Leu Pro Phe Ile Tyr Gly
    50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

```
Ser Pro Leu Arg Arg Ile Ser Ile Lys Ile Leu Val His Ser Leu Phe
            115                 120                 125

Ser Met Leu Ile Met Cys Thr Ile Leu Thr Asn Cys Ile Phe Met Thr
130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
                180                 185                 190

Phe Val Val Ile Val Phe Ala Tyr Leu Thr Glu Phe Val Asn Leu Gly
            195                 200                 205

Asn Val Ser Ala Leu Arg Thr Phe Arg Val Leu Arg Ala Leu Lys Thr
        210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Asn Ser Leu Glu Asn Asn Glu Thr Leu Glu Ser
        275                 280                 285

Ile Met Asn Thr Leu Glu Ser Glu Glu Asp Phe Arg Lys Tyr Phe Tyr
290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
                325                 330                 335

Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
        355                 360                 365

Gln Thr Leu Arg Ala Ala Gly Lys Thr Tyr Met Ile Phe Phe Val Val
370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
            420                 425                 430

Glu Gln Glu Glu Ala Glu Ala Ile Ala Ala Ala Ala Glu Tyr Thr
        435                 440                 445

Ser Ile Arg Arg Ser Arg Ile Met Gly Leu Ser Glu Ser Ser Ser Glu
450                 455                 460

Thr Ser Lys Leu Ser Ser Lys Ser Ala Lys Glu Arg Arg Asn Arg Arg
465                 470                 475                 480

Lys Lys Lys Asn Gln Lys Lys Leu Ser Ser Gly Glu Glu Lys Gly Asp
                485                 490                 495

Ala Glu Lys Leu Ser Lys Ser Glu Ser Glu Asp Ser Ile Arg Arg Lys
            500                 505                 510

Ser Phe His Leu Gly Val Glu Gly His Arg Arg Ala His Glu Lys Arg
        515                 520                 525
```

```
Leu Ser Thr Pro Asn Gln Ser Pro Leu Ser Ile Arg Gly Ser Leu Phe
    530             535                 540

Ser Ala Arg Arg Ser Ser Arg Thr Ser Leu Phe Ser Phe Lys Gly Arg
545             550                 555                 560

Gly Arg Asp Ile Gly Ser Glu Thr Glu Phe Ala Asp Asp Glu His Ser
                565                 570                 575

Ile Phe Gly Asp Asn Glu Ser Arg Arg Gly Ser Leu Phe Val Pro His
            580                 585                 590

Arg Pro Gln Glu Arg Arg Ser Ser Asn Ile Ser Gln Ala Ser Arg Ser
        595                 600                 605

Pro Pro Met Leu Pro Val Asn Gly Lys Met His Ser Ala Val Asp Cys
    610                 615                 620

Asn Gly Val Val Ser Leu Val Asp Gly Arg Ser Ala Leu Met Leu Pro
625             630                 635                 640

Asn Gly Gln Leu Leu Pro Glu Gly Thr Thr Asn Gln Ile His Lys Lys
                645                 650                 655

Arg Arg Cys Ser Ser Tyr Leu Leu Ser Glu Asp Met Leu Asn Asp Pro
            660                 665                 670

Asn Leu Arg Gln Arg Ala Met Ser Arg Ala Ser Ile Leu Thr Asn Thr
        675                 680                 685

Val Glu Glu Leu Glu Glu Ser Arg Gln Lys Cys Pro Pro Trp Trp Tyr
    690                 695                 700

Arg Phe Ala His Lys Phe Leu Ile Trp Asn Cys Ser Pro Tyr Trp Ile
705             710                 715                 720

Lys Phe Lys Lys Cys Ile Tyr Phe Ile Val Met Asp Pro Phe Val Asp
                725                 730                 735

Leu Ala Ile Thr Ile Cys Ile Val Leu Asn Thr Leu Phe Met Ala Met
            740                 745                 750

Glu His His Pro Met Thr Glu Glu Phe Lys Asn Val Leu Ala Ile Gly
        755                 760                 765

Asn Leu Val Phe Thr Gly Ile Phe Ala Ala Glu Met Val Leu Lys Leu
    770                 775                 780

Ile Ala Met Asp Pro Tyr Glu Tyr Phe Gln Val Gly Trp Asn Ile Phe
785             790                 795                 800

Asp Ser Leu Ile Val Thr Leu Ser Leu Val Glu Leu Phe Leu Ala Asp
                805                 810                 815

Val Glu Gly Leu Ser Val Leu Arg Ser Phe Arg Leu Leu Arg Val Phe
            820                 825                 830

Lys Leu Ala Lys Ser Trp Pro Thr Leu Asn Met Leu Ile Lys Ile Ile
        835                 840                 845

Gly Asn Ser Val Gly Ala Leu Gly Asn Leu Thr Leu Val Leu Ala Ile
    850                 855                 860

Ile Val Phe Ile Phe Ala Val Val Gly Met Gln Leu Phe Gly Lys Ser
865             870                 875                 880

Tyr Lys Glu Cys Val Cys Lys Ile Asn Asp Asp Cys Thr Leu Pro Arg
                885                 890                 895

Trp His Met Asn Asp Phe Phe His Ser Phe Leu Ile Val Phe Arg Val
            900                 905                 910

Leu Cys Gly Glu Trp Ile Glu Thr Met Trp Asp Cys Met Glu Val Ala
        915                 920                 925

Gly Gln Ala Met Cys Leu Ile Val Tyr Met Met Val Met Val Ile Gly
    930                 935                 940

Asn Leu Val Val Leu Asn Leu Phe Leu Ala Leu Leu Leu Ser Ser Phe
```

```
                 945              950              955              960
Ser Ser Asp Asn Leu Thr Ala Ile Glu Glu Asp Pro Asp Ala Asn Asn
                965              970              975
Leu Gln Ile Ala Val Thr Arg Ile Lys Lys Gly Ile Asn Tyr Val Lys
                980              985              990
Gln Thr Leu Arg Glu Phe Ile Leu Lys Ala Phe Ser Lys Lys Pro Lys
                995             1000             1005
Ile Ser Arg Glu Ile Arg Gln Ala Glu Asp Leu Asn Thr Lys Lys
           1010             1015             1020
Glu Asn Tyr Ile Ser Asn His Thr Leu Ala Glu Met Ser Lys Gly
           1025             1030             1035
His Asn Phe Leu Lys Glu Lys Asp Lys Ile Ser Gly Phe Gly Ser
           1040             1045             1050
Ser Val Asp Lys His Leu Met Glu Asp Ser Asp Gly Gln Ser Phe
           1055             1060             1065
Ile His Asn Pro Ser Leu Thr Val Thr Val Pro Ile Ala Pro Gly
           1070             1075             1080
Glu Ser Asp Leu Glu Asn Met Asn Ala Glu Glu Leu Ser Ser Asp
           1085             1090             1095
Ser Asp Ser Glu Tyr Ser Lys Val Arg Leu Asn Arg Ser Ser Ser
           1100             1105             1110
Ser Glu Cys Ser Thr Val Asp Asn Pro Leu Pro Gly Glu Gly Glu
           1115             1120             1125
Glu Ala Glu Ala Glu Pro Met Asn Ser Asp Glu Pro Glu Ala Cys
           1130             1135             1140
Phe Thr Asp Gly Cys Val Arg Arg Phe Ser Cys Cys Gln Val Asn
           1145             1150             1155
Ile Glu Ser Gly Lys Gly Lys Ile Trp Trp Asn Ile Arg Lys Thr
           1160             1165             1170
Cys Tyr Lys Ile Val Glu His Ser Trp Phe Glu Ser Phe Ile Val
           1175             1180             1185
Leu Met Ile Leu Leu Ser Ser Gly Ala Leu Ala Phe Glu Asp Ile
           1190             1195             1200
Tyr Ile Glu Arg Lys Lys Thr Ile Lys Ile Ile Leu Glu Tyr Ala
           1205             1210             1215
Asp Lys Ile Phe Thr Tyr Ile Phe Ile Leu Glu Met Leu Leu Lys
           1220             1225             1230
Trp Ile Ala Tyr Gly Tyr Lys Thr Tyr Phe Thr Asn Ala Trp Cys
           1235             1240             1245
Trp Leu Asp Phe Leu Ile Val Asp Val Ser Leu Val Thr Leu Val
           1250             1255             1260
Ala Asn Thr Leu Gly Tyr Ser Asp Leu Gly Pro Ile Lys Ser Leu
           1265             1270             1275
Arg Thr Leu Arg Ala Leu Arg Pro Leu Arg Ala Leu Ser Arg Phe
           1280             1285             1290
Glu Gly Met Arg Val Val Val Asn Ala Leu Ile Gly Ala Ile Pro
           1295             1300             1305
Ser Ile Met Asn Val Leu Leu Val Cys Leu Ile Phe Trp Leu Ile
           1310             1315             1320
Phe Ser Ile Met Gly Val Asn Leu Phe Ala Gly Lys Phe Tyr Glu
           1325             1330             1335
Cys Ile Asn Thr Thr Asp Gly Ser Arg Phe Pro Ala Ser Gln Val
           1340             1345             1350
```

```
Pro Asn Arg Ser Glu Cys Phe Ala Leu Met Asn Val Ser Gln Asn
    1355                1360                1365

Val Arg Trp Lys Asn Leu Lys Val Asn Phe Asp Asn Val Gly Leu
    1370                1375                1380

Gly Tyr Leu Ser Leu Leu Gln Val Ala Thr Phe Lys Gly Trp Thr
    1385                1390                1395

Ile Ile Met Tyr Ala Ala Val Asp Ser Val Asn Val Asp Lys Gln
    1400                1405                1410

Pro Lys Tyr Glu Tyr Ser Leu Tyr Met Tyr Ile Tyr Phe Val Val
    1415                1420                1425

Phe Ile Ile Phe Gly Ser Phe Phe Thr Leu Asn Leu Phe Ile Gly
    1430                1435                1440

Val Ile Ile Asp Asn Phe Asn Gln Gln Lys Lys Lys Leu Gly Gly
    1445                1450                1455

Gln Asp Ile Phe Met Thr Glu Glu Gln Lys Lys Tyr Tyr Asn Ala
    1460                1465                1470

Met Lys Lys Leu Gly Ser Lys Lys Pro Gln Lys Pro Ile Pro Arg
    1475                1480                1485

Pro Gly Asn Lys Ile Gln Gly Cys Ile Phe Asp Leu Val Thr Asn
    1490                1495                1500

Gln Ala Phe Asp Ile Ser Ile Met Val Leu Ile Cys Leu Asn Met
    1505                1510                1515

Val Thr Met Met Val Glu Lys Glu Gly Gln Ser Gln His Met Thr
    1520                1525                1530

Glu Val Leu Tyr Trp Ile Asn Val Val Phe Ile Ile Leu Phe Thr
    1535                1540                1545

Gly Glu Cys Val Leu Lys Leu Ile Ser Leu Arg His Tyr Tyr Phe
    1550                1555                1560

Thr Val Gly Trp Asn Ile Phe Asp Phe Val Val Val Ile Ile Ser
    1565                1570                1575

Ile Val Gly Met Phe Leu Ala Asp Leu Ile Glu Thr Tyr Phe Val
    1580                1585                1590

Ser Pro Thr Leu Phe Arg Val Ile Arg Leu Ala Arg Ile Gly Arg
    1595                1600                1605

Ile Leu Arg Leu Val Lys Gly Ala Lys Gly Ile Arg Thr Leu Leu
    1610                1615                1620

Phe Ala Leu Met Met Ser Leu Pro Ala Leu Phe Asn Ile Gly Leu
    1625                1630                1635

Leu Leu Phe Leu Val Met Phe Ile Tyr Ala Ile Phe Gly Met Ser
    1640                1645                1650

Asn Phe Ala Tyr Val Lys Lys Glu Asp Gly Ile Asn Asp Met Phe
    1655                1660                1665

Asn Phe Glu Thr Phe Gly Asn Ser Met Ile Cys Leu Phe Gln Ile
    1670                1675                1680

Thr Thr Ser Ala Gly Trp Asp Gly Leu Leu Ala Pro Ile Leu Asn
    1685                1690                1695

Ser Lys Pro Pro Asp Cys Asp Pro Lys Lys Val His Pro Gly Ser
    1700                1705                1710

Ser Val Glu Gly Asp Cys Gly Asn Pro Ser Val Gly Ile Phe Tyr
    1715                1720                1725

Phe Val Ser Tyr Ile Ile Ile Ser Phe Leu Val Val Val Asn Met
    1730                1735                1740
```

Tyr Ile Ala Val Ile Leu Glu Asn Phe Ser Val Ala Thr Glu Glu
    1745                1750                1755

Ser Thr Glu Pro Leu Ser Glu Asp Asp Phe Glu Met Phe Tyr Glu
    1760                1765                1770

Val Trp Glu Lys Phe Asp Pro Asp Ala Thr Gln Phe Ile Glu Phe
    1775                1780                1785

Ser Lys Leu Ser Asp Phe Ala Ala Ala Leu Asp Pro Pro Leu Leu
    1790                1795                1800

Ile Ala Lys Pro Asn Lys Val Gln Leu Ile Ala Met Asp Leu Pro
    1805                1810                1815

Met Val Ser Gly Asp Arg Ile His Cys Leu Asp Ile Leu Phe Ala
    1820                1825                1830

Phe Thr Lys Arg Val Leu Gly Glu Ser Gly Glu Met Asp Ser Leu
    1835                1840                1845

Arg Ser Gln Met Glu Glu Arg Phe Met Ser Ala Asn Pro Ser Lys
    1850                1855                1860

Val Ser Tyr Glu Pro Ile Thr Thr Thr Leu Lys Arg Lys Gln Glu
    1865                1870                1875

Asp Val Ser Ala Thr Val Ile Gln Arg Ala Tyr Arg Arg Tyr Arg
    1880                1885                1890

Leu Arg Gln Asn Val Lys Asn Ile Ser Ser Ile Tyr Ile Lys Asp
    1895                1900                1905

Gly Asp Arg Asp Asp Asp Leu Leu Asn Lys Lys Asp Met Ala Phe
    1910                1915                1920

Asp Asn Val Asn Glu Asn Ser Ser Pro Glu Lys Thr Asp Ala Thr
    1925                1930                1935

Ser Ser Thr Thr Ser Pro Pro Ser Tyr Asp Ser Val Thr Lys Pro
    1940                1945                1950

Asp Lys Glu Lys Tyr Glu Gln Asp Arg Thr Glu Lys Glu Asp Lys
    1955                1960                1965

Gly Lys Asp Ser Lys Glu Ser Lys Lys
    1970                1975

<210> SEQ ID NO 80
<211> LENGTH: 20
<212> TYPE: PRT
<213> ORGANISM: Artificial Sequence
<220> FEATURE:
<223> OTHER INFORMATION: Description of Artificial Sequence: Synthetic
      Linker peptide

<400> SEQUENCE: 80

Gly Gly Gly Gly Ser Gly Gly Gly Gly Ser Gly Gly Gly Gly Ser Gly
1               5                   10                  15

Gly Gly Gly Ser
            20

<210> SEQ ID NO 81
<211> LENGTH: 30
<212> TYPE: PRT
<213> ORGANISM: Artificial Sequence
<220> FEATURE:
<223> OTHER INFORMATION: Description of Artificial Sequence: Synthetic
      Linker polypeptide

<400> SEQUENCE: 81

Gly Gly Gly Gly Ser Gly Gly Gly Gly Ser Gly Gly Gly Gly Ser Gly
1               5                   10                  15

-continued

```
Gly Gly Gly Ser Gly Gly Gly Gly Ser Gly Gly Gly Gly Ser
            20                  25                  30
```

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      HRV3C cleavage site peptide

<400> SEQUENCE: 82

```
Leu Glu Val Leu Phe Gln Gly Pro
1               5
```

<210> SEQ ID NO 83
<211> LENGTH: 672
<212> TYPE: PRT
<213> ORGANISM: Artificial Sequence
<220> FEATURE:
<223> OTHER INFORMATION: Description of Artificial Sequence: Synthetic
      NV1G1007 (NV1D2775) Y1Q, W7Q, S11A, M19F polypeptide

<400> SEQUENCE: 83

```
Met Ala Trp Val Trp Thr Leu Leu Phe Leu Met Ala Ala Ala Gln Ser
1               5                   10                  15

Ile Gln Ala Gly Ser His His His His His Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
        195                 200                 205

Leu Asp Glu Leu Arg Asp Glu Gly Lys Ala Ser Ser Ala Lys Gln Arg
    210                 215                 220

Leu Lys Cys Ala Ser Leu Gln Lys Phe Gly Glu Arg Ala Phe Lys Ala
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
            260                 265                 270
```

Cys His Gly Asp Leu Leu Glu Cys Ala Asp Arg Ala Asp Leu Ala
        275                 280                 285

Lys Tyr Ile Cys Glu Asn Gln Asp Ser Ile Ser Ser Lys Leu Lys Glu
290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
                325                 330                 335

Val Glu Ser Lys Asp Val Cys Lys Asn Tyr Ala Glu Ala Lys Asp Val
            340                 345                 350

Phe Leu Gly Met Phe Leu Tyr Glu Tyr Ala Arg Arg His Pro Asp Tyr
        355                 360                 365

Ser Val Val Leu Leu Leu Arg Leu Ala Lys Thr Tyr Glu Thr Thr Leu
370                 375                 380

Glu Lys Cys Cys Ala Ala Ala Asp Pro His Glu Cys Tyr Ala Lys Val
385                 390                 395                 400

Phe Asp Glu Phe Lys Pro Leu Val Glu Glu Pro Gln Asn Leu Ile Lys
                405                 410                 415

Gln Asn Cys Glu Leu Phe Glu Gln Leu Gly Glu Tyr Lys Phe Gln Asn
            420                 425                 430

Ala Leu Leu Val Arg Tyr Thr Lys Lys Val Pro Gln Val Ser Thr Pro
        435                 440                 445

Thr Leu Val Glu Val Ser Arg Asn Leu Gly Lys Val Gly Ser Lys Cys
450                 455                 460

Cys Lys His Pro Glu Ala Lys Arg Met Pro Cys Ala Glu Asp Tyr Leu
465                 470                 475                 480

Ser Val Val Leu Asn Gln Leu Cys Val Leu His Glu Lys Thr Pro Val
                485                 490                 495

Ser Asp Arg Val Thr Lys Cys Cys Thr Glu Ser Leu Val Asn Arg Arg
            500                 505                 510

Pro Cys Phe Ser Ala Leu Glu Val Asp Glu Thr Tyr Val Pro Lys Glu
        515                 520                 525

Phe Asn Ala Glu Thr Phe Thr Phe His Ala Asp Ile Cys Thr Leu Ser
530                 535                 540

Glu Lys Glu Arg Gln Ile Lys Lys Gln Thr Ala Leu Val Glu Leu Val
545                 550                 555                 560

Lys His Lys Pro Lys Ala Thr Lys Glu Gln Leu Lys Ala Val Met Asp
                565                 570                 575

Asp Phe Ala Ala Phe Val Glu Lys Cys Cys Lys Ala Asp Asp Lys Glu
            580                 585                 590

Thr Cys Phe Ala Glu Glu Gly Lys Lys Leu Val Ala Ala Ser Gln Ala
        595                 600                 605

Ala Leu Gly Leu Gly Ser Gly Gly Gly Gly Ser Gly Gly Gly Ser
610                 615                 620

Gly Gly Gly Gly Ser Gly Gly Gly Ser Leu Glu Val Leu Phe Gln
625                 630                 635                 640

Gly Pro Gln Cys Gln Lys Trp Met Gln Thr Cys Asp Ala Glu Arg Lys
                645                 650                 655

Cys Cys Glu Gly Phe Val Cys Arg Leu Trp Cys Lys Lys Lys Leu Trp
            660                 665                 670

<210> SEQ ID NO 84
<211> LENGTH: 2019
<212> TYPE: DNA

<213> ORGANISM: Artificial Sequence
<220> FEATURE:
<223> OTHER INFORMATION: Description of Artificial Sequence: Synthetic
NV1G1007 (NV1D2775) Y1Q, W7Q, S11A, M19F polynucleotide

<400> SEQUENCE: 84

```
atggcttggg tgtggacctt gctattcctg atggcggccg cccaaagtat acaggccggg     60
agccaccacc accaccacca cgacgcccac aagagcgagg tggcccaccg gttcaaggac    120
ctgggcgagg agaacttcaa ggccctggtg ctgatcgcct tcgcccagta cctgcagcag    180
tgccccttcg aggaccacgt gaagctggtg aacgaggtga ccgagttcgc caagacctgc    240
gtggccgacg agagcgccga gaactgcgac aagagcctgc acaccctgtt cggcgacaag    300
ctgtgcaccg tggccaccct gcgggagacc tacggcgaga tggccgactg ctgcgccaag    360
caggagcccg agcggaacga gtgcttcctg cagcacaagg acgacaaccc caacctgccc    420
cggctggtgc ggcccgaggt ggacgtgatg tgcaccgcct tccacgacaa cgaggagacc    480
ttcctgaaga agtacctgta cgagatcgcc cggcggcacc cctacttcta cgcccccgag    540
ctgctgttct tcgccaagcg gtacaaggcc gccttcaccg agtgctgcca ggccgccgac    600
aaggccgcct gcctgctgcc caagctggac gagctgcggg acgagggcaa ggccagcagc    660
gccaagcagc ggctgaagtg cgccagcctg cagaagttcg gcgagcgggc cttcaaggcc    720
tgggccgtgg cccggctgag ccagcggttc cccaaggccg agttcgccga ggtgagcaag    780
ctggtgaccg acctgaccaa ggtgcacacc gagtgctgcc acggcgacct gctggagtgc    840
gccgacgacc gggccgacct ggccaagtac atctgcgaga accaggacag catcagcagc    900
aagctgaagg agtgctgcga gaagcccctg ctggagaaga gccactgcat cgccgaggtg    960
gagaacgacg agatgcccgc cgacctgccc agcctggccg ccgacttcgt ggagagcaag   1020
gacgtgtgca agaactacgc cgaggccaag gacgtgttcc tgggcatgtt cctgtacgag   1080
tacgcccggc ggcaccccga ctacagcgtg gtgctgctgc tgcggctggc caagacctac   1140
gagaccaccc tggagaagtg ctgcgccgcc gccgaccccc acgagtgcta cgccaaggtg   1200
ttcgacgagt tcaagcccct ggtggaggag ccccagaacc tgatcaagca gaactgcgag   1260
ctgttcgagc agctgggcga gtacaagttc cagaacgccc tgctggtgcg gtacaccaag   1320
aaggtgcccc aggtgagcac ccccaccctg gtggaggtga gccggaacct gggcaaggtg   1380
ggcagcaagt gctgcaagca ccccgaggcc aagcggatgc cctgcgccga ggactacctg   1440
agcgtggtgc tgaaccagct gtgcgtgctg cacgagaaga cccccgtgag cgaccgggtg   1500
accaagtgct gcaccgagag cctggtgaac cggcggccct gcttcagcgc cctggaggtg   1560
gacgagacct acgtgcccaa ggagttcaac gccgagacct tcaccttcca cgccgacatc   1620
tgcaccctga gcgagaagga gcggcagatc aagaagcaga ccgccctggt ggagctggtg   1680
aagcacaagc ccaaggccac caaggagcag ctgaaggccg tgatggacga cttcgccgcc   1740
ttcgtggaga agtgctgcaa ggccgacgac aaggagacct gcttcgccga ggagggcaag   1800
aagctggtgg ccgccagcca ggccgccctg ggcctgggca gcggcggcgg cggcagcggc   1860
ggcggcggat ctggtggagg tggcagtgga ggagggggat ccctcgaggt cctctttcag   1920
ggaccacagt gccagaagtg gatgcagaca tgcgacgccg agcgcaagtg ctgcgaaggc   1980
ttcgtgtgtc gcctgtggtg taaaaagaag ttgtggtga                           2019
```

<210> SEQ ID NO 85
<211> LENGTH: 672
<212> TYPE: PRT

<213> ORGANISM: Artificial Sequence
<220> FEATURE:
<223> OTHER INFORMATION: Description of Artificial Sequence: Synthetic
      NV1G1005 (NV1D2772) Y1R, W7Q, S11A, M19F polypeptide

<400> SEQUENCE: 85

| Met | Ala | Trp | Val | Tr

```
Glu Lys Cys Cys Ala Ala Asp Pro His Glu Cys Tyr Ala Lys Val
385                 390                 395                 400

| | | |
|---|---|---|
| cggctggtgc ggcccgaggt ggacgtgatg tgcaccgcct t

-continued

```
Val Ala Asp Glu Ser Ala Glu Asn Cys Asp Lys Ser Leu His Thr Leu
             85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
            115                 120                 125

Phe Leu Gln His Lys Asp Asp Asn Pro Asn Leu Pro Arg Leu Val Arg
130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
            195                 200                 205

Leu Asp Glu Leu Arg Asp Glu Gly Lys Ala Ser Ser Ala Lys Gln Arg
210                 215                 220

Leu Lys Cys Ala Ser Leu Gln Lys Phe Gly Glu Arg Ala Phe Lys Ala
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
            260                 265                 270

Cys His Gly Asp Leu Leu Glu Cys Ala Asp Asp Arg Ala Asp Leu Ala
            275                 280                 285

Lys Tyr Ile Cys Glu Asn Gln Asp Ser Ile Ser Ser Lys Leu Lys Glu
290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
                325                 330                 335

Val Glu Ser Lys Asp Val Cys Lys Asn Tyr Ala Glu Ala Lys Asp Val
            340                 345                 350

Phe Leu Gly Met Phe Leu Tyr Glu Tyr Ala Arg Arg His Pro Asp Tyr
            355                 360                 365

Ser Val Val Leu Leu Leu Arg Leu Ala Lys Thr Tyr Glu Thr Thr Leu
370                 375                 380

Glu Lys Cys Cys Ala Ala Ala Asp Pro His Glu Cys Tyr Ala Lys Val
385                 390                 395                 400

Phe Asp Glu Phe Lys Pro Leu Val Glu Glu Pro Gln Asn Leu Ile Lys
                405                 410                 415

Gln Asn Cys Glu Leu Phe Glu Gln Leu Gly Glu Tyr Lys Phe Gln Asn
            420                 425                 430

Ala Leu Leu Val Arg Tyr Thr Lys Lys Val Pro Gln Val Ser Thr Pro
            435                 440                 445

Thr Leu Val Glu Val Ser Arg Asn Leu Gly Lys Val Gly Ser Lys Cys
450                 455                 460

Cys Lys His Pro Glu Ala Lys Arg Met Pro Cys Ala Glu Asp Tyr Leu
465                 470                 475                 480

Ser Val Val Leu Asn Gln Leu Cys Val Leu His Glu Lys Thr Pro Val
                485                 490                 495
```

| | | | | | | | | | | | | |
|---|---|---|---|---|---|---|---|---|---|---|---|---|
|Ser|Asp|Arg|Val|Thr|Lys|Cys|Cys|Thr|Glu|Ser|Leu|Val|Asn|Arg|Arg|
| | | |500| | | |505| | | |510| |

Pro Cys Phe Ser Ala Leu Glu Val Asp Glu Thr Tyr Val Pro Lys Glu
            515                 520                 525

Phe Asn Ala Glu Thr Phe Thr Phe His Ala Asp Ile Cys Thr Leu Ser
530                 535                 540

Glu Lys Glu Arg Gln Ile Lys Lys Gln Thr Ala Leu Val Glu Leu Val
545                 550                 555                 560

Lys His Lys Pro Lys Ala Thr Lys Glu Gln Leu Lys Ala Val Met Asp
                565                 570                 575

Asp Phe Ala Ala Phe Val Glu Lys Cys Cys Lys Ala Asp Asp Lys Glu
                580                 585                 590

Thr Cys Phe Ala Glu Glu Gly Lys Lys Leu Val Ala Ala Ser Gln Ala
            595                 600                 605

Ala Leu Gly Leu Gly Ser Gly Gly Gly Ser Gly Gly Gly Gly Ser
            610                 615                 620

Gly Gly Gly Gly Ser Gly Gly Gly Ser Leu Glu Val Leu Phe Gln
625                 630                 635                 640

Gly Pro Ser Cys Gln Lys Trp Met Gln Thr Cys Asp Ala Glu Arg Lys
                645                 650                 655

Cys Cys Glu Gly Phe Val Cys Arg Leu Trp Cys Lys Lys Lys Leu Trp
            660                 665                 670

<210> SEQ ID NO 88
<211> LENGTH: 2019
<212> TYPE: DNA
<213> ORGANISM: Artificial Sequence
<220> FEATURE:
<223> OTHER INFORMATION: Description of Artificial Sequence: Synthetic
      NV1G1001 (NV1D2773) Y1S, W7Q, S11A, M19F polynucleotide

<400> SEQUENCE: 88

| | | |
|---|---|---|
|atggcttggg tgtggacctt gctattcctg atggcggccg cccaaagtat acaggccggg|60|
|agccaccacc accaccacca cgacgcccac aagagcgagg tggcccaccg gttcaaggac|120|
|ctgggcgagg agaacttcaa ggccctggtg ctgatcgcct tcgcccagta cctgcagcag|180|
|tgccccttcg aggaccacgt gaagctggtg aacgaggtga ccgagttcgc caagacctgc|240|
|gtggccgacg agagcgccga gaactgcgac aagagcctgc acaccctgtt cggcgacaag|300|
|ctgtgcaccg tggccaccct gcgggagacc tacggcgaga tggccgactg ctgcgccaag|360|
|caggagcccg agcggaacga gtgcttcctg cagcacaagg acgacaaccc caacctgccc|420|
|cggctggtgc ggcccgaggt ggacgtgatg tgcaccgcct ccacgacaa cgaggagacc|480|
|ttcctgaaga gtacctgta cgagatcgcc cggcggcacc cctacttcta cgcccccgag|540|
|ctgctgttct tcgccaagcg gtacaaggcc gccttcaccg agtgctgcca ggccgccgac|600|
|aaggccgcct gcctgctgcc caagctggac gagctgcggg acgagggcaa ggccagcagc|660|
|gccaagcagc ggctgaagtg cgccagcctg cagaagttcg cgagcgggc cttcaaggcc|720|
|tgggccgtgg cccggctgag ccagcggttc cccaaggccg agttcgccga ggtgagcaag|780|
|ctggtgaccg acctgaccaa ggtgcacacc gagtgctgcc acggcgacct gctggagtgc|840|
|gccgacgacc gggccgacct ggccaagtac atctgcgaga accaggacag catcagcagc|900|
|aagctgaagg agtgctgcga aagcccctg ctggagaaga gccactgcat cgccgaggtg|960|
|gagaacgacg agatgcccgc cgacctgccc agcctggccg ccgacttcgt ggagagcaag|1020|
|gacgtgtgca agaactacgc cgaggccaag gacgtgttcc tgggcatgtt cctgtacgag|1080|

```
tacgcccggc ggcaccccga ctacagcgtg gtgctgctgc tgcggctggc caagacctac      1140
gagaccaccc tggagaagtg ctgcgccgcc gccgaccccc acgagtgcta cgccaaggtg      1200
ttcgacgagt tcaagcccct ggtggaggag ccccagaacc tgatcaagca gaactgcgag      1260
ctgttcgagc agctgggcga gtacaagttc cagaacgccc tgctggtgcg gtacaccaag      1320
aaggtgcccc aggtgagcac ccccacccctg gtggaggtga gccggaacct gggcaaggtg      1380
ggcagcaagt gctgcaagca ccccgaggcc aagcggatgc cctgcgccga ggactacctg      1440
agcgtggtgc tgaaccagct gtgcgtgctg cacgagaaga ccccgtgag cgaccgggtg       1500 accaagtgct gcaccgagag cctggtgaac cggcggccct gcttcagcgc cctggaggtg      1560
gacgagacct acgtgcccaa ggagttcaac gccgagacct caccttcca cgccgacatc      1620 tgcacccctga gcgagaagga gcggcagatc aagaagcaga ccgccctggt ggagctggtg      1680
aagcacaagc ccaaggccac caaggagcag ctgaaggccg tgatggacga cttcgccgcc      1740
ttcgtggaga gtgctgcaa ggccgacgac aaggagacct gcttcgccga ggagggcaag      1800
aagctggtgg ccgccagcca ggccgccctg ggcctgggca gcggcggcgg cggcagcggc      1860
ggcggcggat ctggtggagg tggcagtgga ggaggggggat ccctcgaggt cctctttcag      1920
ggaccaagct gccagaagtg gatgcagaca tgcgacgccg agcgcaagtg ctgcgaaggc      1980
ttcgtgtgtc gcctgtggtg taaaaagaag ttgtggtga                             2019

<210> SEQ ID NO 89
<211> LENGTH: 672
<212> TYPE: PRT
<213> ORGANISM: Artificial Sequence
<220> FEATURE:
<223> OTHER INFORMATION: Description of Artificial Sequence: Synthetic
      NV1G1079 (NV1D2889) Y1S,M6F,S11A,M19F polypeptide

<400> SEQUENCE: 89

Met Ala Trp Val Trp Thr Leu Leu Phe Leu Met Ala Ala Ala Gln Ser
1               5                   10                  15

Ile Gln Ala Gly Ser His His His His His His Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190
```

```
Thr Glu Cys Cys Gln Ala Ala Asp Lys Ala Ala Cys Leu Leu Pro Lys
        195                 200                 205

Leu Asp Glu Leu Arg Asp Gly Lys Ala Ser Ser Ala Lys Gln Arg
    210                 215                 220

Leu Lys Cys Ala Ser Leu Gln Lys Phe Gly Glu Arg Ala Phe Lys Ala
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
            260                 265                 270

Cys His Gly Asp Leu Leu Glu Cys Ala Asp Asp Arg Ala Asp Leu Ala
        275                 280                 285

Lys Tyr Ile Cys Glu Asn Gln Asp Ser Ile Ser Ser Lys Leu Lys Glu
    290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
                325                 330                 335

Val Glu Ser Lys Asp Val Cys Lys Asn Tyr Ala Glu Ala Lys Asp Val
            340                 345                 350

Phe Leu Gly Met Phe Leu Tyr Glu Tyr Ala Arg Arg His Pro Asp Tyr
        355                 360                 365

Ser Val Val Leu Leu Leu Arg Leu Ala Lys Thr Tyr Glu Thr Thr Leu
    370                 375                 380

Glu Lys Cys Cys Ala Ala Ala Asp Pro His Glu Cys Tyr Ala Lys Val
385                 390                 395                 400

Phe Asp Glu Phe Lys Pro Leu Val Glu Glu Pro Gln Asn Leu Ile Lys
                405                 410                 415

Gln Asn Cys Glu Leu Phe Glu Gln Leu Gly Glu Tyr Lys Phe Gln Asn
            420                 425                 430

Ala Leu Leu Val Arg Tyr Thr Lys Lys Val Pro Gln Val Ser Thr Pro
        435                 440                 445

Thr Leu Val Glu Val Ser Arg Asn Leu Gly Lys Val Gly Ser Lys Cys
    450                 455                 460

Cys Lys His Pro Glu Ala Lys Arg Met Pro Cys Ala Glu Asp Tyr Leu
465                 470                 475                 480

Ser Val Val Leu Asn Gln Leu Cys Val Leu His Glu Lys Thr Pro Val
                485                 490                 495

Ser Asp Arg Val Thr Lys Cys Cys Thr Glu Ser Leu Val Asn Arg Arg
            500                 505                 510

Pro Cys Phe Ser Ala Leu Glu Val Asp Glu Thr Tyr Val Pro Lys Glu
        515                 520                 525

Phe Asn Ala Glu Thr Phe Thr Phe His Ala Asp Ile Cys Thr Leu Ser
    530                 535                 540

Glu Lys Glu Arg Gln Ile Lys Lys Gln Thr Ala Leu Val Glu Leu Val
545                 550                 555                 560

Lys His Lys Pro Lys Ala Thr Lys Glu Gln Leu Lys Ala Val Met Asp
                565                 570                 575

Asp Phe Ala Ala Phe Val Glu Lys Cys Cys Lys Ala Asp Asp Lys Glu
            580                 585                 590

Thr Cys Phe Ala Glu Glu Gly Lys Lys Leu Val Ala Ala Ser Gln Ala
        595                 600                 605
```

```
        Ala Leu Gly Leu Gly Ser Gly Gly Gly Ser Gly Gly Gly Gly Ser
        610                 615                 620

Gly Gly Gly Gly Ser Gly Gly Gly Ser Leu Glu Val Leu Phe Gln
        625                 630                 635                 640

Gly Pro Ser Cys Gln Lys Trp Phe Trp Thr Cys Asp Ala Glu Arg Lys
                        645                 650                 655

Cys Cys Glu Gly Phe Val Cys Arg Leu Trp Cys Lys Lys Lys Leu Trp
                    660                 665                 670

<210> SEQ ID NO 90
<211> LENGTH: 2019
<212> TYPE: DNA
<213> ORGANISM: Artificial Sequence
<220> FEATURE:
<223> OTHER INFORMATION: Description of Artificial Sequence: Synthetic
      NV1G1079 (NV1D2889) Y1S,M6F,S11A,M19F polynucleotide

<400> SEQUENCE: 90
atggcttggg tgtggacctt gctattcctg atggcggccg cccaaagtat acaggccggg      60
agccaccacc accaccacca cgacgcccac aagagcgagg tggcccaccg gttcaaggac     120
ctgggcgagg agaacttcaa ggccctggtg ctgatcgcct tcgcccagta cctgcagcag     180
tgcccttcg aggaccacgt gaagctggtg aacgaggtga ccgagttcgc caagacctgc     240
gtggccgacg agagcgccga gaactgcgac aagagcctgc acaccctgtt cggcgacaag     300
ctgtgcaccg tggccaccct gcgggagacc tacggcgaga tggccgactg ctgcgccaag     360
caggagcccg agcggaacga gtgcttcctg cagcacaagg acgacaaccc caacctgccc     420
cggctggtgc ggcccgaggt ggacgtgatg tgcaccgcct ccacgacaa cgaggagacc     480
ttcctgaaga gtacctgta cgagatcgcc cggcggcacc cctacttcta cgccccccga      540
ctgctgttct tcgccaagcg gtacaaggcc gccttcaccg agtgctgcca ggccgccgac     600
aaggccgcct gcctgctgcc caagctggac gagctgcggg acgagggcaa ggccagcagc     660
gccaagcagc ggctgaagtg cgccagcctg cagaagttcg gcgagcgggc cttcaaggcc     720
tgggccgtgg cccggctgag ccagcggttc cccaaggccg agttcgccga ggtgagcaag     780
ctggtgaccg acctgaccaa ggtgcacacc gagtgctgcc acggcgacct gctggagtgc     840
gccgacgacc gggccgacct ggccaagtac atctgcgaga accaggacag catcagcagc     900
aagctgaagg agtgctgcga aagcccctg ctggagaaga gccactgcat cgccgaggtg     960
gagaacgacg agatgcccgc cgacctgccc agcctggccg ccgacttcgt ggagagcaag    1020
gacgtgtgca gaactacgc cgaggccaag gacgtgttcc tgggcatgtt cctgtacgag    1080
tacgcccggc ggcaccccga ctacagcgtg gtgctgctgc tgcggctggc caagacctac    1140
gagaccaccc tggagaagtg ctgcgccgcc gccgaccccc acgagtgcta cgccaaggtg    1200
ttcgacgagt tcaagccct ggtggaggag ccccagaacc tgatcaagca gaactgcgag    1260
ctgttcgagc agctgggcga gtacaagttc cagaacgccc tgctggtgcg gtacaccaag    1320
aaggtgcccc aggtgagcac ccccaccctg gtggaggtga ccggaacct gggcaaggtg    1380
ggcagcaagt gctgcaagca ccccgaggcc aagcggatgc cctgcgccga ggactacctg    1440
agcgtggtgc tgaaccagct gtgcgtgctg cacgagaaga cccccgtgag cgaccgggtg    1500
accaagtgct gcaccgagag cctggtgaac cggcggccct gcttcagcgc cctggaggtg    1560
gacgagaccc acgtgcccaa ggagttcaac gccgagacct tcaccttcca cgccgacatc    1620
tgcaccctga cgagaagga cggcagatc aagaagcaga ccgccctggt ggagctggtg    1680
```

```
aagcacaagc ccaaggccac caaggagcag ctgaaggccg tgatggacga cttcgccgcc    1740
ttcgtggaga agtgctgcaa ggccgacgac aaggagacct gcttcgccga ggagggcaag    1800
aagctggtgg ccgccagcca ggccgccctg ggcctgggca gcggcggcgg cggcagcggc    1860
ggcggcggat ctggtggagg tggcagtgga ggaggggggat ccctcgaggt cctctttcag    1920
ggaccaagct gccagaagtg gttctggaca tgcgacgccg agcgcaagtg ctgcgaaggc    1980
ttcgtgtgtc gcctgtggtg taaaaagaag ttgtggtga                           2019
```

<210> SEQ ID NO 91
<211> LENGTH: 672
<212> TYPE: PRT
<213> ORGANISM: Artificial Sequence
<220> FEATURE:
<223> OTHER INFORMATION: Description of Artificial Sequence: Synthetic
      NV1G1107 (NV1D2890) Y1S,M6F,S11A,M19L polypeptide

<400> SEQUENCE: 91

```
Met Ala Trp Val Trp Thr Leu Leu Phe Leu Met Ala Ala Ala Gln Ser
1               5                   10                  15

Ile Gln Ala Gly Ser His His His His His Asp Ala His Lys Ser

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
            325                 330                 335

Val Glu Ser Lys Asp Val Cys Lys Asn Tyr Ala Glu Ala Lys Asp Val
        340                 345                 350

Phe Leu Gly Met Phe Leu Tyr Glu Tyr Ala Arg Arg His Pro Asp Tyr
            355                 360                 365

Ser Val Val Leu Leu Leu Arg Leu Ala Lys Thr Tyr Glu Thr Thr Leu
370                 375                 380

Glu Lys Cys Cys Ala Ala Ala Asp Pro His Glu Cys Tyr Ala Lys Val
385                 390                 395                 400

Phe Asp Glu Phe Lys Pro Leu Val Glu Glu Pro Gln Asn Leu Ile Lys
                405                 410                 415

Gln Asn Cys Glu Leu Phe Glu Gln Leu Gly Glu Tyr Lys Phe Gln Asn
            420                 425                 430

Ala Leu Leu Val Arg Tyr Thr Lys Lys Val Pro Gln Val Ser Thr Pro
        435                 440                 445

Thr Leu Val Glu Val Ser Arg Asn Leu Gly Lys Val Gly Ser Lys Cys
450                 455                 460

Cys Lys His Pro Glu Ala Lys Arg Met Pro Cys Ala Glu Asp Tyr Leu
465                 470                 475                 480

Ser Val Val Leu Asn Gln Leu Cys Val Leu His Glu Lys Thr Pro Val
                485                 490                 495

Ser Asp Arg Val Thr Lys Cys Cys Thr Glu Ser Leu Val Asn Arg Arg
        500                 505                 510

Pro Cys Phe Ser Ala Leu Glu Val Asp Glu Thr Tyr Val Pro Lys Glu
    515                 520                 525

Phe Asn Ala Glu Thr Phe Thr Phe His Ala Asp Ile Cys Thr Leu Ser
530                 535                 540

Glu Lys Glu Arg Gln Ile Lys Lys Gln Thr Ala Leu Val Glu Leu Val
545                 550                 555                 560

Lys His Lys Pro Lys Ala Thr Lys Glu Gln Leu Lys Ala Val Met Asp
                565                 570                 575

Asp Phe Ala Ala Phe Val Glu Lys Cys Cys Lys Ala Asp Asp Lys Glu
            580                 585                 590

Thr Cys Phe Ala Glu Glu Gly Lys Lys Leu Val Ala Ala Ser Gln Ala
        595                 600                 605

Ala Leu Gly Leu Gly Ser Gly Gly Gly Ser Gly Gly Gly Ser
    610                 615                 620

Gly Gly Gly Gly Ser Gly Gly Gly Ser Leu Glu Val Leu Phe Gln
625                 630                 635                 640

Gly Pro Ser Cys Gln Lys Trp Phe Trp Thr Cys Asp Ala Glu Arg Lys
            645                 650                 655

Cys Cys Glu Gly Leu Val Cys Arg Leu Trp Cys Lys Lys Lys Leu Trp
            660                 665                 670

<210> SEQ ID NO 92
<211> LENGTH: 2019
<212> TYPE: DNA
<213> ORGANISM: Artificial Sequence
<220> FEATURE:
<223> OTHER INFORMATION: Description of Artificial Sequence: Synthetic
      NV1G1107 (NV1D2890) Y1S,M6F,S11A,M19L polynucleotide

<400> SEQUENCE: 92

```
atggcttggg tgtggacctt gctattcctg atggcggccg cccaaagtat acaggccggg      60
agccaccacc accaccacca cgacgcccac aagagcgagg tggcccaccg gttcaaggac     120
ctgggcgagg agaacttcaa ggccctggtg ctgatcgcct tcgcccagta cctgcagcag     180
tgccccttcg aggaccacgt gaagctggtg aacgaggtga ccgagttcgc caagacctgc     240
gtggccgacg agagcgccga gaactgcgac aagagcctgc acaccctgtt cggcgacaag     300
ctgtgcaccg tggccaccct gcgggagacc tacgcgaga tggccgactg ctgcgccaag     360
caggagcccg agcggaacga gtgcttcctg cagcacaagg acgacaaccc caacctgccc     420
cggctggtgc ggcccgaggt ggacgtgatg tgcaccgcct tccacgacaa cgaggagacc     480
ttcctgaaga gtacctgta cgagatcgcc cggcggcacc cctacttcta cgcccccgag     540
ctgctgttct cgccaagcg gtacaaggcc gccttcaccg agtgctgcca ggccgccgac     600
aaggccgcct gcctgctgcc caagctggac gagctgcggg acgagggcaa ggccagcagc     660
gccaagcagc ggctgaagtg cgccagcctg cagaagttcg gcgagcgggc cttcaaggcc     720
tgggccgtgg cccggctgag ccagcggttc cccaaggccg agttcgccga ggtgagcaag     780
ctggtgaccg acctgaccaa ggtgcacacc gagtgctgcc acggcgacct gctggagtgc     840
gccgacgacc gggccgacct ggccaagtac atctgcgaga accaggacag catcagcagc     900
aagctgaagg agtgctgcga aagcccctg ctggagaaga ccactgcat cgccgaggtg     960
gagaacgacg agatgcccgc cgacctgccc agcctggccg ccgacttcgt ggagagcaag    1020
gacgtgtgca agaactacgc cgaggccaag acgtgttcc tgggcatgtt cctgtacgag    1080
tacgcccggc ggcaccccga ctacagcgtg gtgctgctgc tgcggctggc caagacctac    1140
gagaccaccc tggagaagtg ctgcgccgcc gccgaccccc acgagtgcta cgccaaggtg    1200
ttcgacgagt tcaagcccct ggtggaggag ccccagaacc tgatcaagca gaactgcgag    1260
ctgttcgagc agctgggcga gtacaagttc cagaacgccc tgctggtgcg gtacaccaag    1320
aaggtgcccc aggtgagcac ccccaccctg gtggaggtga gccggaacct gggcaaggtg    1380
ggcagcaagt gctgcaagca ccccgaggcc aagcggatgc cctgcgccga ggactacctg    1440
agcgtggtgc tgaaccagct gtgcgtgctg cacgagaaga ccccgtgag cgaccgggtg    1500
accaagtgct gcaccgagag cctggtgaac cggcggccct gcttcagcgc cctggaggtg    1560
gacgagacct acgtgcccaa ggagttcaac gccgagacct tcaccttcca cgccgacatc    1620
tgcaccctga gcgagaagga gcggcagatc aagaagcaga ccgccctggt ggagctggtg    1680
aagcacaagc ccaaggccac caaggagcag ctgaaggccg tgatggacga cttcgccgcc    1740
ttcgtggaga agtgctgcaa ggccgacgac aaggagacct gcttcgccga ggagggcaag    1800
aagctggtgg ccgccagcca ggccgccctg ggcctgggca gcggcggcgg cggcagcggc    1860
ggcggcggat ctggtggagg tggcagtgga ggagggggat ccctcgaggt cctctttcag    1920
ggaccaagct gccagaagtg gttctggacc tgcgacgccg agcggaagtg ctgcgagggc    1980
ctggtgtgcc ggctgtggtg caagaagaag ctgtggtga                         2019
```

<210> SEQ ID NO 93
<211> LENGTH: 672
<212> TYPE: PRT
<213> ORGANISM: Artificial Sequence
<220> FEATURE:
<223> OTHER INFORMATION: Description of Artificial Sequence: Synthetic
      NV1G1063 (NV1D2913) Y1R,M6F,W7Q,S11A,M19F polypeptide

<400> SEQUENCE: 93

```
Met Ala Trp Val Trp Thr Leu Leu Phe Leu Met Ala Ala Ala Gln Ser
1               5                   10                  15

Ile Gln Ala Gly Ser His His His His His His Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
        195                 200                 205

Leu Asp Glu Leu Arg Asp Glu Gly Lys Ala Ser Ser Ala Lys Gln Arg
    210                 215                 220

Leu Lys Cys Ala Ser Leu Gln Lys Phe Gly Glu Arg Ala Phe Lys Ala
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
            260                 265                 270

Cys His Gly Asp Leu Leu Glu Cys Ala Asp Asp Arg Ala Asp Leu Ala
        275                 280                 285

Lys Tyr Ile Cys Glu Asn Gln Asp Ser Ile Ser Ser Lys Leu Lys Glu
    290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
                325                 330                 335

Val Glu Ser Lys Asp Val Cys Lys Asn Tyr Ala Glu Ala Lys Asp Val
            340                 345                 350

Phe Leu Gly Met Phe Leu Tyr Glu Tyr Ala Arg Arg His Pro Asp Tyr
        355                 360                 365

Ser Val Val Leu Leu Leu Arg Leu Ala Lys Thr Tyr Glu Thr Thr Leu
    370                 375                 380

Glu Lys Cys Cys Ala Ala Ala Asp Pro His Glu Cys Tyr Ala Lys Val
385                 390                 395                 400

Phe Asp Glu Phe Lys Pro Leu Val Glu Glu Pro Gln Asn Leu Ile Lys
                405                 410                 415
```

```
Gln Asn Cys Glu Leu Phe Glu Gln Leu Gly Glu Tyr Lys Phe Gln Asn
            420                 425                 430

Ala Leu Leu Val Arg Tyr Thr Lys Lys Val Pro Gln Val Ser Thr Pro
        435                 440                 445

Thr Leu Val Glu Val Ser Arg Asn Leu Gly Lys Val Gly Ser Lys Cys
    450                 455                 460

Cys Lys His Pro Glu Ala Lys Arg Met Pro Cys Ala Glu Asp Tyr Leu
465                 470                 475                 480

Ser Val Val Leu Asn Gln Leu Cys Val Leu His Glu Lys Thr Pro Val
                485                 490                 495

Ser Asp Arg Val Thr Lys Cys Cys Thr Glu Ser Leu Val Asn Arg Arg
            500                 505                 510

Pro Cys Phe Ser Ala Leu Glu Val Asp Glu Thr Tyr Val Pro Lys Glu
        515                 520                 525

Phe Asn Ala Glu Thr Phe Thr Phe His Ala Asp Ile Cys Thr Leu Ser
    530                 535                 540

Glu Lys Glu Arg Gln Ile Lys Lys Gln Thr Ala Leu Val Glu Leu Val
545                 550                 555                 560

Lys His Lys Pro Lys Ala Thr Lys Glu Gln Leu Lys Ala Val Met Asp
                565                 570                 575

Asp Phe Ala Ala Phe Val Glu Lys Cys Cys Lys Ala Asp Asp Lys Glu
            580                 585                 590

Thr Cys Phe Ala Glu Glu Gly Lys Lys Leu Val Ala Ala Ser Gln Ala
        595                 600                 605

Ala Leu Gly Leu Gly Ser Gly Gly Gly Gly Ser Gly Gly Gly Gly Ser
    610                 615                 620

Gly Gly Gly Gly Ser Gly Gly Gly Gly Ser Leu Glu Val Leu Phe Gln
625                 630                 635                 640

Gly Pro Arg Cys Gln Lys Trp Phe Gln Thr Cys Asp Ala Glu Arg Lys
                645                 650                 655

Cys Cys Glu Gly Phe Val Cys Arg Leu Trp Cys Lys Lys Lys Leu Trp
            660                 665                 670
```

<210> SEQ ID NO 94
<211> LENGTH: 2019
<212> TYPE: DNA
<213> ORGANISM: Artificial Sequence
<220> FEATURE:
<223> OTHER INFORMATION: Description of Artificial Sequence: Synthetic NV1G1063 (NV1D2913) Y1R,M6F,W7Q,S11A,M19F polynucleotide

<400> SEQUENCE: 94

```
atggcttggg tgtggacctt gctattcctg atggcggccg cccaaagtat acaggccggg      60
agccaccacc accaccacca cgacgcccac aagagcgagg tggcccaccg gttcaaggac     120
ctgggcgagg agaacttcaa ggccctggtg ctgatcgcct tcgcccagta cctgcagcag     180
tgccccttcg aggaccacgt gaagctggtg aacgaggtga ccgagttcgc caagacctgc     240
gtggccgacg agagcgccga gaactgcgac aagagcctgc acaccctgtt cggcgacaag     300
ctgtgcaccg tggccaccct gcgggagacc tacggcgaga tggccgactg ctgcgccaag     360
caggagcccg agcggaacga gtgcttcctg cagcacaagg acgacaaccc caacctgccc     420
cggctggtgc ggcccgaggt ggacgtgatg tgcaccgcct tccacgacaa cgaggagacc     480
ttcctgaaga agtacctgta cgagatcgcc cggcggcacc cctacttcta cgcccccgag     540
ctgctgttct tcgccaagcg gtacaaggcc gccttcaccg agtgctgcca ggccgccgac     600
```

```
aaggccgcct gcctgctgcc caagctggac gagctgcggg acgagggcaa ggccagcagc    660
gccaagcagc ggctgaagtg cgccagcctg cagaagttcg cgagcgggc cttcaaggcc    720 tgggccgtgg cccggctgag ccagcggttc cccaaggccg agttcgccga ggtgagcaag    780
ctggtgaccg acctgaccaa ggtgcacacc gagtgctgcc acggcgacct gctggagtgc    840
gccgacgacc gggccgacct ggccaagtac atctgcgaga accaggacag catcagcagc    900
aagctgaagg agtgctgcga aagcccctg ctggagaaga ccactgcat cgccgaggtg    960 gagaacgacg agatgcccgc cgacctgccc agcctggccg ccgacttcgt ggagagcaag   1020
gacgtgtgca agaactacgc cgaggccaag gacgtgttcc tgggcatgtt cctgtacgag   1080
tacgcccggc ggcaccccga ctacagcgtg gtgctgctgc tgcggctggc caagacctac   1140
gagaccaccc tggagaagtg ctgcgccgcc gccgaccccc acgagtgcta cgccaaggtg   1200
ttcgacgagt tcaagcccct ggtggaggag ccccagaacc tgatcaagca gaactgcgag   1260
ctgttcgagc agctgggcga gtacaagttc cagaacgccc tgctggtgcg gtacaccaag   1320
aaggtgcccc aggtgagcac ccccacccta gtggaggtga ccggaacct gggcaaggtg   1380 ggcagcaagt gctgcaagca ccccgaggcc aagcggatgc cctgcgccga ggactacctg   1440
agcgtggtgc tgaaccagct gtgcgtgctg cacgagaaga ccccgtgag cgaccgggtg   1500 accaagtgct gcaccgagag cctggtgaac cggcggccct gcttcagcgc cctggaggtg   1560
gacgagacct acgtgcccaa ggagttcaac gccgagacct caccttcca cgccgacatc   1620 tgcaccctga gcgagaagga gcggcagatc aagaagcaga ccgccctggt ggagctggtg   1680
aagcacaagc ccaaggccac caaggagcag ctgaaggccg tgatggacga cttcgccgcc   1740
ttcgtggaga gtgctgcaa ggccgacgac aaggagacct gcttcgccga ggagggcaag   1800
aagctggtgg ccgccagcca ggccgccctg ggcctgggca cggcggcgg cggcagcggc   1860 ggcggcggat ctggtggagg tggcagtgga ggaggggat ccctcgaggt cctctttcag   1920
ggaccacggt gccagaagtg gttccagaca tgcgacgccg agcgcaagtg ctgcgaaggc   1980
ttcgtgtgtc gcctgtggtg taaaaagaag ttgtggtga                          2019
```

<210> SEQ ID NO 95
<211> LENGTH: 672
<212> TYPE: PRT
<213> ORGANISM: Artificial Sequence
<220> FEATURE:
<223> OTHER INFORMATION: Description of Artificial Sequence: Synthetic
NV1G1097 (NV1D2810), Y1Q,M6F,W7Q polypeptide

<400> SEQUENCE: 95

Met Ala Trp Val Trp Thr Leu Leu Phe Leu Met Ala Ala Ala Gln Ser
1               5                   10                  15

Ile Gln Ala Gly Ser His His His His His His Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly

```
            100                 105                 110
Glu Met Ala Asp Cys Cys Ala Lys Gln Glu Pro Glu Arg Asn Glu Cys
            115                 120                 125

Phe Leu Gln His Lys Asp Asp Asn Pro Asn Leu Pro Arg Leu Val Arg
            130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
                180                 185                 190

Thr Glu Cys Cys Gln Ala Ala Asp Lys Ala Ala Cys Leu Leu Pro Lys
                195                 200                 205

Leu Asp Glu Leu Arg Asp Glu Gly Lys Ala Ser Ser Ala Lys Gln Arg
            210                 215                 220

Leu Lys Cys Ala Ser Leu Gln Lys Phe Gly Glu Arg Ala Phe Lys Ala
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
                260                 265                 270

Cys His Gly Asp Leu Leu Glu Cys Ala Asp Asp Arg Ala Asp Leu Ala
                275                 280                 285

Lys Tyr Ile Cys Glu Asn Gln Asp Ser Ile Ser Ser Lys Leu Lys Glu
            290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
                325                 330                 335

Val Glu Ser Lys Asp Val Cys Lys Asn Tyr Ala Glu Ala Lys Asp Val
                340                 345                 350

Phe Leu Gly Met Phe Leu Tyr Glu Tyr Ala Arg Arg His Pro Asp Tyr
                355                 360                 365

Ser Val Val Leu Leu Leu Arg Leu Ala Lys Thr Tyr Glu Thr Thr Leu
            370                 375                 380

Glu Lys Cys Cys Ala Ala Ala Asp Pro His Glu Cys Tyr Ala Lys Val
385                 390                 395                 400

Phe Asp Glu Phe Lys Pro Leu Val Glu Glu Pro Gln Asn Leu Ile Lys
                405                 410                 415

Gln Asn Cys Glu Leu Phe Glu Gln Leu Gly Glu Tyr Lys Phe Gln Asn
                420                 425                 430

Ala Leu Leu Val Arg Tyr Thr Lys Lys Val Pro Gln Val Ser Thr Pro
                435                 440                 445

Thr Leu Val Glu Val Ser Arg Asn Leu Gly Lys Val Gly Ser Lys Cys
            450                 455                 460

Cys Lys His Pro Glu Ala Lys Arg Met Pro Cys Ala Glu Asp Tyr Leu
465                 470                 475                 480

Ser Val Val Leu Asn Gln Leu Cys Val Leu His Glu Lys Thr Pro Val
                485                 490                 495

Ser Asp Arg Val Thr Lys Cys Cys Thr Glu Ser Leu Val Asn Arg Arg
                500                 505                 510

Pro Cys Phe Ser Ala Leu Glu Val Asp Glu Thr Tyr Val Pro Lys Glu
                515                 520                 525
```

```
Phe Asn Ala Glu Thr Phe Thr Phe His Ala Asp Ile Cys Thr Leu Ser
        530                 535                 540

Glu Lys Glu Arg Gln Ile Lys Lys Gln Thr Ala Leu Val Glu Leu Val
545                 550                 555                 560

Lys His Lys Pro Lys Ala Thr Lys Glu Gln Leu Lys Ala Val Met Asp
                565                 570                 575

Asp Phe Ala Ala Phe Val Glu Lys Cys Cys Lys Ala Asp Asp Lys Glu
        580                 585                 590

Thr Cys Phe Ala Glu Glu Gly Lys Lys Leu Val Ala Ala Ser Gln Ala
        595                 600                 605

Ala Leu Gly Leu Gly Ser Gly Gly Gly Ser Gly Gly Gly Ser
        610                 615                 620

Gly Gly Gly Gly Ser Gly Gly Gly Ser Leu Glu Val Leu Phe Gln
625                 630                 635                 640

Gly Pro Gln Cys Gln Lys Trp Phe Gln Thr Cys Asp Ser Glu Arg Lys
                645                 650                 655

Cys Cys Glu Gly Met Val Cys Arg Leu Trp Cys Lys Lys Lys Leu Trp
        660                 665                 670
```

<210> SEQ ID NO 96
<211> LENGTH: 1959
<212> TYPE: DNA
<213> ORGANISM: Artificial Sequence
<220> FEATURE:
<223> OTHER INFORMATION: Description of Artificial Sequence: Synthetic
      NV1G1097 (NV1D2810), Y1Q,M6F,W7Q polynucleotide

<400> SEQUENCE: 96

```
gggagccacc accaccacca ccacgacgcc cacaagagcg aggtggccca ccggttcaag    60
gacctgggcg aggagaactt caaggccctg gtgctgatcg ccttcgccca gtacctgcag   120
cagtgcccct tcgaggacca cgtgaagctg gtgaacgagg tgaccgagtt cgccaagacc   180
tgcgtggccg acgagagcgc cgagaactgc gacaagagcc tgcacaccct gttcggcgac   240
aagctgtgca ccgtgccgca cctgcgggag acctacggcg agatggccga ctgctgcgcc   300
aagcaggagc ccgagcggaa cgagtgcttc ctgcagcaca aggacgacaa ccccaacctg   360
ccccggctgg tgcggcccga ggtggacgtg atgtgcaccg ccttccacga caacgaggag   420
accttcctga gaagtaccct gtacgagatc gcccggcggc accctacttt ctacgccccc   480
gagctgctgt tcttcgccaa gcggtacaag gccgccttca ccgagtgctg ccaggccgcc   540
gacaaggccg cctgcctgct gcccaagctg gacgagctgc gggacgaggg caaggccagc   600
agcgccaagc agcggctgaa gtgcgccagc ctgcagaagt tcggcgagcg ggccttcaag   660
gcctgggccg tggcccggct gagccagcgg ttccccaagg ccgagttcgc cgaggtgagc   720
aagctggtga ccgacctgac caaggtgcac accgagtgct gccacggcga cctgctggag   780
tgcgccgacg accgggccga cctggccaag tacatctgcg agaaccagga cagcatcagc   840
agcaagctga aggagtgctg cgagaagccc ctgctggaga gagccactg catcgccgag   900
gtggagaacg acgagatgcc cgccgacctg cccagcctgg ccgccgactt cgtggagagc   960
aaggacgtgt gcaagaacta cgccgaggcc aaggacgtgt tcctgggcat gttcctgtac  1020
gagtacgccc ggcggcaccc cgactacagc gtggtgctgc tgctgcggct ggccaagacc  1080
tacgagacca ccctggagaa gtgctgcgcc gccgccgacc ccacgagtg ctacgccaag  1140
gtgttcgacg agttcaagcc cctggtggag gagccccaga acctgatcaa gcagaactgc  1200
```

```
gagctgttcg agcagctggg cgagtacaag ttccagaacg ccctgctggt gcggtacacc    1260
aagaaggtgc cccaggtgag cacccccacc ctggtggagg tgagccggaa cctgggcaag    1320
gtgggcagca agtgctgcaa gcaccccgag gccaagcgga tgccctgcgc cgaggactac    1380
ctgagcgtgg tgctgaacca gctgtgcgtg ctgcacgaga gaccccccgt gagcgaccgg    1440
gtgaccaagt gctgcaccga gagcctggtg aaccggcggc cctgcttcag cgccctggag    1500
gtggacgaga cctacgtgcc caaggagttc aacgccgaga ccttcacctt ccacgccgac    1560
atctgcaccc tgagcgagaa ggagcggcag atcaagaagc agaccgccct ggtggagctg    1620
gtgaagcaca gcccaaggc caccaaggag cagctgaagg ccgtgatgga cgacttcgcc    1680
gccttcgtgg agaagtgctg caaggccgac gacaaggaga cctgcttcgc cgaggagggc    1740
aagaagctgg tggccgccag ccaggccgcc ctgggcctgg cagcggcgg cggcggcagc    1800 ggcggcggcg gatctggtgg aggtggcagt ggaggagggg gatccctcga ggtcctcttt    1860
cagggaccac agtgccagaa gtggttccag acatgcgaca gcgagcgcaa gtgctgcgaa    1920
ggcatggtgt gtcgcctgtg gtgtaaaaag aagttgtgg                           1959
```

<210> SEQ ID NO 97
<211> LENGTH: 672
<212> TYPE: PRT
<213> ORGANISM: Artificial Sequence
<220> FEATURE:
<223> OTHER INFORMATION: Description of Artificial Sequence: Synthetic
      NV1G1123 (NV1D2882), Y1A,M6F,W7Q,M19L polypeptide

<400> SEQUENCE: 97

```
Met Ala Trp Val Trp Thr Leu Leu Phe Leu Met Ala Ala Ala Gln Ser
1               5                   10                  15

Ile Gln Ala Gly Ser His His His His His Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
        195                 200                 205

Leu Asp Glu Leu Arg Asp Glu Gly Lys Ala Ser Ser Ala Lys Gln Arg
    210                 215                 220
```

```
Leu Lys Cys Ala Ser Leu Gln Lys Phe Gly Glu Arg Ala Phe Lys Ala
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
            260                 265                 270

Cys His Gly Asp Leu Leu Glu Cys Ala Asp Asp Arg Ala Asp Leu Ala
        275                 280                 285

Lys Tyr Ile Cys Glu Asn Gln Asp Ser Ile Ser Ser Lys Leu Lys Glu
    290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
                325                 330                 335

Val Glu Ser Lys Asp Val Cys Lys Asn Tyr Ala Glu Ala Lys Asp Val
            340                 345                 350

Phe Leu Gly Met Phe Leu Tyr Glu Tyr Ala Arg Arg His Pro Asp Tyr
        355                 360                 365

Ser Val Val Leu Leu Leu Arg Leu Ala Lys Thr Tyr Glu Thr Thr Leu
    370                 375                 380

Glu Lys Cys Cys Ala Ala Ala Asp Pro His Glu Cys Tyr Ala Lys Val
385                 390                 395                 400

Phe Asp Glu Phe Lys Pro Leu Val Glu Glu Pro Gln Asn Leu Ile Lys
                405                 410                 415

Gln Asn Cys Glu Leu Phe Glu Gln Leu Gly Glu Tyr Lys Phe Gln Asn
            420                 425                 430

Ala Leu Leu Val Arg Tyr Thr Lys Lys Val Pro Gln Val Ser Thr Pro
        435                 440                 445

Thr Leu Val Glu Val Ser Arg Asn Leu Gly Lys Val Gly Ser Lys Cys
    450                 455                 460

Cys Lys His Pro Glu Ala Lys Arg Met Pro Cys Ala Glu Asp Tyr Leu
465                 470                 475                 480

Ser Val Val Leu Asn Gln Leu Cys Val Leu His Glu Lys Thr Pro Val
                485                 490                 495

Ser Asp Arg Val Thr Lys Cys Cys Thr Glu Ser Leu Val Asn Arg Arg
            500                 505                 510

Pro Cys Phe Ser Ala Leu Glu Val Asp Glu Thr Tyr Val Pro Lys Glu
        515                 520                 525

Phe Asn Ala Glu Thr Phe Thr Phe His Ala Asp Ile Cys Thr Leu Ser
    530                 535                 540

Glu Lys Glu Arg Gln Ile Lys Lys Gln Thr Ala Leu Val Glu Leu Val
545                 550                 555                 560

Lys His Lys Pro Lys Ala Thr Lys Glu Gln Leu Lys Ala Val Met Asp
                565                 570                 575

Asp Phe Ala Ala Phe Val Glu Lys Cys Cys Lys Ala Asp Asp Lys Glu
            580                 585                 590

Thr Cys Phe Ala Glu Glu Gly Lys Lys Leu Val Ala Ala Ser Gln Ala
        595                 600                 605

Ala Leu Gly Leu Gly Ser Gly Gly Gly Ser Gly Gly Gly Ser
    610                 615                 620

Gly Gly Gly Gly Ser Gly Gly Gly Ser Leu Glu Val Leu Phe Gln
625                 630                 635                 640

Gly Pro Ala Cys Gln Lys Trp Phe Gln Thr Cys Asp Ser Glu Arg Lys
```

|       | 645 |     |     |     | 650 |     |     |     | 655 |     |     |     |
|-------|-----|-----|-----|-----|-----|-----|-----|-----|-----|-----|-----|-----|
| Cys Cys Glu Gly Leu Val Cys Arg Leu Trp Cys Lys Lys Lys Leu Trp |
|       | 660 |     |     |     | 665 |     |     |     | 670 |

<210> SEQ ID NO 98
<211> LENGTH: 2019
<212> TYPE: DNA
<213> ORGANISM: Artificial Sequence
<220> FEATURE:
<223> OTHER INFORMATION: Description of Artificial Sequence: Synthetic
    NV1G1123 (NV1D2882), Y1A,M6F,W7Q,M19L polynucleotide

<400> SEQUENCE: 98

```
atggcttggg tgtggacctt gctattcctg atggcggccg cccaaagtat acaggccggg      60
agccaccacc accaccacca cgacgcccac aagagcgagg tggcccaccg gttcaaggac     120
ctgggcgagg agaacttcaa ggccctggtg ctgatcgcct cgcccagta cctgcagcag     180
tgccccttcg aggaccacgt gaagctggtg aacgaggtga ccgagttcgc caagacctgc    240
gtggccgacg agagcgccga gaactgcgac aagagcctgc acaccctgtt cggcgacaag    300
ctgtgcaccg tggccaccct gcgggagacc tacgcgaga tggccgactg ctgcgccaag    360
caggagcccg agcggaacga gtgcttcctg cagcacaagg acgacaaccc caacctgccc    420
cggctggtgc ggcccgaggt ggacgtgatg tgcaccgcct ccacgacaa cgaggagacc    480
ttcctgaaga gtacctgta cgagatcgcc cggcggcacc cctacttcta cccccgag      540
ctgctgttct cgccaagcg gtacaaggcc gccttcaccg agtgctgcca ggccgccgac     600
aaggccgcct gcctgctgcc caagctggac gagctgcggg acgagggcaa ggccagcagc    660
gccaagcagc ggctgaagtg cgccagcctg cagaagttcg gcgagcgggc cttcaaggcc    720
tgggccgtgg cccggctgag ccagcggttc ccaaggccg agttcgccga ggtgagcaag    780
ctggtgaccg acctgaccaa ggtgcacacc gagtgctgcc acggcgacct gctggagtgc    840
gccgacgacc gggccgacct ggccaagtac atctgcgaga accaggacag catcagcagc    900
aagctgaagg agtgctgcga gaagcccctg ctggagaaga ccactgcat cgccgaggtg    960
gagaacgacg agatgcccgc cgacctgccc agcctggccg ccgacttcgt ggagagcaag   1020
gacgtgtgca agaactacgc cgaggccaag gacgtgttcc tgggcatgtt cctgtacgag   1080
tacgcccggc ggcaccccga ctacagcgtg tgctgctgc tgcggctggc caagacctac   1140
gagaccaccc tggagaagtg ctgcgccgcc gccgacccc acgagtgcta cgccaaggtg   1200
ttcgacgagt tcaagcccct ggtggaggag ccccagaacc tgatcaagca gaactgcgag   1260
ctgttcgagc agctgggcga gtacaagttc cagaacgccc tgctggtgcg gtacaccaag   1320
aaggtgcccc aggtgagcac ccccaccctg gtggaggtga ccggaacct gggcaaggtg   1380
ggcagcaagt gctgcaagca ccccgaggcc aagcggatgc cctgcgccga ggactacctg   1440
agcgtggtgc tgaaccagct gtgcgtgctg cacgagaaga cccccgtgag cgaccgggtg   1500
accaagtgct gcaccgagag cctggtgaac cggcggccct gcttcagcgc cctggaggtg   1560
gacgagacct acgtgcccaa ggagttcaac gccgagacct tcaccttcca cgccgacatc   1620
tgcaccctga gcgagaagga gcggcagatc aagaagcaga ccgccctggt ggagctggtg   1680
aagcacaagc ccaaggccac caaggagcag ctgaaggccg tgatggacga cttcgccgcc   1740
ttcgtggaga gtgctgcaa ggccgacgac aaggagacct gcttcgccga ggagggcaag   1800
aagctggtgg ccgccagcca ggccgccctg ggcctgggca gggcggcgg cggcagcggc   1860
ggcggcggat ctggtggagg tggcagtgga ggaggggat ccctcgaggt cctctttcag   1920
```

```
ggaccagcct gccagaagtg gttccagacc tgcgacagcg agcggaagtg ctgcgagggc    1980
ctggtgtgcc ggctgtggtg caagaagaag ctgtggtga                          2019
```

<210> SEQ ID NO 99
<211> LENGTH: 672
<212> TYPE: PRT
<213> ORGANISM: Artificial Sequence
<220> FEATURE:
<223> OTHER INFORMATION: Description of Artificial Sequence: Synthetic
    NV1G1127 (NV1D2870), Y1Q,M6F,W7Q,M19L polypeptide

<400> SEQUENCE: 99

```
Met Ala Trp Val Trp Thr Leu Leu Phe Leu Met Ala Ala Ala Gln Ser
1               5                   10                  15

Ile Gln Ala Gly Ser His His His His His Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
        195                 200                 205

Leu Asp Glu Leu Arg Asp Glu Gly Lys Ala Ser Ser Ala Lys Gln Arg
    210                 215                 220

Leu Lys Cys Ala Ser Leu Gln Lys Phe Gly Glu Arg Ala Phe Lys Ala
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
            260                 265                 270

Cys His Gly Asp Leu Leu Glu Cys Ala Asp Asp Arg Ala Asp Leu Ala
        275                 280                 285

Lys Tyr Ile Cys Glu Asn Gln Asp Ser Ile Ser Ser Lys Leu Lys Glu
    290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
                325                 330                 335
```

| | | | | | | | | | | | |
|---|---|---|---|---|---|---|---|---|---|---|---|
|Val|Glu|Ser|Lys|Asp|Val|Cys|Lys|Asn|Tyr|Ala|Glu|Ala|Lys|Asp|Val|
| | | |340| | | |345| | | |350| | | | |

Val Glu Ser Lys Asp Val Cys Lys Asn Tyr Ala Glu Ala Lys Asp Val
               340               345             350

Phe Leu Gly Met Phe Leu Tyr Glu Tyr Ala Arg Arg His Pro Asp Tyr
               355               360             365

Ser Val Val Leu Leu Leu Arg Leu Ala Lys Thr Tyr Glu Thr Thr Leu
   370                   375               380

Glu Lys Cys Cys Ala Ala Ala Asp Pro His Glu Cys Tyr Ala Lys Val
385                   390               395             400

Phe Asp Glu Phe Lys Pro Leu Val Glu Glu Pro Gln Asn Leu Ile Lys
               405               410             415

Gln Asn Cys Glu Leu Phe Glu Gln Leu Gly Glu Tyr Lys Phe Gln Asn
           420               425             430

Ala Leu Leu Val Arg Tyr Thr Lys Lys Val Pro Gln Val Ser Thr Pro
               435               440             445

Thr Leu Val Glu Val Ser Arg Asn Leu Gly Lys Val Gly Ser Lys Cys
   450                   455               460

Cys Lys His Pro Glu Ala Lys Arg Met Pro Cys Ala Glu Asp Tyr Leu
465                   470               475             480

Ser Val Val Leu Asn Gln Leu Cys Val Leu His Glu Lys Thr Pro Val
               485               490             495

Ser Asp Arg Val Thr Lys Cys Cys Thr Glu Ser Leu Val Asn Arg Arg
           500               505             510

Pro Cys Phe Ser Ala Leu Glu Val Asp Glu Thr Tyr Val Pro Lys Glu
               515               520             525

Phe Asn Ala Glu Thr Phe Thr Phe His Ala Asp Ile Cys Thr Leu Ser
   530                   535               540

Glu Lys Glu Arg Gln Ile Lys Lys Gln Thr Ala Leu Val Glu Leu Val
545                   550               555             560

Lys His Lys Pro Lys Ala Thr Lys Glu Gln Leu Lys Ala Val Met Asp
               565               570             575

Asp Phe Ala Ala Phe Val Glu Lys Cys Cys Lys Ala Asp Asp Lys Glu
           580               585             590

Thr Cys Phe Ala Glu Glu Gly Lys Lys Leu Val Ala Ala Ser Gln Ala
               595               600             605

Ala Leu Gly Leu Gly Ser Gly Gly Gly Gly Ser Gly Gly Gly Gly Ser
610                   615               620

Gly Gly Gly Gly Ser Gly Gly Gly Ser Leu Glu Val Leu Phe Gln
625                   630               635             640

Gly Pro Gln Cys Gln Lys Trp Phe Gln Thr Cys Asp Ser Glu Arg Lys
               645               650             655

Cys Cys Glu Gly Leu Val Cys Arg Leu Trp Cys Lys Lys Lys Leu Trp
           660               665             670

<210> SEQ ID NO 100
<211> LENGTH: 2019
<212> TYPE: DNA
<213> ORGANISM: Artificial Sequence
<220> FEATURE:
<223> OTHER INFORMATION: Description of Artificial Sequence: Synthetic
    NV1G1127 (NV1D2870), Y1Q,M6F,W7Q,M19L polynucleotide

<400> SEQUENCE: 100

```
atggcttggg tgtggacctt gctattcctg atggcggccg cccaaagtat acaggccggg     60
agccaccacc accaccacca cgacgcccac aagagcgagg tggcccaccg gttcaaggac    120
ctgggcgagg agaacttcaa ggccctggtg ctgatcgcct tcgcccagta cctgcagcag    180
```

```
tgcccttcg aggaccacgt gaagctggtg aacgaggtga ccgagttcgc caagacctgc      240
gtggccgacg agagcgccga gaactgcgac aagagcctgc acaccctgtt cggcgacaag      300
ctgtgcaccg tggccaccct gcgggagacc tacggcgaga tggccgactg ctgcgccaag      360
caggagcccg agcggaacga gtgcttcctg cagcacaagg acgacaaccc caacctgccc      420
cggctggtgc ggcccgaggt ggacgtgatg tgcaccgcct ccacgacaa cgaggagacc      480 ttcctgaaga agtacctgta cgagatcgcc cggcggcacc cctacttcta cgcccccgag      540
ctgctgttct cgccaagcg gtacaaggcc gccttcaccg agtgctgcca ggccgccgac      600
aaggccgcct gcctgctgcc caagctggac agctgcgggc gagggcaa ggccagcagc       660 gccaagcagc ggctgaagtg cgccagcctg cagaagttcg gcgagcgggc cttcaaggcc      720
tgggccgtgg cccggctgag ccagcggttc cccaaggccg agttcgccga ggtgagcaag      780
ctggtgaccg acctgaccaa ggtgcacacc gagtgctgcc acggcgacct gctggagtgc      840
gccgacgacc gggccgacct ggccaagtac atctgcgaga accaggacag catcagcagc      900
aagctgaagg agtgctgcga aagcccctg ctggagaaga gccactgcat cgccgaggtg      960
gagaacgacg agatgcccgc cgacctgccc agcctggccg ccgacttcgt ggagagcaag      1020
gacgtgtgca gaactacgc cgaggccaag gacgtgttcc tgggcatgtt cctgtacgag      1080
tacgcccggc ggcaccccga ctacagcgtg gtgctgctgc tgcggctggc caagacctac      1140
gagaccaccc tggagaagtg ctgcgccgcc gccgaccccc acgagtgcta cgccaaggtg      1200
ttcgacgagt tcaagcccct ggtggaggag ccccagaacc tgatcaagca gaactgcgag      1260
ctgttcgagc agctgggcga gtacaagttc cagaacgccc tgctggtgcg gtacaccaag      1320
aaggtgcccc aggtgagcac ccccacccct gtggaggtga ccggaacct gggcaaggtg      1380 ggcagcaagt gctgcaagca ccccgaggcc aagcggatgc cctgcgccga ggactacctg      1440
agcgtggtgc tgaaccagct gtgcgtgctg cacgagaaga cccccgtgag cgaccgggtg      1500
accaagtgct gcaccgagag cctggtgaac cggcggccct gcttcagcgc cctggaggtg      1560
gacgagacct acgtgcccaa ggagttcaac gccgagacct caccttcca cgccgacatc      1620 tgcaccctga gcgagaagga gcggcagatc aagaagcaga ccgccctggt ggagctggtg      1680
aagcacaagc ccaaggccac caaggagcag ctgaaggccg tgatggacga cttcgccgcc      1740
ttcgtggaga agtgctgcaa ggccgacgac aaggagacct gcttcgccga ggagggcaag      1800
aagctggtgg ccgccagcca ggccgccctg ggcctgggca cggcggcgg cggcagcggc      1860 ggcggcggat ctggtggagg tggcagtgga ggaggggat ccctcgaggt cctcttcag       1920 ggaccacagt gccagaagtg gttccagacc tgcgacagcg agcggaagtg ctgcgagggc      1980
ctggtgtgcc ggctgtggtg caagaagaag ctgtggtga                             2019
```

<210> SEQ ID NO 101  
<211> LENGTH: 672  
<212> TYPE: PRT  
<213> ORGANISM: Artificial Sequence  
<220> FEATURE:  
<223> OTHER INFORMATION: Description of Artificial Sequence: Synthetic NV1G1083 (NV1D2878), Y1S,M6F,W7Q,M19L polypeptide

<400> SEQUENCE: 101

Met Ala Trp Val Trp Th

```
Glu Val Ala His Arg Phe Lys Asp Leu Gly Glu Glu Asn Phe Lys Ala
            35                  40                  45

Leu Val Leu Ile Ala Phe Ala Gln Tyr Leu Gln Gln Cys Pro Phe Glu
        50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
        195                 200                 205

Leu Asp Glu Leu Arg Asp Glu Gly Lys Ala Ser Ser Ala Lys Gln Arg
    210                 215                 220

Leu Lys Cys Ala Ser Leu Gln Lys Phe Gly Glu Arg Ala Phe Lys Ala
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
            260                 265                 270

Cys His Gly Asp Leu Leu Glu Cys Ala Asp Asp Arg Ala Asp Leu Ala
        275                 280                 285

Lys Tyr Ile Cys Glu Asn Gln Asp Ser Ile Ser Ser Lys Leu Lys Glu
    290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
                325                 330                 335

Val Glu Ser Lys Asp Val Cys Lys Asn Tyr Ala Glu Ala Lys Asp Val
            340                 345                 350

Phe Leu Gly Met Phe Leu Tyr Glu Tyr Ala Arg Arg His Pro Asp Tyr
        355                 360                 365

Ser Val Val Leu Leu Leu Arg Leu Ala Lys Thr Tyr Glu Thr Thr Leu
    370                 375                 380

Glu Lys Cys Cys Ala Ala Ala Asp Pro His Glu Cys Tyr Ala Lys Val
385                 390                 395                 400

Phe Asp Glu Phe Lys Pro Leu Val Glu Glu Pro Gln Asn Leu Ile Lys
                405                 410                 415

Gln Asn Cys Glu Leu Phe Glu Gln Leu Gly Glu Tyr Lys Phe Gln Asn
            420                 425                 430

Ala Leu Leu Val Arg Tyr Thr Lys Lys Val Pro Gln Val Ser Thr Pro
        435                 440                 445
```

```
Thr Leu Val Glu Val Ser Arg Asn Leu Gly Lys Val Gly Ser Lys Cys
    450                 455                 460
Cys Lys His Pro Glu Ala Lys Arg Met Pro Cys Ala Glu Asp Tyr Leu
465                 470                 475                 480
Ser Val Val Leu Asn Gln Leu Cys Val Leu His Glu Lys Thr Pro Val
                485                 490                 495
Ser Asp Arg Val Thr Lys Cys Cys Thr Glu Ser Leu Val Asn Arg Arg
            500                 505                 510
Pro Cys Phe Ser Ala Leu Glu Val Asp Glu Thr Tyr Val Pro Lys Glu
        515                 520                 525
Phe Asn Ala Glu Thr Phe Thr Phe His Ala Asp Ile Cys Thr Leu Ser
530                 535                 540
Glu Lys Glu Arg Gln Ile Lys Lys Gln Thr Ala Leu Val Glu Leu Val
545                 550                 555                 560
Lys His Lys Pro Lys Ala Thr Lys Glu Gln Leu Lys Ala Val Met Asp
                565                 570                 575
Asp Phe Ala Ala Phe Val Glu Lys Cys Cys Lys Ala Asp Asp Lys Glu
            580                 585                 590
Thr Cys Phe Ala Glu Glu Gly Lys Lys Leu Val Ala Ala Ser Gln Ala
        595                 600                 605
Ala Leu Gly Leu Gly Ser Gly Gly Gly Gly Ser Gly Gly Gly Gly Ser
610                 615                 620
Gly Gly Gly Gly Ser Gly Gly Gly Ser Leu Glu Val Leu Phe Gln
625                 630                 635                 640
Gly Pro Ser Cys Gln Lys Trp Phe Gln Thr Cys Asp Ser Glu Arg Lys
                645                 650                 655
Cys Cys Glu Gly Leu Val Cys Arg Leu Trp Cys Lys Lys Leu Trp
            660                 665                 670

<210> SEQ ID NO 102
<211> LENGTH: 2019
<212> TYPE: DNA
<213> ORGANISM: Artificial Sequence
<220> FEATURE:
<223> OTHER INFORMATION: Description of Artificial Sequence: Synthetic
      NV1G1083 (NV1D2878), Y1S,M6F,W7Q,M19L polynucleotide

<400> SEQUENCE: 102
atggcttggg tgtggacctt gctattcctg atggcggccg cccaaagtat acaggccggg      60
agccaccacc accaccacca cgacgcccac aagagcgagg tggcccaccg gttcaaggac     120
ctgggcgagg agaacttcaa ggccctggtg ctgatcgcct tcgcccagta cctgcagcag     180
tgccccttcg aggaccacgt gaagctggtg aacgaggtga ccgagttcgc caagacctgc     240
gtggccgaca gagccgccga gaactgcgac aagagcctgc acaccctgtt cggcgacaag     300
ctgtgcaccg tggccaccct gcgggagacc tacggcgaga tggccgactg ctgcgccaag     360
caggagcccg agcggaacga gtgcttcctg cagcacaagg acgacaaccc caacctgccc     420
cggctggtgc ggcccgaggt ggacgtgatg tgcaccgcct ccacgacaa cgaggagacc     480 ttcctgaaga gtacctgta cgagatcgcc cggcggcacc cctacttcta cgcccccgag     540
ctgctgttct tcgccaagcg gtacaaggcc gccttcaccg agtgctgcca ggccgccgac     600
aaggccgcct gcctgctgcc caagctggac gagctgcggg acgagggcaa ggccagcagc     660
gccaagcagc ggctgaagtg cgccagcctg cagaagttcg gcgagcgggc cttcaaggcc     720
tgggccgtgg cccggctgag ccagcggttc cccaaggccg agttcgccga ggtgagcaag     780
```

```
ctggtgaccg acctgaccaa ggtgcacacc gagtgctgcc acggcgacct gctggagtgc    840
gccgacgacc gggccgacct ggccaagtac atctgcgaga accaggacag catcagcagc    900
aagctgaagg agtgctgcga gaagccctg ctggagaaga gccactgcat cgccgaggtg    960
gagaacgacg agatgcccgc cgacctgccc agcctggccg ccgacttcgt ggagagcaag    1020
gacgtgtgca agaactacgc cgaggccaag gacgtgttcc tgggcatgtt cctgtacgag    1080
tacgcccggc ggcacccga ctacagcgtg gtgctgctgc tgcggctggc caagacctac    1140
gagaccaccc tggagaagtg ctgcgccgcc gccgacccc acgagtgcta cgccaaggtg    1200
ttcgacgagt tcaagcccct ggtggaggag ccccagaacc tgatcaagca gaactgcgag    1260
ctgttcgagc agctgggcga gtacaagttc cagaacgccc tgctggtgcg gtacaccaag    1320
aaggtgcccc aggtgagcac ccccacccctg gtggaggtga ccggaacct gggcaaggtg    1380
ggcagcaagt gctgcaagca ccccgaggcc aagcggatgc cctgcgccga ggactacctg    1440
agcgtggtgc tgaaccagct gtgcgtgctg cacgagaaga ccccccgtgag cgaccgggtg    1500
accaagtgct gcaccgagag cctggtgaac cggcggccct gcttcagcgc cctggaggtg    1560
gacgagacct acgtgcccaa ggagttcaac gccgagacct tcaccttcca cgccgacatc    1620
tgcaccctga gcgagaagga gcggcagatc aagaagcaga ccgccctggt ggagctggtg    1680
aagcacaagc ccaaggccac caaggagcag ctgaaggccg tgatggacga cttcgccgcc    1740
ttcgtggaga agtgctgcaa ggccgacgac aaggagacct gcttcgccga ggagggcaag    1800
aagctggtgg ccgccagcca ggccgccctg ggcctgggca gcggcggcgg cggcagcggc    1860
ggcggcggat ctggtggagg tggcagtgga ggaggggat ccctcgaggt cctctttcag    1920
ggaccaagct gccagaagtg gttccagaca tgcgacagcg agcgcaagtg ctgcgaaggc    1980
ttagtgtgtc gcctgtggtg taaaaagaag ttgtggtga                           2019
```

<210> SEQ ID NO 103
<211> LENGTH: 672
<212> TYPE: PRT
<213> ORGANISM: Artificial Sequence
<220> FEATURE:
<223> OTHER INFORMATION: Description of Artificial Sequence: Synthetic
      NV1G1153 (NV1D3034) fusion protein

<400> SEQUENCE: 103

Met Ala Trp Val Trp Thr Leu Leu Phe Leu Met Ala Ala Ala Gln Ser
1               5                   10                  15

Ile Gln Ala Gly Ser His His His His His His Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

```
Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
            165                 170                 175

Tyr Ala Pro Glu Leu Leu Phe Phe Ala Lys Arg Tyr Lys Ala Ala Phe
        180                 185                 190

Thr Glu Cys Cys Gln Ala Ala Asp Lys Ala Ala Cys Leu Leu Pro Lys
    195                 200                 205

Leu Asp Glu Leu Arg Asp Glu Gly Lys Ala Ser Ser Ala Lys Gln Arg
210                 215                 220

Leu Lys Cys Ala Ser Leu Gln Lys Phe Gly Glu Arg Ala Phe Lys Ala
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
            260                 265                 270

Cys His Gly Asp Leu Leu Glu Cys Ala Asp Asp Arg Ala Asp Leu Ala
        275                 280                 285

Lys Tyr Ile Cys Glu Asn Gln Asp Ser Ile Ser Ser Lys Leu Lys Glu
    290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
                325                 330                 335

Val Glu Ser Lys Asp Val Cys Lys Asn Tyr Ala Glu Ala Lys Asp Val
            340                 345                 350

Phe Leu Gly Met Phe Leu Tyr Glu Tyr Ala Arg Arg His Pro Asp Tyr
        355                 360                 365

Ser Val Val Leu Leu Leu Arg Leu Ala Lys Thr Tyr Glu Thr Thr Leu
370                 375                 380

Glu Lys Cys Cys Ala Ala Ala Asp Pro His Glu Cys Tyr Ala Lys Val
385                 390                 395                 400

Phe Asp Glu Phe Lys Pro Leu Val Glu Glu Pro Gln Asn Leu Ile Lys
                405                 410                 415

Gln Asn Cys Glu Leu Phe Glu Gln Leu Gly Glu Tyr Lys Phe Gln Asn
            420                 425                 430

Ala Leu Leu Val Arg Tyr Thr Lys Lys Val Pro Gln Val Ser Thr Pro
        435                 440                 445

Thr Leu Val Glu Val Ser Arg Asn Leu Gly Lys Val Gly Ser Lys Cys
    450                 455                 460

Cys Lys His Pro Glu Ala Lys Arg Met Pro Cys Ala Glu Asp Tyr Leu
465                 470                 475                 480

Ser Val Val Leu Asn Gln Leu Cys Val Leu His Glu Lys Thr Pro Val
                485                 490                 495

Ser Asp Arg Val Thr Lys Cys Cys Thr Glu Ser Leu Val Asn Arg Arg
            500                 505                 510

Pro Cys Phe Ser Ala Leu Glu Val Asp Glu Thr Tyr Val Pro Lys Glu
        515                 520                 525

Phe Asn Ala Glu Thr Phe Thr Phe His Ala Asp Ile Cys Thr Leu Ser
    530                 535                 540

Glu Lys Glu Arg Gln Ile Lys Lys Gln Thr Ala Leu Val Glu Leu Val
545                 550                 555                 560
```

```
Lys His Lys Pro Lys Ala Thr Lys Glu Gln Leu Lys Ala Val Met Asp
            565                 570                 575

Asp Phe Ala Ala Phe Val Glu Cys Cys Lys Ala Asp Asp Lys Glu
            580                 585                 590

Thr Cys Phe Ala Glu Glu Gly Lys Lys Leu Val Ala Ala Ser Gln Ala
            595                 600                 605

Ala Leu Gly Leu Gly Ser Gly Gly Gly Ser Gly Gly Gly Gly Ser
        610                 615                 620

Gly Gly Gly Gly Ser Gly Gly Gly Ser Leu Glu Val Leu Phe Gln
625                 630                 635                 640

Gly Pro Gln Cys Gln Lys Trp Met Gln Thr Cys Asp Arg Glu Arg Lys
            645                 650                 655

Cys Cys Glu Gly Phe Val Cys Thr Leu Trp Cys Arg Lys Lys Leu Trp
            660                 665                 670

<210> SEQ ID NO 104
<211> LENGTH: 2019
<212> TYPE: DNA
<213> ORGANISM: Artificial Sequence
<220> FEATURE:
<223> OTHER INFORMATION: Description of Artificial Sequence: Synthetic
      NV1G1153 (NV1D3034) fusion polynucleotide

<400> SEQUENCE: 104
atggcttggg tgtggacctt gctattcctg atggcggccg cccaaagtat acaggccggg     60
agccaccacc accaccacca cgacgcccac aagagcgagg tggcccaccg gttcaaggac    120
ctgggcgaga gaacttcaa ggccctggtg ctgatcgcct cgcccagta cctgcagcag     180 tgcccttcg aggaccacgt gaagctggtg aacgaggtga ccgagttcgc caagacctgc    240
gtggccgacg agagcgccga gaactgcgac aagagcctgc acaccctgtt cggcgacaag    300
ctgtgcaccg tggccaccct gcgggagacc tacggcgaga tggccgactg ctgcgccaag    360
caggagcccg agcggaacga gtgcttcctg cagcacaagg acgacaaccc caacctgccc    420
cggctggtgc ggcccgaggt ggacgtgatg tgcaccgcct ccacgacaa cgaggagacc     480 ttcctgaaga gtacctgta cgagatcgcc cggcggcacc cctacttcta cgcccccgag    540
ctgctgttct tcgccaagcg gtacaaggcc gccttcaccg agtgctgcca ggccgccgac    600
aaggccgcct gcctgctgcc caagctggac gagctgcggg acgagggcaa ggccagcagc    660
gccaagcagc ggctgaagtg cgccagcctg cagaagttcg gcgagcgggc cttcaaggcc    720
tgggccgtgg cccggctgag ccagcggttc cccaaggccg agttcgccga ggtgagcaag    780
ctggtgaccg acctgaccaa ggtgcacacc gagtgctgcc acggcgacct gctggagtgc    840
gccgacgacc gggccgacct ggccaagtac atctgcgaga accaggacag catcagcagc    900
aagctgaagg agtgctgcga aagcccctg ctggagaaga gccactgcat cgccgaggtg    960
gagaacgacg agatgcccgc cgacctgccc agcctggccg ccgacttcgt ggagagcaag   1020
gacgtgtgca gaactacgc cgaggccaag gacgtgttcc tgggcatgtt cctgtacgag   1080
tacgcccggc ggcacccga ctacagcgtg gtgctgctgc tgcggctggc caagacctac   1140
gagaccaccc tggagaagtg ctgcgccgcc gccgaccccc acgagtgcta cgccaaggtg   1200
ttcgacgagt tcaagcccct ggtggaggag ccccagaacc tgatcaagca gaactgcgag   1260
ctgttcgagc agctgggcga gtacaagttc cagaacgccc tgctggtgcg gtacaccaag   1320
aaggtgcccc aggtgagcac ccccaccctg gtggaggtga ccggaacct gggcaaggtg   1380 ggcagcaagt gctgcaagca ccccgaggcc aagcggatgc cctgcgccga ggactacctg   1440
```

```
agcgtggtgc tgaaccagct gtgcgtgctg cacgagaaga cccccgtgag cgaccgggtg      1500
accaagtgct gcaccgagag cctggtgaac cggcggccct gcttcagcgc cctggaggtg      1560
gacgagacct acgtgcccaa ggagttcaac gccgagacct tcaccttcca cgccgacatc      1620
tgcaccctga gcgagaagga gcggcagatc aagaagcaga ccgccctggt ggagctggtg      1680
aagcacaagc ccaaggccac caaggagcag ctgaaggccg tgatggacga cttcgccgcc      1740
ttcgtggaga gtgctgcaa ggccgacgac aaggagacct gcttcgccga ggagggcaag      1800
aagctggtgg ccgccagcca ggccgccctg ggcctgggca gcggcggcgg cggcagcggc      1860
ggcggcggat ctggtggagg tggcagtgga ggaggggggat ccctcgaggt cctctttcag      1920
ggaccacagt gccagaagtg gatgcagacc tgcgaccggg agcggaagtg ctgcgagggc      1980
ttcgtgtgca ccctgtggtg ccggaagaag ctgtggtga                            2019
```

<210> SEQ ID NO 105
<211> LENGTH: 2016
<212> TYPE: PRT
<213> ORGANISM: Homo sapiens

<400> SEQUENCE: 105

```
Met Ala Asn Phe Leu Pro Arg Gly Thr Ser Ser Phe Arg Arg Phe
1               5                   10                  15

Thr Arg Glu Ser Leu Ala Ala Ile Glu Lys Arg Met Ala Glu Lys Gln
            20                  25                  30

Ala Arg Gly Ser Thr Thr Leu Gln Glu Ser Arg Glu Gly Leu Pro Glu
        35                  40                  45

Glu Glu Ala Pro Arg Pro Gln Leu Asp Leu Gln Ala Ser Lys Lys Leu
    50                  55                  60

Pro Asp Leu Tyr Gly Asn Pro Pro Gln Glu Leu Ile Gly Glu Pro Leu
65                  70                  75                  80

Glu Asp Leu Asp Pro Phe Tyr Ser Thr Gln Lys Thr Phe Ile Val Leu
                85                  90                  95

Asn Lys Gly Lys Thr Ile Phe Arg Phe Ser Ala Thr Asn Ala Leu Tyr
            100                 105                 110

Val Leu Ser Pro Phe His Pro Ile Arg Arg Ala Ala Val Lys Ile Leu
        115                 120                 125

Val His Ser Leu Phe Asn Met Leu Ile Met Cys Thr Ile Leu Thr Asn
    130                 135                 140

Cys Val Phe Met Ala Gln His Asp Pro Pro Trp Thr Lys Tyr Val
145                 150                 155                 160

Glu Tyr Thr Phe Thr Ala Ile Tyr Thr Phe Glu Ser Leu Val Lys Ile
                165                 170                 175

Leu Ala Arg Gly Phe Cys Leu His Ala Phe Thr Phe Leu Arg Asp Pro
            180                 185                 190

Trp Asn Trp Leu Asp Phe Ser Val Ile Met Ala Tyr Thr Thr Glu
        195                 200                 205

Phe Val Asp Leu Gly Asn Val Ser Ala Leu Arg Thr Phe Arg Val Leu
    210                 215                 220

Arg Ala Leu Lys Thr Ile Ser Val Ile Ser Gly Leu Lys Thr Ile Val
225                 230                 235                 240

Gly Ala Leu Ile Gln Ser Val Lys Lys Leu Ala Asp Val Met Val Leu
                245                 250                 255

Thr Val Phe Cys Leu Ser Val Phe Ala Leu Ile Gly Leu Gln Leu Phe
            260                 265                 270
```

```
Met Gly Asn Leu Arg His Lys Cys Val Arg Asn Phe Thr Ala Leu Asn
            275                 280                 285

Gly Thr Asn Gly Ser Val Glu Ala Asp Gly Leu Val Trp Glu Ser Leu
        290                 295                 300

Asp Leu Tyr Leu Ser Asp Pro Glu Asn Tyr Leu Leu Lys Asn Gly Thr
305                 310                 315                 320

Ser Asp Val Leu Leu Cys Gly Asn Ser Ser Asp Ala Gly Thr Cys Pro
                325                 330                 335

Glu Gly Tyr Arg Cys Leu Lys Ala Gly Glu Asn Pro Asp His Gly Tyr
            340                 345                 350

Thr Ser Phe Asp Ser Phe Ala Trp Ala Phe Leu Ala Leu Phe Arg Leu
        355                 360                 365

Met Thr Gln Asp Cys Trp Glu Arg Leu Tyr Gln Gln Thr Leu Arg Ser
        370                 375                 380

Ala Gly Lys Ile Tyr Met Ile Phe Phe Met Leu Val Ile Phe Leu Gly
385                 390                 395                 400

Ser Phe Tyr Leu Val Asn Leu Ile Leu Ala Val Val Ala Met Ala Tyr
                405                 410                 415

Glu Glu Gln Asn Gln Ala Thr Ile Ala Glu Thr Glu Glu Lys Glu Lys
            420                 425                 430

Arg Phe Gln Glu Ala Met Glu Met Leu Lys Lys Glu His Glu Ala Leu
        435                 440                 445

Thr Ile Arg Gly Val Asp Thr Val Ser Arg Ser Ser Leu Glu Met Ser
450                 455                 460

Pro Leu Ala Pro Val Asn Ser His Glu Arg Arg Ser Lys Arg Arg Lys
465                 470                 475                 480

Arg Met Ser Ser Gly Thr Glu Glu Cys Gly Glu Asp Arg Leu Pro Lys
                485                 490                 495

Ser Asp Ser Glu Asp Gly Pro Arg Ala Met Asn His Leu Ser Leu Thr
            500                 505                 510

Arg Gly Leu Ser Arg Thr Ser Met Lys Pro Arg Ser Ser Arg Gly Ser
        515                 520                 525

Ile Phe Thr Phe Arg Arg Arg Asp Leu Gly Ser Glu Ala Asp Phe Ala
530                 535                 540

Asp Asp Glu Asn Ser Thr Ala Gly Glu Ser Glu Ser His His Thr Ser
545                 550                 555                 560

Leu Leu Val Pro Trp Pro Leu Arg Arg Thr Ser Ala Gln Gly Gln Pro
                565                 570                 575

Ser Pro Gly Thr Ser Ala Pro Gly His Ala Leu His Gly Lys Lys Asn
            580                 585                 590

Ser Thr Val Asp Cys Asn Gly Val Val Ser Leu Leu Gly Ala Gly Asp
        595                 600                 605

Pro Glu Ala Thr Ser Pro Gly Ser His Leu Leu Arg Pro Val Met Leu
610                 615                 620

Glu His Pro Pro Asp Thr Thr Thr Pro Ser Glu Pro Gly Gly Pro
625                 630                 635                 640

Gln Met Leu Thr Ser Gln Ala Pro Cys Val Asp Gly Phe Glu Glu Pro
                645                 650                 655

Gly Ala Arg Gln Arg Ala Leu Ser Ala Val Ser Val Leu Thr Ser Ala
            660                 665                 670

Leu Glu Glu Leu Glu Glu Ser Arg His Lys Cys Pro Pro Cys Trp Asn
        675                 680                 685
```

```
Arg Leu Ala Gln Arg Tyr Leu Ile Trp Glu Cys Cys Pro Leu Trp Met
    690                 695                 700

Ser Ile Lys Gln Gly Val Lys Leu Val Val Met Asp Pro Phe Thr Asp
705                 710                 715                 720

Leu Thr Ile Thr Met Cys Ile Val Leu Asn Thr Leu Phe Met Ala Leu
                725                 730                 735

Glu His Tyr Asn Met Thr Ser Glu Phe Glu Glu Met Leu Gln Val Gly
            740                 745                 750

Asn Leu Val Phe Thr Gly Ile Phe Thr Ala Glu Met Thr Phe Lys Ile
            755                 760                 765

Ile Ala Leu Asp Pro Tyr Tyr Tyr Phe Gln Gln Gly Trp Asn Ile Phe
770                 775                 780

Asp Ser Ile Ile Val Ile Leu Ser Leu Met Glu Leu Gly Leu Ser Arg
785                 790                 795                 800

Met Ser Asn Leu Ser Val Leu Arg Ser Phe Arg Leu Leu Arg Val Phe
                805                 810                 815

Lys Leu Ala Lys Ser Trp Pro Thr Leu Asn Thr Leu Ile Lys Ile Ile
                820                 825                 830

Gly Asn Ser Val Gly Ala Leu Gly Asn Leu Thr Leu Val Leu Ala Ile
                835                 840                 845

Ile Val Phe Ile Phe Ala Val Val Gly Met Gln Leu Phe Gly Lys Asn
850                 855                 860

Tyr Ser Glu Leu Arg Asp Ser Asp Ser Gly Leu Leu Pro Arg Trp His
865                 870                 875                 880

Met Met Asp Phe Phe His Ala Phe Leu Ile Ile Phe Arg Ile Leu Cys
                885                 890                 895

Gly Glu Trp Ile Glu Thr Met Trp Asp Cys Met Glu Val Ser Gly Gln
                900                 905                 910

Ser Leu Cys Leu Leu Val Phe Leu Leu Val Met Val Ile Gly Asn Leu
                915                 920                 925

Val Val Leu Asn Leu Phe Leu Ala Leu Leu Leu Ser Ser Phe Ser Ala
            930                 935                 940

Asp Asn Leu Thr Ala Pro Asp Glu Asp Arg Glu Met Asn Asn Leu Gln
945                 950                 955                 960

Leu Ala Leu Ala Arg Ile Gln Arg Gly Leu Arg Phe Val Lys Arg Thr
                965                 970                 975

Thr Trp Asp Phe Cys Cys Gly Leu Leu Arg Gln Arg Pro Gln Lys Pro
                980                 985                 990

Ala Ala Leu Ala Ala Gln Gly Gln  Leu Pro Ser Cys Ile Ala Thr Pro
                995                 1000                1005

Tyr Ser  Pro Pro Pro Pro Glu  Thr Glu Lys Val Pro  Pro Thr Arg
    1010                 1015                1020

Lys Glu  Thr Arg Phe Glu Glu  Gly Glu Gln Pro Gly  Gln Gly Thr
    1025                 1030                1035

Pro Gly  Asp Pro Glu Pro Val  Cys Val Pro Ile Ala  Val Ala Glu
    1040                 1045                1050

Ser Asp  Thr Asp Asp Gln Glu  Glu Asp Glu Glu Asn  Ser Leu Gly
    1055                 1060                1065

Thr Glu  Glu Glu Ser Ser Lys  Gln Gln Glu Ser Gln  Pro Val Ser
    1070                 1075                1080

Gly Gly  Pro Glu Ala Pro Pro  Asp Ser Arg Thr Trp  Ser Gln Val
    1085                 1090                1095

Ser Ala  Thr Ala Ser Ser Glu  Ala Glu Ala Ser Ala  Ser Gln Ala
```

-continued

```
                1100                1105                1110
Asp Trp Arg Gln Gln Trp Lys Ala Glu Pro Gln Ala Pro Gly Cys
    1115                1120                1125
Gly Glu Thr Pro Glu Asp Ser Cys Ser Glu Gly Ser Thr Ala Asp
    1130                1135                1140
Met Thr Asn Thr Ala Glu Leu Leu Glu Gln Ile Pro Asp Leu Gly
    1145                1150                1155
Gln Asp Val Lys Asp Pro Glu Asp Cys Phe Thr Glu Gly Cys Val
    1160                1165                1170
Arg Arg Cys Pro Cys Cys Ala Val Asp Thr Thr Gln Ala Pro Gly
    1175                1180                1185
Lys Val Trp Trp Arg Leu Arg Lys Thr Cys Tyr His Ile Val Glu
    1190                1195                1200
His Ser Trp Phe Glu Thr Phe Ile Ile Phe Met Ile Leu Leu Ser
    1205                1210                1215
Ser Gly Ala Leu Ala Phe Glu Asp Ile Tyr Leu Glu Glu Arg Lys
    1220                1225                1230
Thr Ile Lys Val Leu Leu Glu Tyr Ala Asp Lys Met Phe Thr Tyr
    1235                1240                1245
Val Phe Val Leu Glu Met Leu Leu Lys Trp Val Ala Tyr Gly Phe
    1250                1255                1260
Lys Lys Tyr Phe Thr Asn Ala Trp Cys Trp Leu Asp Phe Leu Ile
    1265                1270                1275
Val Asp Val Ser Leu Val Ser Leu Val Ala Asn Thr Leu Gly Phe
    1280                1285                1290
Ala Glu Met Gly Pro Ile Lys Ser Leu Arg Thr Leu Arg Ala Leu
    1295                1300                1305
Arg Pro Leu Arg Ala Leu Ser Arg Phe Glu Gly Met Arg Val Val
    1310                1315                1320
Val Asn Ala Leu Val Gly Ala Ile Pro Ser Ile Met Asn Val Leu
    1325                1330                1335
Leu Val Cys Leu Ile Phe Trp Leu Ile Phe Ser Ile Met Gly Val
    1340                1345                1350
Asn Leu Phe Ala Gly Lys Phe Gly Arg Cys Ile Asn Gln Thr Glu
    1355                1360                1365
Gly Asp Leu Pro Leu Asn Tyr Thr Ile Val Asn Asn Lys Ser Gln
    1370                1375                1380
Cys Glu Ser Leu Asn Leu Thr Gly Glu Leu Tyr Trp Thr Lys Val
    1385                1390                1395
Lys Val Asn Phe Asp Asn Val Gly Ala Gly Tyr Leu Ala Leu Leu
    1400                1405                1410
Gln Val Ala Thr Phe Lys Gly Trp Met Asp Ile Met Tyr Ala Ala
    1415                1420                1425
Val Asp Ser Arg Gly Tyr Glu Glu Gln Pro Gln Trp Glu Tyr Asn
    1430                1435                1440
Leu Tyr Met Tyr Ile Tyr Phe Val Ile Phe Ile Ile Phe Gly Ser
    1445                1450                1455
Phe Phe Thr Leu Asn Leu Phe Ile Gly Val Ile Ile Asp Asn Phe
    1460                1465                1470
Asn Gln Gln Lys Lys Lys Leu Gly Gly Gln Asp Ile Phe Met Thr
    1475                1480                1485
Glu Glu Gln Lys Lys Tyr Tyr Asn Ala Met Lys Lys Leu Gly Ser
    1490                1495                1500
```

-continued

Lys Lys Pro Gln Lys Pro Ile Pro Arg Pro Leu Asn Lys Tyr Gln
1505                1510                1515

Gly Phe Ile Phe Asp Ile Val Thr Lys Gln Ala Phe Asp Val Thr
1520                1525                1530

Ile Met Phe Leu Ile Cys Leu Asn Met Val Thr Met Met Val Glu
1535                1540                1545

Thr Asp Asp Gln Ser Pro Glu Lys Ile Asn Ile Leu Ala Lys Ile
1550                1555                1560

Asn Leu Leu Phe Val Ala Ile Phe Thr Gly Glu Cys Ile Val Lys
1565                1570                1575

Leu Ala Ala Leu Arg His Tyr Tyr Phe Thr Asn Ser Trp Asn Ile
1580                1585                1590

Phe Asp Phe Val Val Val Ile Leu Ser Ile Val Gly Thr Val Leu
1595                1600                1605

Ser Asp Ile Ile Gln Lys Tyr Phe Phe Ser Pro Thr Leu Phe Arg
1610                1615                1620

Val Ile Arg Leu Ala Arg Ile Gly Arg Ile Leu Arg Leu Ile Arg
1625                1630                1635

Gly Ala Lys Gly Ile Arg Thr Leu Leu Phe Ala Leu Met Met Ser
1640                1645                1650

Leu Pro Ala Leu Phe Asn Ile Gly Leu Leu Phe Leu Val Met
1655                1660                1665

Phe Ile Tyr Ser Ile Phe Gly Met Ala Asn Phe Ala Tyr Val Lys
1670                1675                1680

Trp Glu Ala Gly Ile Asp Asp Met Phe Asn Phe Gln Thr Phe Ala
1685                1690                1695

Asn Ser Met Leu Cys Leu Phe Gln Ile Thr Thr Ser Ala Gly Trp
1700                1705                1710

Asp Gly Leu Leu Ser Pro Ile Leu Asn Thr Gly Pro Pro Tyr Cys
1715                1720                1725

Asp Pro Thr Leu Pro Asn Ser Asn Gly Ser Arg Gly Asp Cys Gly
1730                1735                1740

Ser Pro Ala Val Gly Ile Leu Phe Phe Thr Thr Tyr Ile Ile Ile
1745                1750                1755

Ser Phe Leu Ile Val Val Asn Met Tyr Ile Ala Ile Ile Leu Glu
1760                1765                1770

Asn Phe Ser Val Ala Thr Glu Glu Ser Thr Glu Pro Leu Ser Glu
1775                1780                1785

Asp Asp Phe Asp Met Phe Tyr Glu Ile Trp Glu Lys Phe Asp Pro
1790                1795                1800

Glu Ala Thr Gln Phe Ile Glu Tyr Ser Val Leu Ser Asp Phe Ala
1805                1810                1815

Asp Ala Leu Ser Glu Pro Leu Arg Ile Ala Lys Pro Asn Gln Ile
1820                1825                1830

Ser Leu Ile Asn Met Asp Leu Pro Met Val Ser Gly Asp Arg Ile
1835                1840                1845

His Cys Met Asp Ile Leu Phe Ala Phe Thr Lys Arg Val Leu Gly
1850                1855                1860

Glu Ser Gly Glu Met Asp Ala Leu Lys Ile Gln Met Glu Glu Lys
1865                1870                1875

Phe Met Ala Ala Asn Pro Ser Lys Ile Ser Tyr Glu Pro Ile Thr
1880                1885                1890

```
Thr Thr Leu Arg Arg Lys His Glu Glu Val Ser Ala Met Val Ile
1895                1900                1905

Gln Arg Ala Phe Arg Arg His Leu Leu Gln Arg Ser Leu Lys His
    1910                1915                1920

Ala Ser Phe Leu Phe Arg Gln Ala Gly Ser Gly Leu Ser Glu
    1925                1930                1935

Glu Asp Ala Pro Glu Arg Glu Gly Leu Ile Ala Tyr Val Met Ser
    1940                1945                1950

Glu Asn Phe Ser Arg Pro Leu Gly Pro Pro Ser Ser Ser Ser Ile
    1955                1960                1965

Ser Ser Thr Ser Phe Pro Pro Ser Tyr Asp Ser Val Thr Arg Ala
    1970                1975                1980

Thr Ser Asp Asn Leu Gln Val Arg Gly Ser Asp Tyr Ser His Ser
    1985                1990                1995

Glu Asp Leu Ala Asp Phe Pro Pro Ser Pro Asp Arg Asp Arg Glu
    2000                2005                2010

Ser Ile Val
    2015

<210> SEQ ID NO 106
<211> LENGTH: 612
<212> TYPE: PRT
<213> ORGANISM: Homo sapiens

<400> SEQUENCE: 106

Met Ala Trp Val Trp Thr Leu Leu Phe Leu Met Ala Ala Ala Gln Ser
1               5                   10                  15

Ile Gln Ala Gly Ser His His His His His His Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
        195                 200                 205

Leu Asp Glu Leu Arg Asp Glu Gly Lys Ala Ser Ser Ala Lys Gln Arg
    210                 215                 220

Leu Lys Cys Ala Ser Leu Gln Lys Phe Gly Glu Arg Ala Phe Lys Ala
225                 230                 235                 240
```

Trp Ala Val Ala Arg Leu Ser Gln Arg Phe Pro Lys Ala Glu Phe Ala
               245                 250                 255

Glu Val Ser Lys Leu Val Thr Asp Leu Thr Lys Val His Thr Glu Cys
           260                 265                 270

Cys His Gly Asp Leu Leu Glu Cys Ala Asp Arg Ala Asp Leu Ala
       275                 280                 285

Lys Tyr Ile Cys Glu Asn Gln Asp Ser Ile Ser Ser Lys Leu Lys Glu
       290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
               325                 330                 335

Val Glu Ser Lys Asp Val Cys Lys Asn Tyr Ala Glu Ala Lys Asp Val
           340                 345                 350

Phe Leu Gly Met Phe Leu Tyr Glu Tyr Ala Arg Arg His Pro Asp Tyr
           355                 360                 365

Ser Val Val Leu Leu Leu Arg Leu Ala Lys Thr Tyr Glu Thr Thr Leu
       370                 375                 380

Glu Lys Cys Cys Ala Ala Ala Asp Pro His Glu Cys Tyr Ala Lys Val
385                 390                 395                 400

Phe Asp Glu Phe Lys Pro Leu Val Glu Glu Pro Gln Asn Leu Ile Lys
               405                 410                 415

Gln Asn Cys Glu Leu Phe Glu Gln Leu Gly Glu Tyr Lys Phe Gln Asn
           420                 425                 430

Ala Leu Leu Val Arg Tyr Thr Lys Lys Val Pro Gln Val Ser Thr Pro
           435                 440                 445

Thr Leu Val Glu Val Ser Arg Asn Leu Gly Lys Val Gly Ser Lys Cys
       450                 455                 460

Cys Lys His Pro Glu Ala Lys Arg Met Pro Cys Ala Glu Asp Tyr Leu
465                 470                 475                 480

Ser Val Val Leu Asn Gln Leu Cys Val Leu His Glu Lys Thr Pro Val
               485                 490                 495

Ser Asp Arg Val Thr Lys Cys Cys Thr Glu Ser Leu Val Asn Arg Arg
           500                 505                 510

Pro Cys Phe Ser Ala Leu Glu Val Asp Glu Thr Tyr Val Pro Lys Glu
           515                 520                 525

Phe Asn Ala Glu Thr Phe Thr Phe His Ala Asp Ile Cys Thr Leu Ser
       530                 535                 540

Glu Lys Glu Arg Gln Ile Lys Lys Gln Thr Ala Leu Val Glu Leu Val
545                 550                 555                 560

Lys His Lys Pro Lys Ala Thr Lys Glu Gln Leu Lys Ala Val Met Asp
               565                 570                 575

Asp Phe Ala Ala Phe Val Glu Lys Cys Cys Lys Ala Asp Asp Lys Glu
           580                 585                 590

Thr Cys Phe Ala Glu Glu Gly Lys Lys Leu Val Ala Ala Ser Gln Ala
           595                 600                 605

Ala Leu Gly Leu
    610

<210> SEQ ID NO 107
<211> LENGTH: 93
<212> TYPE: DNA
<213> ORGANISM: Thrixopelma pruriens -continued

```
<400> SEQUENCE: 107
tactgccaga agtggatgtg gacatgcgac agcgagcgca agtgctgcga aggcatggtg      60
tgtcgcctgt ggtgtaaaaa gaagttgtgg tga                                   93

<210> SEQ ID NO 108
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 108

His His His His His His
1               5

<210> SEQ ID NO 109
<211> LENGTH: 30
<212> TYPE: PRT
<213> ORGANISM: Artificial sequence
<220> FEATURE:
<223> OTHER INFORMATION: variant (-GP) NV1D2773
<220> FEATURE:
<221> NAME/KEY: MOD_RES
<222> LOCATION: (30)..(30)
<223> OTHER INFORMATION: COOH

<400> SEQUENCE: 109

Ser Cys Gln Lys Trp Met Gln Thr Cys Asp Ala Glu Arg Lys Cys Cys
1               5                   10                  15
Glu Gly Phe Val Cys Arg Leu Trp Cys Lys Lys Lys Leu Trp
            20                  25                  30

<210> SEQ ID NO 110
<211> LENGTH: 30
<212> TYPE: PRT
<213> ORGANISM: Artificial sequence
<220> FEATURE:
<223> OTHER INFORMATION: Variant (-GP) NV1D2773NH2
<220> FEATURE:
<221> NAME/KEY: MOD_RES
<222> LOCATION: (30)..(30)
<223> OTHER INFORMATION: NH2

<400> SEQUENCE: 110

Ser Cys Gln Lys Trp Met Gln Thr Cys Asp Ala Glu Arg Lys Cys Cys
1               5                   10                  15
Glu Gly Phe Val Cys Arg Leu Trp Cys Lys Lys Lys Leu Trp
            20                  25                  30

<210> SEQ ID NO 111
<211> LENGTH: 32
<212> TYPE: PRT
<213> ORGANISM: Artificial sequence
<220> FEATURE:
<223> OTHER INFORMATION: Variant  NV1D2775NH2
<220> FEATURE:
<221> NAME/KEY: MOD_RES
<222> LOCATION: (32)..(32)
<223> OTHER INFORMATION: NH2

<400> SEQUENCE: 111

Gly Pro Gln Cys Gln Lys Trp Met Gln Thr Cys Asp Ala Glu Arg Lys
1               5                   10                  15
Cys Cys Glu Gly Phe Val Cys Arg Leu Trp Cys Lys Lys Lys Leu Trp
            20                  25                  30
```

<210> SEQ ID NO 112
<211> LENGTH: 30
<212> TYPE: PRT
<213> ORGANISM: Artificial sequence
<220> FEATURE:
<223> OTHER INFORMATION: Variant NV1D2890NH2
<220> FEATURE:
<221> NAME/KEY: MOD_RES
<222> LOCATION: (30)..(30)
<223> OTHER INFORMATION: NH2

<400> SEQUENCE: 112

Ser Cys Gln Lys Trp Phe Trp Thr Cys Asp Ala Glu Arg Lys Cys Cys
1               5                   10                  15

Glu Gly Leu Val Cys Arg Leu Trp Cys Lys Lys Lys Leu Trp
            20                  25                  30

<210> SEQ ID NO 113
<211> LENGTH: 32
<212> TYPE: PRT
<213> ORGANISM: Artificial sequence
<220> FEATURE:
<223> OTHER INFORMATION: Variant NV1D2974
<220> FEATURE:
<221> NAME/KEY: MOD_RES
<222> LOCATION: (32)..(32)
<223> OTHER INFORMATION: COOH

<400> SEQUENCE: 113

Gly Pro Gln Cys Gln Lys Trp Met Gln Thr Cys Asp Ala Glu Arg Lys
1               5                   10                  15

Cys Cys Glu Gly Phe Ser Cys Thr Leu Trp Cys Lys Lys Lys Leu Trp
            20                  25                  30

<210> SEQ ID NO 114
<211> LENGTH: 30
<212> TYPE: PRT
<213> ORGANISM: Artificial sequence
<220> FEATURE:
<223> OTHER INFORMATION: Variant (-GP) N-Ac-NV1D2974NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (30)..(30)
<223> OTHER INFORMATION: NH2

<400> SEQUENCE: 114

Gln Cys Gln Lys Trp Met Gln Thr Cys Asp Ala Glu Arg Lys Cys Cys
1               5                   10                  15

Glu Gly Phe Ser Cys Thr Leu Trp Cys Lys Lys Lys Leu Trp
            20                  25                  30

<210> SEQ ID NO 115
<211> LENGTH: 30
<212> TYPE: PRT
<213> ORGANISM: Artificial sequence
<220> FEATURE:
<223> OTHER INFORMATION: Variant (-GP) N-Ac-NV1D2974
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (30)..(30)

<223> OTHER INFORMATION: NH2

<400> SEQUENCE: 115

Gln Cys Gln Lys Trp Met Gln Thr Cys Asp Ala Glu Arg Lys Cys Cys
1               5                   10                  15

Glu Gly Phe Ser Cys Thr Leu Trp Cys Lys Lys Leu Trp
            20                  25                  30

<210> SEQ ID NO 116
<211> LENGTH: 32
<212> TYPE: PRT
<213> ORGANISM: Artificial sequence
<220> FEATURE:
<223> OTHER INFORMATION: Variant NV1D3034
<220> FEATURE:
<221> NAME/KEY: MOD_RES
<222> LOCATION: (32)..(32)
<223> OTHER INFORMATION: COOH

<400> SEQUENCE: 116

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 117
<211> LENGTH: 32
<212> TYPE: PRT
<213> ORGANISM: Artificial sequence
<220> FEATURE:
<223> OTHER INFORMATION: Variant  NV1D3034NH2
<220> FEATURE:
<221> NAME/KEY: MOD_RES
<222> LOCATION: (32)..(32)
<223> OTHER INFORMATION: NH2

<400> SEQUENCE: 117

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 118
<211> LENGTH: 32
<212> TYPE: PRT
<213> ORGANISM: Artificial sequence
<220> FEATURE:
<223> OTHER INFORMATION: NV1D3034-NH-butyl
<220> FEATURE:
<221> NAME/KEY: MOD_RES
<222> LOCATION: (32)..(32)
<223> OTHER INFORMATION: NH-CH2-CH2-CH2-CH3

<400> SEQUENCE: 118

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 119
<211> LENGTH: 32
<212> TYPE: PRT
<213> ORGANISM: Artificial sequence
<220> FEATURE:
<223> OTHER INFORMATION: Variant NV1D3034-NH-methyl
<220> FEATURE:
<221> NAME/KEY: MOD_RES

<222> LOCATION: (32)..(32)
<223> OTHER INFORMATION: NH-CH3

<400> SEQUENCE: 119

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 120
<211> LENGTH: 30
<212> TYPE: PRT
<213> ORGANISM: Artificial sequence
<220> FEATURE:
<223> OTHER INFORMATION: Variant (-GP) N-Ac-NV1D3034
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (30)..(30)
<223> OTHER INFORMATION: COOH

<400> SEQUENCE: 120

Gln Cys Gln Lys Trp Met Gln Thr Cys Asp Arg Glu Arg Lys Cys Cys
1               5                   10                  15

Glu Gly Phe Val Cys Thr Leu Trp Cys Arg Lys Lys Leu Trp
            20                  25                  30

<210> SEQ ID NO 121
<211> LENGTH: 30
<212> TYPE: PRT
<213> ORGANISM: Artificial sequence
<220> FEATURE:
<223> OTHER INFORMATION: Variant  (-GP) N-Ac-NV1D3034NH2
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (30)..(30)
<223> OTHER INFORMATION: NH2

<400> SEQUENCE: 121

Gln Cys Gln Lys Trp Met Gln Thr Cys Asp Arg Glu Arg Lys Cys Cys
1               5                   10                  15

Glu Gly Phe Val Cys Thr Leu Trp Cys Arg Lys Lys Leu Trp
            20                  25                  30

<210> SEQ ID NO 122
<211> LENGTH: 32
<212> TYPE: PRT
<213> ORGANISM: Artificial sequence
<220> FEATURE:
<223> OTHER INFORMATION: Variant NV1D3368
<220> FEATURE:
<221> NAME/KEY: MOD_RES
<222> LOCATION: (32)..(32)
<223> OTHER INFORMATION: COOH

<400> SEQUENCE: 122

Gly Pro Gln Cys Gln Lys Trp Met Gln Thr Cys Asp Arg Thr Arg Lys
1               5                   10                  15

Cys Cys Glu Gly Phe Val Cys Thr Leu Trp Cys Arg Lys Lys Leu Trp
            20                  25                  30

```
<210> SEQ ID NO 123
<211> LENGTH: 32
<212> TYPE: PRT
<213> ORGANISM: Artificial sequence
<220> FEATURE:
<223> OTHER INFORMATION: Variant NV1D3368NH2
<220> FEATURE:
<221> NAME/KEY: MOD_RES
<222> LOCATION: (32)..(32)
<223> OTHER INFORMATION: NH2

<400> SEQUENCE: 123

Gly Pro Gln Cys Gln Lys Trp Met Gln Thr Cys Asp Arg Thr Arg Lys
1               5                   10                  15
Cys Cys Glu Gly Phe Val Cys Thr Leu Trp Cys Arg Lys Lys Leu Trp
            20                  25                  30

<210> SEQ ID NO 124
<211> LENGTH: 32
<212> TYPE: PRT
<213> ORGANISM: Artificial sequence
<220> FEATURE:
<223> OTHER INFORMATION: Variant NV1D2969
<220> FEATURE:
<221> NAME/KEY: MOD_RES
<222> LOCATION: (32)..(32)
<223> OTHER INFORMATION: COOH

<400> SEQUENCE: 124

Gly Pro Ser Cys Gln Lys Trp Met Gln Thr Cys Asp Ala Glu Arg Lys
1               5                   10                  15
Cys Cys Glu Gly Phe Ser Cys Arg Leu Trp Cys Lys Lys Lys Leu Trp
            20                  25                  30

<210> SEQ ID NO 125
<211> LENGTH: 32
<212> TYPE: PRT
<213> ORGANISM: Artificial sequence
<220> FEATURE:
<223> OTHER INFORMATION: Variant NV1D2970
<220> FEATURE:
<221> NAME/KEY: MOD_RES
<222> LOCATION: (32)..(32)
<223> OTHER INFORMATION: COOH

<400> SEQUENCE: 125

Gly Pro Ser Cys Gln Lys Trp Met Gln Thr Cys Asp Ala Glu Arg Lys
1               5                   10                  15
Cys Cys Glu Gly Phe Val Cys Thr Leu Trp Cys Lys Lys Lys Leu Trp
            20                  25                  30

<210> SEQ ID NO 126
<211> LENGTH: 32
<212> TYPE: PRT
<213> ORGANISM: Artificial sequence
<220> FEATURE:
<223> OTHER INFORMATION: Variant NV1D2971
<220> FEATURE:
<221> NAME/KEY: MOD_RES
<222> LOCATION: (32)..(32)
<223> OTHER INFORMATION: COOH

<400> SEQUENCE: 126

Gly Pro Ser Cys Gln Lys Trp Met Gln Thr Cys Asp Ala Glu Arg Lys
1               5                   10                  15
Cys Cys Glu Gly Phe Ser Cys Thr Leu Trp Cys Lys Lys Lys Leu Trp
            20                  25                  30
```

<210> SEQ ID NO 127
<211> LENGTH: 32
<212> TYPE: PRT
<213> ORGANISM: Artificial sequence
<220> FEATURE:
<223> OTHER INFORMATION: Variant NV1D2972
<220> FEATURE:
<221> NAME/KEY: MOD_RES
<222> LOCATION: (32)..(32)
<223> OTHER INFORMATION: COOH

<400> SEQUENCE: 127

Gly Pro Gln Cys Gln Lys Trp Met Gln Thr Cys Asp Ala Glu Arg Lys
1               5                   10                  15

Cys Cys Glu Gly Phe Ser Cys Arg Leu Trp Cys Lys Lys Lys Leu Trp
            20                  25                  30

<210> SEQ ID NO 128
<211> LENGTH: 32
<212> TYPE: PRT
<213> ORGANISM: Artificial sequence
<220> FEATURE:
<223> OTHER INFORMATION: Variant NV1D2973
<220> FEATURE:
<221> NAME/KEY: MOD_RES
<222> LOCATION: (32)..(32)
<223> OTHER INFORMATION: COOH

<400> SEQUENCE: 128

Gly Pro Gln Cys Gln Lys Trp Met Gln Thr Cys Asp Ala Glu Arg Lys
1               5                   10                  15

Cys Cys Glu Gly Phe Val Cys Thr Leu Trp Cys Lys Lys Lys Leu Trp
            20                  25                  30

<210> SEQ ID NO 129
<211> LENGTH: 32
<212> TYPE: PRT
<213> ORGANISM: Artificial sequence
<220> FEATURE:
<223> OTHER INFORMATION: Variant NV1D2974
<220> FEATURE:
<221> NAME/KEY: MOD_RES
<222> LOCATION: (32)..(32)
<223> OTHER INFORMATION: COOH

<400> SEQUENCE: 129

Gly Pro Gln Cys Gln Lys Trp Met Gln Thr Cys Asp Ala Glu Arg Lys
1               5                   10                  15

Cys Cys Glu Gly Phe Ser Cys Thr Leu Trp Cys Lys Lys Lys Leu Trp
            20                  25                  30

<210> SEQ ID NO 130
<211> LENGTH: 32
<212> TYPE: PRT
<213> ORGANISM: Artificial sequence
<220> FEATURE:
<223> OTHER INFORMATION: Variant NV1D2974NH2
<220> FEATURE:
<221> NAME/KEY: MOD_RES
<222> LOCATION: (32)..(32)
<223> OTHER INFORMATION: NH2

<400> SEQUENCE: 130

Gly Pro Gln Cys Gln Lys Trp Met Gln Thr Cys Asp Ala Glu Arg Lys
1               5                   10                  15

Cys Cys Glu Gly Phe Ser Cys Thr Leu Trp Cys Lys Lys Lys Leu Trp

-continued

```
<210> SEQ ID NO 131
<211> LENGTH: 32
<212> TYPE: PRT
<213> ORGANISM: Artificial sequence
<220> FEATURE:
<223> OTHER INFORMATION: Variant NV1D3004
<220> FEATURE:
<221> NAME/KEY: MOD_RES
<222> LOCATION: (32)..(32)
<223> OTHER INFORMATION: COOH

<400> SEQUENCE: 131

Gly Pro Gln Cys Gln Lys Trp Met Gln Thr Cys Asp Arg Glu Arg Lys
1               5                   10                  15

Cys Cys Glu Gly Phe Val Cys Arg Leu Trp Cys Lys Lys Lys Leu Trp
            20                  25                  30

<210> SEQ ID NO 132
<211> LENGTH: 32
<212> TYPE: PRT
<213> ORGANISM: Artificial sequence
<220> FEATURE:
<223> OTHER INFORMATION: Variant NV1D3005
<220> FEATURE:
<221> NAME/KEY: MOD_RES
<222> LOCATION: (32)..(32)
<223> OTHER INFORMATION: COOH

<400> SEQUENCE: 132

Gly Pro Gln Cys Gln Lys Trp Met Gln Thr Cys Asp Ala Asn Arg Lys
1               5                   10                  15

Cys Cys Glu Gly Phe Val Cys Arg Leu Trp Cys Lys Lys Lys Leu Trp
            20                  25                  30

<210> SEQ ID NO 133
<211> LENGTH: 32
<212> TYPE: PRT
<213> ORGANISM: Artificial sequence
<220> FEATURE:
<223> OTHER INFORMATION: Variant NV1D3006
<220> FEATURE:
<221> NAME/KEY: MOD_RES
<222> LOCATION: (32)..(32)
<223> OTHER INFORMATION: COOH

<400> SEQUENCE: 133

Gly Pro Gln Cys Gln Lys Trp Met Gln Thr Cys Asp Ala Arg Arg Lys
1               5                   10                  15

Cys Cys Glu Gly Phe Val Cys Arg Leu Trp Cys Lys Lys Lys Leu Trp
            20                  25                  30

<210> SEQ ID NO 134
<211> LENGTH: 32
<212> TYPE: PRT
<213> ORGANISM: Artificial sequence
<220> FEATURE:
<223> OTHER INFORMATION: Variant NV1D3007
<220> FEATURE:
<221> NAME/KEY: MOD_RES
<222> LOCATION: (32)..(32)
<223> OTHER INFORMATION: COOH

<400> SEQUENCE: 134

Gly Pro Gln Cys Gln Lys Trp Met Gln Thr Cys Asp Ala Glu Arg Lys
1               5                   10                  15
```

Cys Cys Glu Gly Phe Val Cys Arg Leu Trp Cys Arg Lys Lys Leu Trp
            20                  25                  30

<210> SEQ ID NO 135
<211> LENGTH: 32
<212> TYPE: PRT
<213> ORGANISM: Artificial sequence
<220> FEATURE:
<223> OTHER INFORMATION: Variant NV1D3012
<220> FEATURE:
<221> NAME/KEY: MOD_RES
<222> LOCATION: (32)..(32)
<223> OTHER INFORMATION: COOH

<400> SEQUENCE: 135

Gly Pro Gln Cys Gln Lys Trp Met Gln Thr Cys Asp Arg Asn Arg Lys
1               5                   10                  15

Cys Cys Glu Gly Phe Val Cys Arg Leu Trp Cys Lys Lys Lys Leu Trp
            20                  25                  30

<210> SEQ ID NO 136
<211> LENGTH: 32
<212> TYPE: PRT
<213> ORGANISM: Artificial sequence
<220> FEATURE:
<223> OTHER INFORMATION: Variant NV1D3013
<220> FEATURE:
<221> NAME/KEY: MOD_RES
<222> LOCATION: (32)..(32)
<223> OTHER INFORMATION: COOH

<400> SEQUENCE: 136

Gly Pro Gln Cys Gln Lys Trp Met Gln Thr Cys Asp Arg Arg Arg Lys
1               5                   10                  15

Cys Cys Glu Gly Phe Val Cys Arg Leu Trp Cys Lys Lys Lys Leu Trp
            20                  25                  30

<210> SEQ ID NO 137
<211> LENGTH: 32
<212> TYPE: PRT
<213> ORGANISM: Artificial sequence
<220> FEATURE:
<223> OTHER INFORMATION: Variant NV1D3014
<220> FEATURE:
<221> NAME/KEY: MOD_RES
<222> LOCATION: (32)..(32)
<223> OTHER INFORMATION: COOH

<400> SEQUENCE: 137

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Lys Lys Lys Leu Trp
            20                  25                  30

<210> SEQ ID NO 138
<211> LENGTH: 32
<212> TYPE: PRT
<213> ORGANISM: Artificial sequence
<220> FEATURE:
<223> OTHER INFORMATION: Variant NV1D3015
<220> FEATURE:
<221> NAME/KEY: MOD_RES
<222> LOCATION: (32)..(32)
<223> OTHER INFORMATION: COOH

<400> SEQUENCE: 138

Gly Pro Gln Cys Gln Lys Trp Met Gln Thr Cys Asp Arg Glu Arg Lys
1               5                   10                  15

```
Cys Cys Glu Gly Phe Val Cys Arg Leu Trp Cys Arg Lys Lys Leu Trp
            20                  25                  30
```

<210> SEQ ID NO 139
<211> LENGTH: 32
<212> TYPE: PRT
<213> ORGANISM: Artificial sequence
<220> FEATURE:
<223> OTHER INFORMATION: Variant NV1D3016
<220> FEATURE:
<221> NAME/KEY: MOD_RES
<222> LOCATION: (32)..(32)
<223> OTHER INFORMATION: COOH

<400> SEQUENCE: 139

```
Gly Pro Gln Cys Gln Lys Trp Met Gln Thr Cys Asp Ala Asn Arg Lys
1               5                   10                  15

Cys Cys Glu Gly Phe Val Cys Thr Leu Trp Cys Lys Lys Lys Leu Trp
            20                  25                  30
```

<210> SEQ ID NO 140
<211> LENGTH: 32
<212> TYPE: PRT
<213> ORGANISM: Artificial sequence
<220> FEATURE:
<223> OTHER INFORMATION: Variant NV1D3017
<220> FEATURE:
<221> NAME/KEY: MOD_RES
<222> LOCATION: (32)..(32)
<223> OTHER INFORMATION: COOH

<400> SEQUENCE: 140

```
Gly Pro Gln Cys Gln Lys Trp Met Gln Thr Cys Asp Ala Arg Arg Lys
1               5                   10                  15

Cys Cys Glu Gly Phe Val Cys Thr Leu Trp Cys Lys Lys Lys Leu Trp
            20                  25                  30
```

<210> SEQ ID NO 141
<211> LENGTH: 32
<212> TYPE: PRT
<213> ORGANISM: Artificial sequence
<220> FEATURE:
<223> OTHER INFORMATION: Variant NV1D3018
<220> FEATURE:
<221> NAME/KEY: MOD_RES
<222> LOCATION: (32)..(32)
<223> OTHER INFORMATION: COOH

<400> SEQUENCE: 141

```
Gly Pro Gln Cys Gln Lys Trp Met Gln Thr Cys Asp Ala Asn Arg Lys
1               5                   10                  15

Cys Cys Glu Gly Phe Val Cys Arg Leu Trp Cys Arg Lys Lys Leu Trp
            20                  25                  30
```

<210> SEQ ID NO 142
<211> LENGTH: 32
<212> TYPE: PRT
<213> ORGANISM: Artificial sequence
<220> FEATURE:
<223> OTHER INFORMATION: Variant NV1D3019
<220> FEATURE:
<221> NAME/KEY: MOD_RES
<222> LOCATION: (32)..(32)
<223> OTHER INFORMATION: COOH

<400> SEQUENCE: 142

```
Gly Pro Gln Cys Gln Lys Trp Met Gln Thr Cys Asp Ala Arg Arg Lys
```

```
                1               5                  10                  15
```

Cys Cys Glu Gly Phe Val Cys Arg Leu Trp Cys Arg Lys Lys Leu Trp
                20                  25                  30

<210> SEQ ID NO 143
<211> LENGTH: 32
<212> TYPE: PRT
<213> ORGANISM: Artificial sequence
<220> FEATURE:
<223> OTHER INFORMATION: Variant NV1D3020
<220> FEATURE:
<221> NAME/KEY: MOD_RES
<222> LOCATION: (32)..(32)
<223> OTHER INFORMATION: COOH

<400> SEQUENCE: 143

Gly Pro Gln Cys Gln Lys Trp Met Gln Thr Cys Asp Ala Glu Arg Lys
1               5                   10                  15

Cys Cys Glu Gly Phe Val Cys Thr Leu Trp Cys Arg Lys Lys Leu Trp
                20                  25                  30

<210> SEQ ID NO 144
<211> LENGTH: 32
<212> TYPE: PRT
<213> ORGANISM: Artificial sequence
<220> FEATURE:
<223> OTHER INFORMATION: Variant NV1D3030
<220> FEATURE:
<221> NAME/KEY: MOD_RES
<222> LOCATION: (32)..(32)
<223> OTHER INFORMATION: COOH

<400> SEQUENCE: 144

Gly Pro Gln Cys Gln Lys Trp Met Gln Thr Cys Asp Arg Asn Arg Lys
1               5                   10                  15

Cys Cys Glu Gly Phe Val Cys Thr Leu Trp Cys Lys Lys Lys Leu Trp
                20                  25                  30

<210> SEQ ID NO 145
<211> LENGTH: 32
<212> TYPE: PRT
<213> ORGANISM: Artificial sequence
<220> FEATURE:
<223> OTHER INFORMATION: Variant NV1D3031
<220> FEATURE:
<221> NAME/KEY: MOD_RES
<222> LOCATION: (32)..(32)
<223> OTHER INFORMATION: COOH

<400> SEQUENCE: 145

Gly Pro Gln Cys Gln Lys Trp Met Gln Thr Cys Asp Arg Arg Arg Lys
1               5                   10                  15

Cys Cys Glu Gly Phe Val Cys Thr Leu Trp Cys Lys Lys Lys Leu Trp
                20                  25                  30

<210> SEQ ID NO 146
<211> LENGTH: 32
<212> TYPE: PRT
<213> ORGANISM: Artificial sequence
<220> FEATURE:
<223> OTHER INFORMATION: Variant NV1D3032
<220> FEATURE:
<221> NAME/KEY: MOD_RES
<222> LOCATION: (32)..(32)
<223> OTHER INFORMATION: COOH

<400> SEQUENCE: 146

Gly Pro Gln Cys Gln Lys Trp Met Gln Thr Cys Asp Arg Asn Arg Lys
1               5                   10                  15

Cys Cys Glu Gly Phe Val Cys Arg Leu Trp Cys Arg Lys Lys Leu Trp
            20                  25                  30

<210> SEQ ID NO 147
<211> LENGTH: 32
<212> TYPE: PRT
<213> ORGANISM: Artificial sequence
<220> FEATURE:
<223> OTHER INFORMATION: Variant NV1D3033
<220> FEATURE:
<221> NAME/KEY: MOD_RES
<222> LOCATION: (32)..(32)
<223> OTHER INFORMATION: COOH

<400> SEQUENCE: 147

Gly Pro Gln Cys Gln Lys Trp Met Gln Thr Cys Asp Arg Arg Arg Lys
1               5                   10                  15

Cys Cys Glu Gly Phe Val Cys Arg Leu Trp Cys Arg Lys Lys Leu Trp
            20                  25                  30

<210> SEQ ID NO 148
<211> LENGTH: 32
<212> TYPE: PRT
<213> ORGANISM: Artificial sequence
<220> FEATURE:
<223> OTHER INFORMATION: Variant NV1D3035
<220> FEATURE:
<221> NAME/KEY: MOD_RES
<222> LOCATION: (32)..(32)
<223> OTHER INFORMATION: COOH

<400> SEQUENCE: 148

Gly Pro Gln Cys Gln Lys Trp Met Gln Thr Cys Asp Ala Asn Arg Lys
1               5                   10                  15

Cys Cys Glu Gly Phe Val Cys Thr Leu Trp Cys Arg Lys Lys Leu Trp
            20                  25                  30

<210> SEQ ID NO 149
<211> LENGTH: 32
<212> TYPE: PRT
<213> ORGANISM: Artificial sequence
<220> FEATURE:
<223> OTHER INFORMATION: Variant NV1D3036
<220> FEATURE:
<221> NAME/KEY: MOD_RES
<222> LOCATION: (32)..(32)
<223> OTHER INFORMATION: COOH

<400> SEQUENCE: 149

Gly Pro Gln Cys Gln Lys Trp Met Gln Thr Cys Asp Ala Arg Arg Lys
1               5                   10                  15

Cys Cys Glu Gly Phe Val Cys Thr Leu Trp Cys Arg Lys Lys Leu Trp
            20                  25                  30

<210> SEQ ID NO 150
<211> LENGTH: 32
<212> TYPE: PRT
<213> ORGANISM: Artificial sequence
<220> FEATURE:
<223> OTHER INFORMATION: Variant NV1D3044
<220> FEATURE:
<221> NAME/KEY: MOD_RES
<222> LOCATION: (32)..(32)
<223> OTHER INFORMATION: COOH

<400> SEQUENCE: 150

Gly Pro Gln Cys Gln Lys Trp Met Gln Thr Cys Asp Arg Asn Arg Lys
1               5                   10                  15

Cys Cys Glu Gly Phe Val Cys Thr Leu Trp Cys Arg Lys Lys Leu Trp
            20                  25                  30

<210> SEQ ID NO 151
<211> LENGTH: 32
<212> TYPE: PRT
<213> ORGANISM: Artificial sequence
<220> FEATURE:
<223> OTHER INFORMATION: Variant NV1D3045
<220> FEATURE:
<221> NAME/KEY: MOD_RES
<222> LOCATION: (32)..(32)
<223> OTHER INFORMATION: COOH

<400> SEQUENCE: 151

Gly Pro Gln Cys Gln Lys Trp Met Gln Thr Cys Asp Arg Arg Arg Lys
1               5                   10                  15

Cys Cys Glu Gly Phe Val Cys Thr Leu Trp Cys Arg Lys Lys Leu Trp
            20                  25                  30

<210> SEQ ID NO 152
<211> LENGTH: 32
<212> TYPE: PRT
<213> ORGANISM: Artificial sequence
<220> FEATURE:
<223> OTHER INFORMATION: Variant NV1D3048
<220> FEATURE:
<221> NAME/KEY: MOD_RES
<222> LOCATION: (32)..(32)
<223> OTHER INFORMATION: COOH

<400> SEQUENCE: 152

Gly Pro Gln Cys Gln Lys Trp Met Gln Thr Cys Asp Ala Lys Arg Lys
1               5                   10                  15

Cys Cys Glu Gly Phe Val Cys Arg Leu Trp Cys Lys Lys Lys Leu Trp
            20                  25                  30

<210> SEQ ID NO 153
<211> LENGTH: 32
<212> TYPE: PRT
<213> ORGANISM: Artificial sequence
<220> FEATURE:
<223> OTHER INFORMATION: Variant NV1D3050
<220> FEATURE:
<221> NAME/KEY: MOD_RES
<222> LOCATION: (32)..(32)
<223> OTHER INFORMATION: COOH

<400> SEQUENCE: 153

Gly Pro Gln Cys Gln Lys Trp Met Gln Thr Cys Asp Arg Lys Arg Lys
1               5                   10                  15

Cys Cys Glu Gly Phe Val Cys Arg Leu Trp Cys Lys Lys Lys Leu Trp
            20                  25                  30

<210> SEQ ID NO 154
<211> LENGTH: 32
<212> TYPE: PRT
<213> ORGANISM: Artificial sequence
<220> FEATURE:
<223> OTHER INFORMATION: Variant NV1D3051
<220> FEATURE:
<221> NAME/KEY: MOD_RES
<222> LOCATION: (32)..(32)
<223> OTHER INFORMATION: COOH

<400> SEQUENCE: 154

Gly Pro Gln Cys Gln Lys Trp Met Gln Thr Cys Asp Ala Lys Arg Lys
1               5                   10                  15

Cys Cys Glu Gly Phe Val Cys Thr Leu Trp Cys Lys Lys Lys Leu Trp
            20                  25                  30

<210> SEQ ID NO 155
<211> LENGTH: 32
<212> TYPE: PRT
<213> ORGANISM: Artificial sequence
<220> FEATURE:
<223> OTHER INFORMATION: Variant NV1D3052
<220> FEATURE:
<221> NAME/KEY: MOD_RES
<222> LOCATION: (32)..(32)
<223> OTHER INFORMATION: COOH

<400> SEQUENCE: 155

Gly Pro Gln Cys Gln Lys Trp Met Gln Thr Cys Asp Ala Lys Arg Lys
1               5                   10                  15

Cys Cys Glu Gly Phe Val Cys Arg Leu Trp Cys Arg Lys Lys Leu Trp
            20                  25                  30

<210> SEQ ID NO 156
<211> LENGTH: 32
<212> TYPE: PRT
<213> ORGANISM: Artificial sequence
<220> FEATURE:
<223> OTHER INFORMATION: Variant NV1D3056
<220> FEATURE:
<221> NAME/KEY: MOD_RES
<222> LOCATION: (32)..(32)
<223> OTHER INFORMATION: COOH

<400> SEQUENCE: 156

Gly Pro Gln Cys Gln Lys Trp Met Gln Thr Cys Asp Arg Lys Arg Lys
1               5                   10                  15

Cys Cys Glu Gly Phe Val Cys Thr Leu Trp Cys Lys Lys Lys Leu Trp
            20                  25                  30

<210> SEQ ID NO 157
<211> LENGTH: 32
<212> TYPE: PRT
<213> ORGANISM: Artificial sequence
<220> FEATURE:
<223> OTHER INFORMATION: Variant NV1D3057
<220> FEATURE:
<221> NAME/KEY: MOD_RES
<222> LOCATION: (32)..(32)
<223> OTHER INFORMATION: COOH

<400> SEQUENCE: 157

Gly Pro Gln Cys Gln Lys Trp Met Gln Thr Cys Asp Arg Lys Arg Lys
1               5                   10                  15

Cys Cys Glu Gly Phe Val Cys Arg Leu Trp Cys Arg Lys Lys Leu Trp
            20                  25                  30

<210> SEQ ID NO 158
<211> LENGTH: 32
<212> TYPE: PRT
<213> ORGANISM: Artificial sequence
<220> FEATURE:
<223> OTHER INFORMATION: Variant NV1D3058
<220> FEATURE:
<221> NAME/KEY: MOD_RES
<222> LOCATION: (32)..(32)
<223> OTHER INFORMATION: COOH

<400> SEQUENCE: 158

Gly Pro Gln Cys Gln Lys Trp Met Gln Thr Cys Asp Ala Lys Arg Lys
1               5                   10                  15

Cys Cys Glu Gly Phe Val Cys Thr Leu Trp Cys Arg Lys Lys Leu Trp
            20                  25                  30

<210> SEQ ID NO 159
<211> LENGTH: 32
<212> TYPE: PRT
<213> ORGANISM: Artificial sequence
<220> FEATURE:
<223> OTHER INFORMATION: Variant NV1D3062
<220> FEATURE:
<221> NAME/KEY: MOD_RES
<222> LOCATION: (32)..(32)
<223> OTHER INFORMATION: COOH

<400> SEQUENCE: 159

Gly Pro Gln Cys Gln Lys Trp Met Gln Thr Cys Asp Arg Lys Arg Lys
1               5                   10                  15

Cys Cys Glu Gly Phe Val Cys Thr Leu Trp Cys Arg Lys Lys Leu Trp
            20                  25                  30

<210> SEQ ID NO 160
<211> LENGTH: 32
<212> TYPE: PRT
<213> ORGANISM: Artificial sequence
<220> FEATURE:
<223> OTHER INFORMATION: Variant NV1D3109
<220> FEATURE:
<221> NAME/KEY: MOD_RES
<222> LOCATION: (32)..(32)
<223> OTHER INFORMATION: COOH

<400> SEQUENCE: 160

Gly Pro Gln Cys Gln Lys Trp Met Trp Thr Cys Asp Ala Arg Arg Lys
1               5                   10                  15

Cys Cys Glu Gly Phe Val Cys Thr Leu Trp Cys Arg Lys Lys Leu Trp
            20                  25                  30

<210> SEQ ID NO 161
<211> LENGTH: 32
<212> TYPE: PRT
<213> ORGANISM: Artificial sequence
<220> FEATURE:
<223> OTHER INFORMATION: Variant NV1D3121
<220> FEATURE:
<221> NAME/KEY: MOD_RES
<222> LOCATION: (32)..(32)
<223> OTHER INFORMATION: COOH

<400> SEQUENCE: 161

Gly Pro Gln Cys Gln Lys Trp Met Trp Thr Cys Asp Arg Lys Arg Lys
1               5                   10                  15

Cys Cys Glu Gly Phe Val Cys Thr Leu Trp Cys Arg Lys Lys Leu Trp
            20                  25                  30

<210> SEQ ID NO 162
<211> LENGTH: 37
<212> TYPE: PRT
<213> ORGANISM: Artificial sequence
<220> FEATURE:
<223> OTHER INFORMATION: Variant NV1D3249
<220> FEATURE:
<221> NAME/KEY: MOD_RES
<222> LOCATION: (37)..(37)

<223> OTHER INFORMATION: COOH

<400> SEQUENCE: 162

Gly Pro Ala Ala Ala Ala Gln Cys Gln Lys Trp Met Gln Thr Cys
1               5                   10                  15

Asp Ala Glu Arg Lys Cys Cys Glu Gly Phe Val Cys Arg Leu Trp Cys
            20                  25                  30

Lys Lys Lys Leu Trp
        35

<210> SEQ ID NO 163
<211> LENGTH: 37
<212> TYPE: PRT
<213> ORGANISM: Artificial sequence
<220> FEATURE:
<223> OTHER INFORMATION: Variant NV1D3251
<220> FEATURE:
<221> NAME/KEY: MOD_RES
<222> LOCATION: (37)..(37)
<223> OTHER INFORMATION: COOH

<400> SEQUENCE: 163

Gly Pro Ala Pro Ala Pro Ala Gln Cys Gln Lys Trp Met Gln Thr Cys
1               5                   10                  15

Asp Ala Glu Arg Lys Cys Cys Glu Gly Phe Val Cys Arg Leu Trp Cys
            20                  25                  30

Lys Lys Lys Leu Trp
        35

<210> SEQ ID NO 164
<211> LENGTH: 37
<212> TYPE: PRT
<213> ORGANISM: Artificial sequence
<220> FEATURE:
<223> OTHER INFORMATION: Variant NV1D3252
<220> FEATURE:
<221> NAME/KEY: MOD_RES
<222> LOCATION: (37)..(37)
<223> OTHER INFORMATION: COOH

<400> SEQUENCE: 164

Gly Pro Gln Cys Gln Lys Trp Met Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

Ala Pro Ala Pro Ala
        35

<210> SEQ ID NO 165
<211> LENGTH: 37
<212> TYPE: PRT
<213> ORGANISM: Artificial sequence
<220> FEATURE:
<223> OTHER INFORMATION: Variant NV1D3254
<220> FEATURE:
<221> NAME/KEY: MOD_RES
<222> LOCATION: (37)..(37)
<223> OTHER INFORMATION: COOH

<400> SEQUENCE: 165

Gly Pro Gln Cys Gln Lys Trp Met Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

```
Gly Gly Gly Gly Gly
        35
```

<210> SEQ ID NO 166
<211> LENGTH: 64
<212> TYPE: PRT
<213> ORGANISM: Artificial sequence
<220> FEATURE:
<223> OTHER INFORMATION: Variant NV1D3256
<220> FEATURE:
<221> NAME/KEY: MOD_RES
<222> LOCATION: (64)..(64)
<223> OTHER INFORMATION: COOH

<400> SEQUENCE: 166

```
Gly Pro Cys Cys Asn Cys Ser Ser Lys Trp Cys Arg Asp His Ser Arg
1               5                   10                  15

Cys Cys Gly Arg Gly Ser Ala Pro Ala Pro Ala Pro Ala Pro Ala Pro
            20                  25                  30

Gly Ser Gln Cys Gln Lys Trp Met Gln Thr Cys Asp Ala Glu Arg Lys
        35                  40                  45

Cys Cys Glu Gly Phe Val Cys Arg Leu Trp Cys Lys Lys Lys Leu Trp
50                  55                  60
```

<210> SEQ ID NO 167
<211> LENGTH: 62
<212> TYPE: PRT
<213> ORGANISM: Artificial sequence
<220> FEATURE:
<223> OTHER INFORMATION: Variant NV1D3257
<220> FEATURE:
<221> NAME/KEY: MOD_RES
<222> LOCATION: (62)..(62)
<223> OTHER INFORMATION: COOH

<400> SEQUENCE: 167

```
Gly Pro Gln Cys Gln Lys Trp Met Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

Gly Ser Ala Pro Ala Pro Ala Pro Ala Pro Ala Pro Gly Ser Cys Cys
        35                  40                  45

Asn Cys Ser Ser Lys Trp Cys Arg Asp His Ser Arg Cys Cys
        50                  55                  60
```

<210> SEQ ID NO 168
<211> LENGTH: 74
<212> TYPE: PRT
<213> ORGANISM: Artificial sequence
<220> FEATURE:
<223> OTHER INFORMATION: Variant NV1D3259
<220> FEATURE:
<221> NAME/KEY: MOD_RES
<222> LOCATION: (74)..(74)
<223> OTHER INFORMATION: COOH

<400> SEQUENCE: 168

```
Gly Pro Gln Cys Gln Lys Trp Met Gln Thr Cys Asp Ala Glu Arg Lys
1               5                   10                  15

Cys Cys Glu Gly Phe Val Cys Arg Leu Trp Cys Lys Lys Lys Leu Trp
            20                  25                  30

Gly Ser Ala Pro Ala Pro Ala Pro Ala Pro Ala Pro Ala Pro Ala Pro
        35                  40                  45

Ala Pro Ala Pro Ala Pro Gly Ser Cys Cys Asn Cys Ser Ser Lys Trp
```

```
                50                  55                  60
Cys Arg Asp His Ser Arg Cys Cys Gly Arg
65                  70

<210> SEQ ID NO 169
<211> LENGTH: 74
<212> TYPE: PRT
<213> ORGANISM: Artificial sequence
<220> FEATURE:
<223> OTHER INFORMATION: Variant NV1D3260
<220> FEATURE:
<221> NAME/KEY: MOD_RES
<222> LOCATION: (74)..(74)
<223> OTHER INFORMATION: COOH

<400> SEQUENCE: 169

Gly Pro Cys Cys Asn Cys Ser Ser Lys Trp Cys Arg Asp His Ser Arg
1               5                   10                  15

Cys Cys Gly Arg Gly Ser Ala Pro Ala Pro Ala Pro Ala Pro Ala Pro
                20                  25                  30

Ala Pro Ala Pro Ala Pro Ala Pro Gly Ser Gln Cys Gln Lys
            35                  40                  45

Trp Met Gln Thr Cys Asp Ala Glu Arg Lys Cys Cys Glu Gly Phe Val
            50                  55                  60

Cys Arg Leu Trp Cys Lys Lys Lys Leu Trp
65                  70

<210> SEQ ID NO 170
<211> LENGTH: 72
<212> TYPE: PRT
<213> ORGANISM: Artificial sequence
<220> FEATURE:
<223> OTHER INFORMATION: Variant NV1D3261
<220> FEATURE:
<221> NAME/KEY: MOD_RES
<222> LOCATION: (72)..(72)
<223> OTHER INFORMATION: COOH

<400> SEQUENCE: 170

Gly Pro Gln Cys Gln Lys Trp Met Gln Thr Cys Asp Ala Glu Arg Lys
1               5                   10                  15

Cys Cys Glu Gly Phe Val Cys Arg Leu Trp Cys Lys Lys Lys Leu Trp
                20                  25                  30

Gly Ser Ala Pro Ala Pro Ala Pro Ala Pro Ala Pro Ala Pro Ala Pro
            35                  40                  45

Ala Pro Ala Pro Gly Ser Cys Cys Asn Cys Ser Ser Lys Trp
            50                  55                  60

Cys Arg Asp His Ser Arg Cys Cys
65                  70

<210> SEQ ID NO 171
<211> LENGTH: 72
<212> TYPE: PRT
<213> ORGANISM: Artificial sequence
<220> FEATURE:
<223> OTHER INFORMATION: Variant NV1D3262
<220> FEATURE:
<221> NAME/KEY: MOD_RES
<222> LOCATION: (72)..(72)
<223> OTHER INFORMATION: COOH

<400> SEQUENCE: 171

Gly Pro Cys Cys Asn Cys Ser Ser Lys Trp Cys Arg Asp His Ser Arg
1               5                   10                  15
```

```
Cys Cys Gly Ser Ala Pro Ala Pro Ala Pro Ala Pro
            20              25              30

Ala Pro Ala Pro Ala Pro Gly Ser Gln Cys Gln Lys Trp Met
        35              40              45

Gln Thr Cys Asp Ala Glu Arg Lys Cys Cys Gly Phe Val Cys Arg
 50              55              60

Leu Trp Cys Lys Lys Lys Leu Trp
 65              70
```

<210> SEQ ID NO 172
<211> LENGTH: 32
<212> TYPE: PRT
<213> ORGANISM: Artificial sequence
<220> FEATURE:
<223> OTHER INFORMATION: Variant NV1D3339
<220> FEATURE:
<221> NAME/KEY: MOD_RES
<222> LOCATION: (32)..(32)
<223> OTHER INFORMATION: COOH

<400> SEQUENCE: 172

```
Gly Pro Gln Cys Arg Lys Trp Met Gln Thr Cys Asp Arg Glu Arg Lys
 1               5                  10                  15

Cys Cys Glu Gly Phe Val Cys Thr Leu Trp Cys Arg Lys Lys Leu Trp
            20                  25                  30
```

<210> SEQ ID NO 173
<211> LENGTH: 32
<212> TYPE: PRT
<213> ORGANISM: Artificial sequence
<220> FEATURE:
<223> OTHER INFORMATION: Variant NV1D3340
<220> FEATURE:
<221> NAME/KEY: MOD_RES
<222> LOCATION: (32)..(32)
<223> OTHER INFORMATION: COOH

<400> SEQUENCE: 173

```
Gly Pro Gln Cys Lys Lys Trp Met Gln Thr Cys Asp Arg Glu Arg Lys
 1               5                  10                  15

Cys Cys Glu Gly Phe Val Cys Thr Leu Trp Cys Arg Lys Lys Leu Trp
            20                  25                  30
```

<210> SEQ ID NO 174
<211> LENGTH: 32
<212> TYPE: PRT
<213> ORGANISM: Artificial sequence
<220> FEATURE:
<223> OTHER INFORMATION: Variant NV1D3341
<220> FEATURE:
<221> NAME/KEY: MOD_RES
<222> LOCATION: (32)..(32)
<223> OTHER INFORMATION: COOH

<400> SEQUENCE: 174

```
Gly Pro Gln Cys Thr Lys Trp Met Gln Thr Cys Asp Arg Glu Arg Lys
 1               5                  10                  15

Cys Cys Glu Gly Phe Val Cys Thr Leu Trp Cys Arg Lys Lys Leu Trp
            20                  25                  30
```

<210> SEQ ID NO 175
<211> LENGTH: 32
<212> TYPE: PRT
<213> ORGANISM: Artificial sequence
<220> FEATURE:

<223> OTHER INFORMATION: Variant NV1D3342
<220> FEATURE:
<221> NAME/KEY: MOD_RES
<222> LOCATION: (32)..(32)
<223> OTHER INFORMATION: COOH

<400> SEQUENCE: 175

Gly Pro Gln Cys Ala Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 176
<211> LENGTH: 32
<212> TYPE: PRT
<213> ORGANISM: Artificial sequence
<220> FEATURE:
<223> OTHER INFORMATION: Variant NV1D3344
<220> FEATURE:
<221> NAME/KEY: MOD_RES
<222> LOCATION: (32)..(32)
<223> OTHER INFORMATION: COOH

<400> SEQUENCE: 176

Gly Pro Gln Cys Glu Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 177
<211> LENGTH: 32
<212> TYPE: PRT
<213> ORGANISM: Artificial sequence
<220> FEATURE:
<223> OTHER INFORMATION: Variant NV1D3345
<220> FEATURE:
<221> NAME/KEY: MOD_RES
<222> LOCATION: (32)..(32)
<223> OTHER INFORMATION: COOH

<400> SEQUENCE: 177

Gly Pro Gln Cys Ser Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 178
<211> LENGTH: 32
<212> TYPE: PRT
<213> ORGANISM: Artificial sequence
<220> FEATURE:
<223> OTHER INFORMATION: Variant NV1D3346
<220> FEATURE:
<221> NAME/KEY: MOD_RES
<222> LOCATION: (32)..(32)
<223> OTHER INFORMATION: COOH

<400> SEQUENCE: 178

Gly Pro Gln Cys Gln Arg Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 179
<211> LENGTH: 32
<212> TYPE: PRT
<213> ORGANISM: Artificial sequence

```
<220> FEATURE:
<223> OTHER INFORMATION: Variant NV1D3347
<220> FEATURE:
<221> NAME/KEY: MOD_RES
<222> LOCATION: (32)..(32)
<223> OTHER INFORMATION: COOH

<400> SEQUENCE: 179

Gly Pro Gln Cys Gln Thr Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 180
<211> LENGTH: 32
<212> TYPE: PRT
<213> ORGANISM: Artificial sequence
<220> FEATURE:
<223> OTHER INFORMATION: Variant NV1D3348
<220> FEATURE:
<221> NAME/KEY: MOD_RES
<222> LOCATION: (32)..(32)
<223> OTHER INFORMATION: COOH

<400> SEQUENCE: 180

Gly Pro Gln Cys Gln Ala Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 181
<211> LENGTH: 32
<212> TYPE: PRT
<213> ORGANISM: Artificial sequence
<220> FEATURE:
<223> OTHER INFORMATION: Variant NV1D3349
<220> FEATURE:
<221> NAME/KEY: MOD_RES
<222> LOCATION: (32)..(32)
<223> OTHER INFORMATION: COOH

<400> SEQUENCE: 181

Gly Pro Gln Cys Gln Asp Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 182
<211> LENGTH: 32
<212> TYPE: PRT
<213> ORGANISM: Artificial sequence
<220> FEATURE:
<223> OTHER INFORMATION: Variant NV1D3350
<220> FEATURE:
<221> NAME/KEY: MOD_RES
<222> LOCATION: (32)..(32)
<223> OTHER INFORMATION: COOH

<400> SEQUENCE: 182

Gly Pro Gln Cys Gln Glu Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 183
<211> LENGTH: 32
<212> TYPE: PRT
```

<213> ORGANISM: Artificial sequence
<220> FEATURE:
<223> OTHER INFORMATION: Variant NV1D3351
<220> FEATURE:
<221> NAME/KEY: MOD_RES
<222> LOCATION: (32)..(32)
<223> OTHER INFORMATION: COOH

<400> SEQUENCE: 183

Gly Pro Gln Cys Gln Gln Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 184
<211> LENGTH: 32
<212> TYPE: PRT
<213> ORGANISM: Artificial sequence
<220> FEATURE:
<223> OTHER INFORMATION: Variant NV1D3352
<220> FEATURE:
<221> NAME/KEY: MOD_RES
<222> LOCATION: (32)..(32)
<223> OTHER INFORMATION: COOH

<400> SEQUENCE: 184

Gly Pro Gln Cys Gln Ser Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 185
<211> LENGTH: 32
<212> TYPE: PRT
<213> ORGANISM: Artificial sequence
<220> FEATURE:
<223> OTHER INFORMATION: Variant NV1D3353
<220> FEATURE:
<221> NAME/KEY: MOD_RES
<222> LOCATION: (32)..(32)
<223> OTHER INFORMATION: COOH

<400> SEQUENCE: 185

Gly Pro Gln Cys Gln Lys Trp Met Gln Arg Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 186
<211> LENGTH: 32
<212> TYPE: PRT
<213> ORGANISM: Artificial sequence
<220> FEATURE:
<223> OTHER INFORMATION: Variant NV1D3354
<220> FEATURE:
<221> NAME/KEY: MOD_RES
<222> LOCATION: (32)..(32)
<223> OTHER INFORMATION: COOH

<400> SEQUENCE: 186

Gly Pro Gln Cys Gln Lys Trp Met Gln Lys Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 187
<211> LENGTH: 32

```
<212> TYPE: PRT
<213> ORGANISM: Artificial sequence
<220> FEATURE:
<223> OTHER INFORMATION: Variant NV1D3356
<220> FEATURE:
<221> NAME/KEY: MOD_RES
<222> LOCATION: (32)..(32)
<223> OTHER INFORMATION: COOH

<400> SEQUENCE: 187
```

Gly Pro Gln Cys Gln Lys Trp Met Gln Asp Cys Asp Arg Glu Arg Lys
1               5                   10                  15

Cys Cys Glu Gly Phe Val Cys Thr Leu Trp Cys Arg Lys Lys Leu Trp
            20                  25                  30

```
<210> SEQ ID NO 188
<211> LENGTH: 32
<212> TYPE: PRT
<213> ORGANISM: Artificial sequence
<220> FEATURE:
<223> OTHER INFORMATION: Variant NV1D3357
<220> FEATURE:
<221> NAME/KEY: MOD_RES
<222> LOCATION: (32)..(32)
<223> OTHER INFORMATION: COOH

<400> SEQUENCE: 188
```

Gly Pro Gln Cys Gln Lys Trp Met Gln Glu Cys Asp Arg Glu Arg Lys
1               5                   10                  15

Cys Cys Glu Gly Phe Val Cys Thr Leu Trp Cys Arg Lys Lys Leu Trp
            20                  25                  30

```
<210> SEQ ID NO 189
<211> LENGTH: 32
<212> TYPE: PRT
<213> ORGANISM: Artificial sequence
<220> FEATURE:
<223> OTHER INFORMATION: Variant NV1D3358
<220> FEATURE:
<221> NAME/KEY: MOD_RES
<222> LOCATION: (32)..(32)
<223> OTHER INFORMATION: COOH

<400> SEQUENCE: 189
```

Gly Pro Gln Cys Gln Lys Trp Met Gln Gln Cys Asp Arg Glu Arg Lys
1               5                   10                  15

Cys Cys Glu Gly Phe Val Cys Thr Leu Trp Cys Arg Lys Lys Leu Trp
            20                  25                  30

```
<210> SEQ ID NO 190
<211> LENGTH: 32
<212> TYPE: PRT
<213> ORGANISM: Artificial sequence
<220> FEATURE:
<223> OTHER INFORMATION: Variant NV1D3359
<220> FEATURE:
<221> NAME/KEY: MOD_RES
<222> LOCATION: (32)..(32)
<223> OTHER INFORMATION: COOH

<400> SEQUENCE: 190
```

Gly Pro Gln Cys Gln Lys Trp Met Gln Ser Cys Asp Arg Glu Arg Lys
1               5                   10                  15

Cys Cys Glu Gly Phe Val Cys Thr Leu Trp Cys Arg Lys Lys Leu Trp
            20                  25                  30

```
<210> SEQ ID NO 191
```

```
<211> LENGTH: 32
<212> TYPE: PRT
<213> ORGANISM: Artificial sequence
<220> FEATURE:
<223> OTHER INFORMATION: Variant NV1D3360
<220> FEATURE:
<221> NAME/KEY: MOD_RES
<222> LOCATION: (32)..(32)
<223> OTHER INFORMATION: COOH

<400> SEQUENCE: 191

Gly Pro Gln Cys Gln Lys Trp Met Gln Thr Cys Arg Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 192
<211> LENGTH: 32
<212> TYPE: PRT
<213> ORGANISM: Artificial sequence
<220> FEATURE:
<223> OTHER INFORMATION: Variant NV1D3361
<220> FEATURE:
<221> NAME/KEY: MOD_RES
<222> LOCATION: (32)..(32)
<223> OTHER INFORMATION: COOH

<400> SEQUENCE: 192

Gly Pro Gln Cys Gln Lys Trp Met Gln Thr Cys Lys Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 193
<211> LENGTH: 32
<212> TYPE: PRT
<213> ORGANISM: Artificial sequence
<220> FEATURE:
<223> OTHER INFORMATION: Variant NV1D3362
<220> FEATURE:
<221> NAME/KEY: MOD_RES
<222> LOCATION: (32)..(32)
<223> OTHER INFORMATION: COOH

<400> SEQUENCE: 193

Gly Pro Gln Cys Gln Lys Trp Met Gln Thr Cys Thr Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 194
<211> LENGTH: 32
<212> TYPE: PRT
<213> ORGANISM: Artificial sequence
<220> FEATURE:
<223> OTHER INFORMATION: Variant NV1D3363
<220> FEATURE:
<221> NAME/KEY: MOD_RES
<222> LOCATION: (32)..(32)
<223> OTHER INFORMATION: COOH

<400> SEQUENCE: 194

Gly Pro Gln Cys Gln Lys Trp Met Gln Thr Cys Ala Arg Glu Arg Lys
1               5                   10                  15

Cys Cys Glu Gly Phe Val Cys Thr Leu Trp Cys Arg Lys Lys Leu Trp
            20                  25                  30
```

```
<210> SEQ ID NO 195
<211> LENGTH: 32
<212> TYPE: PRT
<213> ORGANISM: Artificial sequence
<220> FEATURE:
<223> OTHER INFORMATION: Variant NV1D3365
<220> FEATURE:
<221> NAME/KEY: MOD_RES
<222> LOCATION: (32)..(32)
<223> OTHER INFORMATION: COOH

<400> SEQUENCE: 195

Gly Pro Gln Cys Gln Lys Trp Met Gln Thr Cys Gln Arg Glu Arg Lys
 1               5                  10                  15

Cys Cys Glu Gly Phe Val Cys Thr Leu Trp Cys Arg Lys Lys Leu Trp
            20                  25                  30

<210> SEQ ID NO 196
<211> LENGTH: 32
<212> TYPE: PRT
<213> ORGANISM: Artificial sequence
<220> FEATURE:
<223> OTHER INFORMATION: Variant NV1D3366
<220> FEATURE:
<221> NAME/KEY: MOD_RES
<222> LOCATION: (32)..(32)
<223> OTHER INFORMATION: COOH

<400> SEQUENCE: 196

Gly Pro Gln Cys Gln Lys Trp Met Gln Thr Cys Ser Arg Glu Arg Lys
 1               5                  10                  15

Cys Cys Glu Gly Phe Val Cys Thr Leu Trp Cys Arg Lys Lys Leu Trp
            20                  25                  30

<210> SEQ ID NO 197
<211> LENGTH: 32
<212> TYPE: PRT
<213> ORGANISM: Artificial sequence
<220> FEATURE:
<223> OTHER INFORMATION: Variant NV1D3367
<220> FEATURE:
<221> NAME/KEY: MOD_RES
<222> LOCATION: (32)..(32)
<223> OTHER INFORMATION: COOH

<400> SEQUENCE: 197

Gly Pro Gln Cys Gln Lys Trp Met Gln Thr Cys Asp Arg Gln Arg Lys
 1               5                  10                  15

Cys Cys Glu Gly Phe Val Cys Thr Leu Trp Cys Arg Lys Lys Leu Trp
            20                  25                  30

<210> SEQ ID NO 198
<211> LENGTH: 32
<212> TYPE: PRT
<213> ORGANISM: Artificial sequence
<220> FEATURE:
<223> OTHER INFORMATION: Variant NV1D3368
<220> FEATURE:
<221> NAME/KEY: MOD_RES
<222> LOCATION: (32)..(32)
<223> OTHER INFORMATION: COOH

<400> SEQUENCE: 198

Gly Pro Gln Cys Gln Lys Trp Met Gln Thr Cys Asp Arg Thr Arg Lys
 1               5                  10                  15

Cys Cys Glu Gly Phe Val Cys Thr Leu Trp Cys Arg Lys Lys Leu Trp
            20                  25                  30
```

<210> SEQ ID NO 199
<211> LENGTH: 32
<212> TYPE: PRT
<213> ORGANISM: Artificial sequence
<220> FEATURE:
<223> OTHER INFORMATION: Variant NV1D3369
<220> FEATURE:
<221> NAME/KEY: MOD_RES
<222> LOCATION: (32)..(32)
<223> OTHER INFORMATION: COOH

<400> SEQUENCE: 199

Gly Pro Gln Cys Gln Lys Trp Met Gln Thr Cys Asp Arg Glu Lys Lys
1               5                   10                  15

Cys Cys Glu Gly Phe Val Cys Thr Leu Trp Cys Arg Lys Lys Leu Trp
            20                  25                  30

<210> SEQ ID NO 200
<211> LENGTH: 32
<212> TYPE: PRT
<213> ORGANISM: Artificial sequence
<220> FEATURE:
<223> OTHER INFORMATION: Variant NV1D3370
<220> FEATURE:
<221> NAME/KEY: MOD_RES
<222> LOCATION: (32)..(32)
<223> OTHER INFORMATION: COOH

<400> SEQUENCE: 200

Gly Pro Gln Cys Gln Lys Trp Met Gln Thr Cys Asp Arg Glu Thr Lys
1               5                   10                  15

Cys Cys Glu Gly Phe Val Cys Thr Leu Trp Cys Arg Lys Lys Leu Trp
            20                  25                  30

<210> SEQ ID NO 201
<211> LENGTH: 32
<212> TYPE: PRT
<213> ORGANISM: Artificial sequence
<220> FEATURE:
<223> OTHER INFORMATION: Variant NV1D3371
<220> FEATURE:
<221> NAME/KEY: MOD_RES
<222> LOCATION: (32)..(32)
<223> OTHER INFORMATION: COOH

<400> SEQUENCE: 201

Gly Pro Gln Cys Gln Lys Trp Met Gln Thr Cys Asp Arg Glu Ala Lys
1               5                   10                  15

Cys Cys Glu Gly Phe Val Cys Thr Leu Trp Cys Arg Lys Lys Leu Trp
            20                  25                  30

<210> SEQ ID NO 202
<211> LENGTH: 32
<212> TYPE: PRT
<213> ORGANISM: Artificial sequence
<220> FEATURE:
<223> OTHER INFORMATION: Variant NV1D3372
<220> FEATURE:
<221> NAME/KEY: MOD_RES
<222> LOCATION: (32)..(32)
<223> OTHER INFORMATION: COOH

<400> SEQUENCE: 202

Gly Pro Gln Cys Gln Lys Trp Met Gln Thr Cys Asp Arg Glu Asp Lys
1               5                   10                  15

Cys Cys Glu Gly Phe Val Cys Thr Leu Trp Cys Arg Lys Lys Leu Trp
            20                  25                  30

```
<210> SEQ ID NO 203
<211> LENGTH: 32
<212> TYPE: PRT
<213> ORGANISM: Artificial sequence
<220> FEATURE:
<223> OTHER INFORMATION: Variant NV1D3374
<220> FEATURE:
<221> NAME/KEY: MOD_RES
<222> LOCATION: (32)..(32)
<223> OTHER INFORMATION: COOH

<400> SEQUENCE: 203

Gly Pro Gln Cys Gln Lys Trp Met Gln Thr Cys Asp Arg Glu Gln Lys
1               5                   10                  15

Cys Cys Glu Gly Phe Val Cys Thr Leu Trp Cys Arg Lys Lys Leu Trp
            20                  25                  30

<210> SEQ ID NO 204
<211> LENGTH: 32
<212> TYPE: PRT
<213> ORGANISM: Artificial sequence
<220> FEATURE:
<223> OTHER INFORMATION: Variant NV1D3375
<220> FEATURE:
<221> NAME/KEY: MOD_RES
<222> LOCATION: (32)..(32)
<223> OTHER INFORMATION: COOH

<400> SEQUENCE: 204

Gly Pro Gln Cys Gln Lys Trp Met Gln Thr Cys Asp Arg Glu Ser Lys
1               5                   10                  15

Cys Cys Glu Gly Phe Val Cys Thr Leu Trp Cys Arg Lys Lys Leu Trp
            20                  25                  30

<210> SEQ ID NO 205
<211> LENGTH: 32
<212> TYPE: PRT
<213> ORGANISM: Artificial sequence
<220> FEATURE:
<223> OTHER INFORMATION: Variant NV1D3376
<220> FEATURE:
<221> NAME/KEY: MOD_RES
<222> LOCATION: (32)..(32)
<223> OTHER INFORMATION: COOH

<400> SEQUENCE: 205

Gly Pro Gln Cys Gln Lys Trp Met Gln Thr Cys Asp Arg Glu Arg Arg
1               5                   10                  15

Cys Cys Glu Gly Phe Val Cys Thr Leu Trp Cys Arg Lys Lys Leu Trp
            20                  25                  30

<210> SEQ ID NO 206
<211> LENGTH: 32
<212> TYPE: PRT
<213> ORGANISM: Artificial sequence
<220> FEATURE:
<223> OTHER INFORMATION: Variant NV1D3377
<220> FEATURE:
<221> NAME/KEY: MOD_RES
<222> LOCATION: (32)..(32)
<223> OTHER INFORMATION: COOH

<400> SEQUENCE: 206

Gly Pro Gln Cys Gln Lys Trp Met Gln Thr Cys Asp Arg Glu Arg Thr
1               5                   10                  15

Cys Cys Glu Gly Phe Val Cys Thr Leu Trp Cys Arg Lys Lys Leu Trp
```

20                  25                  30

<210> SEQ ID NO 207
<211> LENGTH: 32
<212> TYPE: PRT
<213> ORGANISM: Artificial sequence
<220> FEATURE:
<223> OTHER INFORMATION: Variant NV1D3378
<220> FEATURE:
<221> NAME/KEY: MOD_RES
<222> LOCATION: (32)..(32)
<223> OTHER INFORMATION: COOH

<400> SEQUENCE: 207

Gly Pro Gln Cys Gln Lys Trp Met Gln Thr Cys Asp Arg Glu Arg Ala
1               5                   10                  15

Cys Cys Glu Gly Phe Val Cys Thr Leu Trp Cys Arg Lys Lys Leu Trp
            20                  25                  30

<210> SEQ ID NO 208
<211> LENGTH: 32
<212> TYPE: PRT
<213> ORGANISM: Artificial sequence
<220> FEATURE:
<223> OTHER INFORMATION: Variant NV1D3379
<220> FEATURE:
<221> NAME/KEY: MOD_RES
<222> LOCATION: (32)..(32)
<223> OTHER INFORMATION: COOH

<400> SEQUENCE: 208

Gly Pro Gln Cys Gln Lys Trp Met Gln Thr Cys Asp Arg Glu Arg Asp
1               5                   10                  15

Cys Cys Glu Gly Phe Val Cys Thr Leu Trp Cys Arg Lys Lys Leu Trp
            20                  25                  30

<210> SEQ ID NO 209
<211> LENGTH: 32
<212> TYPE: PRT
<213> ORGANISM: Artificial sequence
<220> FEATURE:
<223> OTHER INFORMATION: Variant NV1D3380
<220> FEATURE:
<221> NAME/KEY: MOD_RES
<222> LOCATION: (32)..(32)
<223> OTHER INFORMATION: COOH

<400> SEQUENCE: 209

Gly Pro Gln Cys Gln Lys Trp Met Gln Thr Cys Asp Arg Glu Arg Glu
1               5                   10                  15

Cys Cys Glu Gly Phe Val Cys Thr Leu Trp Cys Arg Lys Lys Leu Trp
            20                  25                  30

<210> SEQ ID NO 210
<211> LENGTH: 32
<212> TYPE: PRT
<213> ORGANISM: Artificial sequence
<220> FEATURE:
<223> OTHER INFORMATION: Variant NV1D3381
<220> FEATURE:
<221> NAME/KEY: MOD_RES
<222> LOCATION: (32)..(32)
<223> OTHER INFORMATION: COOH

<400> SEQUENCE: 210

Gly Pro Gln Cys Gln Lys Trp Met Gln Thr Cys Asp Arg Glu Arg Gln
1               5                   10                  15

Cys Cys Glu Gly Phe Val Cys Thr Leu Trp Cys Arg Lys Lys Leu Trp
            20                  25                  30

<210> SEQ ID NO 211
<211> LENGTH: 32
<212> TYPE: PRT
<213> ORGANISM: Artificial sequence
<220> FEATURE:
<223> OTHER INFORMATION: Variant NV1D3382
<220> FEATURE:
<221> NAME/KEY: MOD_RES
<222> LOCATION: (32)..(32)
<223> OTHER INFORMATION: COOH

<400> SEQUENCE: 211

Gly Pro Gln Cys Gln Lys Trp Met Gln Thr Cys Asp Arg Glu Arg Ser
1               5                   10                  15

Cys Cys Glu Gly Phe Val Cys Thr Leu Trp Cys Arg Lys Lys Leu Trp
            20                  25                  30

<210> SEQ ID NO 212
<211> LENGTH: 32
<212> TYPE: PRT
<213> ORGANISM: Artificial sequence
<220> FEATURE:
<223> OTHER INFORMATION: Variant NV1D3383
<220> FEATURE:
<221> NAME/KEY: MOD_RES
<222> LOCATION: (32)..(32)
<223> OTHER INFORMATION: COOH

<400> SEQUENCE: 212

Gly Pro Gln Cys Gln Lys Trp Met Gln Thr Cys Asp Arg Glu Arg Lys
1               5                   10                  15

Cys Cys Arg Gly Phe Val Cys Thr Leu Trp Cys Arg Lys Lys Leu Trp
            20                  25                  30

<210> SEQ ID NO 213
<211> LENGTH: 32
<212> TYPE: PRT
<213> ORGANISM: Artificial sequence
<220> FEATURE:
<223> OTHER INFORMATION: Variant NV1D3384
<220> FEATURE:
<221> NAME/KEY: MOD_RES
<222> LOCATION: (32)..(32)
<223> OTHER INFORMATION: COOH

<400> SEQUENCE: 213

Gly Pro Gln Cys Gln Lys Trp Met Gln Thr Cys Asp Arg Glu Arg Lys
1               5                   10                  15

Cys Cys Lys Gly Phe Val Cys Thr Leu Trp Cys Arg Lys Lys Leu Trp
            20                  25                  30

<210> SEQ ID NO 214
<211> LENGTH: 32
<212> TYPE: PRT
<213> ORGANISM: Artificial sequence
<220> FEATURE:
<223> OTHER INFORMATION: Variant NV1D3385
<220> FEATURE:
<221> NAME/KEY: MOD_RES
<222> LOCATION: (32)..(32)
<223> OTHER INFORMATION: COOH

<400> SEQUENCE: 214

Gly Pro Gln Cys Gln Lys Trp Met Gln Thr Cys Asp Arg Glu Arg Lys
1               5                   10                  15

Cys Cys Thr Gly Phe Val Cys Thr Leu Trp Cys Arg Lys Lys Leu Trp
            20                  25                  30

<210> SEQ ID NO 215
<211> LENGTH: 32
<212> TYPE: PRT
<213> ORGANISM: Artificial sequence
<220> FEATURE:
<223> OTHER INFORMATION: Variant NV1D3386
<220> FEATURE:
<221> NAME/KEY: MOD_RES
<222> LOCATION: (32)..(32)
<223> OTHER INFORMATION: COOH

<400> SEQUENCE: 215

Gly Pro Gln Cys Gln Lys Trp Met Gln Thr Cys Asp Arg Glu Arg Lys
1               5                   10                  15

Cys Cys Ala Gly Phe Val Cys Thr Leu Trp Cys Arg Lys Lys Leu Trp
            20                  25                  30

<210> SEQ ID NO 216
<211> LENGTH: 32
<212> TYPE: PRT
<213> ORGANISM: Artificial sequence
<220> FEATURE:
<223> OTHER INFORMATION: Variant NV1D3387
<220> FEATURE:
<221> NAME/KEY: MOD_RES
<222> LOCATION: (32)..(32)
<223> OTHER INFORMATION: COOH

<400> SEQUENCE: 216

Gly Pro Gln Cys Gln Lys Trp Met Gln Thr Cys Asp Arg Glu Arg Lys
1               5                   10                  15

Cys Cys Asp Gly Phe Val Cys Thr Leu Trp Cys Arg Lys Lys Leu Trp
            20                  25                  30

<210> SEQ ID NO 217
<211> LENGTH: 32
<212> TYPE: PRT
<213> ORGANISM: Artificial sequence
<220> FEATURE:
<223> OTHER INFORMATION: Variant NV1D3388
<220> FEATURE:
<221> NAME/KEY: MOD_RES
<222> LOCATION: (32)..(32)
<223> OTHER INFORMATION: COOH

<400> SEQUENCE: 217

Gly Pro Gln Cys Gln Lys Trp Met Gln Thr Cys Asp Arg Glu Arg Lys
1               5                   10                  15

Cys Cys Gln Gly Phe Val Cys Thr Leu Trp Cys Arg Lys Lys Leu Trp
            20                  25                  30

<210> SEQ ID NO 218
<211> LENGTH: 32
<212> TYPE: PRT
<213> ORGANISM: Artificial sequence
<220> FEATURE:
<223> OTHER INFORMATION: Variant NV1D3389
<220> FEATURE:
<221> NAME/KEY: MOD_RES
<222> LOCATION: (32)..(32)
<223> OTHER INFORMATION: COOH

<400> SEQUENCE: 218

Gly Pro Gln Cys Gln Lys Trp Met Gln Thr Cys Asp Arg Glu Arg Lys

```
            1               5                  10                 15
Cys Cys Ser Gly Phe Val Cys Thr Leu Trp Cys Arg Lys Lys Leu Trp
            20                 25                 30

<210> SEQ ID NO 219
<211> LENGTH: 32
<212> TYPE: PRT
<213> ORGANISM: Artificial sequence
<220> FEATURE:
<223> OTHER INFORMATION: Variant NV1D3390
<220> FEATURE:
<221> NAME/KEY: MOD_RES
<222> LOCATION: (32)..(32)
<223> OTHER INFORMATION: COOH

<400> SEQUENCE: 219

Gly Pro Gln Cys Gln Lys Trp Met Gln Thr Cys Asp Arg Glu Arg Lys
1               5                  10                 15

Cys Cys Glu Arg Phe Val Cys Thr Leu Trp Cys Arg Lys Lys Leu Trp
            20                 25                 30

<210> SEQ ID NO 220
<211> LENGTH: 32
<212> TYPE: PRT
<213> ORGANISM: Artificial sequence
<220> FEATURE:
<223> OTHER INFORMATION: Variant NV1D3391
<220> FEATURE:
<221> NAME/KEY: MOD_RES
<222> LOCATION: (32)..(32)
<223> OTHER INFORMATION: COOH

<400> SEQUENCE: 220

Gly Pro Gln Cys Gln Lys Trp Met Gln Thr Cys Asp Arg Glu Arg Lys
1               5                  10                 15

Cys Cys Glu Lys Phe Val Cys Thr Leu Trp Cys Arg Lys Lys Leu Trp
            20                 25                 30

<210> SEQ ID NO 221
<211> LENGTH: 32
<212> TYPE: PRT
<213> ORGANISM: Artificial sequence
<220> FEATURE:
<223> OTHER INFORMATION: Variant NV1D3392
<220> FEATURE:
<221> NAME/KEY: MOD_RES
<222> LOCATION: (32)..(32)
<223> OTHER INFORMATION: COOH

<400> SEQUENCE: 221

Gly Pro Gln Cys Gln Lys Trp Met Gln Thr Cys Asp Arg Glu Arg Lys
1               5                  10                 15

Cys Cys Glu Thr Phe Val Cys Thr Leu Trp Cys Arg Lys Lys Leu Trp
            20                 25                 30

<210> SEQ ID NO 222
<211> LENGTH: 32
<212> TYPE: PRT
<213> ORGANISM: Artificial sequence
<220> FEATURE:
<223> OTHER INFORMATION: Variant NV1D3393
<220> FEATURE:
<221> NAME/KEY: MOD_RES
<222> LOCATION: (32)..(32)
<223> OTHER INFORMATION: COOH

<400> SEQUENCE: 222
```

Gly Pro Gln Cys Gln Lys Trp Met Gln Thr Cys Asp Arg Glu Arg Lys
1               5                   10                  15

Cys Cys Glu Ala Phe Val Cys Thr Leu Trp Cys Arg Lys Lys Leu Trp
            20                  25                  30

<210> SEQ ID NO 223
<211> LENGTH: 32
<212> TYPE: PRT
<213> ORGANISM: Artificial sequence
<220> FEATURE:
<223> OTHER INFORMATION: Variant NV1D3394
<220> FEATURE:
<221> NAME/KEY: MOD_RES
<222> LOCATION: (32)..(32)
<223> OTHER INFORMATION: COOH

<400> SEQUENCE: 223

Gly Pro Gln Cys Gln Lys Trp Met Gln Thr Cys Asp Arg Glu Arg Lys
1               5                   10                  15

Cys Cys Glu Asp Phe Val Cys Thr Leu Trp Cys Arg Lys Lys Leu Trp
            20                  25                  30

<210> SEQ ID NO 224
<211> LENGTH: 32
<212> TYPE: PRT
<213> ORGANISM: Artificial sequence
<220> FEATURE:
<223> OTHER INFORMATION: Variant NV1D3396
<220> FEATURE:
<221> NAME/KEY: MOD_RES
<222> LOCATION: (32)..(32)
<223> OTHER INFORMATION: COOH

<400> SEQUENCE: 224

Gly Pro Gln Cys Gln Lys Trp Met Gln Thr Cys Asp Arg Glu Arg Lys
1               5                   10                  15

Cys Cys Glu Gln Phe Val Cys Thr Leu Trp Cys Arg Lys Lys Leu Trp
            20                  25                  30

<210> SEQ ID NO 225
<211> LENGTH: 32
<212> TYPE: PRT
<213> ORGANISM: Artificial sequence
<220> FEATURE:
<223> OTHER INFORMATION: Variant NV1D3397
<220> FEATURE:
<221> NAME/KEY: MOD_RES
<222> LOCATION: (32)..(32)
<223> OTHER INFORMATION: COOH

<400> SEQUENCE: 225

Gly Pro Gln Cys Gln Lys Trp Met Gln Thr Cys Asp Arg Glu Arg Lys
1               5                   10                  15

Cys Cys Glu Ser Phe Val Cys Thr Leu Trp Cys Arg Lys Lys Leu Trp
            20                  25                  30

<210> SEQ ID NO 226
<211> LENGTH: 32
<212> TYPE: PRT
<213> ORGANISM: Artificial sequence
<220> FEATURE:
<223> OTHER INFORMATION: Variant NV1D3398
<220> FEATURE:
<221> NAME/KEY: MOD_RES
<222> LOCATION: (32)..(32)
<223> OTHER INFORMATION: COOH

<400> SEQUENCE: 226

Gly Pro Gln Cys Gln Lys Trp Met Gln Thr Cys Asp Arg Glu Arg Lys
1               5                   10                  15

Cys Cys Glu Gly Phe Ser Cys Thr Leu Trp Cys Arg Lys Lys Leu Trp
            20                  25                  30

<210> SEQ ID NO 227
<211> LENGTH: 32
<212> TYPE: PRT
<213> ORGANISM: Artificial sequence
<220> FEATURE:
<223> OTHER INFORMATION: Variant NV1D3399
<220> FEATURE:
<221> NAME/KEY: MOD_RES
<222> LOCATION: (32)..(32)
<223> OTHER INFORMATION: COOH

<400> SEQUENCE: 227

Gly Pro Gln Cys Gln Lys Trp Met Gln Thr Cys Asp Arg Glu Arg Lys
1               5                   10                  15

Cys Cys Glu Gly Phe Thr Cys Thr Leu Trp Cys Arg Lys Lys Leu Trp
            20                  25                  30

<210> SEQ ID NO 228
<211> LENGTH: 32
<212> TYPE: PRT
<213> ORGANISM: Artificial sequence
<220> FEATURE:
<223> OTHER INFORMATION: Variant NV1D3400
<220> FEATURE:
<221> NAME/KEY: MOD_RES
<222> LOCATION: (32)..(32)
<223> OTHER INFORMATION: COOH

<400> SEQUENCE: 228

Gly Pro Gln Cys Gln Lys Trp Met Gln Thr Cys Asp Arg Glu Arg Lys
1               5                   10                  15

Cys Cys Glu Gly Phe Gln Cys Thr Leu Trp Cys Arg Lys Lys Leu Trp
            20                  25                  30

<210> SEQ ID NO 229
<211> LENGTH: 32
<212> TYPE: PRT
<213> ORGANISM: Artificial sequence
<220> FEATURE:
<223> OTHER INFORMATION: Variant NV1D3401
<220> FEATURE:
<221> NAME/KEY: MOD_RES
<222> LOCATION: (32)..(32)
<223> OTHER INFORMATION: COOH

<400> SEQUENCE: 229

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Arg Lys Leu Trp
            20                  25                  30

<210> SEQ ID NO 230
<211> LENGTH: 32
<212> TYPE: PRT
<213> ORGANISM: Artificial sequence
<220> FEATURE:
<223> OTHER INFORMATION: Variant NV1D3403
<220> FEATURE:
<221> NAME/KEY: MOD_RES
<222> LOCATION: (32)..(32)
<223> OTHER INFORMATION: COOH

<400> SEQUENCE: 230

Gly Pro Gln Cys Gln Lys Trp Met Gln Thr Cys Asp Arg Glu Arg Lys
1               5                   10                  15
Cys Cys Glu Gly Phe Val Cys Thr Leu Trp Cys Arg Ala Lys Leu Trp
            20                  25                  30

<210> SEQ ID NO 231
<211> LENGTH: 32
<212> TYPE: PRT
<213> ORGANISM: Artificial sequence
<220> FEATURE:
<223> OTHER INFORMATION: Variant NV1D3408
<220> FEATURE:
<221> NAME/KEY: MOD_RES
<222> LOCATION: (32)..(32)
<223> OTHER INFORMATION: COOH

<400> SEQUENCE: 231

Gly Pro Gln Cys Gln Lys Trp Met Gln Thr Cys Asp Arg Glu Arg Lys
1               5                   10                  15
Cys Cys Glu Gly Phe Val Cys Thr Leu Trp Cys Arg Lys Arg Leu Trp
            20                  25                  30

<210> SEQ ID NO 232
<211> LENGTH: 32
<212> TYPE: PRT
<213> ORGANISM: Artificial sequence
<220> FEATURE:
<223> OTHER INFORMATION: Variant NV1D3409
<220> FEATURE:
<221> NAME/KEY: MOD_RES
<222> LOCATION: (32)..(32)
<223> OTHER INFORMATION: COOH

<400> SEQUENCE: 232

Gly Pro Gln Cys Gln Lys Trp Met Gln Thr Cys Asp Arg Glu Arg Lys
1               5                   10                  15
Cys Cys Glu Gly Phe Val Cys Thr Leu Trp Cys Arg Lys Thr Leu Trp
            20                  25                  30

<210> SEQ ID NO 233
<211> LENGTH: 32
<212> TYPE: PRT
<213> ORGANISM: Artificial sequence
<220> FEATURE:
<223> OTHER INFORMATION: Variant NV1D3410
<220> FEATURE:
<221> NAME/KEY: MOD_RES
<222> LOCATION: (32)..(32)
<223> OTHER INFORMATION: COOH

<400> SEQUENCE: 233

Gly Pro Gln Cys Gln Lys Trp Met Gln Thr Cys Asp Arg Glu Arg Lys
1               5                   10                  15
Cys Cys Glu Gly Phe Val Cys Thr Leu Trp Cys Arg Lys Ala Leu Trp
            20                  25                  30

<210> SEQ ID NO 234
<211> LENGTH: 32
<212> TYPE: PRT
<213> ORGANISM: Artificial sequence
<220> FEATURE:
<223> OTHER INFORMATION: Variant NV1D3413
<220> FEATURE:
<221> NAME/KEY: MOD_RES
<222> LOCATION: (32)..(32)
<223> OTHER INFORMATION: COOH

<400> SEQUENCE: 234

Gly Pro Gln Cys Gln Lys Trp Met Gln Thr Cys Asp Arg Glu Arg Lys
1               5                   10                  15
Cys Cys Glu Gly Phe Val Cys Thr Leu Trp Cys Arg Lys Gln Leu Trp
            20                  25                  30

<210> SEQ ID NO 235
<211> LENGTH: 32
<212> TYPE: PRT
<213> ORGANISM: Artificial sequence
<220> FEATURE:
<223> OTHER INFORMATION: Variant NV1D3414
<220> FEATURE:
<221> NAME/KEY: MOD_RES
<222> LOCATION: (32)..(32)
<223> OTHER INFORMATION: COOH

<400> SEQUENCE: 235

Gly Pro Gln Cys Gln Lys Trp Met Gln Thr Cys Asp Arg Glu Arg Lys
1               5                   10                  15
Cys Cys Glu Gly Phe Val Cys Thr Leu Trp Cys Arg Lys Ser Leu Trp
            20                  25                  30

<210> SEQ ID NO 236
<211> LENGTH: 32
<212> TYPE: PRT
<213> ORGANISM: Artificial sequence
<220> FEATURE:
<223> OTHER INFORMATION: Variant NV1D3419
<220> FEATURE:
<221> NAME/KEY: MOD_RES
<222> LOCATION: (32)..(32)
<223> OTHER INFORMATION: COOH

<400> SEQUENCE: 236

Gly Pro Gln Cys Gln Lys Trp Met Gln Thr Cys Asp Arg Glu Arg Lys
1               5                   10                  15
Cys Cys Glu Gly Phe Val Cys Thr Leu Trp Cys Arg Lys Lys Leu Asp
            20                  25                  30

<210> SEQ ID NO 237
<211> LENGTH: 32
<212> TYPE: PRT
<213> ORGANISM: Artificial sequence
<220> FEATURE:
<223> OTHER INFORMATION: Variant NV1D3423
<220> FEATURE:
<221> NAME/KEY: MOD_RES
<222> LOCATION: (32)..(32)
<223> OTHER INFORMATION: COOH

<400> SEQUENCE: 237

Gly Pro Gln Cys Gln Lys Trp Met Gln Thr Cys Arg Arg Arg Arg Lys
1               5                   10                  15
Cys Cys Glu Gly Phe Val Cys Thr Leu Trp Cys Arg Lys Lys Leu Trp
            20                  25                  30

<210> SEQ ID NO 238
<211> LENGTH: 32
<212> TYPE: PRT
<213> ORGANISM: Artificial sequence
<220> FEATURE:
<223> OTHER INFORMATION: Variant NV1D3424
<220> FEATURE:
<221> NAME/KEY: MOD_RES
<222> LOCATION: (32)..(32)

```
<223> OTHER INFORMATION: COOH

<400> SEQUENCE: 238

Gly Pro Gln Cys Gln Lys Trp Met Gln Thr Cys Lys Arg Lys Arg Lys
1               5                   10                  15

Cys Cys Glu Gly Phe Val Cys Thr Leu Trp Cys Arg Lys Lys Leu Trp
            20                  25                  30

<210> SEQ ID NO 239
<211> LENGTH: 32
<212> TYPE: PRT
<213> ORGANISM: Artificial sequence
<220> FEATURE:
<223> OTHER INFORMATION: Variant NV1D3425
<220> FEATURE:
<221> NAME/KEY: MOD_RES
<222> LOCATION: (32)..(32)
<223> OTHER INFORMATION: COOH

<400> SEQUENCE: 239

Gly Pro Gln Cys Gln Lys Trp Met Gln Thr Cys Arg Arg Arg Asp Lys
1               5                   10                  15

Cys Cys Glu Gly Phe Val Cys Thr Leu Trp Cys Arg Lys Lys Leu Trp
            20                  25                  30

<210> SEQ ID NO 240
<211> LENGTH: 32
<212> TYPE: PRT
<213> ORGANISM: Artificial sequence
<220> FEATURE:
<223> OTHER INFORMATION: Variant NV1D3426
<220> FEATURE:
<221> NAME/KEY: MOD_RES
<222> LOCATION: (32)..(32)
<223> OTHER INFORMATION: COOH

<400> SEQUENCE: 240

Gly Pro Gln Cys Gln Lys Trp Met Gln Thr Cys Lys Arg Lys Asp Lys
1               5                   10                  15

Cys Cys Glu Gly Phe Val Cys Thr Leu Trp Cys Arg Lys Lys Leu Trp
            20                  25                  30

<210> SEQ ID NO 241
<211> LENGTH: 32
<212> TYPE: PRT
<213> ORGANISM: Artificial sequence
<220> FEATURE:
<223> OTHER INFORMATION: Variant NV1D3427
<220> FEATURE:
<221> NAME/KEY: MOD_RES
<222> LOCATION: (32)..(32)
<223> OTHER INFORMATION: COOH

<400> SEQUENCE: 241

Gly Pro Gln Cys Gln Lys Trp Met Gln Thr Cys Arg Arg Arg Glu Lys
1               5                   10                  15

Cys Cys Glu Gly Phe Val Cys Thr Leu Trp Cys Arg Lys Lys Leu Trp
            20                  25                  30

<210> SEQ ID NO 242
<211> LENGTH: 32
<212> TYPE: PRT
<213> ORGANISM: Artificial sequence
<220> FEATURE:
<223> OTHER INFORMATION: Variant NV1D3428
<220> FEATURE:
<221> NAME/KEY: MOD_RES
```

```
<222> LOCATION: (32)..(32)
<223> OTHER INFORMATION: COOH

<400> SEQUENCE: 242

Gly Pro Gln Cys Gln Lys Trp Met Gln Thr Cys Lys Arg Lys Glu Lys
1               5                   10                  15

Cys Cys Glu Gly Phe Val Cys Thr Leu Trp Cys Arg Lys Lys Leu Trp
            20                  25                  30

<210> SEQ ID NO 243
<211> LENGTH: 32
<212> TYPE: PRT
<213> ORGANISM: Artificial sequence
<220> FEATURE:
<223> OTHER INFORMATION: Variant NV1D3430
<220> FEATURE:
<221> NAME/KEY: MOD_RES
<222> LOCATION: (32)..(32)
<223> OTHER INFORMATION: COOH

<400> SEQUENCE: 243

Gly Pro Gln Cys Gln Asp Trp Met Gln Thr Cys Asp Arg Glu Arg Lys
1               5                   10                  15

Cys Cys Lys Gly Phe Val Cys Thr Leu Trp Cys Arg Lys Lys Leu Trp
            20                  25                  30

<210> SEQ ID NO 244
<211> LENGTH: 32
<212> TYPE: PRT
<213> ORGANISM: Artificial sequence
<220> FEATURE:
<223> OTHER INFORMATION: Variant NV1D3431
<220> FEATURE:
<221> NAME/KEY: MOD_RES
<222> LOCATION: (32)..(32)
<223> OTHER INFORMATION: COOH

<400> SEQUENCE: 244

Gly Pro Gln Cys Gln Glu Trp Met Gln Thr Cys Asp Arg Glu Arg Lys
1               5                   10                  15

Cys Cys Lys Gly Phe Val Cys Thr Leu Trp Cys Arg Lys Lys Leu Trp
            20                  25                  30

<210> SEQ ID NO 245
<211> LENGTH: 32
<212> TYPE: PRT
<213> ORGANISM: Artificial sequence
<220> FEATURE:
<223> OTHER INFORMATION: Variant NV1D3432
<220> FEATURE:
<221> NAME/KEY: MOD_RES
<222> LOCATION: (32)..(32)
<223> OTHER INFORMATION: COOH

<400> SEQUENCE: 245

Gly Pro Gln Cys Gln Glu Trp Met Gln Thr Cys Asp Arg Glu Arg Lys
1               5                   10                  15

Cys Cys Arg Gly Phe Val Cys Thr Leu Trp Cys Arg Lys Lys Leu Trp
            20                  25                  30

<210> SEQ ID NO 246
<211> LENGTH: 32
<212> TYPE: PRT
<213> ORGANISM: Artificial sequence
<220> FEATURE:
<223> OTHER INFORMATION: Variant NV1D3439
<220> FEATURE:
```

```
<221> NAME/KEY: MOD_RES
<222> LOCATION: (32)..(32)
<223> OTHER INFORMATION: COOH

<400> SEQUENCE: 246

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Gly
            20                  25                  30

<210> SEQ ID NO 247
<211> LENGTH: 32
<212> TYPE: PRT
<213> ORGANISM: Artificial sequence
<220> FEATURE:
<223> OTHER INFORMATION: Variant NV1D3465
<220> FEATURE:
<221> NAME/KEY: MOD_RES
<222> LOCATION: (32)..(32)
<223> OTHER INFORMATION: COOH

<400> SEQUENCE: 247

Gly Pro Gln Cys Gln Lys Phe Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 248
<211> LENGTH: 32
<212> TYPE: PRT
<213> ORGANISM: Artificial sequence
<220> FEATURE:
<223> OTHER INFORMATION: Variant NV1D3466
<220> FEATURE:
<221> NAME/KEY: MOD_RES
<222> LOCATION: (32)..(32)
<223> OTHER INFORMATION: COOH

<400> SEQUENCE: 248

Gly Pro Gln Cys Gln Lys Trp Met Gln Thr Cys Asp Glu Glu Arg Lys
1               5                   10                  15

Cys Cys Glu Gly Phe Val Cys Thr Leu Trp Cys Arg Lys Lys Leu Trp
            20                  25                  30

<210> SEQ ID NO 249
<211> LENGTH: 32
<212> TYPE: PRT
<213> ORGANISM: Artificial sequence
<220> FEATURE:
<223> OTHER INFORMATION: Variant NV1D3467
<220> FEATURE:
<221> NAME/KEY: MOD_RES
<222> LOCATION: (32)..(32)
<223> OTHER INFORMATION: COOH

<400> SEQUENCE: 249

Gly Pro Gln Cys Gln Lys Trp Met Gln Thr Cys Asp Arg Glu Arg Lys
1               5                   10                  15

Cys Cys Gly Gly Phe Val Cys Thr Leu Trp Cys Arg Lys Lys Leu Trp
            20                  25                  30

<210> SEQ ID NO 250
<211> LENGTH: 32
<212> TYPE: PRT
<213> ORGANISM: Artificial sequence
<220> FEATURE:
<223> OTHER INFORMATION: Variant NV1D3470
```

```
<220> FEATURE:
<221> NAME/KEY: MOD_RES
<222> LOCATION: (32)..(32)
<223> OTHER INFORMATION: COOH

<400> SEQUENCE: 250

Gly Pro Gln Cys Gln Lys Trp Met Gln Thr Cys Asp Arg Glu Arg Lys
1               5                   10                  15
Cys Cys Glu Gly Leu Val Cys Thr Leu Trp Cys Arg Lys Lys Leu Trp
            20                  25                  30

<210> SEQ ID NO 251
<211> LENGTH: 44
<212> TYPE: PRT
<213> ORGANISM: Artificial sequence
<220> FEATURE:
<223> OTHER INFORMATION: Variant NV1D3510
<220> FEATURE:
<221> NAME/KEY: MOD_RES
<222> LOCATION: (44)..(44)
<223> OTHER INFORMATION: COOH

<400> SEQUENCE: 251

Gly Pro Gln Cys Gln Lys Trp Met Gln Thr Cys Asp Arg Glu Arg Lys
1               5                   10                  15
Cys Cys Glu Gly Phe Val Cys Thr Leu Trp Cys Arg Lys Lys Leu Trp
            20                  25                  30
Ala Pro Ala Pro Ala Ser Pro Gly Ala Arg Ala Phe
        35                  40

<210> SEQ ID NO 252
<211> LENGTH: 39
<212> TYPE: PRT
<213> ORGANISM: Artificial sequence
<220> FEATURE:
<223> OTHER INFORMATION: Variant NV1D3511
<220> FEATURE:
<221> NAME/KEY: MOD_RES
<222> LOCATION: (39)..(39)
<223> OTHER INFORMATION: COOH

<400> SEQUENCE: 252

Gly Pro Gln Cys Gln Lys Trp Met Gln Thr Cys Asp Arg Glu Arg Lys
1               5                   10                  15
Cys Cys Glu Gly Phe Val Cys Thr Leu Trp Cys Arg Lys Lys Leu Trp
            20                  25                  30
Ser Pro Gly Ala Arg Ala Phe
        35

<210> SEQ ID NO 253
<211> LENGTH: 49
<212> TYPE: PRT
<213> ORGANISM: Artificial sequence
<220> FEATURE:
<223> OTHER INFORMATION: Variant NV1D3512
<220> FEATURE:
<221> NAME/KEY: MOD_RES
<222> LOCATION: (49)..(49)
<223> OTHER INFORMATION: COOH

<400> SEQUENCE: 253

Gly Pro Gln Cys Gln Lys Trp Met Gln Thr Cys Asp Arg Glu Arg Lys
1               5                   10                  15
Cys Cys Glu Gly Phe Val Cys Thr Leu Trp Cys Arg Lys Lys Leu Trp
            20                  25                  30
```

Ala Pro Ala Pro Ala Pro Ala Pro Ala Pro Asp Gly Pro Trp Arg Lys
            35                  40                  45

Met

<210> SEQ ID NO 254
<211> LENGTH: 44
<212> TYPE: PRT
<213> ORGANISM: Artificial sequence
<220> FEATURE:
<223> OTHER INFORMATION: Variant NV1D3513
<220> FEATURE:
<221> NAME/KEY: MOD_RES
<222> LOCATION: (44)..(44)
<223> OTHER INFORMATION: COOH

<400> SEQUENCE: 254

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Ala Pro Ala Pro Ala Asp Gly Pro Trp Arg Lys Met
            35                  40

<210> SEQ ID NO 255
<211> LENGTH: 39
<212> TYPE: PRT
<213> ORGANISM: Artificial sequence
<220> FEATURE:
<223> OTHER INFORMATION: Variant NV1D3514
<220> FEATURE:
<221> NAME/KEY: MOD_RES
<222> LOCATION: (39)..(39)
<223> OTHER INFORMATION: COOH

<400> SEQUENCE: 255

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Asp Gly Pro Trp Arg Lys Met
            35

<210> SEQ ID NO 256
<211> LENGTH: 49
<212> TYPE: PRT
<213> ORGANISM: Artificial sequence
<220> FEATURE:
<223> OTHER INFORMATION: Variant NV1D3515
<220> FEATURE:
<221> NAME/KEY: MOD_RES
<222> LOCATION: (49)..(49)
<223> OTHER INFORMATION: COOH

<400> SEQUENCE: 256

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Ala Pro Ala Pro Ala Pro Ala Pro Ala Pro Phe Gly Gln Lys Ala Ser
            35                  40                  45

Ser

<210> SEQ ID NO 257
<211> LENGTH: 44

```
<212> TYPE: PRT
<213> ORGANISM: Artificial sequence
<220> FEATURE:
<223> OTHER INFORMATION: Variant NV1D3516
<220> FEATURE:
<221> NAME/KEY: MOD_RES
<222> LOCATION: (44)..(44)
<223> OTHER INFORMATION: COOH

<400> SEQUENCE: 257

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Ala Pro Ala Pro Ala Phe Gly Gln Lys Ala Ser Ser
        35                  40

<210> SEQ ID NO 258
<211> LENGTH: 39
<212> TYPE: PRT
<213> ORGANISM: Artificial sequence
<220> FEATURE:
<223> OTHER INFORMATION: Variant NV1D3517
<220> FEATURE:
<221> NAME/KEY: MOD_RES
<222> LOCATION: (39)..(39)
<223> OTHER INFORMATION: COOH

<400> SEQUENCE: 258

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Phe Gly Gln Lys Ala Ser Ser
        35

<210> SEQ ID NO 259
<211> LENGTH: 58
<212> TYPE: PRT
<213> ORGANISM: Artificial sequence
<220> FEATURE:
<223> OTHER INFORMATION: Variant NV1D3518
<220> FEATURE:
<221> NAME/KEY: MOD_RES
<222> LOCATION: (58)..(58)
<223> OTHER INFORMATION: COOH

<400> SEQUENCE: 259

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Ala Pro Ala Pro Ala Pro Ala Pro Ala Pro Gln Arg Phe Val Thr Gly
        35                  40                  45

His Phe Gly Gly Leu Tyr Pro Ala Asn Gly
    50                  55

<210> SEQ ID NO 260
<211> LENGTH: 53
<212> TYPE: PRT
<213> ORGANISM: Artificial sequence
<220> FEATURE:
<223> OTHER INFORMATION: Variant NV1D3519
<220> FEATURE:
<221> NAME/KEY: MOD_RES
<222> LOCATION: (53)..(53)
```

<223> OTHER INFORMATION: COOH

<400> SEQUENCE: 260

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Ala Pro Ala Pro Ala Gln Arg Phe Val Thr Gly His Phe Gly Gly Leu
        35                  40                  45

Tyr Pro Ala Asn Gly
    50

<210> SEQ ID NO 261
<211> LENGTH: 48
<212> TYPE: PRT
<213> ORGANISM: Artificial sequence
<220> FEATURE:
<223> OTHER INFORMATION: Variant NV1D3520
<220> FEATURE:
<221> NAME/KEY: MOD_RES
<222> LOCATION: (48)..(48)
<223> OTHER INFORMATION: COOH

<400> SEQUENCE: 261

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Gln Arg Phe Val Thr Gly His Phe Gly Gly Leu Tyr Pro Ala Asn Gly
        35                  40                  45

<210> SEQ ID NO 262
<211> LENGTH: 53
<212> TYPE: PRT
<213> ORGANISM: Artificial sequence
<220> FEATURE:
<223> OTHER INFORMATION: Variant NV1D3521
<220> FEATURE:
<221> NAME/KEY: MOD_RES
<222> LOCATION: (53)..(53)
<223> OTHER INFORMATION: COOH

<400> SEQUENCE: 262

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Ala Pro Ala Pro Ala Pro Ala Pro Ala Pro Arg Arg Arg Arg Arg
        35                  40                  45

Arg Arg Arg Arg Arg
    50

<210> SEQ ID NO 263
<211> LENGTH: 43
<212> TYPE: PRT
<213> ORGANISM: Artificial sequence
<220> FEATURE:
<223> OTHER INFORMATION: Variant NV1D3523
<220> FEATURE:
<221> NAME/KEY: MOD_RES
<222> LOCATION: (43)..(43)
<223> OTHER INFORMATION: COOH

<400> SEQUENCE: 263

```
Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Arg Arg Arg Arg Arg Arg Arg Arg Arg
        35                  40
```

<210> SEQ ID NO 264
<211> LENGTH: 53
<212> TYPE: PRT
<213> ORGANISM: Artificial sequence
<220> FEATURE:
<223> OTHER INFORMATION: Variant NV1D3524
<220> FEATURE:
<221> NAME/KEY: MOD_RES
<222> LOCATION: (53)..(53)
<223> OTHER INFORMATION: COOH

<400> SEQUENCE: 264

```
Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Ala Pro Ala Pro Ala Pro Ala Pro Ala Pro Tyr Gly Arg Lys Lys Arg
        35                  40                  45

Arg Gln Arg Arg Arg
    50
```

<210> SEQ ID NO 265
<211> LENGTH: 48
<212> TYPE: PRT
<213> ORGANISM: Artificial sequence
<220> FEATURE:
<223> OTHER INFORMATION: Variant NV1D3525
<220> FEATURE:
<221> NAME/KEY: MOD_RES
<222> LOCATION: (48)..(48)
<223> OTHER INFORMATION: COOH

<400> SEQUENCE: 265

```
Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Ala Pro Ala Pro Ala Tyr Gly Arg Lys Lys Arg Arg Gln Arg Arg Arg
        35                  40                  45
```

<210> SEQ ID NO 266
<211> LENGTH: 43
<212> TYPE: PRT
<213> ORGANISM: Artificial sequence
<220> FEATURE:
<223> OTHER INFORMATION: Variant NV1D3526
<220> FEATURE:
<221> NAME/KEY: MOD_RES
<222> LOCATION: (43)..(43)
<223> OTHER INFORMATION: COOH

<400> SEQUENCE: 266

```
Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Tyr Gly Arg Lys Lys Arg Arg Gln Arg Arg Arg
```

35          40

<210> SEQ ID NO 267
<211> LENGTH: 42
<212> TYPE: PRT
<213> ORGANISM: Artificial sequence
<220> FEATURE:
<223> OTHER INFORMATION: Variant NV1D3527
<220> FEATURE:
<221> NAME/KEY: MOD_RES
<222> LOCATION: (42)..(42)
<223> OTHER INFORMATION: COOH

<400> SEQUENCE: 267

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Ala Pro Ala Pro Ala Pro Ala Pro Ala Pro
        35                  40

<210> SEQ ID NO 268
<211> LENGTH: 37
<212> TYPE: PRT
<213> ORGANISM: Artificial sequence
<220> FEATURE:
<223> OTHER INFORMATION: Variant NV1D3528
<220> FEATURE:
<221> NAME/KEY: MOD_RES
<222> LOCATION: (37)..(37)
<223> OTHER INFORMATION: COOH

<400> SEQUENCE: 268

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Ala Pro Ala Pro Ala
        35

<210> SEQ ID NO 269
<211> LENGTH: 32
<212> TYPE: PRT
<213> ORGANISM: Artificial sequence
<220> FEATURE:
<223> OTHER INFORMATION: Variant NV1D3529
<220> FEATURE:
<221> NAME/KEY: MOD_RES
<222> LOCATION: (32)..(32)
<223> OTHER INFORMATION: COOH

<400> SEQUENCE: 269

Gly Pro Arg Cys Gln Lys Trp Met Gln Thr Cys Asp Ala Lys Arg Lys
1               5                   10                  15

Cys Cys Glu Gly Phe Val Cys Thr Leu Trp Cys Arg Lys Lys Leu Trp
            20                  25                  30

<210> SEQ ID NO 270
<211> LENGTH: 32
<212> TYPE: PRT
<213> ORGANISM: Artificial sequence
<220> FEATURE:
<223> OTHER INFORMATION: Variant NV1D3530
<220> FEATURE:
<221> NAME/KEY: MOD_RES
<222> LOCATION: (32)..(32)
<223> OTHER INFORMATION: COOH

<400> SEQUENCE: 270

Gly Pro Ser Cys Gln Lys Trp Met Gln Thr Cys Asp Ala Lys Arg Lys
1               5                   10                  15

Cys Cys Glu Gly Phe Val Cys Thr Leu Trp Cys Arg Lys Lys Leu Trp
            20                  25                  30

<210> SEQ ID NO 271
<211> LENGTH: 32
<212> TYPE: PRT
<213> ORGANISM: Artificial sequence
<220> FEATURE:
<223> OTHER INFORMATION: Variant NV1D3531
<220> FEATURE:
<221> NAME/KEY: MOD_RES
<222> LOCATION: (32)..(32)
<223> OTHER INFORMATION: COOH

<400> SEQUENCE: 271

Gly Pro Tyr Cys Gln Lys Trp Met Gln Thr Cys Asp Ala Lys Arg Lys
1               5                   10                  15

Cys Cys Glu Gly Phe Val Cys Thr Leu Trp Cys Arg Lys Lys Leu Trp
            20                  25                  30

<210> SEQ ID NO 272
<211> LENGTH: 32
<212> TYPE: PRT
<213> ORGANISM: Artificial sequence
<220> FEATURE:
<223> OTHER INFORMATION: Variant NV1D3532
<220> FEATURE:
<221> NAME/KEY: MOD_RES
<222> LOCATION: (32)..(32)
<223> OTHER INFORMATION: COOH

<400> SEQUENCE: 272

Gly Pro Ala Cys Gln Lys Trp Met Gln Thr Cys Asp Ala Lys Arg Lys
1               5                   10                  15

Cys Cys Glu Gly Phe Val Cys Thr Leu Trp Cys Arg Lys Lys Leu Trp
            20                  25                  30

<210> SEQ ID NO 273
<211> LENGTH: 32
<212> TYPE: PRT
<213> ORGANISM: Artificial sequence
<220> FEATURE:
<223> OTHER INFORMATION: Variant NV1D3533
<220> FEATURE:
<221> NAME/KEY: MOD_RES
<222> LOCATION: (32)..(32)
<223> OTHER INFORMATION: COOH

<400> SEQUENCE: 273

Gly Pro Gln Cys Gln Lys Trp Met Gln Thr Cys Asp Ala Lys Arg Lys
1               5                   10                  15

Cys Cys Glu Gly Phe Ser Cys Thr Leu Trp Cys Arg Lys Lys Leu Trp
            20                  25                  30

<210> SEQ ID NO 274
<211> LENGTH: 32
<212> TYPE: PRT
<213> ORGANISM: Artificial sequence
<220> FEATURE:
<223> OTHER INFORMATION: Variant NV1D3534
<220> FEATURE:
<221> NAME/KEY: MOD_RES
<222> LOCATION: (32)..(32)

<223> OTHER INFORMATION: COOH

<400> SEQUENCE: 274

Gly Pro Arg Cys Gln Lys Trp Met Gln Thr Cys Asp Ala Lys Arg Lys
1               5                   10                  15

Cys Cys Glu Gly Phe Ser Cys Thr Leu Trp Cys Arg Lys Lys Leu Trp
            20                  25                  30

<210> SEQ ID NO 275
<211> LENGTH: 32
<212> TYPE: PRT
<213> ORGANISM: Artificial sequence
<220> FEATURE:
<223> OTHER INFORMATION: Variant NV1D3535
<220> FEATURE:
<221> NAME/KEY: MOD_RES
<222> LOCATION: (32)..(32)
<223> OTHER INFORMATION: COOH

<400> SEQUENCE: 275

Gly Pro Ser Cys Gln Lys Trp Met Gln Thr Cys Asp Ala Lys Arg Lys
1               5                   10                  15

Cys Cys Glu Gly Phe Ser Cys Thr Leu Trp Cys Arg Lys Lys Leu Trp
            20                  25                  30

<210> SEQ ID NO 276
<211> LENGTH: 32
<212> TYPE: PRT
<213> ORGANISM: Artificial sequence
<220> FEATURE:
<223> OTHER INFORMATION: Variant NV1D3536
<220> FEATURE:
<221> NAME/KEY: MOD_RES
<222> LOCATION: (32)..(32)
<223> OTHER INFORMATION: COOH

<400> SEQUENCE: 276

Gly Pro Tyr Cys Gln Lys Trp Met Gln Thr Cys Asp Ala Lys Arg Lys
1               5                   10                  15

Cys Cys Glu Gly Phe Ser Cys Thr Leu Trp Cys Arg Lys Lys Leu Trp
            20                  25                  30

<210> SEQ ID NO 277
<211> LENGTH: 32
<212> TYPE: PRT
<213> ORGANISM: Artificial sequence
<220> FEATURE:
<223> OTHER INFORMATION: Variant NV1D3537
<220> FEATURE:
<221> NAME/KEY: MOD_RES
<222> LOCATION: (32)..(32)
<223> OTHER INFORMATION: COOH

<400> SEQUENCE: 277

Gly Pro Ala Cys Gln Lys Trp Met Gln Thr Cys Asp Ala Lys Arg Lys
1               5                   10                  15

Cys Cys Glu Gly Phe Ser Cys Thr Leu Trp Cys Arg Lys Lys Leu Trp
            20                  25                  30

<210> SEQ ID NO 278
<211> LENGTH: 32
<212> TYPE: PRT
<213> ORGANISM: Artificial sequence
<220> FEATURE:
<223> OTHER INFORMATION: Variant NV1D3538
<220> FEATURE:
<221> NAME/KEY: MOD_RES

```
<222> LOCATION: (32)..(32)
<223> OTHER INFORMATION: COOH

<400> SEQUENCE: 278

Gly Pro Arg Cys Gln Lys Trp Met Gln Thr Cys Asp Arg Asn Arg Lys
1               5                   10                  15

Cys Cys Glu Gly Phe Val Cys Thr Leu Trp Cys Arg Lys Lys Leu Trp
            20                  25                  30

<210> SEQ ID NO 279
<211> LENGTH: 32
<212> TYPE: PRT
<213> ORGANISM: Artificial sequence
<220> FEATURE:
<223> OTHER INFORMATION: Variant NV1D3539
<220> FEATURE:
<221> NAME/KEY: MOD_RES
<222> LOCATION: (32)..(32)
<223> OTHER INFORMATION: COOH

<400> SEQUENCE: 279

Gly Pro Ser Cys Gln Lys Trp Met Gln Thr Cys Asp Arg Asn Arg Lys
1               5                   10                  15

Cys Cys Glu Gly Phe Val Cys Thr Leu Trp Cys Arg Lys Lys Leu Trp
            20                  25                  30

<210> SEQ ID NO 280
<211> LENGTH: 32
<212> TYPE: PRT
<213> ORGANISM: Artificial sequence
<220> FEATURE:
<223> OTHER INFORMATION: Variant NV1D3540
<220> FEATURE:
<221> NAME/KEY: MOD_RES
<222> LOCATION: (32)..(32)
<223> OTHER INFORMATION: COOH

<400> SEQUENCE: 280

Gly Pro Tyr Cys Gln Lys Trp Met Gln Thr Cys Asp Arg Asn Arg Lys
1               5                   10                  15

Cys Cys Glu Gly Phe Val Cys Thr Leu Trp Cys Arg Lys Lys Leu Trp
            20                  25                  30

<210> SEQ ID NO 281
<211> LENGTH: 32
<212> TYPE: PRT
<213> ORGANISM: Artificial sequence
<220> FEATURE:
<223> OTHER INFORMATION: Variant NV1D3541
<220> FEATURE:
<221> NAME/KEY: MOD_RES
<222> LOCATION: (32)..(32)
<223> OTHER INFORMATION: COOH

<400> SEQUENCE: 281

Gly Pro Ala Cys Gln Lys Trp Met Gln Thr Cys Asp Arg Asn Arg Lys
1               5                   10                  15

Cys Cys Glu Gly Phe Val Cys Thr Leu Trp Cys Arg Lys Lys Leu Trp
            20                  25                  30

<210> SEQ ID NO 282
<211> LENGTH: 32
<212> TYPE: PRT
<213> ORGANISM: Artificial sequence
<220> FEATURE:
<223> OTHER INFORMATION: Variant NV1D3542
<220> FEATURE:
```

```
<221> NAME/KEY: MOD_RES
<222> LOCATION: (32)..(32)
<223> OTHER INFORMATION: COOH

<400> SEQUENCE: 282

Gly Pro Gln Cys Gln Lys Trp Met Gln Thr Cys Asp Arg Asn Arg Lys
1               5                   10                  15

Cys Cys Glu Gly Phe Ser Cys Thr Leu Trp Cys Arg Lys Lys Leu Trp
            20                  25                  30

<210> SEQ ID NO 283
<211> LENGTH: 32
<212> TYPE: PRT
<213> ORGANISM: Artificial sequence
<220> FEATURE:
<223> OTHER INFORMATION: Variant NV1D3543
<220> FEATURE:
<221> NAME/KEY: MOD_RES
<222> LOCATION: (32)..(32)
<223> OTHER INFORMATION: COOH

<400> SEQUENCE: 283

Gly Pro Arg Cys Gln Lys Trp Met Gln Thr Cys Asp Arg Asn Arg Lys
1               5                   10                  15

Cys Cys Glu Gly Phe Ser Cys Thr Leu Trp Cys Arg Lys Lys Leu Trp
            20                  25                  30

<210> SEQ ID NO 284
<211> LENGTH: 32
<212> TYPE: PRT
<213> ORGANISM: Artificial sequence
<220> FEATURE:
<223> OTHER INFORMATION: Variant NV1D3544
<220> FEATURE:
<221> NAME/KEY: MOD_RES
<222> LOCATION: (32)..(32)
<223> OTHER INFORMATION: COOH

<400> SEQUENCE: 284

Gly Pro Ser Cys Gln Lys Trp Met Gln Thr Cys Asp Arg Asn Arg Lys
1               5                   10                  15

Cys Cys Glu Gly Phe Ser Cys Thr Leu Trp Cys Arg Lys Lys Leu Trp
            20                  25                  30

<210> SEQ ID NO 285
<211> LENGTH: 32
<212> TYPE: PRT
<213> ORGANISM: Artificial sequence
<220> FEATURE:
<223> OTHER INFORMATION: Variant NV1D3545
<220> FEATURE:
<221> NAME/KEY: MOD_RES
<222> LOCATION: (32)..(32)
<223> OTHER INFORMATION: COOH

<400> SEQUENCE: 285

Gly Pro Tyr Cys Gln Lys Trp Met Gln Thr Cys Asp Arg Asn Arg Lys
1               5                   10                  15

Cys Cys Glu Gly Phe Ser Cys Thr Leu Trp Cys Arg Lys Lys Leu Trp
            20                  25                  30

<210> SEQ ID NO 286
<211> LENGTH: 32
<212> TYPE: PRT
<213> ORGANISM: Artificial sequence
<220> FEATURE:
<223> OTHER INFORMATION: Variant NV1D3546
```

<220> FEATURE:
<221> NAME/KEY: MOD_RES
<222> LOCATION: (32)..(32)
<223> OTHER INFORMATION: COOH

<400> SEQUENCE: 286

Gly Pro Ala Cys Gln Lys Trp Met Gln Thr Cys Asp Arg Asn Arg Lys
1               5                   10                  15
Cys Cys Glu Gly Phe Ser Cys Thr Leu Trp Cys Arg Lys Lys Leu Trp
            20                  25                  30

<210> SEQ ID NO 287
<211> LENGTH: 32
<212> TYPE: PRT
<213> ORGANISM: Artificial sequence
<220> FEATURE:
<223> OTHER INFORMATION: Variant NV1D3547
<220> FEATURE:
<221> NAME/KEY: MOD_RES
<222> LOCATION: (32)..(32)
<223> OTHER INFORMATION: COOH

<400> SEQUENCE: 287

Gly Pro Arg Cys Gln Lys Trp Met Gln Thr Cys Asp Arg Glu Arg Lys
1               5                   10                  15
Cys Cys Glu Gly Phe Val Cys Thr Leu Trp Cys Arg Lys Lys Leu Trp
            20                  25                  30

<210> SEQ ID NO 288
<211> LENGTH: 32
<212> TYPE: PRT
<213> ORGANISM: Artificial sequence
<220> FEATURE:
<223> OTHER INFORMATION: Variant NV1D3548
<220> FEATURE:
<221> NAME/KEY: MOD_RES
<222> LOCATION: (32)..(32)
<223> OTHER INFORMATION: COOH

<400> SEQUENCE: 288

Gly Pro Ser Cys Gln Lys Trp Met Gln Thr Cys Asp Arg Glu Arg Lys
1               5                   10                  15
Cys Cys Glu Gly Phe Val Cys Thr Leu Trp Cys Arg Lys Lys Leu Trp
            20                  25                  30

<210> SEQ ID NO 289
<211> LENGTH: 32
<212> TYPE: PRT
<213> ORGANISM: Artificial sequence
<220> FEATURE:
<223> OTHER INFORMATION: Variant NV1D3549
<220> FEATURE:
<221> NAME/KEY: MOD_RES
<222> LOCATION: (32)..(32)
<223> OTHER INFORMATION: COOH

<400> SEQUENCE: 289

Gly Pro Tyr Cys Gln Lys Trp Met Gln Thr Cys Asp Arg Glu Arg Lys
1               5                   10                  15
Cys Cys Glu Gly Phe Val Cys Thr Leu Trp Cys Arg Lys Lys Leu Trp
            20                  25                  30

<210> SEQ ID NO 290
<211> LENGTH: 32
<212> TYPE: PRT
<213> ORGANISM: Artificial sequence
<220> FEATURE:

```
<223> OTHER INFORMATION: Variant NV1D3550
<220> FEATURE:
<221> NAME/KEY: MOD_RES
<222> LOCATION: (32)..(32)
<223> OTHER INFORMATION: COOH

<400> SEQUENCE: 290

Gly Pro Ala Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

<210> SEQ ID NO 291
<211> LENGTH: 32
<212> TYPE: PRT
<213> ORGANISM: Artificial sequence
<220> FEATURE:
<223> OTHER INFORMATION: Variant NV1D3551
<220> FEATURE:
<221> NAME/KEY: MOD_RES
<222> LOCATION: (32)..(32)
<223> OTHER INFORMATION: COOH

<400> SEQUENCE: 291

Gly Pro Arg Cys Gln Lys Trp Met Gln Thr Cys Asp Arg Glu Arg Lys
1               5                   10                  15

Cys Cys Glu Gly Phe Ser Cys Thr Leu Trp Cys Arg Lys Lys Leu Trp
            20                  25                  30

<210> SEQ ID NO 292
<211> LENGTH: 32
<212> TYPE: PRT
<213> ORGANISM: Artificial sequence
<220> FEATURE:
<223> OTHER INFORMATION: Variant NV1D3552
<220> FEATURE:
<221> NAME/KEY: MOD_RES
<222> LOCATION: (32)..(32)
<223> OTHER INFORMATION: COOH

<400> SEQUENCE: 292

Gly Pro Ser Cys Gln Lys Trp Met Gln Thr Cys Asp Arg Glu Arg Lys
1               5                   10                  15

Cys Cys Glu Gly Phe Ser Cys Thr Leu Trp Cys Arg Lys Lys Leu Trp
            20                  25                  30

<210> SEQ ID NO 293
<211> LENGTH: 32
<212> TYPE: PRT
<213> ORGANISM: Artificial sequence
<220> FEATURE:
<223> OTHER INFORMATION: Variant NV1D3553
<220> FEATURE:
<221> NAME/KEY: MOD_RES
<222> LOCATION: (32)..(32)
<223> OTHER INFORMATION: COOH

<400> SEQUENCE: 293

Gly Pro Tyr Cys Gln Lys Trp Met Gln Thr Cys Asp Arg Glu Arg Lys
1               5                   10                  15

Cys Cys Glu Gly Phe Ser Cys Thr Leu Trp Cys Arg Lys Lys Leu Trp
            20                  25                  30

<210> SEQ ID NO 294
<211> LENGTH: 32
<212> TYPE: PRT
<213> ORGANISM: Artificial sequence
```

```
<220> FEATURE:
<223> OTHER INFORMATION: Variant NV1D3554
<220> FEATURE:
<221> NAME/KEY: MOD_RES
<222> LOCATION: (32)..(32)
<223> OTHER INFORMATION: COOH

<400> SEQUENCE: 294

Gly Pro Ala Cys Gln Lys Trp Met Gln Thr Cys Asp Arg Glu Arg Lys
1               5                   10                  15

Cys Cys Glu Gly Phe Ser Cys Thr Leu Trp Cys Arg Lys Lys Leu Trp
            20                  25                  30

<210> SEQ ID NO 295
<211> LENGTH: 32
<212> TYPE: PRT
<213> ORGANISM: Artificial sequence
<220> FEATURE:
<223> OTHER INFORMATION: Variant NV1D3555
<220> FEATURE:
<221> NAME/KEY: MOD_RES
<222> LOCATION: (32)..(32)
<223> OTHER INFORMATION: COOH

<400> SEQUENCE: 295

Gly Pro Arg Cys Gln Lys Trp Met Gln Thr Cys Asp Ala Glu Arg Lys
1               5                   10                  15

Cys Cys Glu Gly Phe Ser Cys Thr Leu Trp Cys Lys Lys Lys Leu Trp
            20                  25                  30

<210> SEQ ID NO 296
<211> LENGTH: 32
<212> TYPE: PRT
<213> ORGANISM: Artificial sequence
<220> FEATURE:
<223> OTHER INFORMATION: Variant NV1D3556
<220> FEATURE:
<221> NAME/KEY: MOD_RES
<222> LOCATION: (32)..(32)
<223> OTHER INFORMATION: COOH

<400> SEQUENCE: 296

Gly Pro Tyr Cys Gln Lys Trp Met Gln Thr Cys Asp Ala Glu Arg Lys
1               5                   10                  15

Cys Cys Glu Gly Phe Ser Cys Thr Leu Trp Cys Lys Lys Lys Leu Trp
            20                  25                  30

<210> SEQ ID NO 297
<211> LENGTH: 32
<212> TYPE: PRT
<213> ORGANISM: Artificial sequence
<220> FEATURE:
<223> OTHER INFORMATION: Variant NV1D3558
<220> FEATURE:
<221> NAME/KEY: MOD_RES
<222> LOCATION: (32)..(32)
<223> OTHER INFORMATION: COOH

<400> SEQUENCE: 297

Gly Pro Arg Cys Gln Lys Trp Met Gln Thr Cys Asp Ala Asn Arg Lys
1               5                   10                  15

Cys Cys Glu Gly Phe Ser Cys Thr Leu Trp Cys Lys Lys Lys Leu Trp
            20                  25                  30

<210> SEQ ID NO 298
<211> LENGTH: 32
<212> TYPE: PRT
```

```
<213> ORGANISM: Artificial sequence
<220> FEATURE:
<223> OTHER INFORMATION: Variant NV1D3559
<220> FEATURE:
<221> NAME/KEY: MOD_RES
<222> LOCATION: (32)..(32)
<223> OTHER INFORMATION: COOH

<400> SEQUENCE: 298

Gly Pro Ser Cys Gln Lys Trp Met Gln Thr Cys Asp Ala Asn Arg Lys
1               5                   10                  15

Cys Cys Glu Gly Phe Ser Cys Thr Leu Trp Cys Lys Lys Lys Leu Trp
            20                  25                  30

<210> SEQ ID NO 299
<211> LENGTH: 32
<212> TYPE: PRT
<213> ORGANISM: Artificial sequence
<220> FEATURE:
<223> OTHER INFORMATION: Variant NV1D3560
<220> FEATURE:
<221> NAME/KEY: MOD_RES
<222> LOCATION: (32)..(32)
<223> OTHER INFORMATION: COOH

<400> SEQUENCE: 299

Gly Pro Tyr Cys Gln Lys Trp Met Gln Thr Cys Asp Ala Asn Arg Lys
1               5                   10                  15

Cys Cys Glu Gly Phe Ser Cys Thr Leu Trp Cys Lys Lys Lys Leu Trp
            20                  25                  30

<210> SEQ ID NO 300
<211> LENGTH: 32
<212> TYPE: PRT
<213> ORGANISM: Artificial sequence
<220> FEATURE:
<223> OTHER INFORMATION: Variant NV1D3561
<220> FEATURE:
<221> NAME/KEY: MOD_RES
<222> LOCATION: (32)..(32)
<223> OTHER INFORMATION: COOH

<400> SEQUENCE: 300

Gly Pro Ala Cys Gln Lys Trp Met Gln Thr Cys Asp Ala Asn Arg Lys
1               5                   10                  15

Cys Cys Glu Gly Phe Ser Cys Thr Leu Trp Cys Lys Lys Lys Leu Trp
            20                  25                  30

<210> SEQ ID NO 301
<211> LENGTH: 32
<212> TYPE: PRT
<213> ORGANISM: Artificial sequence
<220> FEATURE:
<223> OTHER INFORMATION: variant NV1D3562
<220> FEATURE:
<221> NAME/KEY: MOD_RES
<222> LOCATION: (32)..(32)
<223> OTHER INFORMATION: COOH

<400> SEQUENCE: 301

Gly Pro Arg Cys Gln Lys Trp Met Gln Thr Cys Asp Ala Arg Arg Lys
1               5                   10                  15

Cys Cys Glu Gly Phe Ser Cys Thr Leu Trp Cys Lys Lys Lys Leu Trp
            20                  25                  30

<210> SEQ ID NO 302
<211> LENGTH: 32
```

```
<212> TYPE: PRT
<213> ORGANISM: Artificial sequence
<220> FEATURE:
<223> OTHER INFORMATION: Variant NV1D3563
<220> FEATURE:
<221> NAME/KEY: MOD_RES
<222> LOCATION: (32)..(32)
<223> OTHER INFORMATION: COOH

<400> SEQUENCE: 302

Gly Pro Ser Cys Gln Lys Trp Met Gln Thr Cys Asp Ala Arg Arg Lys
1               5                   10                  15

Cys Cys Glu Gly Phe Ser Cys Thr Leu Trp Cys Lys Lys Lys Leu Trp
            20                  25                  30

<210> SEQ ID NO 303
<211> LENGTH: 32
<212> TYPE: PRT
<213> ORGANISM: Artificial sequence
<220> FEATURE:
<223> OTHER INFORMATION: Variant NV1D3564
<220> FEATURE:
<221> NAME/KEY: MOD_RES
<222> LOCATION: (32)..(32)
<223> OTHER INFORMATION: COOH

<400> SEQUENCE: 303

Gly Pro Tyr Cys Gln Lys Trp Met Gln Thr Cys Asp Ala Arg Arg Lys
1               5                   10                  15

Cys Cys Glu Gly Phe Ser Cys Thr Leu Trp Cys Lys Lys Lys Leu Trp
            20                  25                  30

<210> SEQ ID NO 304
<211> LENGTH: 32
<212> TYPE: PRT
<213> ORGANISM: Artificial sequence
<220> FEATURE:
<223> OTHER INFORMATION: Variant NV1D3565
<220> FEATURE:
<221> NAME/KEY: MOD_RES
<222> LOCATION: (32)..(32)
<223> OTHER INFORMATION: COOH

<400> SEQUENCE: 304

Gly Pro Ala Cys Gln Lys Trp Met Gln Thr Cys Asp Ala Arg Arg Lys
1               5                   10                  15

Cys Cys Glu Gly Phe Ser Cys Thr Leu Trp Cys Lys Lys Lys Leu Trp
            20                  25                  30

<210> SEQ ID NO 305
<211> LENGTH: 32
<212> TYPE: PRT
<213> ORGANISM: Artificial sequence
<220> FEATURE:
<223> OTHER INFORMATION: Variant NV1D3566
<220> FEATURE:
<221> NAME/KEY: MOD_RES
<222> LOCATION: (32)..(32)
<223> OTHER INFORMATION: COOH

<400> SEQUENCE: 305

Gly Pro Arg Cys Gln Lys Trp Met Gln Thr Cys Asp Ala Glu Arg Lys
1               5                   10                  15

Cys Cys Glu Gly Phe Val Cys Thr Leu Trp Cys Lys Lys Lys Leu Trp
            20                  25                  30

<210> SEQ ID NO 306
```

```
<211> LENGTH: 32
<212> TYPE: PRT
<213> ORGANISM: Artificial sequence
<220> FEATURE:
<223> OTHER INFORMATION: Variant NV1D3568
<220> FEATURE:
<221> NAME/KEY: MOD_RES
<222> LOCATION: (32)..(32)
<223> OTHER INFORMATION: COOH

<400> SEQUENCE: 306

Gly Pro Ala Cys Gln Lys Trp Met Gln Thr Cys Asp Ala Glu Arg Lys
1               5                   10                  15

Cys Cys Glu Gly Phe Val Cys Thr Leu Trp Cys Lys Lys Lys Leu Trp
            20                  25                  30

<210> SEQ ID NO 307
<211> LENGTH: 32
<212> TYPE: PRT
<213> ORGANISM: Artificial sequence
<220> FEATURE:
<223> OTHER INFORMATION: Variant NV1D3569
<220> FEATURE:
<221> NAME/KEY: MOD_RES
<222> LOCATION: (32)..(32)
<223> OTHER INFORMATION: COOH

<400> SEQUENCE: 307

Gly Pro Arg Cys Gln Lys Trp Met Gln Thr Cys Asp Ala Arg Arg Lys
1               5                   10                  15

Cys Cys Glu Gly Phe Val Cys Thr Leu Trp Cys Lys Lys Lys Leu Trp
            20                  25                  30

<210> SEQ ID NO 308
<211> LENGTH: 32
<212> TYPE: PRT
<213> ORGANISM: Artificial sequence
<220> FEATURE:
<223> OTHER INFORMATION: Variant NV1D3570
<220> FEATURE:
<221> NAME/KEY: MOD_RES
<222> LOCATION: (32)..(32)
<223> OTHER INFORMATION: COOH

<400> SEQUENCE: 308

Gly Pro Ser Cys Gln Lys Trp Met Gln Thr Cys Asp Ala Arg Arg Lys
1               5                   10                  15

Cys Cys Glu Gly Phe Val Cys Thr Leu Trp Cys Lys Lys Lys Leu Trp
            20                  25                  30

<210> SEQ ID NO 309
<211> LENGTH: 32
<212> TYPE: PRT
<213> ORGANISM: Artificial sequence
<220> FEATURE:
<223> OTHER INFORMATION: Variant NV1D3571
<220> FEATURE:
<221> NAME/KEY: MOD_RES
<222> LOCATION: (32)..(32)
<223> OTHER INFORMATION: COOH

<400> SEQUENCE: 309

Gly Pro Tyr Cys Gln Lys Trp Met Gln Thr Cys Asp Ala Arg Arg Lys
1               5                   10                  15

Cys Cys Glu Gly Phe Val Cys Thr Leu Trp Cys Lys Lys Lys Leu Trp
            20                  25                  30
```

```
<210> SEQ ID NO 310
<211> LENGTH: 32
<212> TYPE: PRT
<213> ORGANISM: Artificial sequence
<220> FEATURE:
<223> OTHER INFORMATION: variant NV1D3572
<220> FEATURE:
<221> NAME/KEY: MOD_RES
<222> LOCATION: (32)..(32)
<223> OTHER INFORMATION: COOH

<400> SEQUENCE: 310
```

Gly Pro Ala Cys Gln Lys Trp Met Gln Thr Cys Asp Ala Arg Arg Lys
1               5                   10                  15

Cys Cys Glu Gly Phe Val Cys Thr Leu Trp Cys Lys Lys Lys Leu Trp
            20                  25                  30

```
<210> SEQ ID NO 311
<211> LENGTH: 32
<212> TYPE: PRT
<213> ORGANISM: Artificial sequence
<220> FEATURE:
<223> OTHER INFORMATION: Variant NV1D3573
<220> FEATURE:
<221> NAME/KEY: MOD_RES
<222> LOCATION: (32)..(32)
<223> OTHER INFORMATION: COOH

<400> SEQUENCE: 311
```

Gly Pro Arg Cys Gln Lys Trp Met Gln Thr Cys Asp Ala Asn Arg Lys
1               5                   10                  15

Cys Cys Glu Gly Phe Val Cys Thr Leu Trp Cys Lys Lys Lys Leu Trp
            20                  25                  30

```
<210> SEQ ID NO 312
<211> LENGTH: 32
<212> TYPE: PRT
<213> ORGANISM: Artificial sequence
<220> FEATURE:
<223> OTHER INFORMATION: Variant NV1D3574
<220> FEATURE:
<221> NAME/KEY: MOD_RES
<222> LOCATION: (32)..(32)
<223> OTHER INFORMATION: COOH

<400> SEQUENCE: 312
```

Gly Pro Ser Cys Gln Lys Trp Met Gln Thr Cys Asp Ala Asn Arg Lys
1               5                   10                  15

Cys Cys Glu Gly Phe Val Cys Thr Leu Trp Cys Lys Lys Lys Leu Trp
            20                  25                  30

```
<210> SEQ ID NO 313
<211> LENGTH: 32
<212> TYPE: PRT
<213> ORGANISM: Artificial sequence
<220> FEATURE:
<223> OTHER INFORMATION: Variant NV1D3575
<220> FEATURE:
<221> NAME/KEY: MOD_RES
<222> LOCATION: (32)..(32)
<223> OTHER INFORMATION: COOH

<400> SEQUENCE: 313
```

Gly Pro Tyr Cys Gln Lys Trp Met Gln Thr Cys Asp Ala Asn Arg Lys
1               5                   10                  15

Cys Cys Glu Gly Phe Val Cys Thr Leu Trp Cys Lys Lys Lys Leu Trp
            20                  25                  30

<210> SEQ ID NO 314
<211> LENGTH: 32
<212> TYPE: PRT
<213> ORGANISM: Artificial sequence
<220> FEATURE:
<223> OTHER INFORMATION: Variant NV1D3576
<220> FEATURE:
<221> NAME/KEY: MOD_RES
<222> LOCATION: (32)..(32)
<223> OTHER INFORMATION: COOH

<400> SEQUENCE: 314

Gly Pro Ala Cys Gln Lys Trp Met Gln Thr Cys Asp Ala Asn Arg Lys
1               5                   10                  15

Cys Cys Glu Gly Phe Val Cys Thr Leu Trp Cys Lys Lys Lys Leu Trp
            20                  25                  30

<210> SEQ ID NO 315
<211> LENGTH: 32
<212> TYPE: PRT
<213> ORGANISM: Artificial sequence
<220> FEATURE:
<223> OTHER INFORMATION: Variant NV1D3577
<220> FEATURE:
<221> NAME/KEY: MOD_RES
<222> LOCATION: (32)..(32)
<223> OTHER INFORMATION: COOH

<400> SEQUENCE: 315

Gly Pro Arg Cys Gln Lys Trp Met Gln Thr Cys Asp Ala Glu Arg Lys
1               5                   10                  15

Cys Cys Glu Gly Phe Ser Cys Arg Leu Trp Cys Lys Lys Lys Leu Trp
            20                  25                  30

<210> SEQ ID NO 316
<211> LENGTH: 32
<212> TYPE: PRT
<213> ORGANISM: Artificial sequence
<220> FEATURE:
<223> OTHER INFORMATION: Variant NV1D3578
<220> FEATURE:
<221> NAME/KEY: MOD_RES
<222> LOCATION: (32)..(32)
<223> OTHER INFORMATION: COOH

<400> SEQUENCE: 316

Gly Pro Tyr Cys Gln Lys Trp Met Gln Thr Cys Asp Ala Glu Arg Lys
1               5                   10                  15

Cys Cys Glu Gly Phe Ser Cys Arg Leu Trp Cys Lys Lys Lys Leu Trp
            20                  25                  30

<210> SEQ ID NO 317
<211> LENGTH: 32
<212> TYPE: PRT
<213> ORGANISM: Artificial sequence
<220> FEATURE:
<223> OTHER INFORMATION: Variant NV1D3579
<220> FEATURE:
<221> NAME/KEY: MOD_RES
<222> LOCATION: (32)..(32)
<223> OTHER INFORMATION: COOH

<400> SEQUENCE: 317

Gly Pro Ala Cys Gln Lys Trp Met Gln Thr Cys Asp Ala Glu Arg Lys
1               5                   10                  15

Cys Cys Glu Gly Phe Ser Cys Arg Leu Trp Cys Lys Lys Lys Leu Trp
            20                  25                  30

<210> SEQ ID NO 318
<211> LENGTH: 32
<212> TYPE: PRT
<213> ORGANISM: Artificial sequence
<220> FEATURE:
<223> OTHER INFORMATION: Variant NV1D3580
<220> FEATURE:
<221> NAME/KEY: MOD_RES
<222> LOCATION: (32)..(32)
<223> OTHER INFORMATION: COOH

<400> SEQUENCE: 318

Gly Pro Arg Cys Gln Lys Trp Met Gln Thr Cys Asp Ala Arg Arg Lys
1               5                   10                  15

Cys Cys Glu Gly Phe Ser Cys Arg Leu Trp Cys Lys Lys Lys Leu Trp
            20                  25                  30

<210> SEQ ID NO 319
<211> LENGTH: 32
<212> TYPE: PRT
<213> ORGANISM: Artificial sequence
<220> FEATURE:
<223> OTHER INFORMATION: Variant NV1D3581
<220> FEATURE:
<221> NAME/KEY: MOD_RES
<222> LOCATION: (32)..(32)
<223> OTHER INFORMATION: COOH

<400> SEQUENCE: 319

Gly Pro Ser Cys Gln Lys Trp Met Gln Thr Cys Asp Ala Arg Arg Lys
1               5                   10                  15

Cys Cys Glu Gly Phe Ser Cys Arg Leu Trp Cys Lys Lys Lys Leu Trp
            20                  25                  30

<210> SEQ ID NO 320
<211> LENGTH: 32
<212> TYPE: PRT
<213> ORGANISM: Artificial sequence
<220> FEATURE:
<223> OTHER INFORMATION: Variant NV1D3582
<220> FEATURE:
<221> NAME/KEY: MOD_RES
<222> LOCATION: (32)..(32)
<223> OTHER INFORMATION: COOH

<400> SEQUENCE: 320

Gly Pro Tyr Cys Gln Lys Trp Met Gln Thr Cys Asp Ala Arg Arg Lys
1               5                   10                  15

Cys Cys Glu Gly Phe Ser Cys Arg Leu Trp Cys Lys Lys Lys Leu Trp
            20                  25                  30

<210> SEQ ID NO 321
<211> LENGTH: 32
<212> TYPE: PRT
<213> ORGANISM: Artificial sequence
<220> FEATURE:
<223> OTHER INFORMATION: Variant NV1D3583
<220> FEATURE:
<221> NAME/KEY: MOD_RES
<222> LOCATION: (32)..(32)
<223> OTHER INFORMATION: COOH

<400> SEQUENCE: 321

Gly Pro Ala Cys Gln Lys Trp Met Gln Thr Cys Asp Ala Arg Arg Lys
1               5                   10                  15

Cys Cys Glu Gly Phe Ser Cys Arg Leu Trp Cys Lys Lys Lys Leu Trp

-continued

```
              20                  25                  30
```

<210> SEQ ID NO 322
<211> LENGTH: 32
<212> TYPE: PRT
<213> ORGANISM: Artificial sequence
<220> FEATURE:
<223> OTHER INFORMATION: Variant NV1D3584
<220> FEATURE:
<221> NAME/KEY: MOD_RES
<222> LOCATION: (32)..(32)
<223> OTHER INFORMATION: COOH

<400> SEQUENCE: 322

```
Gly Pro Arg Cys Gln Lys Trp Met Gln Thr Cys Asp Ala Asn Arg Lys
1               5                  10                  15

Cys Cys Glu Gly Phe Ser Cys Arg Leu Trp Cys Lys Lys Lys Leu Trp
            20                  25                  30
```

<210> SEQ ID NO 323
<211> LENGTH: 32
<212> TYPE: PRT
<213> ORGANISM: Artificial sequence
<220> FEATURE:
<223> OTHER INFORMATION: Variant NV1D3585
<220> FEATURE:
<221> NAME/KEY: MOD_RES
<222> LOCATION: (32)..(32)
<223> OTHER INFORMATION: COOH

<400> SEQUENCE: 323

```
Gly Pro Ser Cys Gln Lys Trp Met Gln Thr Cys Asp Ala Asn Arg Lys
1               5                  10                  15

Cys Cys Glu Gly Phe Ser Cys Arg Leu Trp Cys Lys Lys Lys Leu Trp
            20                  25                  30
```

<210> SEQ ID NO 324
<211> LENGTH: 32
<212> TYPE: PRT
<213> ORGANISM: Artificial sequence
<220> FEATURE:
<223> OTHER INFORMATION: Variant NV1D3586
<220> FEATURE:
<221> NAME/KEY: MOD_RES
<222> LOCATION: (32)..(32)
<223> OTHER INFORMATION: COOH

<400> SEQUENCE: 324

```
Gly Pro Tyr Cys Gln Lys Trp Met Gln Thr Cys Asp Ala Asn Arg Lys
1               5                  10                  15

Cys Cys Glu Gly Phe Ser Cys Arg Leu Trp Cys Lys Lys Lys Leu Trp
            20                  25                  30
```

<210> SEQ ID NO 325
<211> LENGTH: 32
<212> TYPE: PRT
<213> ORGANISM: Artificial sequence
<220> FEATURE:
<223> OTHER INFORMATION: Variant NV1D3586NH2
<220> FEATURE:
<221> NAME/KEY: MOD_RES
<222> LOCATION: (32)..(32)
<223> OTHER INFORMATION: NH2

<400> SEQUENCE: 325

```
Gly Pro Tyr Cys Gln Lys Trp Met Gln Thr Cys Asp Ala Asn Arg Lys
1               5                  10                  15
```

Cys Cys Glu Gly Phe Ser Cys Arg Leu Trp Cys Lys Lys Lys Leu Trp
            20                  25                  30

<210> SEQ ID NO 326
<211> LENGTH: 32
<212> TYPE: PRT
<213> ORGANISM: Artificial sequence
<220> FEATURE:
<223> OTHER INFORMATION: Variant NV1D3587
<220> FEATURE:
<221> NAME/KEY: MOD_RES
<222> LOCATION: (32)..(32)
<223> OTHER INFORMATION: COOH

<400> SEQUENCE: 326

Gly Pro Ala Cys Gln Lys Trp Met Gln Thr Cys Asp Ala Asn Arg Lys
1               5                   10                  15

Cys Cys Glu Gly Phe Ser Cys Arg Leu Trp Cys Lys Lys Lys Leu Trp
            20                  25                  30

<210> SEQ ID NO 327
<211> LENGTH: 48
<212> TYPE: PRT
<213> ORGANISM: Artificial sequence
<220> FEATURE:
<223> OTHER INFORMATION: Variant NV1D3772
<220> FEATURE:
<221> NAME/KEY: MOD_RES
<222> LOCATION: (48)..(48)
<223> OTHER INFORMATION: COOH

<400> SEQUENCE: 327

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Ser His Ser Asn Thr Gln Thr Leu Ala Lys Ala Pro Glu His Thr Gly
            35                  40                  45

<210> SEQ ID NO 328
<211> LENGTH: 68
<212> TYPE: PRT
<213> ORGANISM: Artificial sequence
<220> FEATURE:
<223> OTHER INFORMATION: Variant NV1D3774
<220> FEATURE:
<221> NAME/KEY: MOD_RES
<222> LOCATION: (68)..(68)
<223> OTHER INFORMATION: COOH

<400> SEQUENCE: 328

Gly Pro Ser His Ser Asn Thr Gln Thr Leu Ala Lys Ala Pro Glu His
1               5                   10                  15

Thr Gly Ala Pro Ala Pro Ala Pro Ala Pro Ala Pro Ala Pro Ala Pro
            20                  25                  30

Ala Pro Ala Pro Ala Pro Gln Cys Gln Lys Trp Met Gln Thr Cys Asp
            35                  40                  45

Arg Glu Arg Lys Cys Cys Glu Gly Phe Val Cys Thr Leu Trp Cys Arg
    50                  55                  60

Lys Lys Leu Trp
65

<210> SEQ ID NO 329
<211> LENGTH: 58
<212> TYPE: PRT

<213> ORGANISM: Artificial sequence
<220> FEATURE:
<223> OTHER INFORMATION: Variant NV1D3775
<220> FEATURE:
<221> NAME/KEY: MOD_RES
<222> LOCATION: (58)..(58)
<223> OTHER INFORMATION: COOH

<400> SEQUENCE: 329

Gly Pro Ser His Ser Asn Thr Gln Thr Leu Ala Lys Ala Pro Glu His
1               5                   10                  15

Thr Gly Ala Pro Ala Pro Ala Pro Ala Pro Gln Cys Gln Lys
            20                  25                  30

Trp Met Gln Thr Cys Asp Arg Glu Arg Lys Cys Cys Gly Phe Val
            35                  40                  45

Cys Thr Leu Trp Cys Arg Lys Lys Leu Trp
        50                  55

<210> SEQ ID NO 330
<211> LENGTH: 48
<212> TYPE: PRT
<213> ORGANISM: Artificial sequence
<220> FEATURE:
<223> OTHER INFORMATION: Variant NV1D3777
<220> FEATURE:
<221> NAME/KEY: MOD_RES
<222> LOCATION: (48)..(48)
<223> OTHER INFORMATION: COOH

<400> SEQUENCE: 330

Gly Pro Ser His Ser Asn Thr Gln Thr Leu Ala Lys Ala Pro Glu His
1               5                   10                  15

Thr Gly Gln Cys Gln Lys Trp Met Gln Thr Cys Asp Arg Glu Arg Lys
            20                  25                  30

Cys Cys Glu Gly Phe Val Cys Thr Leu Trp Cys Arg Lys Lys Leu Trp
            35                  40                  45

<210> SEQ ID NO 331
<211> LENGTH: 32
<212> TYPE: PRT
<213> ORGANISM: Artificial sequence
<220> FEATURE:
<223> OTHER INFORMATION: Variant NV1D3782
<220> FEATURE:
<221> NAME/KEY: MOD_RES
<222> LOCATION: (32)..(32)
<223> OTHER INFORMATION: COOH

<400> SEQUENCE: 331

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Ala Trp
            20                  25                  30

<210> SEQ ID NO 332
<211> LENGTH: 37
<212> TYPE: PRT
<213> ORGANISM: Artificial sequence
<220> FEATURE:
<223> OTHER INFORMATION: Variant NV1D3788
<220> FEATURE:
<221> NAME/KEY: MOD_RES
<222> LOCATION: (37)..(37)
<223> OTHER INFORMATION: COOH

<400> SEQUENCE: 332

Gly Pro Ala Ala Ala Ala Gln Cys Gln Lys Trp Met Gln Thr Cys
1               5                   10                  15

Asp Arg Glu Arg Lys Cys Cys Glu Gly Phe Val Cys Thr Leu Trp Cys
            20                  25                  30

Arg Lys Lys Leu Trp
        35

<210> SEQ ID NO 333
<211> LENGTH: 37
<212> TYPE: PRT
<213> ORGANISM: Artificial sequence
<220> FEATURE:
<223> OTHER INFORMATION: Variant NV1D3789
<220> FEATURE:
<221> NAME/KEY: MOD_RES
<222> LOCATION: (37)..(37)
<223> OTHER INFORMATION: COOH

<400> SEQUENCE: 333

Gly Pro Ala Pro Ala Pro Ala Gln Cys Gln Lys Trp Met Gln Thr Cys
1               5                   10                  15

Asp Arg Glu Arg Lys Cys Cys Glu Gly Phe Val Cys Thr Leu Trp Cys
            20                  25                  30

Arg Lys Lys Leu Trp
        35

<210> SEQ ID NO 334
<211> LENGTH: 37
<212> TYPE: PRT
<213> ORGANISM: Artificial sequence
<220> FEATURE:
<223> OTHER INFORMATION: Variant NV1D3791
<220> FEATURE:
<221> NAME/KEY: MOD_RES
<222> LOCATION: (37)..(37)
<223> OTHER INFORMATION: COOH

<400> SEQUENCE: 334

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Ala Ala Ala Ala Ala
        35

<210> SEQ ID NO 335
<211> LENGTH: 37
<212> TYPE: PRT
<213> ORGANISM: Artificial sequence
<220> FEATURE:
<223> OTHER INFORMATION: Variant NV1D3792
<220> FEATURE:
<221> NAME/KEY: MOD_RES
<222> LOCATION: (37)..(37)
<223> OTHER INFORMATION: COOH

<400> SEQUENCE: 335

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Gly Gly Gly Gly Gly
        35

-continued

```
<210> SEQ ID NO 336
<211> LENGTH: 74
<212> TYPE: PRT
<213> ORGANISM: Artificial sequence
<220> FEATURE:
<223> OTHER INFORMATION: Variant NV1D3793
<220> FEATURE:
<221> NAME/KEY: MOD_RES
<222> LOCATION: (74)..(74)
<223> OTHER INFORMATION: COOH

<400> SEQUENCE: 336

Gly Pro Cys Cys Asn Cys Ser Ser Lys Trp Cys Arg Asp His Ser Arg
1               5                   10                  15

Cys Cys Gly Arg Gly Ser Ala Pro Ala Pro Ala Pro Ala Pro Ala Pro
            20                  25                  30

Ala Pro Ala Pro Ala Pro Ala Pro Gly Ser Gln Cys Gln Lys
        35                  40                  45

Trp Met Gln Thr Cys Asp Arg Glu Arg Lys Cys Cys Glu Gly Phe Val
        50                  55                  60

Cys Thr Leu Trp Cys Arg Lys Lys Leu Trp
65                  70

<210> SEQ ID NO 337
<211> LENGTH: 72
<212> TYPE: PRT
<213> ORGANISM: Artificial sequence
<220> FEATURE:
<223> OTHER INFORMATION: Variant NV1D3795
<220> FEATURE:
<221> NAME/KEY: MOD_RES
<222> LOCATION: (72)..(72)
<223> OTHER INFORMATION: COOH

<400> SEQUENCE: 337

Gly Pro Cys Cys Asn Cys Ser Ser Lys Trp Cys Arg Asp His Ser Arg
1               5                   10                  15

Cys Cys Gly Ser Ala Pro Ala Pro Ala Pro Ala Pro Ala Pro Ala Pro
            20                  25                  30

Ala Pro Ala Pro Ala Pro Gly Ser Gln Cys Gln Lys Trp Met
        35                  40                  45

Gln Thr Cys Asp Arg Glu Arg Lys Cys Cys Glu Gly Phe Val Cys Thr
        50                  55                  60

Leu Trp Cys Arg Lys Lys Leu Trp
65                  70

<210> SEQ ID NO 338
<211> LENGTH: 62
<212> TYPE: PRT
<213> ORGANISM: Artificial sequence
<220> FEATURE:
<223> OTHER INFORMATION: Variant NV1D3796
<220> FEATURE:
<221> NAME/KEY: MOD_RES
<222> LOCATION: (62)..(62)
<223> OTHER INFORMATION: COOH

<400> SEQUENCE: 338

Gly Pro Cys Cys Asn Cys Ser Ser Lys Trp Cys Arg Asp His Ser Arg
1               5                   10                  15

Cys Cys Gly Ser Ala Pro Ala Pro Ala Pro Ala Pro Ala Pro Gly Ser
            20                  25                  30

Gln Cys Gln Lys Trp Met Gln Thr Cys Asp Arg Glu Arg Lys Cys Cys
        35                  40                  45
```

Glu Gly Phe Val Cys Thr Leu Trp Cys Arg Lys Lys Leu Trp
    50                  55                  60

<210> SEQ ID NO 339
<211> LENGTH: 72
<212> TYPE: PRT
<213> ORGANISM: Artificial sequence
<220> FEATURE:
<223> OTHER INFORMATION: Variant NV1D3797
<220> FEATURE:
<221> NAME/KEY: MOD_RES
<222> LOCATION: (72)..(72)
<223> OTHER INFORMATION: COOH

<400> SEQUENCE: 339

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Gly Ser Ala Pro Ala Pro Ala Pro Ala Pro Ala Pro Ala Pro Ala Pro
        35                  40                  45

Ala Pro Ala Pro Ala Pro Gly Ser Cys Cys Asn Cys Ser Ser Lys Trp
    50                  55                  60

Cys Arg Asp His Ser Arg Cys Cys
65                  70

<210> SEQ ID NO 340
<211> LENGTH: 74
<212> TYPE: PRT
<213> ORGANISM: Artificial sequence
<220> FEATURE:
<223> OTHER INFORMATION: Variant NV1D3798
<220> FEATURE:
<221> NAME/KEY: MOD_RES
<222> LOCATION: (74)..(74)
<223> OTHER INFORMATION: COOH

<400> SEQUENCE: 340

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Gly Ser Ala Pro Ala Pro Ala Pro Ala Pro Ala Pro Ala Pro Ala Pro
        35                  40                  45

Ala Pro Ala Pro Ala Pro Gly Ser Cys Cys Asn Cys Ser Ser Lys Trp
    50                  55                  60

Cys Arg Asp His Ser Arg Cys Cys Gly Arg
65                  70

<210> SEQ ID NO 341
<211> LENGTH: 62
<212> TYPE: PRT
<213> ORGANISM: Artificial sequence
<220> FEATURE:
<223> OTHER INFORMATION: Variant NV1D3799
<220> FEATURE:
<221> NAME/KEY: MOD_RES
<222> LOCATION: (62)..(62)
<223> OTHER INFORMATION: COOH

<400> SEQUENCE: 341

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Gly Ser Ala Pro Ala Pro Ala Pro Ala Pro Gly Ser Cys Cys
            35                  40                  45

Asn Cys Ser Ser Lys Trp Cys Arg Asp His Ser Arg Cys Cys
 50                  55                  60

<210> SEQ ID NO 342
<211> LENGTH: 64
<212> TYPE: PRT
<213> ORGANISM: Artificial sequence
<220> FEATURE:
<223> OTHER INFORMATION: Variant NV1D3800
<220> FEATURE:
<221> NAME/KEY: MOD_RES
<222> LOCATION: (64)..(64)
<223> OTHER INFORMATION: COOH

<400> SEQUENCE: 342

Gly Pro Gln Cys Gln Lys Trp Met Gln Thr Cys Asp Arg Glu Arg Lys
 1               5                  10                  15

Cys Cys Glu Gly Phe Val Cys Thr Leu Trp Cys Arg Lys Lys Leu Trp
            20                  25                  30

Gly Ser Ala Pro Ala Pro Ala Pro Ala Pro Gly Ser Cys Cys
            35                  40                  45

Asn Cys Ser Ser Lys Trp Cys Arg Asp His Ser Arg Cys Cys Gly Arg
 50                  55                  60

<210> SEQ ID NO 343
<211> LENGTH: 49
<212> TYPE: PRT
<213> ORGANISM: Artificial sequence
<220> FEATURE:
<223> OTHER INFORMATION: Variant NV1D3801
<220> FEATURE:
<221> NAME/KEY: MOD_RES
<222> LOCATION: (49)..(49)
<223> OTHER INFORMATION: COOH

<400> SEQUENCE: 343

Gly Pro Ser Pro Gly Ala Arg Ala Phe Ala Pro Ala Pro Ala
 1               5                  10                  15

Pro Ala Pro Gln Cys Gln Lys Trp Met Gln Thr Cys Asp Arg Glu Arg
            20                  25                  30

Lys Cys Cys Glu Gly Phe Val Cys Thr Leu Trp Cys Arg Lys Lys Leu
            35                  40                  45

Trp

<210> SEQ ID NO 344
<211> LENGTH: 44
<212> TYPE: PRT
<213> ORGANISM: Artificial sequence
<220> FEATURE:
<223> OTHER INFORMATION: Variant NV1D3802
<220> FEATURE:
<221> NAME/KEY: MOD_RES
<222> LOCATION: (44)..(44)
<223> OTHER INFORMATION: COOH

<400> SEQUENCE: 344

Gly Pro Ser Pro Gly Ala Arg Ala Phe Ala Pro Ala Pro Ala Gln Cys
 1               5                  10                  15

Gln Lys Trp Met Gln Thr Cys Asp Arg Glu Arg Lys Cys Cys Glu Gly
            20                  25                  30

```
<210> SEQ ID NO 345
<211> LENGTH: 39
<212> TYPE: PRT
<213> ORGANISM: Artificial sequence
<220> FEATURE:
<223> OTHER INFORMATION: Variant NV1D3803
<220> FEATURE:
<221> NAME/KEY: MOD_RES
<222> LOCATION: (39)..(39)
<223> OTHER INFORMATION: COOH

<400> SEQUENCE: 345

Gly Pro Ser Pro Gly Ala Arg Ala Phe Gln Cys Gln Lys Trp Met Gln
1               5                   10                  15

Thr Cys Asp Arg Glu Arg Lys Cys Cys Glu Gly Phe Val Cys Thr Leu
            20                  25                  30

Trp Cys Arg Lys Lys Leu Trp
        35

<210> SEQ ID NO 346
<211> LENGTH: 49
<212> TYPE: PRT
<213> ORGANISM: Artificial sequence
<220> FEATURE:
<223> OTHER INFORMATION: Variant NV1D3804
<220> FEATURE:
<221> NAME/KEY: MOD_RES
<222> LOCATION: (49)..(49)
<223> OTHER INFORMATION: COOH

<400> SEQUENCE: 346

Gly Pro Asp Gly Pro Trp Arg Lys Met Ala Pro Ala Pro Ala Pro Ala
1               5                   10                  15

Pro Ala Pro Gln Cys Gln Lys Trp Met Gln Thr Cys Asp Arg Glu Arg
            20                  25                  30

Lys Cys Cys Glu Gly Phe Val Cys Thr Leu Trp Cys Arg Lys Lys Leu
        35                  40                  45

Trp

<210> SEQ ID NO 347
<211> LENGTH: 44
<212> TYPE: PRT
<213> ORGANISM: Artificial sequence
<220> FEATURE:
<223> OTHER INFORMATION: Variant NV1D3805
<220> FEATURE:
<221> NAME/KEY: MOD_RES
<222> LOCATION: (44)..(44)
<223> OTHER INFORMATION: COOH

<400> SEQUENCE: 347

Gly Pro Asp Gly Pro Trp Arg Lys Met Ala Pro Ala Pro Ala Gln Cys
1               5                   10                  15

Gln Lys Trp Met Gln Thr Cys Asp Arg Glu Arg Lys Cys Cys Glu Gly
            20                  25                  30

Phe Val Cys Thr Leu Trp Cys Arg Lys Lys Leu Trp
        35                  40

<210> SEQ ID NO 348
<211> LENGTH: 39
<212> TYPE: PRT
```

<213> ORGANISM: Artificial sequence
<220> FEATURE:
<223> OTHER INFORMATION: Variant NV1D3806
<220> FEATURE:
<221> NAME/KEY: MOD_RES
<222> LOCATION: (39)..(39)
<223> OTHER INFORMATION: COOH

<400> SEQUENCE: 348

Gly Pro Asp Gly Pro Trp Arg Lys Met Gln Cys Gln Lys Trp Met Gln
1               5                   10                  15

Thr Cys Asp Arg Glu Arg Lys Cys Cys Glu Gly Phe Val Cys Thr Leu
            20                  25                  30

Trp Cys Arg Lys Lys Leu Trp
        35

<210> SEQ ID NO 349
<211> LENGTH: 44
<212> TYPE: PRT
<213> ORGANISM: Artificial sequence
<220> FEATURE:
<223> OTHER INFORMATION: Variant NV1D3808
<220> FEATURE:
<221> NAME/KEY: MOD_RES
<222> LOCATION: (44)..(44)
<223> OTHER INFORMATION: COOH

<400> SEQUENCE: 349

Gly Pro Phe Gly Gln Lys Ala Ser Ser Ala Pro Ala Pro Ala Gln Cys
1               5                   10                  15

Gln Lys Trp Met Gln Thr Cys Asp Arg Glu Arg Lys Cys Cys Glu Gly
            20                  25                  30

Phe Val Cys Thr Leu Trp Cys Arg Lys Lys Leu Trp
        35                  40

<210> SEQ ID NO 350
<211> LENGTH: 39
<212> TYPE: PRT
<213> ORGANISM: Artificial sequence
<220> FEATURE:
<223> OTHER INFORMATION: Variant NV1D3809
<220> FEATURE:
<221> NAME/KEY: MOD_RES
<222> LOCATION: (39)..(39)
<223> OTHER INFORMATION: COOH

<400> SEQUENCE: 350

Gly Pro Phe Gly Gln Lys Ala Ser Ser Gln Cys Gln Lys Trp Met Gln
1               5                   10                  15

Thr Cys Asp Arg Glu Arg Lys Cys Cys Glu Gly Phe Val Cys Thr Leu
            20                  25                  30

Trp Cys Arg Lys Lys Leu Trp
        35

<210> SEQ ID NO 351
<211> LENGTH: 58
<212> TYPE: PRT
<213> ORGANISM: Artificial sequence
<220> FEATURE:
<223> OTHER INFORMATION: Variant NV1D3810
<220> FEATURE:
<221> NAME/KEY: MOD_RES
<222> LOCATION: (58)..(58)
<223> OTHER INFORMATION: COOH

<400> SEQUENCE: 351

```
Gly Pro Gln Arg Phe Val Thr Gly His Phe Gly Gly Leu Tyr Pro Ala
1               5                   10                  15

Asn Gly Ala Pro Ala Pro Ala Pro Ala Pro Gln Cys Gln Lys
            20              25                  30

Trp Met Gln Thr Cys Asp Arg Glu Arg Lys Cys Cys Glu Gly Phe Val
        35                  40                  45

Cys Thr Leu Trp Cys Arg Lys Lys Leu Trp
    50                  55
```

<210> SEQ ID NO 352
<211> LENGTH: 53
<212> TYPE: PRT
<213> ORGANISM: Artificial sequence
<220> FEATURE:
<223> OTHER INFORMATION: Variant NV1D3811
<220> FEATURE:
<221> NAME/KEY: MOD_RES
<222> LOCATION: (53)..(53)
<223> OTHER INFORMATION: COOH

<400> SEQUENCE: 352

```
Gly Pro Gln Arg Phe Val Thr Gly His Phe Gly Gly Leu Tyr Pro Ala
1               5                   10                  15

Asn Gly Ala Pro Ala Pro Ala Gln Cys Gln Lys Trp Met Gln Thr Cys
            20                  25                  30

Asp Arg Glu Arg Lys Cys Cys Glu Gly Phe Val Cys Thr Leu Trp Cys
        35                  40                  45

Arg Lys Lys Leu Trp
    50
```

<210> SEQ ID NO 353
<211> LENGTH: 48
<212> TYPE: PRT
<213> ORGANISM: Artificial sequence
<220> FEATURE:
<223> OTHER INFORMATION: Variant NV1D3812
<220> FEATURE:
<221> NAME/KEY: MOD_RES
<222> LOCATION: (48)..(48)
<223> OTHER INFORMATION: COOH

<400> SEQUENCE: 353

```
Gly Pro Gln Arg Phe Val Thr Gly His Phe Gly Gly Leu Tyr Pro Ala
1               5                   10                  15

Asn Gly Gln Cys Gln Lys Trp Met Gln Thr Cys Asp Arg Glu Arg Lys
            20                  25                  30

Cys Cys Glu Gly Phe Val Cys Thr Leu Trp Cys Arg Lys Lys Leu Trp
        35                  40                  45
```

<210> SEQ ID NO 354
<211> LENGTH: 53
<212> TYPE: PRT
<213> ORGANISM: Artificial sequence
<220> FEATURE:
<223> OTHER INFORMATION: Variant NV1D3813
<220> FEATURE:
<221> NAME/KEY: MOD_RES
<222> LOCATION: (53)..(53)
<223> OTHER INFORMATION: COOH

<400> SEQUENCE: 354

```
Gly Pro Arg Arg Arg Arg Arg Arg Arg Arg Arg Ala Pro Ala
1               5                   10                  15

Pro Ala Pro Ala Pro Ala Pro Gln Cys Gln Lys Trp Met Gln Thr Cys
```

-continued

```
                    20                  25                  30
Asp Arg Glu Arg Lys Cys Cys Glu Gly Phe Val Cys Thr Leu Trp Cys
        35                  40                  45

Arg Lys Lys Leu Trp
        50
```

<210> SEQ ID NO 355
<211> LENGTH: 48
<212> TYPE: PRT
<213> ORGANISM: Artificial sequence
<220> FEATURE:
<223> OTHER INFORMATION: Variant NV1D3814
<220> FEATURE:
<221> NAME/KEY: MOD_RES
<222> LOCATION: (48)..(48)
<223> OTHER INFORMATION: COOH

<400> SEQUENCE: 355

```
Gly Pro Arg Arg Arg Arg Arg Arg Arg Arg Arg Arg Ala Pro Ala
1               5                   10                  15

Pro Ala Gln Cys Gln Lys Trp Met Gln Thr Cys Asp Arg Glu Arg Lys
            20                  25                  30

Cys Cys Glu Gly Phe Val Cys Thr Leu Trp Cys Arg Lys Lys Leu Trp
        35                  40                  45
```

<210> SEQ ID NO 356
<211> LENGTH: 43
<212> TYPE: PRT
<213> ORGANISM: Artificial sequence
<220> FEATURE:
<223> OTHER INFORMATION: Variant NV1D3815
<220> FEATURE:
<221> NAME/KEY: MOD_RES
<222> LOCATION: (43)..(43)
<223> OTHER INFORMATION: COOH

<400> SEQUENCE: 356

```
Gly Pro Arg Arg Arg Arg Arg Arg Arg Arg Arg Gln Cys Gln
1               5                   10                  15

Lys Trp Met Gln Thr Cys Asp Arg Glu Arg Lys Cys Cys Glu Gly Phe
            20                  25                  30

Val Cys Thr Leu Trp Cys Arg Lys Lys Leu Trp
        35                  40
```

<210> SEQ ID NO 357
<211> LENGTH: 43
<212> TYPE: PRT
<213> ORGANISM: Artificial sequence
<220> FEATURE:
<223> OTHER INFORMATION: Variant NV1D3818
<220> FEATURE:
<221> NAME/KEY: MOD_RES
<222> LOCATION: (43)..(43)
<223> OTHER INFORMATION: COOH

<400> SEQUENCE: 357

```
Gly Pro Tyr Gly Arg Lys Lys Arg Arg Gln Arg Arg Gln Cys Gln
1               5                   10                  15

Lys Trp Met Gln Thr Cys Asp Arg Glu Arg Lys Cys Cys Glu Gly Phe
            20                  25                  30

Val Cys Thr Leu Trp Cys Arg Lys Lys Leu Trp
        35                  40
```

<210> SEQ ID NO 358

```
<211> LENGTH: 42
<212> TYPE: PRT
<213> ORGANISM: Artificial sequence
<220> FEATURE:
<223> OTHER INFORMATION: Variant NV1D3819
<220> FEATURE:
<221> NAME/KEY: MOD_RES
<222> LOCATION: (42)..(42)
<223> OTHER INFORMATION: COOH

<400> SEQUENCE: 358

Gly Pro Ala Pro Ala Pro Ala Pro Ala Pro Gln Cys Gln Lys
1               5                   10                  15

Trp Met Gln Thr Cys Asp Arg Glu Arg Lys Cys Cys Glu Gly Phe Val
            20                  25                  30

Cys Thr Leu Trp Cys Arg Lys Lys Leu Trp
        35                  40

<210> SEQ ID NO 359
<211> LENGTH: 107
<212> TYPE: PRT
<213> ORGANISM: Artificial sequence
<220> FEATURE:
<223> OTHER INFORMATION: Variant NV1D3822
<220> FEATURE:
<221> NAME/KEY: MOD_RES
<222> LOCATION: (107)..(107)
<223> OTHER INFORMATION: COOH

<400> SEQUENCE: 359

Gly Pro Gly Trp Cys Gly Asp Pro Gly Ala Thr Cys Gly Lys Leu Arg
1               5                   10                  15

Leu Tyr Cys Cys Ser Gly Phe Cys Asp Ser Tyr Thr Lys Thr Cys Lys
            20                  25                  30

Asp Lys Ser Ser Ala Gly Gly Gly Ser Ala Pro Ala Pro Ala Pro
        35                  40                  45

Ala Pro Ala Pro Ala Pro Ala Pro Ala Pro Ala Pro Ala Pro Ala Pro
    50                  55                  60

Ala Pro Ala Pro Ala Pro Ala Pro Gly Gly Gly Ser Gln Cys Gln
65                  70                  75                  80

Lys Trp Met Gln Thr Cys Asp Arg Glu Arg Lys Cys Cys Glu Gly Phe
                85                  90                  95

Val Cys Thr Leu Trp Cys Arg Lys Lys Leu Trp
            100                 105

<210> SEQ ID NO 360
<211> LENGTH: 107
<212> TYPE: PRT
<213> ORGANISM: Artificial sequence
<220> FEATURE:
<223> OTHER INFORMATION: Variant NV1D3823
<220> FEATURE:
<221> NAME/KEY: MOD_RES
<222> LOCATION: (107)..(107)
<223> OTHER INFORMATION: COOH

<400> SEQUENCE: 360

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Gly Gly Gly Gly Ser Ala Pro Ala Pro Ala Pro Ala Pro Ala Pro Ala
        35                  40                  45
```

```
Pro Ala Pro Ala Pro Ala Pro Ala Pro Ala Pro Ala
        50                  55                  60

Pro Ala Pro Gly Gly Gly Ser Gly Trp Cys Gly Asp Pro Gly Ala
65                  70                  75                  80

Thr Cys Gly Lys Leu Arg Leu Tyr Cys Cys Ser Gly Phe Cys Asp Ser
                85                  90                  95

Tyr Thr Lys Thr Cys Lys Asp Lys Ser Ser Ala
            100                 105
```

<210> SEQ ID NO 361
<211> LENGTH: 107
<212> TYPE: PRT
<213> ORGANISM: Artificial sequence
<220> FEATURE:
<223> OTHER INFORMATION: Variant NV1D3824
<220> FEATURE:
<221> NAME/KEY: MOD_RES
<222> LOCATION: (107)..(107)
<223> OTHER INFORMATION: COOH

<400> SEQUENCE: 361

```
Gly Pro Gly Trp Cys Gly Asp Pro Gly Ala Thr Cys Gly Lys Leu Arg
1               5                   10                  15

Leu Tyr Cys Cys Ser Gly Phe Cys Asp Ala Tyr Thr Lys Thr Cys Lys
            20                  25                  30

Asp Lys Ser Ser Ala Gly Gly Gly Ser Ala Pro Ala Pro Ala Pro
            35                  40                  45

Ala Pro Ala Pro Ala Pro Ala Pro Ala Pro Ala Pro Ala Pro
        50                  55                  60

Ala Pro Ala Pro Ala Pro Ala Pro Gly Gly Gly Ser Gln Cys Gln
65                  70                  75                  80

Lys Trp Met Gln Thr Cys Asp Arg Glu Arg Lys Cys Cys Glu Gly Phe
                85                  90                  95

Val Cys Thr Leu Trp Cys Arg Lys Lys Leu Trp
            100                 105
```

<210> SEQ ID NO 362
<211> LENGTH: 107
<212> TYPE: PRT
<213> ORGANISM: Artificial sequence
<220> FEATURE:
<223> OTHER INFORMATION: Variant NV1D3825
<220> FEATURE:
<221> NAME/KEY: MOD_RES
<222> LOCATION: (107)..(107)
<223> OTHER INFORMATION: COOH

<400> SEQUENCE: 362

```
Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Gly Gly Gly Gly Ser Ala Pro Ala Pro Ala Pro Ala Pro Ala
            35                  40                  45

Pro Ala Pro Ala Pro Ala Pro Ala Pro Ala Pro Ala Pro Ala
        50                  55                  60

Pro Ala Pro Gly Gly Gly Ser Gly Trp Cys Gly Asp Pro Gly Ala
65                  70                  75                  80

Thr Cys Gly Lys Leu Arg Leu Tyr Cys Cys Ser Gly Phe Cys Asp Ala
                85                  90                  95
```

Tyr Thr Lys Thr Cys Lys Asp Lys Ser Ser Ala
                100                 105

<210> SEQ ID NO 363
<211> LENGTH: 107
<212> TYPE: PRT
<213> ORGANISM: Artificial sequence
<220> FEATURE:
<223> OTHER INFORMATION: Variant NV1D3826
<220> FEATURE:
<221> NAME/KEY: MOD_RES
<222> LOCATION: (107)..(107)
<223> OTHER INFORMATION: COOH

<400> SEQUENCE: 363

Gly Pro Gly Trp Cys Gly Asp Pro Gly Ala Thr Cys Gly Lys Leu Arg
1               5                   10                  15

Leu Tyr Cys Cys Ser Gly Phe Cys Asp Cys Tyr Thr Lys Thr Cys Lys
            20                  25                  30

Asp Lys Ser Ser Ala Gly Gly Gly Ser Ala Pro Ala Pro Ala Pro Ala Pro
        35                  40                  45

Ala Pro Ala Pro Ala Pro Ala Pro Ala Pro Ala Pro Ala Pro
    50                  55                  60

Ala Pro Ala Pro Ala Pro Gly Gly Gly Ser Gln Cys Gln
65                  70                  75                  80

Lys Trp Met Gln Thr Cys Asp Arg Glu Arg Lys Cys Cys Glu Gly Phe
                85                  90                  95

Val Cys Thr Leu Trp Cys Arg Lys Lys Leu Trp
                100                 105

<210> SEQ ID NO 364
<211> LENGTH: 84
<212> TYPE: PRT
<213> ORGANISM: Artificial sequence
<220> FEATURE:
<223> OTHER INFORMATION: Variant NV1D3828
<220> FEATURE:
<221> NAME/KEY: MOD_RES
<222> LOCATION: (84)..(84)
<223> OTHER INFORMATION: COOH

<400> SEQUENCE: 364

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Gly Ser Gly Gly Gly Ser Ala Pro Ala Pro Ala Pro Ala Pro Ala
        35                  40                  45

Pro Ala Pro Ala Pro Ala Pro Ala Pro Gly Gly Gly Ser
    50                  55                  60

Gly Ser Cys Cys Asn Cys Ser Ser Lys Trp Cys Arg Asp His Ser Arg
65                  70                  75                  80

Cys Cys Gly Arg

<210> SEQ ID NO 365
<211> LENGTH: 82
<212> TYPE: PRT
<213> ORGANISM: Artificial sequence
<220> FEATURE:
<223> OTHER INFORMATION: Variant NV1D3829
<220> FEATURE:
<221> NAME/KEY: MOD_RES
<222> LOCATION: (82)..(82)

<223> OTHER INFORMATION: COOH

<400> SEQUENCE: 365

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Gly Ser Gly Gly Gly Ser Ala Pro Ala Pro Ala Pro Ala
        35                  40                  45

Pro Ala Pro Ala Pro Ala Pro Ala Pro Gly Gly Gly Ser
50                  55                  60

Gly Ser Cys Cys Asn Cys Ser Ser Lys Trp Cys Arg Asp His Ser Arg
65                  70                  75                  80

Cys Cys

<210> SEQ ID NO 366
<211> LENGTH: 84
<212> TYPE: PRT
<213> ORGANISM: Artificial sequence
<220> FEATURE:
<223> OTHER INFORMATION: Variant NV1D3830
<220> FEATURE:
<221> NAME/KEY: MOD_RES
<222> LOCATION: (84)..(84)
<223> OTHER INFORMATION: COOH

<400> SEQUENCE: 366

Gly Pro Cys Cys Asn Cys Ser Ser Lys Trp Cys Arg Asp His Ser Arg
1               5                   10                  15

Cys Cys Gly Arg Gly Ser Gly Gly Gly Ser Ala Pro Ala Pro Ala
            20                  25                  30

Pro Ala Pro Ala Pro Ala Pro Ala Pro Ala Pro Ala Pro Gly
        35                  40                  45

Gly Gly Ser Gly Ser Gln Cys Gln Lys Trp Met Gln Thr Cys Asp
50                  55                  60

Arg Glu Arg Lys Cys Cys Glu Gly Phe Val Cys Thr Leu Trp Cys Arg
65                  70                  75                  80

Lys Lys Leu Trp

<210> SEQ ID NO 367
<211> LENGTH: 61
<212> TYPE: PRT
<213> ORGANISM: Artificial sequence
<220> FEATURE:
<223> OTHER INFORMATION: Variant NV1D3832
<220> FEATURE:
<221> NAME/KEY: MOD_RES
<222> LOCATION: (61)..(61)
<223> OTHER INFORMATION: COOH

<400> SEQUENCE: 367

Gly Pro Cys Arg Thr Ile Gly Pro Ser Val Cys Ala Pro Ala Pro Ala
1               5                   10                  15

Pro Ala Pro Ala Pro Ala Pro Ala Pro Ala Pro Ala Pro Gln
            20                  25                  30

Cys Gln Lys Trp Met Gln Thr Cys Asp Arg Glu Arg Lys Cys Cys Glu
        35                  40                  45

Gly Phe Val Cys Thr Leu Trp Cys Arg Lys Lys Leu Trp
50                  55                  60

```
<210> SEQ ID NO 368
<211> LENGTH: 51
<212> TYPE: PRT
<213> ORGANISM: Artificial sequence
<220> FEATURE:
<223> OTHER INFORMATION: Variant NV1D3833
<220> FEATURE:
<221> NAME/KEY: MOD_RES
<222> LOCATION: (51)..(51)
<223> OTHER INFORMATION: COOH

<400> SEQUENCE: 368
```

Gly Pro Cys Arg Thr Ile Gly Pro Ser Val Cys Ala Pro Ala Pro Ala
1               5                   10                  15

Pro Ala Pro Ala Pro Gln Cys Gln Lys Trp Met Gln Thr Cys Asp Arg
            20                  25                  30

Glu Arg Lys Cys Cys Glu Gly Phe Val Cys Thr Leu Trp Cys Arg Lys
        35                  40                  45

Lys Leu Trp
    50

```
<210> SEQ ID NO 369
<211> LENGTH: 46
<212> TYPE: PRT
<213> ORGANISM: Artificial sequence
<220> FEATURE:
<223> OTHER INFORMATION: Variant NV1D3834
<220> FEATURE:
<221> NAME/KEY: MOD_RES
<222> LOCATION: (46)..(46)
<223> OTHER INFORMATION: COOH

<400> SEQUENCE: 369
```

Gly Pro Cys Arg Thr Ile Gly Pro Ser Val Cys Ala Pro Ala Pro Ala
1               5                   10                  15

Gln Cys Gln Lys Trp Met Gln Thr Cys Asp Arg Glu Arg Lys Cys Cys
            20                  25                  30

Glu Gly Phe Val Cys Thr Leu Trp Cys Arg Lys Lys Leu Trp
        35                  40                  45

```
<210> SEQ ID NO 370
<211> LENGTH: 41
<212> TYPE: PRT
<213> ORGANISM: Artificial sequence
<220> FEATURE:
<223> OTHER INFORMATION: Variant NV1D3835
<220> FEATURE:
<221> NAME/KEY: MOD_RES
<222> LOCATION: (41)..(41)
<223> OTHER INFORMATION: COOH

<400> SEQUENCE: 370
```

Gly Pro Cys Arg Thr Ile Gly Pro Ser Val Cys Gln Cys Gln Lys Trp
1               5                   10                  15

Met Gln Thr Cys Asp Arg Glu Arg Lys Cys Cys Glu Gly Phe Val Cys
            20                  25                  30

Thr Leu Trp Cys Arg Lys Lys Leu Trp
        35                  40

```
<210> SEQ ID NO 371
<211> LENGTH: 46
<212> TYPE: PRT
<213> ORGANISM: Artificial sequence
<220> FEATURE:
<223> OTHER INFORMATION: Variant NV1D3838
<220> FEATURE:
```

<221> NAME/KEY: MOD_RES
<222> LOCATION: (46)..(46)
<223> OTHER INFORMATION: COOH

<400> SEQUENCE: 371

Gly Pro Gln Cys Gln Lys Trp Met Gln Thr Cys Asp Arg Glu Arg Lys
1               5                   10                  15

Cys Cys Glu Gly Phe Val Cys Thr Leu Trp Cys Arg Lys Lys Leu Trp
            20                  25                  30

Ala Pro Ala Pro Ala Cys Arg Thr Ile Gly Pro Ser Val Cys
        35                  40                  45

<210> SEQ ID NO 372
<211> LENGTH: 7
<212> TYPE: PRT
<213> ORGANISM: Artificial sequence
<220> FEATURE:
<223> OTHER INFORMATION: N-terminal extension

<400> SEQUENCE: 372

Gly Pro Ala Ala Ala Ala Ala
1               5

<210> SEQ ID NO 373
<211> LENGTH: 7
<212> TYPE: PRT
<213> ORGANISM: Artificial sequence
<220> FEATURE:
<223> OTHER INFORMATION: N-terminal extension

<400> SEQUENCE: 373

Gly Pro Ala Pro Ala Pro Ala
1               5

<210> SEQ ID NO 374
<211> LENGTH: 6
<212> TYPE: PRT
<213> ORGANISM: Artificial sequence
<220> FEATURE:
<223> OTHER INFORMATION: N-terminal extension

<400> SEQUENCE: 374

Gly Gly Gly Gly Gly Gly
1               5

<210> SEQ ID NO 375
<211> LENGTH: 18
<212> TYPE: PRT
<213> ORGANISM: Artificial sequence
<220> FEATURE:
<223> OTHER INFORMATION: N-terminal extension

<400> SEQUENCE: 375

Gly Pro Cys Cys Asn Cys Ser Ser Lys Trp Cys Arg Asp His Ser Arg
1               5                   10                  15

Cys Cys

<210> SEQ ID NO 376
<211> LENGTH: 9
<212> TYPE: PRT
<213> ORGANISM: Artificial sequence
<220> FEATURE:
<223> OTHER INFORMATION: N-terminal extension

<400> SEQUENCE: 376

```
Gly Pro Ser Pro Gly Ala Arg Ala Phe
1               5
```

<210> SEQ ID NO 377
<211> LENGTH: 9
<212> TYPE: PRT
<213> ORGANISM: Artificial sequence
<220> FEATURE:
<223> OTHER INFORMATION: N-terminal extension

<400> SEQUENCE: 377

```
Gly Pro Asp Gly Pro Trp Arg Lys Met
1               5
```

<210> SEQ ID NO 378
<211> LENGTH: 9
<212> TYPE: PRT
<213> ORGANISM: Artificial sequence
<220> FEATURE:
<223> OTHER INFORMATION: N-terminal extension

<400> SEQUENCE: 378

```
Gly Pro Phe Gly Gln Lys Ala Ser Ser
1               5
```

<210> SEQ ID NO 379
<211> LENGTH: 11
<212> TYPE: PRT
<213> ORGANISM: Artificial sequence
<220> FEATURE:
<223> OTHER INFORMATION: N-terminal extension

<400> SEQUENCE: 379

```
Gly Pro Cys Arg Thr Ile Gly Pro Ser Val Cys
1               5                   10
```

<210> SEQ ID NO 380
<211> LENGTH: 18
<212> TYPE: PRT
<213> ORGANISM: Artificial sequence
<220> FEATURE:
<223> OTHER INFORMATION: N-terminal extension

<400> SEQUENCE: 380

```
Gly Pro Ser His Ser Asn Thr Gln Thr Leu Ala Lys Ala Pro Glu His
1               5                   10                  15

Thr Gly
```

<210> SEQ ID NO 381
<211> LENGTH: 18
<212> TYPE: PRT
<213> ORGANISM: Artificial sequence
<220> FEATURE:
<223> OTHER INFORMATION: N-terminal extension

<400> SEQUENCE: 381

```
Gly Pro Gln Arg Phe Val Thr Gly His Phe Gly Gly Leu Tyr Pro Ala
1               5                   10                  15

Asn Gly
```

<210> SEQ ID NO 382
<211> LENGTH: 37
<212> TYPE: PRT
<213> ORGANISM: Artificial sequence
<220> FEATURE:
<223> OTHER INFORMATION: N-terminal extension

<400> SEQUENCE: 382

Gly Pro Gly Trp Cys Gly Asp Pro Gly Ala Thr Cys Gly Lys Leu Arg
1               5                   10                  15

Leu Tyr Cys Cys Ser Gly Phe Cys Asp Ser Tyr Thr Lys Thr Cys Lys
            20                  25                  30

Asp Lys Ser Ser Ala
            35

<210> SEQ ID NO 383
<211> LENGTH: 10
<212> TYPE: PRT
<213> ORGANISM: Artificial sequence
<220> FEATURE:
<223> OTHER INFORMATION: N-terminal extension

<400> SEQUENCE: 383

Ala Pro Ala Pro Ala Pro Ala Pro Ala Pro
1               5                   10

<210> SEQ ID NO 384
<211> LENGTH: 13
<212> TYPE: PRT
<213> ORGANISM: Artificial sequence
<220> FEATURE:
<223> OTHER INFORMATION: N-terminal extension

<400> SEQUENCE: 384

Gly Pro Tyr Gly Arg Lys Lys Arg Arg Gln Arg Arg Arg
1               5                   10

<210> SEQ ID NO 385
<211> LENGTH: 13
<212> TYPE: PRT
<213> ORGANISM: Artificial sequence
<220> FEATURE:
<223> OTHER INFORMATION: N-terminal extension

<400> SEQUENCE: 385

Gly Pro Arg Arg Arg Arg Arg Arg Arg Arg Arg Arg Arg
1               5                   10

<210> SEQ ID NO 386
<211> LENGTH: 9
<212> TYPE: PRT
<213> ORGANISM: Artificial sequence
<220> FEATURE:
<223> OTHER INFORMATION: C-terminal extension

<400> SEQUENCE: 386

Cys Arg Thr Ile Gly Pro Ser Val Cys
1               5

<210> SEQ ID NO 387
<211> LENGTH: 11
<212> TYPE: PRT
<213> ORGANISM: Artificial sequence
<220> FEATURE:
<223> OTHER INFORMATION: C-terminal extension

<400> SEQUENCE: 387

Tyr Gly Arg Lys Lys Arg Arg Gln Arg Arg Arg
1               5                   10

<210> SEQ ID NO 388

```
<211> LENGTH: 7
<212> TYPE: PRT
<213> ORGANISM: Artificial sequence
<220> FEATURE:
<223> OTHER INFORMATION: C-terminal extension

<400> SEQUENCE: 388

Asp Gly Pro Trp Arg Lys Met
1               5

<210> SEQ ID NO 389
<211> LENGTH: 16
<212> TYPE: PRT
<213> ORGANISM: Artificial sequence
<220> FEATURE:
<223> OTHER INFORMATION: C-terminal extension

<400> SEQUENCE: 389

Cys Cys Asn Cys Ser Ser Lys Trp Cys Arg Asp His Ser Arg Cys Cys
1               5                   10                  15

<210> SEQ ID NO 390
<211> LENGTH: 11
<212> TYPE: PRT
<213> ORGANISM: Artificial sequence
<220> FEATURE:
<223> OTHER INFORMATION: C-terminal extension

<400> SEQUENCE: 390

Arg Arg Arg Arg Arg Arg Arg Arg Arg Arg Arg
1               5                   10

<210> SEQ ID NO 391
<211> LENGTH: 16
<212> TYPE: PRT
<213> ORGANISM: Artificial sequence
<220> FEATURE:
<223> OTHER INFORMATION: C-terminal extension

<400> SEQUENCE: 391

Ser His Ser Asn Thr Gln Thr Leu Ala Lys Ala Pro Glu His Thr Gly
1               5                   10                  15

<210> SEQ ID NO 392
<211> LENGTH: 5
<212> TYPE: PRT
<213> ORGANISM: Artificial sequence
<220> FEATURE:
<223> OTHER INFORMATION: C-terminal extension

<400> SEQUENCE: 392

Ala Pro Ala Pro Ala
1               5

<210> SEQ ID NO 393
<211> LENGTH: 5
<212> TYPE: PRT
<213> ORGANISM: Artificial sequence
<220> FEATURE:
<223> OTHER INFORMATION: C-terminal extension

<400> SEQUENCE: 393

Ala Ala Ala Ala Ala
1               5

<210> SEQ ID NO 394
<211> LENGTH: 7
```

```
<212> TYPE: PRT
<213> ORGANISM: Artificial sequence
<220> FEATURE:
<223> OTHER INFORMATION: C-terminal extension

<400> SEQUENCE: 394

Phe Gly Gln Lys Ala Ser Ser
1               5

<210> SEQ ID NO 395
<211> LENGTH: 16
<212> TYPE: PRT
<213> ORGANISM: Artificial sequence
<220> FEATURE:
<223> OTHER INFORMATION: C-terminal extension

<400> SEQUENCE: 395

Gln Arg Phe Val Thr Gly His Phe Gly Gly Leu Tyr Pro Ala Asn Gly
1               5                   10                  15

<210> SEQ ID NO 396
<211> LENGTH: 7
<212> TYPE: PRT
<213> ORGANISM: Artificial sequence
<220> FEATURE:
<223> OTHER INFORMATION: C-terminal extension

<400> SEQUENCE: 396

Ser Pro Gly Ala Arg Ala Phe
1               5

<210> SEQ ID NO 397
<211> LENGTH: 37
<212> TYPE: PRT
<213> ORGANISM: Artificial sequence
<220> FEATURE:
<223> OTHER INFORMATION: C-terminal extension

<400> SEQUENCE: 397

Gly Pro Gly Trp Cys Gly Asp Pro Gly Ala Thr Cys Gly Lys Leu Arg
1               5                   10                  15

Leu Tyr Cys Cys Ser Gly Phe Cys Asp Ala Tyr Thr Lys Thr Cys Lys
            20                  25                  30

Asp Lys Ser Ser Ala
        35

<210> SEQ ID NO 398
<211> LENGTH: 14
<212> TYPE: PRT
<213> ORGANISM: Artificial sequence
<220> FEATURE:
<223> OTHER INFORMATION: Linker

<400> SEQUENCE: 398

Gly Ser Ala Pro Ala Pro Ala Pro Ala Pro Ala Pro Gly Ser
1               5                   10

<210> SEQ ID NO 399
<211> LENGTH: 24
<212> TYPE: PRT
<213> ORGANISM: Artificial sequence
<220> FEATURE:
<223> OTHER INFORMATION: Linker

<400> SEQUENCE: 399

Gly Ser Ala Pro Ala Pro Ala Pro Ala Pro Ala Pro Ala Pro
```

```
1               5                   10                  15
Ala Pro Ala Pro Ala Pro Gly Ser
            20

<210> SEQ ID NO 400
<211> LENGTH: 40
<212> TYPE: PRT
<213> ORGANISM: Artificial sequence
<220> FEATURE:
<223> OTHER INFORMATION: Linker

<400> SEQUENCE: 400

Gly Gly Gly Gly Ser Ala Pro Ala Pro Ala Pro Ala Pro Ala Pro Ala
1               5                   10                  15

Pro Ala Pro Ala Pro Ala Pro Ala Pro Ala Pro Ala Pro Ala Pro Ala
            20                  25                  30

Pro Ala Pro Gly Gly Gly Gly Ser
        35                  40

<210> SEQ ID NO 401
<211> LENGTH: 34
<212> TYPE: PRT
<213> ORGANISM: Artificial sequence
<220> FEATURE:
<223> OTHER INFORMATION: Linker

<400> SEQUENCE: 401

Gly Ser Gly Gly Gly Gly Ser Ala Pro Ala Pro Ala Pro Ala Pro Ala
1               5                   10                  15

Pro Ala Pro Ala Pro Ala Pro Ala Pro Ala Pro Gly Gly Gly Gly Ser
            20                  25                  30

Gly Ser

<210> SEQ ID NO 402
<211> LENGTH: 20
<212> TYPE: PRT
<213> ORGANISM: Artificial sequence
<220> FEATURE:
<223> OTHER INFORMATION: Linker

<400> SEQUENCE: 402

Ala Pro Ala Pro Ala Pro Ala Pro Ala Pro Ala Pro Ala Pro Ala Pro
1               5                   10                  15

Ala Pro Ala Pro
            20

<210> SEQ ID NO 403
<211> LENGTH: 32
<212> TYPE: PRT
<213> ORGANISM: Artificial sequence
<220> FEATURE:
<223> OTHER INFORMATION: Genus protoxin-II sequence
<220> FEATURE:
<221> NAME/KEY: MISC_FEATURE
<222> LOCATION: (1)..(1)
<223> OTHER INFORMATION: Xaa is Gly, Pro, Ala or deleted
<220> FEATURE:
<221> NAME/KEY: MISC_FEATURE
<222> LOCATION: (2)..(2)
<223> OTHER INFORMATION: Xaa is Pro, Ala or deleted
<220> FEATURE:
<221> NAME/KEY: MISC_FEATURE
<222> LOCATION: (3)..(3)
<223> OTHER INFORMATION: Xaa is Ser, Qln, Ala, Arg or Tyr
<220> FEATURE:
<221> NAME/KEY: MISC_FEATURE

```
<222> LOCATION: (5)..(5)
<223> OTHER INFORMATION: Xaa is Gln, Arg, Lys, Ala or Ser
<220> FEATURE:
<221> NAME/KEY: MISC_FEATURE
<222> LOCATION: (6)..(6)
<223> OTHER INFORMATION: Xaa is  Lys, Ser, Gln or Arg
<220> FEATURE:
<221> NAME/KEY: MISC_FEATURE
<222> LOCATION: (8)..(8)
<223> OTHER INFORMATION: Xaa is  Met or Phe
<220> FEATURE:
<221> NAME/KEY: MISC_FEATURE
<222> LOCATION: (10)..(10)
<223> OTHER INFORMATION: Xaa is  Thr, Ser, Arg, Lys or Gln
<220> FEATURE:
<221> NAME/KEY: MISC_FEATURE
<222> LOCATION: (12)..(12)
<223> OTHER INFORMATION: Xaa is  Asp or Thr
<220> FEATURE:
<221> NAME/KEY: MISC_FEATURE
<222> LOCATION: (13)..(13)
<223> OTHER INFORMATION: Xaa is Ser, Ala or Arg
<220> FEATURE:
<221> NAME/KEY: MISC_FEATURE
<222> LOCATION: (14)..(14)
<223> OTHER INFORMATION: Xaa is Glu, Arg, Asn, Lys, Thr or Gln
<220> FEATURE:
<221> NAME/KEY: MISC_FEATURE
<222> LOCATION: (15)..(15)
<223> OTHER INFORMATION: Xaa is Arg or Lys
<220> FEATURE:
<221> NAME/KEY: MISC_FEATURE
<222> LOCATION: (16)..(16)
<223> OTHER INFORMATION: Xaa is Lys, Gln, Ser or Ala
<220> FEATURE:
<221> NAME/KEY: MISC_FEATURE
<222> LOCATION: (19)..(19)
<223> OTHER INFORMATION: Xaa is Glu, Gln or Asp
<220> FEATURE:
<221> NAME/KEY: MISC_FEATURE
<222> LOCATION: (20)..(20)
<223> OTHER INFORMATION: Xaa is Glu or Gln
<220> FEATURE:
<221> NAME/KEY: MISC_FEATURE
<222> LOCATION: (22)..(22)
<223> OTHER INFORMATION: Xaa is Val or Ser
<220> FEATURE:
<221> NAME/KEY: MISC_FEATURE
<222> LOCATION: (24)..(24)
<223> OTHER INFORMATION: Xaa is Arg or Thr
<220> FEATURE:
<221> NAME/KEY: MISC_FEATURE
<222> LOCATION: (28)..(28)
<223> OTHER INFORMATION: Xaa is Lys or Arg

<400> SEQUENCE: 403

Xaa Xaa Xaa Cys Xaa Xaa Trp Xaa Gln Xaa Cys Xaa Xaa Xaa Xaa Xaa
1               5                   10                  15

Cys Cys Xaa Xaa Phe Xaa Cys Xaa Leu Trp Cys Xaa Lys Lys Leu Trp
            20                  25                  30

<210> SEQ ID NO 404
<211> LENGTH: 32
<212> TYPE: PRT
<213> ORGANISM: Artificial sequence
<220> FEATURE:
<223> OTHER INFORMATION: Protoxin-II genus 2
<220> FEATURE:
<221> NAME/KEY: MISC_FEATURE
<222> LOCATION: (5)..(5)
<223> OTHER INFORMATION: Xaa is Gln, Arg, Lys, Ala or Ser
<220> FEATURE:
<221> NAME/KEY: MISC_FEATURE
<222> LOCATION: (6)..(6)
<223> OTHER INFORMATION: Xaa is Lys, Ser, Gln or Arg
<220> FEATURE:
```

<221> NAME/KEY: MISC_FEATURE
<222> LOCATION: (8)..(8)
<223> OTHER INFORMATION: Xaa is Met or Phe
<220> FEATURE:
<221> NAME/KEY: MISC_FEATURE
<222> LOCATION: (10)..(10)
<223> OTHER INFORMATION: Xaa is Thr, Ser, Arg, Lys or Qln
<220> FEATURE:
<221> NAME/KEY: MISC_FEATURE
<222> LOCATION: (12)..(12)
<223> OTHER INFORMATION: Xaa is Asp or Thr
<220> FEATURE:
<221> NAME/KEY: MISC_FEATURE
<222> LOCATION: (13)..(13)
<223> OTHER INFORMATION: Xaa is  Ser, Ala or Arg
<220> FEATURE:
<221> NAME/KEY: MISC_FEATURE
<222> LOCATION: (14)..(14)
<223> OTHER INFORMATION: Xaa is Glu, Arg, Asn, Lys, Thr or Qln
<220> FEATURE:
<221> NAME/KEY: MISC_FEATURE
<222> LOCATION: (15)..(15)
<223> OTHER INFORMATION: Xaa is Arg or Lys
<220> FEATURE:
<221> NAME/KEY: MISC_FEATURE
<222> LOCATION: (16)..(16)
<223> OTHER INFORMATION: Xaa is Lys, Qln, Ser or Ala
<220> FEATURE:
<221> NAME/KEY: MISC_FEATURE
<222> LOCATION: (19)..(19)
<223> OTHER INFORMATION: Xaa is Glu, Qln or Asp
<220> FEATURE:
<221> NAME/KEY: MISC_FEATURE
<222> LOCATION: (20)..(20)
<223> OTHER INFORMATION: Xaa is is Gly or Qln
<220> FEATURE:
<221> NAME/KEY: MISC_FEATURE
<222> LOCATION: (22)..(22)
<223> OTHER INFORMATION: Xaa is Val or Ser
<220> FEATURE:
<221> NAME/KEY: MISC_FEATURE
<222> LOCATION: (24)..(24)
<223> OTHER INFORMATION: Xaa is Arg or Thr
<220> FEATURE:
<221> NAME/KEY: MISC_FEATURE
<222> LOCATION: (28)..(28)
<223> OTHER INFORMATION: Xaa is Lys or Arg

<400> SEQUENCE: 404

Gly Pro Gln Cys Xaa Xaa Trp Xaa Gln Xaa Cys Xaa Xaa Xaa Xaa Xaa
1               5                   10                  15

Cys Cys Xaa Xaa Phe Xaa Cys Xaa Leu Trp Cys Xaa Lys Lys Leu Trp
            20                  25                  30

<210> SEQ ID NO 405
<211> LENGTH: 32
<212> TYPE: PRT
<213> ORGANISM: Artificial sequence
<220> FEATURE:
<223> OTHER INFORMATION: Protoxin-II genus 3
<220> FEATURE:
<221> NAME/KEY: MISC_FEATURE
<222> LOCATION: (3)..(3)
<223> OTHER INFORMATION: Xaa is Tyr, Qln, Ala, Ser or Arg
<220> FEATURE:
<221> NAME/KEY: MISC_FEATURE
<222> LOCATION: (10)..(10)
<223> OTHER INFORMATION: Xaa is Thr or Ser
<220> FEATURE:
<221> NAME/KEY: MISC_FEATURE
<222> LOCATION: (13)..(13)
<223> OTHER INFORMATION: Xaa is Ser, Arg or Ala
<220> FEATURE:
<221> NAME/KEY: MISC_FEATURE
<222> LOCATION: (14)..(14)
<223> OTHER INFORMATION: Xaa is Glu, Thr or Asn -continued

```
<220> FEATURE:
<221> NAME/KEY: MISC_FEATURE
<222> LOCATION: (19)..(19)
<223> OTHER INFORMATION: Xaa is Glu or Qln
<220> FEATURE:
<221> NAME/KEY: MISC_FEATURE
<222> LOCATION: (22)..(22)
<223> OTHER INFORMATION: Xaa is Val or Ser
<220> FEATURE:
<221> NAME/KEY: MISC_FEATURE
<222> LOCATION: (24)..(24)
<223> OTHER INFORMATION: Xaa is Arg or Thr
<220> FEATURE:
<221> NAME/KEY: MISC_FEATURE
<222> LOCATION: (28)..(28)
<223> OTHER INFORMATION: Xaa is Lys or Arg

<400> SEQUENCE: 405

Gly Pro Xaa Cys Gln Lys Trp Met Gln Xaa Cys Asp Xaa Xaa Arg Lys
1               5                   10                  15

Cys Cys Xaa Gly Phe Xaa Cys Xaa Leu Trp Cys Xaa Lys Lys Leu Trp
            20                  25                  30

<210> SEQ ID NO 406
<211> LENGTH: 32
<212> TYPE: PRT
<213> ORGANISM: Artificial sequence
<220> FEATURE:
<223> OTHER INFORMATION: Protoxin-II genus 4
<220> FEATURE:
<221> NAME/KEY: MISC_FEATURE
<222> LOCATION: (10)..(10)
<223> OTHER INFORMATION: Xaa is Thr or

```
Phe Thr Pro Glu Ser Leu Ala Asn Ile Glu Arg Arg Ile Ala Glu Ser
                 20                  25                  30

Lys Leu Lys Lys Pro Pro Lys Ala Asp Gly Ser His Arg Glu Asp Asp
             35                  40                  45

Glu Asp Ser Lys Pro Lys Pro Asn Ser Asp Leu Glu Ala Gly Lys Ser
 50                  55                  60

Leu Pro Phe Ile Tyr Gly Asp Ile Pro Gln Gly Leu Val Ala Val Pro
 65                  70                  75                  80

Leu Glu Asp Phe Asp Pro Tyr Tyr Leu Thr Gln Lys Thr Phe Val Val
                 85                  90                  95

Leu Asn Arg Gly Lys Thr Leu Phe Arg Phe Ser Ala Thr Pro Ala Leu
            100                 105                 110

Tyr Ile Leu Ser Pro Phe Asn Leu Ile Arg Arg Ile Ala Ile Lys Ile
            115                 120                 125

Leu Ile His Ser Val Phe Ser Met Ile Ile Met Cys Thr Ile Leu Thr
130                 135                 140

Asn Cys Val Phe Met Thr Phe Ser Asn Pro Pro Asp Trp Ser Lys Asn
145                 150                 155                 160

Val Glu Tyr Thr Phe Thr Gly Ile Tyr Thr Phe Glu Ser Leu Val Lys
                165                 170                 175

Ile Ile Ala Arg Gly Phe Cys Ile Asp Gly Phe Thr Phe Leu Arg Asp
            180                 185                 190

Pro Trp Asn Trp Leu Asp Phe Ser Val Ile Met Met Ala Tyr Ile Thr
            195                 200                 205

Glu Phe Val Asn Leu Gly Asn Val Ser Ala Leu Arg Thr Phe Arg Val
210                 215                 220

Leu Arg Ala Leu Lys Thr Ile Ser Val Ile Pro Gly Leu Lys Thr Ile
225                 230                 235                 240

Val Gly Ala Leu Ile Gln Ser Val Lys Lys Leu Ser Asp Val Met Ile
                245                 250                 255

Leu Thr Val Phe Cys Leu Ser Val Phe Ala Leu Ile Gly Leu Gln Leu
            260                 265                 270

Phe Met Gly Asn Leu Arg Asn Lys Cys Val Val Trp Pro Ile Asn Phe
            275                 280                 285

Asn Glu Ser Tyr Leu Glu Asn Gly Thr Lys Gly Phe Asp Trp Glu Glu
290                 295                 300

Tyr Ile Asn Asn Lys Thr Asn Phe Tyr Thr Val Pro Gly Met Leu Glu
305                 310                 315                 320

Pro Leu Leu Cys Gly Asn Ser Ser Asp Ala Gly Gln Cys Pro Glu Gly
                325                 330                 335

Tyr Gln Cys Met Lys Ala Gly Arg Asn Pro Asn Tyr Tyr Thr Ser
            340                 345                 350

Phe Asp Thr Phe Ser Trp Ala Phe Leu Ala Leu Phe Arg Leu Met Thr
            355                 360                 365

Gln Asp Tyr Trp Glu Asn Leu Tyr Gln Leu Thr Leu Arg Ala Ala Gly
            370                 375                 380

Lys Thr Tyr Met Ile Phe Phe Val Leu Val Ile Phe Val Gly Ser Phe
385                 390                 395                 400

Tyr Leu Val Asn Leu Ile Leu Ala Val Val Ala Met Ala Tyr Glu Glu
                405                 410                 415

Gln Asn Gln Ala Thr Leu Glu Glu Ala Glu Gln Lys Glu Ala Glu Phe
            420                 425                 430
```

```
Lys Ala Met Leu Glu Gln Leu Lys Gln Gln Glu Ala Gln Ala
            435                 440                 445
Ala Ala Met Ala Thr Ser Ala Gly Thr Val Ser Glu Asp Ala Ile Glu
450                 455                 460
Glu Glu Gly Glu Glu Gly Gly Gly Ser Pro Arg Ser Ser Ser Glu Ile
465                 470                 475                 480
Ser Lys Leu Ser Ser Lys Ser Ala Lys Glu Arg Arg Asn Arg Arg Lys
                485                 490                 495
Lys Arg Lys Gln Lys Glu Leu Ser Gly Glu Glu Lys Gly Asp Pro
            500                 505                 510
Glu Lys Val Phe Lys Ser Glu Ser Glu Asp Gly Met Arg Arg Lys Ala
            515                 520                 525
Phe Arg Leu Pro Asp Asn Arg Ile Gly Arg Lys Phe Ser Ile Met Asn
            530                 535                 540
Gln Ser Leu Leu Ser Ile Pro Gly Ser Pro Phe Leu Ser Arg His Asn
545                 550                 555                 560
Ser Lys Ser Ser Ile Phe Ser Phe Arg Gly Pro Gly Arg Phe Arg Asp
                565                 570                 575
Pro Gly Ser Glu Asn Glu Phe Ala Asp Asp Glu His Ser Thr Val Glu
            580                 585                 590
Glu Ser Glu Gly Arg Arg Asp Ser Leu Phe Ile Pro Ile Arg Ala Arg
            595                 600                 605
Glu Arg Arg Ser Ser Tyr Ser Gly Tyr Ser Gly Tyr Ser Gln Gly Ser
            610                 615                 620
Arg Ser Ser Arg Ile Phe Pro Ser Leu Arg Arg Ser Val Lys Arg Asn
625                 630                 635                 640
Ser Thr Val Asp Cys Asn Gly Val Val Ser Leu Ile Gly Gly Pro Gly
                645                 650                 655
Ser His Ile Gly Gly Arg Leu Leu Pro Glu Ala Thr Glu Val Glu
            660                 665                 670
Ile Lys Lys Lys Gly Pro Gly Ser Leu Leu Val Ser Met Asp Gln Leu
            675                 680                 685
Ala Ser Tyr Gly Arg Lys Asp Arg Ile Asn Ser Ile Met Ser Val Val
            690                 695                 700
Thr Asn Thr Leu Val Glu Glu Leu Glu Glu Ser Gln Arg Lys Cys Pro
705                 710                 715                 720
Pro Cys Trp Tyr Lys Phe Ala Asn Thr Phe Leu Ile Trp Glu Cys His
                725                 730                 735
Pro Tyr Trp Ile Lys Leu Lys Glu Ile Val Asn Leu Ile Val Met Asp
            740                 745                 750
Pro Phe Val Asp Leu Ala Ile Thr Ile Cys Ile Val Leu Asn Thr Leu
            755                 760                 765
Phe Met Ala Met Glu His His Pro Met Thr Pro Gln Phe Glu His Val
770                 775                 780
Leu Ala Val Gly Asn Leu Val Phe Thr Gly Ile Phe Thr Ala Glu Met
785                 790                 795                 800
Phe Leu Lys Leu Ile Ala Met Asp Pro Tyr Tyr Tyr Phe Gln Glu Gly
                805                 810                 815
Trp Asn Ile Phe Asp Gly Phe Ile Val Ser Leu Ser Leu Met Glu Leu
            820                 825                 830
Ser Leu Ala Asp Val Glu Gly Leu Ser Val Leu Arg Ser Phe Arg Leu
            835                 840                 845
Leu Arg Val Phe Lys Leu Ala Lys Ser Trp Pro Thr Leu Asn Met Leu
```

```
                    850             855             860
Ile Lys Ile Ile Gly Asn Ser Val Gly Ala Leu Gly Asn Leu Thr Leu
865                 870             875                 880

Val Leu Ala Ile Ile Val Phe Ile Phe Ala Val Val Gly Met Gln Leu
                    885             890                 895

Phe Gly Lys Ser Tyr Lys Glu Cys Val Cys Lys Ile Asn Gln Asp Cys
                900             905             910

Glu Leu Pro Arg Trp His Met His Asp Phe Phe His Ser Phe Leu Ile
            915             920             925

Val Phe Arg Val Leu Cys Gly Glu Trp Ile Glu Thr Met Trp Asp Cys
        930             935             940

Met Glu Val Ala Gly Gln Ala Met Cys Leu Ile Val Phe Met Met Val
945             950             955             960

Met Val Ile Gly Asn Leu Val Val Leu Asn Leu Phe Leu Ala Leu Leu
                965             970             975

Leu Ser Ser Phe Ser Ala Asp Asn Leu Ala Ala Thr Asp Asp Asp Gly
                980             985             990

Glu Met Asn Asn Leu Gln Ile Ser Val Ile Arg Ile Lys Lys Gly Val
            995             1000            1005

Ala Trp Thr Lys Leu Lys Val His Ala Phe Met Gln Ala His Phe
    1010            1015           1020

Lys Gln Arg Glu Ala Asp Glu Val Lys Pro Leu Asp Glu Leu Tyr
    1025            1030           1035

Glu Lys Lys Ala Asn Cys Ile Ala Asn His Thr Gly Ala Asp Ile
    1040            1045           1050

His Arg Asn Gly Asp Phe Gln Lys Asn Gly Asn Gly Thr Thr Ser
    1055            1060           1065

Gly Ile Gly Ser Ser Val Glu Lys Tyr Ile Ile Asp Glu Asp His
    1070            1075           1080

Met Ser Phe Ile Asn Asn Pro Asn Leu Thr Val Arg Val Pro Ile
    1085            1090           1095

Ala Val Gly Glu Ser Asp Phe Glu Asn Leu Asn Thr Glu Asp Val
    1100            1105           1110

Ser Ser Glu Ser Asp Pro Glu Gly Ser Lys Asp Lys Leu Asp Asp
    1115            1120           1125

Thr Ser Ser Ser Glu Gly Ser Thr Ile Asp Ile Lys Pro Glu Val
    1130            1135           1140

Glu Glu Val Pro Val Glu Gln Pro Glu Glu Tyr Leu Asp Pro Asp
    1145            1150           1155

Ala Cys Phe Thr Glu Gly Cys Val Gln Arg Phe Lys Cys Cys Gln
    1160            1165           1170

Val Asn Ile Glu Glu Gly Leu Gly Lys Ser Trp Trp Ile Leu Arg
    1175            1180           1185

Lys Thr Cys Phe Leu Ile Val Glu His Asn Trp Phe Glu Thr Phe
    1190            1195           1200

Ile Ile Phe Met Ile Leu Leu Ser Ser Gly Ala Leu Ala Phe Glu
    1205            1210           1215

Asp Ile Tyr Ile Glu Gln Arg Lys Thr Ile Arg Thr Ile Leu Glu
    1220            1225           1230

Tyr Ala Asp Lys Val Phe Thr Tyr Ile Phe Ile Leu Glu Met Leu
    1235            1240           1245

Leu Lys Trp Thr Ala Tyr Gly Phe Val Lys Phe Phe Thr Asn Ala
    1250            1255           1260
```

-continued

Trp Cys Trp Leu Asp Phe Leu Ile Val Ala Val Ser Leu Val Ser
1265                1270                1275

Leu Ile Ala Asn Ala Leu Gly Tyr Ser Glu Leu Gly Ala Ile Lys
1280                1285                1290

Ser Leu Arg Thr Leu Arg Ala Leu Arg Pro Leu Arg Ala Leu Ser
1295                1300                1305

Arg Phe Glu Gly Met Arg Val Val Val Asn Ala Leu Val Gly Ala
1310                1315                1320

Ile Pro Ser Ile Met Asn Val Leu Leu Val Cys Leu Ile Phe Trp
1325                1330                1335

Leu Ile Phe Ser Ile Met Gly Val Asn Leu Phe Ala Gly Lys Tyr
1340                1345                1350

His Tyr Cys Phe Asn Glu Thr Ser Glu Ile Arg Phe Glu Ile Glu
1355                1360                1365

Asp Val Asn Asn Lys Thr Glu Cys Glu Lys Leu Met Glu Gly Asn
1370                1375                1380

Asn Thr Glu Ile Arg Trp Lys Asn Val Lys Ile Asn Phe Asp Asn
1385                1390                1395

Val Gly Ala Gly Tyr Leu Ala Leu Leu Gln Val Ala Thr Phe Lys
1400                1405                1410

Gly Trp Met Asp Ile Met Tyr Ala Ala Val Asp Ser Arg Lys Pro
1415                1420                1425

Asp Glu Gln Pro Lys Tyr Glu Asp Asn Ile Tyr Met Tyr Ile Tyr
1430                1435                1440

Phe Val Ile Phe Ile Ile Phe Gly Ser Phe Phe Thr Leu Asn Leu
1445                1450                1455

Phe Ile Gly Val Ile Ile Asp Asn Phe Asn Gln Gln Lys Lys Lys
1460                1465                1470

Phe Gly Gly Gln Asp Ile Phe Met Thr Glu Glu Gln Lys Lys Tyr
1475                1480                1485

Tyr Asn Ala Met Lys Lys Leu Gly Ser Lys Lys Pro Gln Lys Pro
1490                1495                1500

Ile Pro Arg Pro Leu Asn Lys Ile Gln Gly Ile Val Phe Asp Phe
1505                1510                1515

Val Thr Gln Gln Ala Phe Asp Ile Val Ile Met Met Leu Ile Cys
1520                1525                1530

Leu Asn Met Val Thr Met Met Val Glu Thr Asp Thr Gln Ser Lys
1535                1540                1545

Gln Met Glu Asn Ile Leu Tyr Trp Ile Asn Leu Val Phe Val Ile
1550                1555                1560

Phe Phe Thr Cys Glu Cys Val Leu Lys Met Phe Ala Leu Arg His
1565                1570                1575

Tyr Tyr Phe Thr Ile Gly Trp Asn Ile Phe Asp Phe Val Val Val
1580                1585                1590

Ile Leu Ser Ile Val Gly Met Phe Leu Ala Asp Ile Ile Glu Lys
1595                1600                1605

Tyr Phe Val Ser Pro Thr Leu Phe Arg Val Ile Arg Leu Ala Arg
1610                1615                1620

Ile Gly Arg Ile Leu Arg Leu Ile Lys Gly Ala Lys Gly Ile Arg
1625                1630                1635

Thr Leu Leu Phe Ala Leu Met Met Ser Leu Pro Ala Leu Phe Asn
1640                1645                1650

```
        -continued

Ile Gly Leu Leu Leu Phe Leu Val Met Phe Ile Phe Ser Ile Phe
    1655                1660                1665

Gly Met Ser Asn Phe Ala Tyr Val Lys His Glu Ala Gly Ile Asp
    1670                1675                1680

Asp Met Phe Asn Phe Glu Thr Phe Gly Asn Ser Met Ile Cys Leu
    1685                1690                1695

Phe Gln Ile Thr Thr Ser Ala Gly Trp Asp Gly Leu Leu Leu Pro
    1700                1705                1710

Ile Leu Asn Arg Pro Pro Asp Cys Ser Leu Asp Lys Glu His Pro
    1715                1720                1725

Gly Ser Gly Phe Lys Gly Asp Cys Gly Asn Pro Ser Val Gly Ile
    1730                1735                1740

Phe Phe Phe Val Ser Tyr Ile Ile Ser Phe Leu Ile Val Val
    1745                1750                1755

Asn Met Tyr Ile Ala Ile Ile Leu Glu Asn Phe Ser Val Ala Thr
    1760                1765                1770

Glu Glu Ser Ala Asp Pro Leu Ser Glu Asp Asp Phe Glu Thr Phe
    1775                1780                1785

Tyr Glu Ile Trp Glu Lys Phe Asp Pro Asp Ala Thr Gln Phe Ile
    1790                1795                1800

Glu Tyr Cys Lys Leu Ala Asp Phe Ala Asp Ala Leu Glu His Pro
    1805                1810                1815

Leu Arg Val Pro Lys Pro Asn Thr Ile Glu Leu Ile Ala Met Asp
    1820                1825                1830

Leu Pro Met Val Ser Gly Asp Arg Ile His Cys Leu Asp Ile Leu
    1835                1840                1845

Phe Ala Phe Thr Lys Arg Val Leu Gly Asp Ser Gly Glu Leu Asp
    1850                1855                1860

Ile Leu Arg Gln Gln Met Glu Glu Arg Phe Val Ala Ser Asn Pro
    1865                1870                1875

Ser Lys Val Ser Tyr Glu Pro Ile Thr Thr Thr Leu Arg Arg Lys
    1880                1885                1890

Gln Glu Glu Val Ser Ala Val Val Leu Gln Arg Ala Tyr Arg Gly
    1895                1900                1905

His Leu Ala Arg Arg Gly Phe Ile Cys Lys Lys Thr Thr Ser Asn
    1910                1915                1920

Lys Leu Glu Asn Gly Gly Thr His Arg Glu Lys Lys Glu Ser Thr
    1925                1930                1935

Pro Ser Thr Ala Ser Leu Pro Ser Tyr Asp Ser Val Thr Lys Pro
    1940                1945                1950

Glu Lys Glu Lys Gln Gln Arg Ala Glu Glu Gly Arg Arg Glu Arg
    1955                1960                1965

Ala Lys Arg Gln Lys Glu Val Arg Glu Ser Lys Cys
    1970                1975                1980
```

PROTOXIN-II VARIANTS AND METHODS OF USE

CROSS REFERENCE TO RELATED APPLICATIONS

The instant application is a continuation of U.S. application Ser. No. 14/505,592, filed on Oct. 3, 2014, which claims priority of the benefits of the filing of U.S. Provisional Application Ser. No. 61/886,100, filed Oct. 3, 2013. The complete disclosures of the aforementioned related U.S. patent applications are hereby incorporated herein by reference for all purposes.

SEQUENCE LISTING

The instant application contains a Sequence Listing which has been submitted in the parent application in ASCII format via EFS-WEB and is hereby incorporated herein by reference in its entirety for use as the ACII copy in this application. Said ASCII copy, created on Oct. 23, 2014, is named U.S. Ser. No. 14/505,592.txt—and is 331.27 kilobytes in size and contains no new matter.

FIELD OF THE INVENTION

The present invention relates to Protoxin-II variants, synthetic polynucleotides encoding them, and methods of making and using the foregoing.

BACKGROUND OF THE INVENTION

Voltage-gated sodium channels (VGSC) are present in all excitable cells including cardiac and skeletal muscle cells and central and peripheral neurons. In neuronal cells, sodium channels are responsible for amplifying sub-threshold depolarizations and generating the rapid upstroke of the action potential. As such, sodium channels are essential to the initiation and propagation of electrical signals in the nervous system. Aberrant sodium channel function is thought to underlie a variety of medical disorders (Hibner and Jentsch, Hum Mol Genet 11:2435-45, 2002), including epilepsy (Yogeeswari et al., Curr Drug Targets 5:589-602, 2004), arrhythmia (Tfelt-Hansen et al., J Cardiovasc Electrophysiol 21:107-15, 2010), myotonia (Cannon and Bean, J Clin Invest 120:80-3, 2010), and pain (Cregg et al., J Physiol 588:1897-904, 2010). Sodium channels are typically a complex of various subunits, the principle one being the pore-forming alpha-subunit, which is alone sufficient for function.

Nine known members of the family of voltage-gated sodium channel alpha subunits exist in humans, Nav1.1-Nav1.9. The Nav1.x subfamily can be pharmacologically subdivided into two groups, the tetrodotoxin (TTX)-sensitive and TTX-resistant. Nav1.7, (a.k.a. PN1 or hNE) is encoded by the SCN9A gene, is TTX-sensitive and is primarily expressed in peripheral sympathetic and sensory neurons. Nav1.7 accumulates at nerve fiber endings and amplifies small sub-threshold depolarizations and acts as a threshold channel that regulates excitability.

Nav1.7 function is implicated in various pain states, including acute, inflammatory and/or neuropathic pain. In man, gain of function mutations of Nav1.7 have been linked to primary erythermalgia (PE), a disease characterized by burning pain and inflammation of the extremities (Yang et al., J Med Genet 41:171-4, 2004), and paroxysmal extreme pain disorder (PEPD)(Fertleman et al., Neuron 52:767-74, 2006). Consistent with this observation, non-selective sodium channel blockers lidocaine, mexiletine and carbamazepine can provide symptomatic relief in these painful disorders (Legroux-Crespel et al., Ann Dermatol Venereol 130:429-33, 2003; Fertleman et al., Neuron 52:767-74, 2006).

Loss-of-function mutations of Nav1.7 in humans cause congenital indifference to pain (CIP), a rare autosomal recessive disorder characterized by a complete indifference or insensitivity to painful stimuli (Cox et al., Nature 444: 894-8, 2006; Goldberg et al, Clin Genet 71:311-9, 2007; Ahmad et al., Hum Mol Genet 16:2114-21, 2007).

Single nucleotide polymorphisms in the coding region of SCN9A have been associated with increased nociceptor excitability and pain sensitivity. For example, a polymorphism rs6746030 resulting in R1150W substitution in human Nav1.7 has been associated with osteoarthritis pain, lumbar discectomy pain, phantom pain, and pancreatitis pain (Reimann et al., Proc Natl Acad Sci USA 107:5148-53, 2010). DRG neurons expressing the R1150W mutant Nav1.7 display increased firing frequency in response to depolarization (Estacion et al., Ann Neurol 66:862-6, 2009). A disabling form of fibromyalgia has been associated with SCN9A sodium channel polymorphism rs6754031, indicating that some patients with severe fibromyalgia may have a dorsal root ganglia sodium channelopathy (Vargas-Alarcon et al., BMC Musculoskelet Disord 13:23, 2012).

In mice, deletion of the SCN9A gene in nociceptive neurons leads to reduction in mechanical and thermal pain thresholds and reduction or abolition of inflammatory pain responses (Nassar et al., Proc Natl Acad Sci USA 101: 12706-11, 2004). Ablating SCN9A in all sensory neurons abolished mechanical pain, inflammatory pain and reflex withdrawal responses to heat. Deleting SCN9A in both sensory and sympathetic neurons abolished mechanical, thermal and neuropathic pain, and recapitulated the pain-free phenotype seen in humans with Nav1.7 loss-of-function mutations (Minett et al., Nat Commun 3:791, 2012). Nav1.7 inhibitors or blockers may therefore be useful in the treatment of a wide range of pain associated with various disorders.

Spider venoms are known to contain a large number of sodium channel blocking peptides, including Huwentoxin-IV (HwTx-IV) (Peng et al., J Biol Chem 277:47564-71, 2002), Protoxin-I, Protoxin-II (Middleton et al., Biochemistry 41:14734-47, 2002) and Phrixotoxin-III (Bosmans et al., Mol Pharmacol 69:419-29, 2006). There is a need for identification of additional Nav1.7 blockers for treatment of a wide range of pain indications. In particular, there is a need for new Nav1.7 blockers with selectivity for Nav1.7 over other voltage gated sodium channel isoforms.

SUMMARY OF THE INVENTION

One embodiment of the invention is an isolated Protoxin-II variant comprising the sequence (SEQ ID NO: 403)
$X_1X_2X_3CX_4X_5WX_6QX_7CX_8X_9X_{10}X_{11}X_{12}CCX_{13}X_{14}FX_{15}CX_{16}$
$LWCX_{17}KKLW$, wherein
$X_1$ is G, P, A or deleted;
$X_2$ is P, A or deleted;
$X_3$ is S, Q, A, R or Y;
$X_4$ is Q, R, K, A or S;
$X_5$ is K, S, Q or R;

X₆ is M or F;
X₇ is T, S, R, K or Q;
X₈ is D or T;
X₉ is S, A or R;
X₁₀ is E, R, N, K, T or Q;
X₁₁ is R or K;
X₁₂ is K, Q, S or A;
X₁₃ is E, Q or D;
X₁₄ is G or Q;
X₁₅ is V or S;
X₁₆ is R or T; and
X₁₇ is K or R;
optionally having an N-terminal extension or a C-terminal extension,
wherein the polypeptide inhibits human Nav1.7 activity with an $IC_{50}$ value of about $1 \times 10^{-7}$ M or less, wherein the $IC_{50}$ value is measured using a FLIPR® Tetra membrane depolarization assay using fluorescence resonance energy transfer (FRET) in the presence of $25 \times 10^{-6}$ M 3-veratroylveracevine in HEK293 cells stably expressing human Nav1.7.

Another embodiment of the invention is an isolated Protoxin-II variant comprising the amino acid sequence that is 90%, 91%, 92%, 93%, 94%, 95%, 96%, 97%, 98% or 99% identical to the amino acid sequence of SEQ ID NO: 78 (GPQCQKWMQTCDRERKC-CEGFVCTLWCRKKLW-COOH), wherein
the amino acid sequence has Q at position 1, Q at position 7 and F at position 19, when residue numbering is according to SEQ ID NO: 1;
the polypeptide inhibits human Nav1.7 activity with an $IC_{50}$ value of about $30 \times 10^{-9}$ M or less, wherein the $IC_{50}$ value is measured using a FLIPR® Tetra membrane depolarization assay using fluorescence resonance energy transfer (FRET) in the presence of $25 \times 10^{-6}$ M 3-veratroylveracevine in HEK293 cells stably expressing human Nav1.7; and the polypeptide selectively inhibits Nav1.7.

Another embodiment of the invention is a polynucleotide encoding the Protoxin-II variant of the invention.

Another embodiment of the invention is a vector comprising the isolated polynucleotide of the invention.

Another embodiment of the invention is a host cell comprising the vector of the invention.

Another embodiment of the invention is a method for producing the Protoxin-II variant of the invention, comprising culturing the host cell of the invention and recovering the Protoxin-II variant from the cell.

Another embodiment of the invention is a pharmaceutical composition comprising the isolated Protoxin-II variant of the invention and a pharmaceutically acceptable excipient.

Another embodiment of the invention is a method of treating Nav1.7-mediated pain in a subject, comprising administering to a subject an effective amount of the Protoxin-II variant of the invention to treat the Nav1.7-mediated pain.

BRIEF DESCRIPTION OF THE DRAWINGS

FIG. 1 shows the genus amino acid sequence of Protoxin-II variants that inhibit Nav1.7 with an $IC_{50}$ value of 30 nM or less in a FLIPR Tetra assay. Residue numbering is according to wild-type Protoxin-II of SEQ ID NO: 1. Genus SEQ ID NO: 403.

FIG. 2 shows the $IC_{50}$ values for Nav1.7 and Nav1.6 inhibition in a QPatch assay, and selectivity of each variant calculated by ratio of $IC_{50}$ (Nav1.6)/$IC_{50}$ (Nav1.7) obtained in QPatch assay. SE: standard error.

FIG. 3 shows the sequences and the genus sequence of Protoxin-II variants that inhibit Nav1.7 with an $IC_{50}$ value of 30 nM or less in a FLIPR Tetra assay, and are over 30-fold selective over Nav1.6. Selectivity of each variant was calculated by ratio of $IC_{50}$ (Nav1.6)/$IC_{50}$9av1.7) obtained in QPatch assay. Residue numbering is according to wild-type Protoxin-II of SEQ ID NO: 1.

DETAILED DESCRIPTION OF THE INVENTION

Figure 4A:
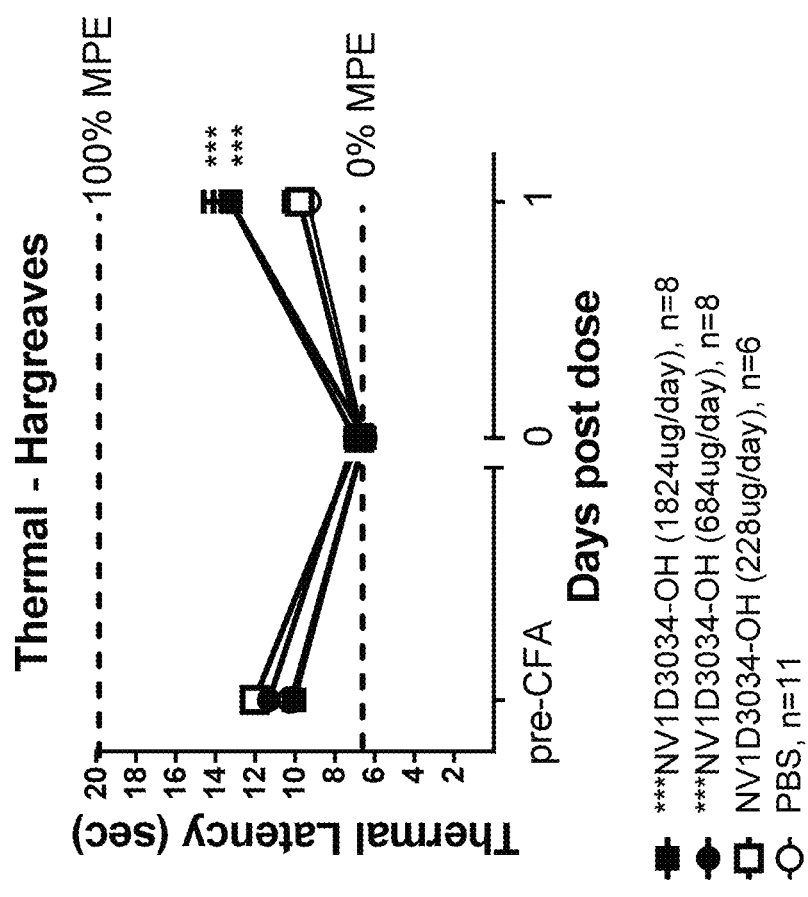
FIG. 4A shows efficacy of NV1D3034 (NV1D3034-OH) (SEQ ID NO: 78) against CFA-induced thermal hyperalgesia assessed by measurement of paw withdrawal latency in the Hargreaves test before (pre-CFA) and after CFA injection (0) and 1-day after peptide administration (1). ***$P<0.001$ vs. PBS, two-way ANOVA followed by Bonferroni's multiple comparison.

All publications, including but not limited to patents and patent applications, cited in this specification are herein incorporated by reference as though fully set forth.

As used herein and in the claims, the singular forms "a," "and," and "the" include plural reference unless the context clearly dictates otherwise.

Unless defined otherwise, all technical and scientific terms used herein have the same meaning as commonly understood by one of ordinary skill in the art to which an invention belongs. Although any compositions and methods similar or equivalent to those described herein can be used in the practice or testing of the invention, exemplary compositions and methods are described herein.

The term "polypeptide" means a molecule that comprises at least two amino acid residues linked by a peptide bond to form a polypeptide. Small polypeptides of less than 50 amino acids may be referred to as "peptides". Polypeptides may also be referred as "proteins".

The term "polynucleotide" means a molecule comprising a chain of nucleotides covalently linked by a sugar-phosphate backbone or other equivalent covalent chemistry. Double and single-stranded DNAs and RNAs are typical examples of polynucleotides.

The term "complementary sequence" means a second isolated polynucleotide sequence that is antiparallel to a first isolated polynucleotide sequence and that comprises nucleotides complementary to the nucleotides in the first polynucleotide sequence.

The term "vector" means a non-natural polynucleotide capable of being duplicated within a biological system or that can be moved between such systems. Vector polynucleotides typically contain a cDNA encoding a protein of interest and additional elements, such as origins of replication, polyadenylation signal or selection markers, that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

The term "expression vector" means a vector that can be utilized in a biological system or a reconstituted biological system to direct the translation of a polypeptide encoded by a polynucleotide sequence present in the expression vector.

The term "variant" as used herein refers to a polypeptide or a polynucleotide that differs from wild type Protoxin-II polypeptide of SEQ ID NO: 1 or the polynucleotide encoding the wild type Protoxin-II having the sequence of SEQ ID NO: 107 by one or more modifications for example, substitutions, insertions or deletions of nucleotides or amino acids.

Throughout the specification, residues that are substituted in the Protoxin-II variants are numbered corresponding to their position in the wild-type Protoxin-II of SEQ ID NO: 1. For example, "Y1A" in the specification refers to the substitution of tyrosine at residue position that corresponds to the position 1 in the wild type Protoxin-II of SEQ ID NO:1 with alanine.

"Complementary DNA" or "cDNA" refers to a well-known synthetic polynucleotide that shares the arrangement of sequence elements found in native mature mRNA species with contiguous exons, with the intervening introns present in genomic DNA are removed. The codons encoding the initiator methionine may or may not be present in cDNA. cDNA may be synthesized for example by reverse transcription or synthetic gene assembly.

"Synthetic" or "non-natural" as used herein refers to a polynucleotide or a polypeptide molecule not present in nature.

"Nav1.7" (also referred to as hNE or PN1) or "hNav1.7" as used herein refers to the well-known human sodium channel protein type 9 subunit alpha having a sequence shown in GenBank accession number NP_002968.1 and in SEQ ID NO: 79.

The term "wild type Protoxin-II" or "wild type ProTx-II" as used herein refers to the tarantula *Thrixopelma pruriens* (Peruvian green velvet tarantula) toxin peptide having the amino acid sequence YCQKWMWTCDSERKCCEGMVCRLWCKKKLW-COOH (SEQ ID NO: 1) as described in Middleton et al., Biochemistry 41(50):14734-47, 2002.

The term "recombinant Protoxin-II" or recombinant ProTx-II" as used herein refers to the recombinant Protoxin-II obtained from expression and subsequent cleavage of a Protoxin-II fusion protein having the sequence of GPYCQKWMWTCDSERKCCEGMVCRLWCKKKLW-OH as shown in SEQ ID NO: 2. Recombinant Protoxin-II incorporates a two amino acid N-terminal extension (residues G and P) when compared to the wild type Protoxin-II.

"Blocks human Nav1.7 activity" or "inhibits human Nav1.7 activity" as used herein refers to the ability of the Protoxin-II variant of the invention to reduce membrane depolarization induced by veratridine (3-veratroylveracevine) with an $IC_{50}$ value of about $1\times10^{-7}$ M or less in a FLIPR® Tetra membrane depolarization assay using fluorescence resonance energy transfer (FRET), where veratridine-induced depolarization is measured as a reduction in FRET signal using DISBAC2(3) ([bis-(1,3-diethylthiobarbituric acid) trimethine oxonol]) as an acceptor and PTS18 (trisodium 8-octadecyloxypyrene-1,3,6-trisulfonate) as a donor by exciting the donor at 390-420 nm and measuring FRET at 515-575 nm in a cell line stably expressing human Nav1.7.

"FLIPR® Tetra membrane depolarization assay" as used herein is the assay described in Example 3.

The term "substantially identical" as used herein means that the two Protoxin-II variant amino acid sequences being compared are identical or have "insubstantial differences"

Insubstantial differences are substitutions of 1, 2, 3, 4, 5, 6, or 7 amino acids in the Protoxin-II variant amino acid sequence that do not adversely affect peptide properties. Amino acid sequences substantially identical to the Protoxin-II variants disclosed herein are within the scope of the application. In some embodiments, the sequence identity can be about 80%, 81%, 82%, 83%, 84%, 85%, 86%, 87%, 88%, 89%, 90%, 91%, 92%, 93%, 94%, 95%, 96%, 97%, 98%, 99% or higher. Percent identity can be determined for example by pairwise alignment using the default settings of the AlignX module of Vector NTI v.9.0.0 (Invitrogen, Carslbad, Calif.). The protein sequences of the present invention may be used as a query sequence to perform a search against public or patent databases, for example, to identify related sequences. Exemplary programs used to perform such searches are the XBLAST or BLASTP programs (http_// www_ncbi_nlm/nih_gov), or the GenomeQuest™ (GenomeQuest, Westborough, Mass.) suite using the default settings.

Conventional one and three-letter amino acid codes are used herein as shown in Table 1.

TABLE 1

| Amino acid | Three letter code | One letter code |
|---|---|---|
| Alanine | Ala | A |
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The present invention provides isolated Protoxin-II (ProTx-II) variant polypeptides that inhibit human Nav1.7 activity, polynucleotides encoding them, vectors, host cells, and methods of using the polynucleotides and polypeptides of the invention. The polypeptides of the invention inhibit depolarization resulting from Nav1.7 activation, and therefore may be useful in the treatment of various conditions associated with pain and conditions associated with sensory or sympathetic neuron dysfunction.

The variants of the invention are potent inhibitors of Nav1.7. The current invention is based, at least in part, on the finding that certain residue substitutions in Protoxin-II enhance selectivity, synthetic yield and/or homogeneity without adversely affecting the potency of the generated Protoxin-II variants, specifically W7 and M19, and additionally residues Y1 and S11, and further additionally residues E12, R22 and (residue numbering according to SEQ ID NO: 1).

One embodiment of the invention is an isolated Protoxin-II variant, wherein the Protoxin-II variant inhibits human Nav1.7 activity with an $IC_{50}$ value of about $1\times10^{-7}$ M or less, about $1\times10^{-8}$ M or less, about $1\times10^{-9}$ M or less, about $1\times10^{-10}$ M or less, about $1\times10^{-11}$ M or less, or about $1\times10^{-12}$ M or less, wherein the $IC_{50}$ value is measured using a FLIPR® Tetra membrane depolarization assay using fluorescence resonance energy transfer (FRET) in the presence of $25\times10^{-6}$ M 3-veratroylveracevine in HEK293 cells stably expressing human Nav1.7.

Another embodiment of the invention is an isolated Protoxin-II variant comprising the sequence (SEQ ID NO: 403)
$X_1X_2X_3CX_4X_5WX_6QX_7CX_8X_9X_{10}X_{11}X_{12}CCX_{13}X_{14}FX_{15}CX_{16}LWCX_{17}KKLW$, wherein
$X_1$ is G, P, A or deleted;
$X_2$ is P, A or deleted;
$X_3$ is S, Q, A, R or Y;
$X_4$ is Q, R, K, A or S;
$X_5$ is K, S, Q or R;
$X_6$ is M or F;
$X_7$ is T, S, R, K or Q;
$X_8$ is D or T;
$X_9$ is S, A or R;
$X_{10}$ is E, R, N, K, T or Q;
$X_{11}$ is R or K;
$X_{12}$ is K, Q, S or A;
$X_{13}$ is E, Q or D;
$X_{14}$ is G or Q;
$X_{15}$ is V or S;
$X_{16}$ is R or T; and
$X_{17}$ is K or R;
optionally having an N-terminal extension or a C-terminal extension,
wherein the polypeptide inhibits human Nav1.7 activity with an $IC_{50}$ value of about $1\times10^{-7}$ M or less, wherein the $IC_{50}$ value is measured using a FLIPR® Tetra membrane depolarization assay using fluorescence resonance energy transfer (FRET) in the presence of $25\times10^{-6}$ M 3-veratroylveracevine in HEK293 cells stably expressing human Nav1.7.

In some embodiments, the N-terminal extension comprises the amino acid sequences of SEQ ID NOs: 372, 373, 374, 375, 376, 377, 378, 379, 380, 381, 382, 383, 384 or 385.

In some embodiments, the C-terminal extension comprises the amino acid sequence of SEQ ID NOs: 374, 386, 387, 388, 389, 390, 391, 392, 393, 394, 395, 396 or 397.

In some embodiments, the N-terminal and/or the C-terminal extension is conjugated to the Protoxin-II variant via a linker.

In some embodiments, the linker comprises the amino acid sequence of SEQ ID NOs: 383, 392, 398, 399, 400, 401 or 402.

In some embodiments, the N-terminal extension consists of the amino acid sequences of SEQ ID NOs: 372, 373, 374, 375, 376, 377, 378, 379, 380, 381, 382, 383, 384 or 385.

In some embodiments, the C-terminal extension consists of the amino acid sequence of SEQ ID NOs: 374, 386, 387, 388, 389, 390, 391, 392, 393, 394, 395, 396 or 397.

In some embodiments, the linker consists of the amino acid sequence of SEQ ID NOs: 383, 392, 398, 399, 400, 401 or 402.

The Protoxin-II variants of the invention are potent Nav1.7 inhibitors. Recombinant Protoxin-II (SEQ ID NO: 2) has an $IC_{50}$ value of about $4\times10^{-9}$ M for human Nav1.7 in a veratridine-induced depolarization inhibition assay measuring decline in FRET (fluorescence resonance energy transfer) in cells stably expressing Nav1.7 using FLIPR® Tetra instrument (Molecular Devices) using experimental details described in Example 3. A Protoxin-II variant is "a potent" Nav1.7 inhibitor when the $IC_{50}$ value in the assay described above and in Experiment 3 is about $30 \times 10^{-9}$ M or less i.e. within 10 fold of recombinant Protoxin-II. For clarity, an $IC_{50}$ of $30 \times 10^{-9}$ M is identical to $IC_{50}$ of $3.0 \times 10^{-8}$ M.

The Protoxin-II variant polypeptides of the invention may be produced by chemical synthesis, such as solid phase peptide synthesis, on an automated peptide synthesizer. Alternatively, the polypeptides of the invention may be obtained from polynucleotides encoding the polypeptides by the use of cell-free expression systems such as reticulocyte lysate based expression systems, or by recombinant expression systems. Those skilled in the art will recognize other techniques for obtaining the polypeptides of the invention. In an exemplary method, the Protoxin-II variants of the invention are generated by expressing them as human serum albumin (HSA) fusion proteins utilizing a glycine-rich linker such as $(GGGGS)_4$ (SEQ ID NO:80) or $(GGGGS)_6$ (SEQ ID NO: 81) coupled to a protease cleavable linker such as a recognition sequence for HRV3C protease (Recombinant type 14 3C protease from human rhinovirus) LEVLFQGP (HRV3C linker) (SEQ ID NO: 82), and cleaving the expressed fusion proteins with the HRV3C protease to release the recombinant Protoxin-II variant peptides. Hexahistidine (SEQ ID NO: 108) or other tags may be used to facilitate purification using well known methods.

Protoxin-II variants of the invention may be purified using methods described herein. In an exemplary method, Protoxin-II variants of the invention expressed as HSA fusion proteins and cleaved with HRV3C protease may be purified using sold phase extraction (SPE) as described herein.

Generation of the Protoxin-II variants optionally having N-terminal and/or C-terminal extensions, and Protoxin-II variant fusion proteins is typically achieved at the nucleic acid level. The polynucleotides may be synthesized using chemical gene synthesis according to methods described in U.S. Pat. Nos. 6,521,427 and 6,670,127, utilizing degenerate oligonucleotides to generate the desired variants, or by standard PCR cloning and mutagenesis. Libraries of variants may be generated by standard cloning techniques to clone the polynucleotides encoding the Protoxin-II variants into the vector for expression.

The Protoxin-II variants may incorporate additional N- and/or C-terminal amino acids when compared to the wild type Protoxin-II of SEQ ID NO: 1, for example resulting from cloning and/or expression schemes. For example, cleavage from HSA after expression of the variant as HSA-linker-HRV3C cleavable peptide-Protoxin-II variant fusion protein may result in the incorporation of additional two residues to the N-terminus of each Protoxin-II variant, such as G and P.

The Protoxin-II variants of the invention are tested for their ability to inhibit human Nav1.7 using methods described herein. An exemplary assay is a veratridine-induced depolarization inhibition assay measuring decline in FRET (fluorescence resonance energy transfer) in cells stably expressing Nav1.7. Another exemplary assay employs electrophysiological recordings to measure changes in Nav1.7-mediated currents using well known patch clamp techniques and as described herein.

Another embodiment of the invention is an isolated Protoxin-II variant comprising the amino acid sequence of SEQ ID NOs: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 109, 110, 111, 112, 113, 114, 115, 116, 117, 118, 119, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 35, 357, 358, 359, 360, 361, 362, 363, 364, 365, 366, 367, 368 367, 370 or 371.

The Protoxin-II variants of the invention may inhibit human Nav1.7 with an $IC_{50}$ value of about $1 \times 10^{-7}$ M or less, about $1 \times 10^{-8}$ M about $1 \times 10^{-9}$ or less, about $1 \times 10^{-10}$ M or less, about $1 \times 10^{-11}$ M or less, or about $1 \times 10^{-12}$ M or less. Exemplary variants demonstrating the range of $IC_{50}$ values are variants having amino acid sequences shown in SEQ ID NOs: 30, 40, 44, 52, 56, 56, 59, 65, 78, 109, 110, 111, 117, 118, 119, 120, 121, 122, 123, 124, 125, 126, 127, 128, 129, 131, 132, 133, 134, 135, 136, 137, 138, 139, 140, 141, 142, 143, 144, 145, 146, 147, 148, 149, 150, 151, 152, 153, 154, 155, 156, 157, 158, 159, 162, 165, 166, 167, 168, 169, 170, 171, 172, 173, 174, 175, 177, 178, 179, 180, 182, 183, 184, 185, 186, 189, 190, 193, 195, 197, 199, 206, 207, 208, 209, 210, 211, 212, 213, 214, 215, 216, 217, 218, 224, 226, 227, 231, 232, 243, 244, 245, 247, 249, 252, 255, 258, 261, 263, 264, 265, 266, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 332, 334, 335, 336, 337, 339, 340, 341, 342, 346, 351, 358, 359, 364, 366, 367, or 368.

Table 2 and Table 3 show the sequences of select Protoxin-II variants.

TABLE 2

| Protein name | Protoxin-II variant peptide name | SEQ ID NO: | Protein amino acid sequence |
|---|---|---|---|
| | wild type | 1 | YCQKWMWTCDSERKCCEGMVCRLWCKKKLW-COOH |
| | NV1D12 | 2 | GPYCQKWMWTCDSERKCCEGMVCRLWCKKKLW-COOH |

TABLE 2-continued

| Protein name | Protoxin-II variant peptide name | SEQ ID NO: | Protein amino acid sequence |
|---|---|---|---|
| | NV1D748 | 3 | GPACQKWMWTCDSERKCCEGMVCRLWCKKKLW-COOH |
| | NV1D751 | 4 | GPQCQKWMWTCDSERKCCEGMVCRLWCKKKLW-COOH |
| | NV1D2292 | 5 | GPRCQKWMWTCDSERKCCEGMVCRLWCKKKLW-COOH |
| | NV1D750 | 6 | GPSCQKWMWTCDSERKCCEGMVCRLWCKKKLW-COOH |
| | NV1D1328 | 7 | GPYCQKWFWTCDSERKCCEGMVCRLWCKKKLW-COOH |
| | NV1D774 | 8 | GPYCQKWMQTCDSERKCCEGMVCRLWCKKKLW-COOH |
| | NV1D786 | 9 | GPYCQKWMWTCDAERKCCEGMVCRLWCKKKLW-COOH |
| | NV1D2300 | 10 | GPYCQKWMWTCDRERKCCEGMVCRLWCKKKLW-COOH |
| | NV1D791 | 11 | GPYCQKWMWTCDSKRKCCEGMVCRLWCKKKLW-COOH |
| | NV1D1332 | 12 | GPYCQKWMWTCDSNRKCCEGMVCRLWCKKKLW-COOH |
| | NV1D2512 | 13 | GPYCQKWMWTCDSERKCCEGFVCRLWCKKKLW-COOH |
| | NV1D1336 | 14 | GPYCQKWMWTCDSERKCCEGLVCRLWCKKKLW-COOH |
| | NV1D1337 | 15 | GPYCQKWMWTCDSERKCCEGMVCTLWCKKKLW-COOH |
| | NV1D2308 | 16 | GPYCQKWMWTCDSERKCCEGMVCRLWCRKKLW-COOH |
| NV1G953 | NV1D2670 | 17 | GPACQKWMQTCDSERKCCEGMVCRLWCKKKLW-COOH |
| NV1G951 | NV1D2674 | 18 | GPACQKWMWTCDAERKCCEGMVCRLWCKKKLW-COOH |
| NV1G909 | NV1D2664 | 19 | GPACQKWMWTCDSERKCCEGFVCRLWCKKKLW-COOH |
| NV1G963 | NV1D2671 | 20 | GPQCQKWMQTCDSERKCCEGMVCRLWCKKKLW-COOH |
| NV1G949 | NV1D2675 | 21 | GPQCQKWMWTCDAERKCCEGMVCRLWCKKKLW-COOH |
| NV1G977 | NV1D2665 | 22 | GPQCQKWMWTCDSERKCCEGFVCRLWCKKKLW-COOH |
| NV1G957 | NV1D2668 | 23 | GPRCQKWMQTCDSERKCCEGMVCRLWCKKKLW-COOH |
| NV1G965 | NV1D2672 | 24 | GPRCQKWMWTCDAERKCCEGMVCRLWCKKKLW-COOH |
| NV1G973 | NV1D2662 | 25 | GPRCQKWMWTCDSERKCCEGFVCRLWCKKKLW-COOH |
| NV1G975 | NV1D2669 | 26 | GPSCQKWMQTCDSERKCCEGMVCRLWCKKKLW-COOH |
| NV1G971 | NV1D2673 | 27 | GPSCQKWMWTCDAERKCCEGMVCRLWCKKKLW-COOH |
| NV1G995 | NV1D2663 | 28 | GPSCQKWMWTCDSERKCCEGFVCRLWCKKKLW-COOH |
| NV1G961 | NV1D2676 | 29 | GPYCQKWMQTCDAERKCCEGMVCRLWCKKKLW-COOH |
| NV1G911 | NV1D2666 | 30 | GPYCQKWMQTCDSERKCCEGFVCRLWCKKKLW-COOH |
| | NV1D2816 | 31 | GPACQKWFQTCDSERKCCEGMVCRLWCKKKLW-COOH |
| NV1G905 | NV1D2735 | 32 | GPACQKWMQTCDSERKCCEGFVCRLWCKKKLW-COOH |
| NV1G919 | NV1D2739 | 33 | GPACQKWMWTCDAERKCCEGFVCRLWCKKKLW-COOH |
| NV1G979 | NV1D2731 | 34 | GPACQKWMQTCDAERKCCEGMVCRLWCKKKLW-COOH |
| | NV1D2810 | 35 | GPQCQKWFQTCDSERKCCEGMVCRLWCKKKLW-COOH |
| NV1G1099 | NV1D2732 | 36 | GPQCQKWMQTCDAERKCCEGMVCRLWCKKKLW-COOH |
| NV1G1011 | NV1D2740 | 37 | GPQCQKWMWTCDAERKCCEGFVCRLWCKKKLW-COOH |
| | NV1D2819 | 38 | GPRCQKWFWTCDAERKCCEGMVCRLWCKKKLW-COOH |
| NV1G1105 | NV1D2729 | 39 | GPRCQKWMQTCDAERKCCEGMVCRLWCKKKLW-COOH |

TABLE 2-continued

| Protein name | Protoxin-II variant peptide name | SEQ ID NO: | Protein amino acid sequence |
|---|---|---|---|
| NV1G1013 | NV1D2733 | 40 | GPRCQKWMQTCDSERKCCEGFVCRLWCKKKLW-COOH |
|  | NV1D2814 | 41 | GPSCQKWFQTCDSERKCCEGMVCRLWCKKKLW-COOH |
|  | NV1D2820 | 42 | GPSCQKWFWTCDAERKCCEGMVCRLWCKKKLW-COOH |
| NV1G983 | NV1D2730 | 43 | GPSCQKWMQTCDAERKCCEGMVCRLWCKKKLW-COOH |
| NV1G1003 | NV1D2734 | 44 | GPSCQKWMQTCDSERKCCEGFVCRLWCKKKLW-COOH |
| NV1G1009 | NV1D2738 | 45 | GPSCQKWMWTCDAERKCCEGFVCRLWCKKKLW-COOH |
|  | NV1D2851 | 46 | GPYCQKWFKTCDAERKCCEGMVCRLWCKKKLW-COOH |
|  | NV1D2850 | 47 | GPYCQKWFQTCDAERKCCEGMVCRLWCKKKLW-COOH |
| NV1G987 | NV1D2667 | 48 | GPYCQKWMWTCDAERKCCEGFVCRLWCKKKLW-COOH |
|  | NV1D2867 | 49 | GPACQKWFQTCDAERKCCEGMVCRLWCKKKLW-COOH |
|  | NV1D2881 | 50 | GPACQKWFQTCDSERKCCEGFVCRLWCKKKLW-COOH |
|  | NV1D2882 | 51 | GPACQKWFQTCDSERKCCEGLVCRLWCKKKLW-COOH |
| NV1G899 | NV1D2774 | 52 | GPACQKWMQTCDAERKCCEGFVCRLWCKKKLW-COOH |
| NV1G1077 | NV1D2902 | 53 | GPACQKWMQTCDAERKCCEGLVCRLWCKKKLW-COOH |
|  | NV1D2861 | 54 | GPQCQKWFQTCDAERKCCEGMVCRLWCKKKLW-COOH |
|  | NV1D2870 | 55 | GPQCQKWFQTCDSERKCCEGLVCRLWCKKKLW-COOH |
| NV1G1007 | NV1D2775 | 56 | GPQCQKWMQTCDAERKCCEGFVCRLWCKKKLW-COOH |
| NV1G1067 | NV1D2893 | 57 | GPQCQKWMQTCDAERKCCEGLVCRLWCKKKLW-COOH |
|  | NV1D2887 | 58 | GPRCQKWFWTCDAERKCCEGFVCRLWCKKKLW-COOH |
| NV1G1005 | NV1D2772 | 59 | GPRCQKWMQTCDAERKCCEGFVCRLWCKKKLW-COOH |
| NV1G1061 | NV1D2896 | 60 | GPRCQKWMQTCDAERKCCEGLVCRLWCKKKLW-COOH |
|  | NV1D2877 | 61 | GPSCQKWFQTCDSERKCCEGFVCRLWCKKKLW-COOH |
|  | NV1D2878 | 62 | GPSCQKWFQTCDSERKCCEGLVCRLWCKKKLW-COOH |
|  | NV1D2889 | 63 | GPSCQKWFWTCDAERKCCEGFVCRLWCKKKLW-COOH |
|  | NV1D2889 | 64 | GPSCQKWFWTCDAERKCCEGFVCRLWCKKKLW-COOH |
| NV1G1001 | NV1D2773 | 65 | GPSCQKWMQTCDAERKCCEGFVCRLWCKKKLW-COOH |
|  | NV1D2890 | 66 | GPSCQKWFWTCDAERKCCEGLVCRLWCKKKLW-COOH |
| NV1G1109 | NV1D2899 | 67 | GPSCQKWMQTCDAERKCCEGLVCRLWCKKKLW-COOH |
|  | NV1D2905 | 68 | GPYCQKWFQTCDAERKCCEGFVCRLWCKKKLW-COOH |
|  | NV1D2906 | 69 | GPYCQKWFQTCDAERKCCEGLVCRLWCKKKLW-COOH |
|  | NV1D2921 | 70 | GPACQKWFQTCDAERKCCEGFVCRLWCKKKLW-COOH |
|  | NV1D2922 | 71 | GPACQKWFQTCDAERKCCEGLVCRLWCKKKLW-COOH |
|  | NV1D2909 | 72 | GPQCQKWFQTCDAERKCCEGFVCRLWCKKKLW-COOH |
|  | NV1D2910 | 73 | GPQCQKWFQTCDAERKCCEGLVCRLWCKKKLW-COOH |
|  | NV1D2913 | 74 | GPRCQKWFQTCDAERKCCEGFVCRLWCKKKLW-COOH |
|  | NV1D2914 | 75 | GPRCQKWFQTCDAERKCCEGLVCRLWCKKKLW-COOH |
|  | NV1D2917 | 76 | GPSCQKWFQTCDAERKCCEGFVCRLWCKKKLW-COOH |
|  | NV1D2918 | 77 | GPSCQKWFQTCDAERKCCEGLVCRLWCKKKLW-COOH |

TABLE 2-continued

| Protein name | Protoxin-II variant peptide name | SEQ ID NO: | Protein amino acid sequence |
|---|---|---|---|
| NV1G1153 | NV1D3034 | 78 | GPQCQKWMQTCDRERKCCEGFVCTLWCRKKLW-COOH |
| (-GP)NV1G1001 | (-GP)NV1D2773 | 109 | SCQKWMQTCDAERKCCEGFVCRLWCKKKLW-COOH |
| (-GP)NV1G1001-NH-Me | (-GP)NV1D2773-NH2 | 110 | SCQKWMQTCDAERKCCEGFVCRLWCKKKLW-NH2 |
| NV1G1007-NH2 | NV1D2775-NH2 | 111 | GPQCQKWMQTCDAERKCCEGFVCRLWCKKKLW-NH2 |
| NV1G1107-NH2 | NV1D2890-NH2 | 112 | SCQKWFWTCDAERKCCEGLVCRLWCKKKLW-NH2 |
| NV1G1137 | NV1D2974 | 113 | GPQCQKWMQTCDAERKCCEGFSCTLWCKKKLW-COOH |
| (-GP)N-Ac-NV1G1137-NH2 | (-GP)N-Ac-NV1D2974-NH2 | 114 | Ac-QCQKWMQTCDAERKCCEGFSCTLWCKKKLW-NH2 |
| (-GP)N-Ac-NV1G1137- | (-GP)N-Ac-NV1D2974 | 115 | Ac-QCQKWMQTCDAERKCCEGFSCTLWCKKKLW-COOH |
| NV1G1153 | NV1D3034 | 116 | GPQCQKWMQTCDRERKCCEGFVCTLWCRKKLW-COOH |
| NV1G1153-NH2 | NV1D3034-NH2 | 117 | GPQCQKWMQTCDRERKCCEGFVCTLWCRKKLW-NH2 |
| NV1G1153-NH-butyl | NV1D3034-NH-butyl | 118 | GPQCQKWMQTCDRERKCCEGFVCTLWCRKKLW-NH-butyl |
| NV1G1153-NH-methyl | NV1D3034-NH-methyl | 119 | GPQCQKWMQTCDRERKCCEGFVCTLWCRKKLW-NH-methyl |
| (-GP)N-Ac-NV1G1153 | (-GP)N-Ac-NV1D3034 | 120 | Ac-QCQKWMQTCDRERKCCEGFVCTLWCRKKLW-COOH |
| (-GP)N-Ac-NV1G1153-NH2 | (-GP)N-Ac-NV1D3034-NH2 | 121 | Ac-QCQKWMQTCDRERKCCEGFVCTLWCRKKLW-NH2 |
| NV1G1818 | NV1D3368 | 122 | GPQCQKWMQTCDRTRKCCEGFVCTLWCRKKLW-COOH |
| NV1G1818-NH2 | NV1D3368-NH2 | 123 | GPQCQKWMQTCDRTRKCCEGFVCTLWCRKKLW-NH2 |
| NV1G1147 | NV1D2969 | 124 | GPSCQKWMQTCDAERKCCEGFSCRLWCKKKLW-COOH |
| NV1G1145 | NV1D2970 | 125 | GPSCQKWMQTCDAERKCCEGFVCTLWCKKKLW-COOH |
| NV1G1143 | NV1D2971 | 126 | GPSCQKWMQTCDAERKCCEGFSCTLWCKKKLW-COOH |
| NV1G1141 | NV1D2972 | 127 | GPQCQKWMQTCDAERKCCEGFSCRLWCKKKLW-COOH |
| NV1G1139 | NV1D2973 | 128 | GPQCQKWMQTCDAERKCCEGFVCTLWCKKKLW-COOH |
| NV1G1137 | NV1D2974 | 129 | GPQCQKWMQTCDAERKCCEGFSCTLWCKKKLW-COOH |
| NV1G1137-NH2 | NV1D2974-NH2 | 130 | GPQCQKWMQTCDAERKCCEGFSCTLWCKKKLW-NH2 |
| NV1G1517 | NV1D3004 | 131 | GPQCQKWMQTCDRERKCCEGFVCRLWCKKKLW-COOH |
| NV1G1515 | NV1D3005 | 132 | GPQCQKWMQTCDANRKCCEGFVCRLWCKKKLW-COOH |
| NV1G1519 | NV1D3006 | 133 | GPQCQKWMQTCDARRKCCEGFVCRLWCKKKLW-COOH |
| NV1G1513 | NV1D3007 | 134 | GPQCQKWMQTCDAERKCCEGFVCRLWCKKKLW-COOH |
| NV1G1523 | NV1D3012 | 135 | GPQCQKWMQTCDRNRKCCEGFVCRLWCKKKLW-COOH |
| NV1G1525 | NV1D3013 | 136 | GPQCQKWMQTCDRRRKCCEGFVCRLWCKKKLW-COOH |
| NV1G1255 | NV1D3014 | 137 | GPQCQKWMQTCDRERKCCEGFVCTLWCKKKLW-COOH |
| NV1G1187 | NV1D3015 | 138 | GPQCQKWMQTCDRERKCCEGFVCRLWCKKKLW-COOH |
| NV1G1257 | NV1D3016 | 139 | GPQCQKWMQTCDANRKCCEGFVCTLWCKKKLW-COOH |
| NV1G1221 | NV1D3017 | 140 | GPQCQKWMQTCDARRKCCEGFVCTLWCKKKLW-COOH |
| NV1G1521 | NV1D3018 | 141 | GPQCQKWMQTCDANRKCCEGFVCRLWCRKKLW-COOH |

TABLE 2-continued

| Protein name | Protoxin-II variant peptide name | SEQ ID NO: | Protein amino acid sequence |
|---|---|---|---|
| NV1G1531 | NV1D3019 | 142 | GPQCQKWMQTCDARRKCCEGFVCRLWCRKKLW-COOH |
| NV1G1239 | NV1D3020 | 143 | GPQCQKWMQTCDAERKCCEGFVCTLWCRKKLW-COOH |
| NV1G1583 | NV1D3030 | 144 | GPQCQKWMQTCDRNRKCCEGFVCTLWCKKKLW-COOH |
| NV1G1527 | NV1D3031 | 145 | GPQCQKWMQTCDRRRKCCEGFVCTLWCKKKLW-COOH |
| NV1G1511 | NV1D3032 | 146 | GPQCQKWMQTCDRNRKCCEGFVCRLWCRKKLW-COOH |
| NV1G1509 | NV1D3033 | 147 | GPQCQKWMQTCDRRRKCCEGFVCRLWCRKKLW-COOH |
| NV1G1231 | NV1D3035 | 148 | GPQCQKWMQTCDANRKCCEGFVCTLWCRKKLW-COOH |
| NV1G1211 | NV1D3036 | 149 | GPQCQKWMQTCDARRKCCEGFVCTLWCRKKLW-COOH |
| NV1G1267 | NV1D3044 | 150 | GPQCQKWMQTCDRNRKCCEGFVCTLWCRKKLW-COOH |
| NV1G1269 | NV1D3045 | 151 | GPQCQKWMQTCDRRRKCCEGFVCTLWCRKKLW-COOH |
| NV1G1215 | NV1D3048 | 152 | GPQCQKWMQTCDAKRKCCEGFVCRLWCKKKLW-COOH |
| NV1G1593 | NV1D3050 | 153 | GPQCQKWMQTCDRKRKCCEGFVCRLWCKKKLW-COOH |
| NV1G1263 | NV1D3051 | 154 | GPQCQKWMQTCDAKRKCCEGFVCTLWCKKKLW-COOH |
| NV1G1585 | NV1D3052 | 155 | GPQCQKWMQTCDAKRKCCEGFVCRLWCRKKLW-COOH |
| NV1G1623 | NV1D3056 | 156 | GPQCQKWMQTCDRKRKCCEGFVCTLWCKKKLW-COOH |
| NV1G1613 | NV1D3057 | 157 | GPQCQKWMQTCDRKRKCCEGFVCRLWCRKKLW-COOH |
| NV1G1259 | NV1D3058 | 158 | GPQCQKWMQTCDAKRKCCEGFVCTLWCRKKLW-COOH |
| NV1G1265 | NV1D3062 | 159 | GPQCQKWMQTCDRKRKCCEGFVCTLWCRKKLW-COOH |
| NV1G1273 | NV1D3109 | 160 | GPQCQKWMWTCDARRKCCEGFVCTLWCRKKLW-COOH |
| NV1G1225 | NV1D3121 | 161 | GPQCQKWMWTCDRKRKCCEGFVCTLWCRKKLW-COOH |
| NV1G1886 | NV1D3249 | 162 | GPAAAAAQCQKWMQTCDAERKCCEGFVCRLWCKKKLW-COOH |
| NV1G1633 | NV1D3251 | 163 | GPAPAPAQCQKWMQTCDAERKCCEGFVCRLWCKKKLW-COOH |
| NV1G1631 | NV1D3252 | 164 | GPQCQKWMQTCDAERKCCEGFVCRLWCKKKLWAPAPA-COOH |
| NV1G1885 | NV1D3254 | 165 | GPQCQKWMQTCDAERKCCEGFVCRLWCKKKLWGGGGG-COOH |
| NV1G1884 | NV1D3256 | 166 | GPCCNCSSKWCRDHSRCCGRGSAPAPAPAPAPGSQCQKWMQTCDAERKCCEGFVCRLWCKKKLW-COOH |
| NV1G1881 | NV1D3257 | 167 | GPQCQKWMQTCDAERKCCEGFVCRLWCKKKLWGSAPAPAPAPAPGSCCNCSSKWCRDHSRCC-COOH |
| NV1G1879 | NV1D3259 | 168 | GPQCQKWMQTCDAERKCCEGFVCRLWCKKKLWGSAPAPAPAPAPAPAPAPAPGSCCNCSSKWCRDHSRCCGR-COOH |
| NV1G1883 | NV1D3260 | 169 | GPCCNCSSKWCRDHSRCCGRGSAPAPAPAPAPAPAPAPAPAPGSQCQKWMQTCDAERKCCEGFVCRLWCKKKLW-COOH |
| NV1G1880 | NV1D3261 | 170 | GPQCQKWMQTCDAERKCCEGFVCRLWCKKKLWGSAPAPAPAPAPAPAPAPAPGSCCNCSSKWCRDHSRCC-COOH |
| NV1G1882 | NV1D3262 | 171 | GPCCNCSSKWCRDHSRCCGSAPAPAPAPAPAPAPAPAPAPGSQCQKWMQTCDAERKCCEGFVCRLWCKKKLW-COOH |

TABLE 2-continued

| Protein name | Protoxin-II variant peptide name | SEQ ID NO: | Protein amino acid sequence |
|---|---|---|---|
| NV1G1776 | NV1D3339 | 172 | GPQCRKWMQTCDRERKCCEGFVCTLWCRKKLW-COOH |
| NV1G1775 | NV1D3340 | 173 | GPQCKKWMQTCDRERKCCEGFVCTLWCRKKLW-COOH |
| NV1G1768 | NV1D3341 | 174 | GPQCTKWMQTCDRERKCCEGFVCTLWCRKKLW-COOH |
| NV1G1777 | NV1D3342 | 175 | GPQCAKWMQTCDRERKCCEGFVCTLWCRKKLW-COOH |
| NV1G1770 | NV1D3344 | 176 | GPQCEKWMQTCDRERKCCEGFVCTLWCRKKLW-COOH |
| NV1G1767 | NV1D3345 | 177 | GPQCSKWMQTCDRERKCCEGFVCTLWCRKKLW-COOH |
| NV1G1769 | NV1D3346 | 178 | GPQCQRWMQTCDRERKCCEGFVCTLWCRKKLW-COOH |
| NV1G1774 | NV1D3347 | 179 | GPQCQTWMQTCDRERKCCEGFVCTLWCRKKLW-COOH |
| NV1G1771 | NV1D3348 | 180 | GPQCQAWMQTCDRERKCCEGFVCTLWCRKKLW-COOH |
| NV1G1778 | NV1D3349 | 181 | GPQCQDWMQTCDRERKCCEGFVCTLWCRKKLW-COOH |
| NV1G1773 | NV1D3350 | 182 | GPQCQEWMQTCDRERKCCEGFVCTLWCRKKLW-COOH |
| NV1G1779 | NV1D3351 | 183 | GPQCQQWMQTCDRERKCCEGFVCTLWCRKKLW-COOH |
| NV1G1772 | NV1D3352 | 184 | GPQCQSWMQTCDRERKCCEGFVCTLWCRKKLW-COOH |
| NV1G1868 | NV1D3353 | 185 | GPQCQKWMQRCDRERKCCEGFVCTLWCRKKLW-COOH |
| NV1G1824 | NV1D3354 | 186 | GPQCQKWMQKCDRERKCCEGFVCTLWCRKKLW-COOH |
| NV1G1863 | NV1D3356 | 187 | GPQCQKWMQDCDRERKCCEGFVCTLWCRKKLW-COOH |
| NV1G1826 | NV1D3357 | 188 | GPQCQKWMQECDRERKCCEGFVCTLWCRKKLW-COOH |
| NV1G1810 | NV1D3358 | 189 | GPQCQKWMQQCDRERKCCEGFVCTLWCRKKLW-COOH |
| NV1G1836 | NV1D3359 | 190 | GPQCQKWMQSCDRERKCCEGFVCTLWCRKKLW-COOH |
| NV1G1834 | NV1D3360 | 191 | GPQCQKWMQTCRRERKCCEGFVCTLWCRKKLW-COOH |
| NV1G1829 | NV1D3361 | 192 | GPQCQKWMQTCKRERKCCEGFVCTLWCRKKLW-COOH |
| NV1G1820 | NV1D3362 | 193 | GPQCQKWMQTCTRERKCCEGFVCTLWCRKKLW-COOH |
| NV1G1828 | NV1D3363 | 194 | GPQCQKWMQTCARERKCCEGFVCTLWCRKKLW-COOH |
| NV1G1827 | NV1D3365 | 195 | GPQCQKWMQTCQRERKCCEGFVCTLWCRKKLW-COOH |
| NV1G1857 | NV1D3366 | 196 | GPQCQKWMQTCSRERKCCEGFVCTLWCRKKLW-COOH |
| NV1G1823 | NV1D3367 | 197 | GPQCQKWMQTCDRQRKCCEGFVCTLWCRKKLW-COOH |
| NV1G1818 | NV1D3368 | 198 | GPQCQKWMQTCDRTRKCCEGFVCTLWCRKKLW-COOH |
| NV1G1811 | NV1D3369 | 199 | GPQCQKWMQTCDREKKCCEGFVCTLWCRKKLW-COOH |
| NV1G1853 | NV1D3370 | 200 | GPQCQKWMQTCDRETKCCEGFVCTLWCRKKLW-COOH |
| NV1G1817 | NV1D3371 | 201 | GPQCQKWMQTCDREAKCCEGFVCTLWCRKKLW-COOH |
| NV1G1814 | NV1D3372 | 202 | GPQCQKWMQTCDREDKCCEGFVCTLWCRKKLW-COOH |
| NV1G1831 | NV1D3374 | 203 | GPQCQKWMQTCDREQKCCEGFVCTLWCRKKLW-COOH |
| NV1G1819 | NV1D3375 | 204 | GPQCQKWMQTCDRESKCCEGFVCTLWCRKKLW-COOH |
| NV1G1859 | NV1D3376 | 205 | GPQCQKWMQTCDRERRCCEGFVCTLWCRKKLW-COOH |
| NV1G1825 | NV1D3377 | 206 | GPQCQKWMQTCDRERTCCEGFVCTLWCRKKLW-COOH |
| NV1G1821 | NV1D3378 | 207 | GPQCQKWMQTCDRERACCEGFVCTLWCRKKLW-COOH |
| NV1G1835 | NV1D3379 | 208 | GPQCQKWMQTCDRERDCCEGFVCTLWCRKKLW-COOH |
| NV1G1815 | NV1D3380 | 209 | GPQCQKWMQTCDRERECCEGFVCTLWCRKKLW-COOH |

TABLE 2-continued

| Protein name | Protoxin-II variant peptide name | SEQ ID NO: | Protein amino acid sequence |
|---|---|---|---|
| NV1G1833 | NV1D3381 | 210 | GPQCQKWMQTCDRERQCCEGFVCTLWCRKKLW-COOH |
| NV1G1812 | NV1D3382 | 211 | GPQCQKWMQTCDRERSCCEGFVCTLWCRKKLW-COOH |
| NV1G1782 | NV1D3383 | 212 | GPQCQKWMQTCDRERKCCRGFVCTLWCRKKLW-COOH |
| NV1G1783 | NV1D3384 | 213 | GPQCQKWMQTCDRERKCCKGFVCTLWCRKKLW-COOH |
| NV1G1785 | NV1D3385 | 214 | GPQCQKWMQTCDRERKCCTGFVCTLWCRKKLW-COOH |
| NV1G1784 | NV1D3386 | 215 | GPQCQKWMQTCDRERKCCAGFVCTLWCRKKLW-COOH |
| NV1G1780 | NV1D3387 | 216 | GPQCQKWMQTCDRERKCCDGFVCTLWCRKKLW-COOH |
| NV1G1781 | NV1D3388 | 217 | GPQCQKWMQTCDRERKCCQGFVCTLWCRKKLW-COOH |
| NV1G1786 | NV1D3389 | 218 | GPQCQKWMQTCDRERKCCSGFVCTLWCRKKLW-COOH |
| NV1G1851 | NV1D3390 | 219 | GPQCQKWMQTCDRERKCCERFVCTLWCRKKLW-COOH |
| NV1G1852 | NV1D3391 | 220 | GPQCQKWMQTCDRERKCCEKFVCTLWCRKKLW-COOH |
| NV1G1854 | NV1D3392 | 221 | GPQCQKWMQTCDRERKCCETFVCTLWCRKKLW-COOH |
| NV1G1860 | NV1D3393 | 222 | GPQCQKWMQTCDRERKCCEAFVCTLWCRKKLW-COOH |
| NV1G1789 | NV1D3394 | 223 | GPQCQKWMQTCDRERKCCEDFVCTLWCRKKLW-COOH |
| NV1G1787 | NV1D3396 | 224 | GPQCQKWMQTCDRERKCCEQFVCTLWCRKKLW-COOH |
| NV1G1856 | NV1D3397 | 225 | GPQCQKWMQTCDRERKCCESFVCTLWCRKKLW-COOH |
| NV1G1855 | NV1D3398 | 226 | GPQCQKWMQTCDRERKCCEGFSCTLWCRKKLW-COOH |
| NV1G1788 | NV1D3399 | 227 | GPQCQKWMQTCDRERKCCEGFTCTLWCRKKLW-COOH |
| NV1G1849 | NV1D3400 | 228 | GPQCQKWMQTCDRERKCCEGFQCTLWCRKKLW-COOH |
| NV1G1795 | NV1D3401 | 229 | GPQCQKWMQTCDRERKCCEGFVCTLWCRRKLW-COOH |
| NV1G1803 | NV1D3403 | 230 | GPQCQKWMQTCDRERKCCEGFVCTLWCRAKLW-COOH |
| NV1G1807 | NV1D3408 | 231 | GPQCQKWMQTCDRERKCCEGFVCTLWCRKRLW-COOH |
| NV1G1806 | NV1D3409 | 232 | GPQCQKWMQTCDRERKCCEGFVCTLWCRKTLW-COOH |
| NV1G1805 | NV1D3410 | 233 | GPQCQKWMQTCDRERKCCEGFVCTLWCRKALW-COOH |
| NV1G1809 | NV1D3413 | 234 | GPQCQKWMQTCDRERKCCEGFVCTLWCRKQLW-COOH |
| NV1G1850 | NV1D3414 | 235 | GPQCQKWMQTCDRERKCCEGFVCTLWCRKSLW-COOH |
| NV1G1793 | NV1D3419 | 236 | GPQCQKWMQTCDRERKCCEGFVCTLWCRKKLD-COOH |
| NV1G1822 | NV1D3423 | 237 | GPQCQKWMQTCRRRKCCEGFVCTLWCRKKLW-COOH |
| NV1G1813 | NV1D3424 | 238 | GPQCQKWMQTCKRKRKCCEGFVCTLWCRKKLW-COOH |
| NV1G1840 | NV1D3425 | 239 | GPQCQKWMQTCRRRDKCCEGFVCTLWCRKKLW-COOH |
| NV1G1848 | NV1D3426 | 240 | GPQCQKWMQTCKRKDKCCEGFVCTLWCRKKLW-COOH |
| NV1G1841 | NV1D3427 | 241 | GPQCQKWMQTCRRREKCCEGFVCTLWCRKKLW-COOH |
| NV1G1844 | NV1D3428 | 242 | GPQCQKWMQTCKRKEKCCEGFVCTLWCRKKLW-COOH |
| NV1G1842 | NV1D3430 | 243 | GPQCQDWMQTCDRERKCCKGFVCTLWCRKKLW-COOH |
| NV1G1846 | NV1D3431 | 244 | GPQCQEWMQTCDRERKCCKGFVCTLWCRKKLW-COOH |
| NV1G1843 | NV1D3432 | 245 | GPQCQEWMQTCDRERKCCRGFVCTLWCRKKLW-COOH |
| NV1G1892 | NV1D3439 | 246 | GPQCQKWMQTCDRERKCCEGFVCTLWCRKKLG-COOH |

TABLE 2-continued

| Protein name | Protoxin-II variant peptide name | SEQ ID NO: | Protein amino acid sequence |
|---|---|---|---|
| NV1G1916 | NV1D3465 | 247 | GPQCQKFMQTCDRERKCCEGFVCTLWCRKKLW-COOH |
| NV1G1922 | NV1D3466 | 248 | GPQCQKWMQTCDEERKCCEGFVCTLWCRKKLW-COOH |
| NV1G1915 | NV1D3467 | 249 | GPQCQKWMQTCDRERKCCGGFVCTLWCRKKLW-COOH |
| NV1G1924 | NV1D3470 | 250 | GPQCQKWMQTCDRERKCCEGLVCTLWCRKKLW-COOH |
| NV1G1709 | NV1D3510 | 251 | GPQCQKWMQTCDRERKCCEGFVCTLWCRKKLWAPAPAS PGARAF-COOH |
| NV1G1681 | NV1D3511 | 252 | GPQCQKWMQTCDRERKCCEGFVCTLWCRKKLWSPGARA F-COOH |
| NV1G1693 | NV1D3512 | 253 | GPQCQKWMQTCDRERKCCEGFVCTLWCRKKLWAPAPAP APAPDGPWRKM-COOH |
| NV1G1705 | NV1D3513 | 254 | GPQCQKWMQTCDRERKCCEGFVCTLWCRKKLWAPAPAD GPWRKM-COOH |
| NV1G1689 | NV1D3514 | 255 | GPQCQKWMQTCDRERKCCEGFVCTLWCRKKLWDGPWRK M-COOH |
| NV1G1711 | NV1D3515 | 256 | GPQCQKWMQTCDRERKCCEGFVCTLWCRKKLWAPAPAP APAPFGQKASS-COOH |
| NV1G1685 | NV1D3516 | 257 | GPQCQKWMQTCDRERKCCEGFVCTLWCRKKLWAPAPAF GQKASS-COOH |
| NV1G1697 | NV1D3517 | 258 | GPQCQKWMQTCDRERKCCEGFVCTLWCRKKLWFGQKAS S-COOH |
| NV1G1695 | NV1D3518 | 259 | GPQCQKWMQTCDRERKCCEGFVCTLWCRKKLWAPAPAP APAPQRFVTGHFGGLYPANG-COOH |
| NV1G1701 | NV1D3519 | 260 | GPQCQKWMQTCDRERKCCEGFVCTLWCRKKLWAPAPAQ RFVTGHFGGLYPANG-COOH |
| NV1G1691 | NV1D3520 | 261 | GPQCQKWMQTCDRERKCCEGFVCTLWCRKKLWQRFVTG HFGGLYPANG-COOH |
| NV1G1679 | NV1D3521 | 262 | GPQCQKWMQTCDRERKCCEGFVCTLWCRKKLWAPAPAP APAPRRRRRRRRRRR-COOH |
| NV1G1683 | NV1D3523 | 263 | GPQCQKWMQTCDRERKCCEGFVCTLWCRKKLWRRRRRR RRRRR-COOH |
| NV1G1707 | NV1D3524 | 264 | GPQCQKWMQTCDRERKCCEGFVCTLWCRKKLWAPAPAP APAPYGRKKRRQRRR-COOH |
| NV1G1713 | NV1D3525 | 265 | GPQCQKWMQTCDRERKCCEGFVCTLWCRKKLWAPAPAY GRKKRRQRRR-COOH |
| NV1G1687 | NV1D3526 | 266 | GPQCQKWMQTCDRERKCCEGFVCTLWCRKKLWYGRKKR RQRRR-COOH |
| NV1G1699 | NV1D3527 | 267 | GPQCQKWMQTCDRERKCCEGFVCTLWCRKKLWAPAPAP APAP-COOH |
| NV1G1675 | NV1D3528 | 268 | GPQCQKWMQTCDRERKCCEGFVCTLWCRKKLWAPAPA- COOH |
| NV1G1754 | NV1D3529 | 269 | GPRCQKWMQTCDAKRKCCEGFVCTLWCRKKLW-COOH |
| NV1G1748 | NV1D3530 | 270 | GPSCQKWMQTCDAKRKCCEGFVCTLWCRKKLW-COOH |
| NV1G1747 | NV1D3531 | 271 | GPYCQKWMQTCDAKRKCCEGFVCTLWCRKKLW-COOH |
| NV1G1752 | NV1D3532 | 272 | GPACQKWMQTCDAKRKCCEGFVCTLWCRKKLW-COOH |
| NV1G1722 | NV1D3533 | 273 | GPQCQKWMQTCDAKRKCCEGFSCTLWCRKKLW-COOH |
| NV1G1744 | NV1D3534 | 274 | GPRCQKWMQTCDAKRKCCEGFSCTLWCRKKLW-COOH |
| NV1G1742 | NV1D3535 | 275 | GPSCQKWMQTCDAKRKCCEGFSCTLWCRKKLW-COOH |

TABLE 2-continued

| Protein name | Protoxin-II variant peptide name | SEQ ID NO: | Protein amino acid sequence |
|---|---|---|---|
| NV1G1723 | NV1D3536 | 276 | GPYCQKWMQTCDAKRKCCEGFSCTLWCRKKLW-COOH |
| NV1G1745 | NV1D3537 | 277 | GPACQKWMQTCDAKRKCCEGFSCTLWCRKKLW-COOH |
| NV1G1757 | NV1D3538 | 278 | GPRCQKWMQTCDRNRKCCEGFVCTLWCRKKLW-COOH |
| NV1G1762 | NV1D3539 | 279 | GPSCQKWMQTCDRNRKCCEGFVCTLWCRKKLW-COOH |
| NV1G1763 | NV1D3540 | 280 | GPYCQKWMQTCDRNRKCCEGFVCTLWCRKKLW-COOH |
| NV1G1728 | NV1D3541 | 281 | GPACQKWMQTCDRNRKCCEGFVCTLWCRKKLW-COOH |
| NV1G1730 | NV1D3542 | 282 | GPQCQKWMQTCDRNRKCCEGFSCTLWCRKKLW-COOH |
| NV1G1760 | NV1D3543 | 283 | GPRCQKWMQTCDRNRKCCEGFSCTLWCRKKLW-COOH |
| NV1G1727 | NV1D3544 | 284 | GPSCQKWMQTCDRNRKCCEGFSCTLWCRKKLW-COOH |
| NV1G1729 | NV1D3545 | 285 | GPYCQKWMQTCDRNRKCCEGFSCTLWCRKKLW-COOH |
| NV1G1867 | NV1D3546 | 286 | GPACQKWMQTCDRNRKCCEGFSCTLWCRKKLW-COOH |
| NV1G1759 | NV1D3547 | 287 | GPRCQKWMQTCDRERKCCEGFVCTLWCRKKLW-COOH |
| NV1G1758 | NV1D3548 | 288 | GPSCQKWMQTCDRERKCCEGFVCTLWCRKKLW-COOH |
| NV1G1766 | NV1D3549 | 289 | GPYCQKWMQTCDRERKCCEGFVCTLWCRKKLW-COOH |
| NV1G1761 | NV1D3550 | 290 | GPACQKWMQTCDRERKCCEGFVCTLWCRKKLW-COOH |
| NV1G1726 | NV1D3551 | 291 | GPRCQKWMQTCDRERKCCEGFSCTLWCRKKLW-COOH |
| NV1G1721 | NV1D3552 | 292 | GPSCQKWMQTCDRERKCCEGFSCTLWCRKKLW-COOH |
| NV1G1765 | NV1D3553 | 293 | GPYCQKWMQTCDRERKCCEGFSCTLWCRKKLW-COOH |
| NV1G1764 | NV1D3554 | 294 | GPACQKWMQTCDRERKCCEGFSCTLWCRKKLW-COOH |
| NV1G1732 | NV1D3555 | 295 | GPRCQKWMQTCDAERKCCEGFSCTLWCKKKLW-COOH |
| NV1G1862 | NV1D3556 | 296 | GPYCQKWMQTCDAERKCCEGFSCTLWCKKKLW-COOH |
| NV1G1751 | NV1D3558 | 297 | GPRCQKWMQTCDANRKCCEGFSCTLWCKKKLW-COOH |
| NV1G1866 | NV1D3559 | 298 | GPSCQKWMQTCDANRKCCEGFSCTLWCKKKLW-COOH |
| NV1G1865 | NV1D3560 | 299 | GPYCQKWMQTCDANRKCCEGFSCTLWCKKKLW-COOH |
| NV1G1716 | NV1D3561 | 300 | GPACQKWMQTCDANRKCCEGFSCTLWCKKKLW-COOH |
| NV1G1724 | NV1D3562 | 301 | GPRCQKWMQTCDARRKCCEGFSCTLWCKKKLW-COOH |
| NV1G1717 | NV1D3563 | 302 | GPSCQKWMQTCDARRKCCEGFSCTLWCKKKLW-COOH |
| NV1G1743 | NV1D3564 | 303 | GPYCQKWMQTCDARRKCCEGFSCTLWCKKKLW-COOH |
| NV1G1720 | NV1D3565 | 304 | GPACQKWMQTCDARRKCCEGFSCTLWCKKKLW-COOH |
| NV1G1735 | NV1D3566 | 305 | GPRCQKWMQTCDAERKCCEGFVCTLWCKKKLW-COOH |
| NV1G1734 | NV1D3568 | 306 | GPACQKWMQTCDAERKCCEGFVCTLWCKKKLW-COOH |
| NV1G1741 | NV1D3569 | 307 | GPRCQKWMQTCDARRKCCEGFVCTLWCKKKLW-COOH |
| NV1G1719 | NV1D3570 | 308 | GPSCQKWMQTCDARRKCCEGFVCTLWCKKKLW-COOH |
| NV1G1718 | NV1D3571 | 309 | GPYCQKWMQTCDARRKCCEGFVCTLWCKKKLW-COOH |
| NV1G1725 | NV1D3572 | 310 | GPACQKWMQTCDARRKCCEGFVCTLWCKKKLW-COOH |
| NV1G1869 | NV1D3573 | 311 | GPRCQKWMQTCDANRKCCEGFVCTLWCKKKLW-COOH |
| NV1G1755 | NV1D3574 | 312 | GPSCQKWMQTCDANRKCCEGFVCTLWCKKKLW-COOH |

TABLE 2-continued

| Protein name | Protoxin-II variant peptide name | SEQ ID NO: | Protein amino acid sequence |
|---|---|---|---|
| NV1G1756 | NV1D3575 | 313 | GPYCQKWMQTCDANRKCCEGFVCTLWCKKKLW-COOH |
| NV1G1746 | NV1D3576 | 314 | GPACQKWMQTCDANRKCCEGFVCTLWCKKKLW-COOH |
| NV1G1733 | NV1D3577 | 315 | GPRCQKWMQTCDAERKCCEGFSCRLWCKKKLW-COOH |
| NV1G1738 | NV1D3578 | 316 | GPYCQKWMQTCDAERKCCEGFSCRLWCKKKLW-COOH |
| NV1G1737 | NV1D3579 | 317 | GPACQKWMQTCDAERKCCEGFSCRLWCKKKLW-COOH |
| NV1G1740 | NV1D3580 | 318 | GPRCQKWMQTCDARRKCCEGFSCRLWCKKKLW-COOH |
| NV1G1864 | NV1D3581 | 319 | GPSCQKWMQTCDARRKCCEGFSCRLWCKKKLW-COOH |
| NV1G1739 | NV1D3582 | 320 | GPYCQKWMQTCDARRKCCEGFSCRLWCKKKLW-COOH |
| NV1G1870 | NV1D3583 | 321 | GPACQKWMQTCDARRKCCEGFSCRLWCKKKLW-COOH |
| NV1G1715 | NV1D3584 | 322 | GPRCQKWMQTCDANRKCCEGFSCRLWCKKKLW-COOH |
| NV1G1753 | NV1D3585 | 323 | GPSCQKWMQTCDANRKCCEGFSCRLWCKKKLW-COOH |
| NV1G1750 | NV1D3586 | 324 | GPYCQKWMQTCDANRKCCEGFSCRLWCKKKLW-COOH |
| NV1G1750-NH2 | NV1D3586-NH2 | 325 | GPYCQKWMQTCDANRKCCEGFSCRLWCKKKLW-NH2 |
| NV1G1749 | NV1D3587 | 326 | GPACQKWMQTCDANRKCCEGFSCRLWCKKKLW-COOH |
| NV1G1871 | NV1D3772 | 327 | GPQCQKWMQTCDRERKCCEGFVCTLWCRKKLWSHSNTQ TLAKAPEHTG-COOH |
| NV1G1839 | NV1D3774 | 328 | GPSHSNTQTLAKAPEHTGAPAPAPAPAPAPAPAPAPAP QCQKWMQTCDRERKCCEGFVCTLWCRKKLW-COOH |
| NV1G1877 | NV1D3775 | 329 | GPSHSNTQTLAKAPEHTGAPAPAPAPAPQCQKWMQTCD RERKCCEGFVCTLWCRKKLW-COOH |
| NV1G1872 | NV1D3777 | 330 | GPSHSNTQTLAKAPEHTGQCQKWMQTCDRERKCCEGFV CTLWCRKKLW-COOH |
| NV1G1941 | NV1D3782 | 331 | GPQCQKWMQTCDRERKCCEGFVCTLWCRKKAW-COOH |
| NV1G1990 | NV1D3788 | 332 | GPAAAAAQCQKWMQTCDRERKCCEGFVCTLWCRKKLW- COOH |
| NV1G1991 | NV1D3789 | 333 | GPAPAPAQCQKWMQTCDRERKCCEGFVCTLWCRKKLW- COOH |
| NV1G1989 | NV1D3791 | 334 | GPQCQKWMQTCDRERKCCEGFVCTLWCRKKLWAAAAA- COOH |
| NV1G1993 | NV1D3792 | 335 | GPQCQKWMQTCDRERKCCEGFVCTLWCRKKLWGGGGG- COOH |
| NV1G1967 | NV1D3793 | 336 | GPCCNCSSKWCRDHSRCCGRGSAPAPAPAPAPAPAPAP APAPGSQCQKWMQTCDRERKCCEGFVCTLWCRKKLW- COOH |
| NV1G1969 | NV1D3795 | 337 | GPCCNCSSKWCRDHSRCCGSAPAPAPAPAPAPAPAPAP APGSQCQKWMQTCDRERKCCEGFVCTLWCRKKLW- COOH |
| NV1G1974 | NV1D3796 | 338 | GPCCNCSSKWCRDHSRCCGSAPAPAPAPAPGSQCQKWM QTCDRERKCCEGFVCTLWCRKKLW-COOH |
| NV1G1950 | NV1D3797 | 339 | GPQCQKWMQTCDRERKCCEGFVCTLWCRKKLWGSAPAP APAPAPAPAPAPAPGSCCNCSSKWCRDHSRCC- COOH |
| NV1G1948 | NV1D3798 | 340 | GPQCQKWMQTCDRERKCCEGFVCTLWCRKKLWGSAPAP APAPAPAPAPAPAPGSCCNCSSKWCRDHSRCCGR- COOH |
| NV1G2057 | NV1D3799 | 341 | GPQCQKWMQTCDRERKCCEGFVCTLWCRKKLWGSAPAP APAPAPGSCCNCSSKWCRDHSRCC-COOH |

TABLE 2-continued

| Protein name | Protoxin-II variant peptide name | SEQ ID NO: | Protein amino acid sequence |
|---|---|---|---|
| NV1G1954 | NV1D3800 | 342 | GPQCQKWMQTCDRERKCCEGFVCTLWCRKKLWGSAPAPAPAPAPGSCCNCSSKWCRDHSRCCGR-COOH |
| NV1G1956 | NV1D3801 | 343 | GPSPGARAFAPAPAPAPAPQCQKWMQTCDRERKCCEGFVCTLWCRKKLW-COOH |
| NV1G1961 | NV1D3802 | 344 | GPSPGARAFAPAPAQCQKWMQTCDRERKCCEGFVCTLWCRKKLW-COOH |
| NV1G1960 | NV1D3803 | 345 | GPSPGARAFQCQKWMQTCDRERKCCEGFVCTLWCRKKLW-COOH |
| NV1G1977 | NV1D3804 | 346 | GPDGPWRKMAPAPAPAPAPQCQKWMQTCDRERKCCEGFVCTLWCRKKLW-COOH |
| NV1G1982 | NV1D3805 | 347 | GPDGPWRKMAPAPAQCQKWMQTCDRERKCCEGFVCTLWCRKKLW-COOH |
| NV1G1984 | NV1D3806 | 348 | GPDGPWRKMQCQKWMQTCDRERKCCEGFVCTLWCRKKLW-COOH |
| NV1G1985 | NV1D3808 | 349 | GPFGQKASSAPAPAQCQKWMQTCDRERKCCEGFVCTLWCRKKLW-COOH |
| NV1G1983 | NV1D3809 | 350 | GPFGQKASSQCQKWMQTCDRERKCCEGFVCTLWCRKKLW-COOH |
| NV1G1973 | NV1D3810 | 351 | GPQRFVTGHFGGLYPANGAPAPAPAPAPQCQKWMQTCDRERKCCEGFVCTLWCRKKLW-COOH |
| NV1G1976 | NV1D3811 | 352 | GPQRFVTGHFGGLYPANGAPAPAQCQKWMQTCDRERKCCEGFVCTLWCRKKLW-COOH |
| NV1G1980 | NV1D3812 | 353 | GPQRFVTGHFGGLYPANGQCQKWMQTCDRERKCCEGFVCTLWCRKKLW-COOH |
| NV1G1952 | NV1D3813 | 354 | GPRRRRRRRRRRRAPAPAPAPAPQCQKWMQTCDRERKCCEGFVCTLWCRKKLW-COOH |
| NV1G1957 | NV1D3814 | 355 | GPRRRRRRRRRRRAPAPAQCQKWMQTCDRERKCCEGFVCTLWCRKKLW-COOH |
| NV1G1981 | NV1D3815 | 356 | GPRRRRRRRRRRRQCQKWMQTCDRERKCCEGFVCTLWCRKKLW-COOH |
| NV1G1959 | NV1D3818 | 357 | GPYGRKKRRQRRRQCQKWMQTCDRERKCCEGFVCTLWCRKKLW-COOH |
| NV1G1986 | NV1D3819 | 358 | GPAPAPAPAPAPQCQKWMQTCDRERKCCEGFVCTLWCRKKLW-COOH |
| NV1G1968 | NV1D3822 | 359 | GPGWCGDPGATCGKLRLYCCSGFCDSYTKTCKDKSSAGGGGSAPAPAPAPAPAPAPAPAPAPAPAPAPAPGGGGSQCQKWMQTCDRERKCCEGFVCTLWCRKKLW-COOH |
| NV1G1945 | NV1D3823 | 360 | GPQCQKWMQTCDRERKCCEGFVCTLWCRKKLWGGGGSAPAPAPAPAPAPAPAPAPAPAPAPAPAPAPGGGGSGWCGDPGATCGKLRLYCCSGFCDSYTKTCKDKSSA-COOH |
| NV1G1972 | NV1D3824 | 361 | GPGWCGDPGATCGKLRLYCCSGFCDAYTKTCKDKSSAGGGGSAPAPAPAPAPAPAPAPAPAPAPAPAPAPGGGGSQCQKWMQTCDRERKCCEGFVCTLWCRKKLW-COOH |
| NV1G1946 | NV1D3825 | 362 | GPQCQKWMQTCDRERKCCEGFVCTLWCRKKLWGGGGSAPAPAPAPAPAPAPAPAPAPAPAPAPAPAPGGGGSGWCGDPGATCGKLRLYCCSGFCDAYTKTCKDKSSA-COOH |
| NV1G1970 | NV1D3826 | 363 | GPGWCGDPGATCGKLRLYCCSGFCDCYTKTCKDKSSAGGGGSAPAPAPAPAPAPAPAPAPAPAPAPAPAPGGGGSQCQKWMQTCDRERKCCEGFVCTLWCRKKLW-COOH |
| NV1G1949 | NV1D3828 | 364 | GPQCQKWMQTCDRERKCCEGFVCTLWCRKKLWGSGGGGSAPAPAPAPAPAPAPAPAPGGGGSGSCCNCSSKWCRDHSRCCGR-COOH |

TABLE 2-continued

| Protein name | Protoxin-II variant peptide name | SEQ ID NO: | Protein amino acid sequence |
|---|---|---|---|
| NV1G1951 | NV1D3829 | 365 | GPQCQKWMQTCDRERKCCEGFVCTLWCRKKLWGSGGGG SAPAPAPAPAPAPAPAPAPAPAPAPGGGGSGSCCNCSSKWCR DHSRCC-COOH |
| NV1G1971 | NV1D3830 | 366 | GPCCNCSSKWCRDHSRCCGRGSGGGGSAPAPAPAPAPA PAPAPAPAPGGGGSGSQCQKWMQTCDRERKCCEGFVCT LWCRKKLW-COOH |
| NV1G1975 | NV1D3832 | 367 | GPCRTIGPSVCAPAPAPAPAPAPAPAPAPAPCQKWMQ TCDRERKCCEGFVCTLWCRKKLW-COOH |
| NV1G1978 | NV1D3833 | 368 | GPCRTIGPSVCAPAPAPAPAPCQKWMQTCDRERKCCE GFVCTLWCRKKLW-COOH |
| NV1G1979 | NV1D3834 | 369 | GPCRTIGPSVCAPAPAQCQKWMQTCDRERKCCEGFVCT LWCRKKLW-COOH |
| NV1G2043 | NV1D3835 | 370 | GPCRTIGPSVCQCQKWMQTCDRERKCCEGFVCTLWCRK KLW-COOH |
| NV1G1955 | NV1D3838 | 371 | GPQCQKWMQTCDRERKCCEGFVCTLWCRKKLWAPAPAC RTIGPSVC-COOH |

In some embodiments, the isolated Protoxin-II variant inhibits human Nav1.7 activity with an $IC_{50}$ value of about $3 \times 10^{-8}$ M or less.

In some embodiments, the isolated Protoxin-II variant inhibits human Nav1.7 activity with an $IC_{50}$ value of between about $3 \times 10^{-8}$ M to about $1 \times 10^{-9}$ M.

Another embodiment of the invention is an isolated Protoxin-II variant comprising the amino acid sequence (SEQ ID NO: 404)
$GPQCX_1X_2WX_3QX_4Cx_5X_6X_7X_8X_9CCX_{10}X_{11}FX_{12}CX_{13}LWCX_{14}KKLW$, wherein
$X_1$ is Q, R, K, A or S;
$X_2$ is K, S, Q or R;
$X_3$ is M or F;
$X_4$ is T, S, R, K or Q;
$X_5$ is D or T;
$X_6$ is S, A or R;
$X_7$ is E, R, N, K, T or Q;
$X_8$ is R or K;
$X_9$ is K, Q, S or A;
$X_{10}$ is E, Q or D;
$X_{11}$ is G or Q;
$X_{12}$ is V or S;
$X_{13}$ is R or T; and
$X_{14}$ is K or R.

Exemplary Protoxin-II variants that inhibit human Nav1.7 activity with an $IC_{50}$ value of about $30 \times 10^{-9}$ M or less are variants comprising the amino acid sequences of SEQ ID NOs: 56, 78, 111, 114, 117, 118, 119, 122, 123, 129, 130, 131, 132, 133, 134, 135, 136, 138, 139, 140, 141, 142, 145, 146, 147, 149, 150, 151, 152, 153, 154, 156, 158, 159, 165, 172, 173, 175, 177, 178, 183, 184, 185, 186, 189, 190, 193, 197, 199, 207, 210, 211, 216, 217, 224, 266, 273, 282 or 335.

In some embodiments, the isolated Protoxin-II variant selectively inhibits human Nav1.7. The Protoxin-II variants of the invention may be more selective towards Nav1.7 when compared to the recombinant Protoxin-II (SEQ ID NO: 2). In the QPatch electrophysiology assay, recombinant Protoxin-II has an $IC_{50}$ of about $2.2 \times 10^{-9}$ M for Nav1.7 and an $IC_{50}$ of about $62 \times 10^{-9}$ M for Nav1.6, and therefore the ratio of $IC_{50}$ for Nav1.6 to $IC_{50}$ for Nav1.7 about 28 fold. "Selectivity" or "selective" or "more selective" or "selectively blocks" or "selectively inhibits" when used herein refers to a Protoxin-II variant that has a ratio of $IC_{50}$ for Nav1.6 to $IC_{50}$ for Nav1.7 ($IC_{50}$ (Nav1.6)/$IC_{50}$ (Nav1.7)) equal or over about 30. $IC_{50}$ for Nav1.6 may be assayed in a QPatch electrophysiology assay using cell lines stably expressing Nav1.6 using similar methods to those described for Nav1.7.

Residue positions in Protoxin-II that can be mutagenized to improve selectivity include residues 7 and 19, and optionally residues 1 and 11, and further optionally 12, 20, 22 and 26 (residue numbering according to SEQ ID NO: 1). Exemplary substitutions to improve selectivity are Y1Q, W7Q, S11R, S11A, E12T, M19F, V20S, R22T, and K26R. Exemplary Protoxin-II variants with improved selectivity are variants of SEQ ID NOs: 56, 59, 65, 78, 111, 114, 117, 118, 119, 121, 122, 123, 129, 130, 133, 150, 190, 217, 281, 324, 325 or 326.

Another embodiment of the invention is an isolated Protoxin-II variant comprising the sequence (SEQ ID NO: 405)
$GPX_1CQKWMQX_2CDX_3X_4RKCCX_5GFX_6CX_7LWCX_8KKLW$;

wherein
$X_1$ is Y, Q, A, S or R;
$X_2$ is T or S;
$X_3$ is S, R or A;
$X_4$ is E, T or N;
$X_5$ is E or Q;
$X_6$ is V or S;
$X_7$ is R or T; and
$X_8$ is K or R;
wherein the Protoxin-II variant inhibits human Nav1.7 activity with an $IC_{50}$ value of about $3 \times 10^{-8}$ M or less, and selectively inhibits human Nav1.7.

In some embodiments, the isolated Protoxin-II variant comprises the sequence

GPQCQKWMQX$_1$CDX$_2$X$_3$RKCCX$_4$GFX$_5$CX$_6$LWCX$_8$KKLW; (SEQ ID NO: 406)

wherein
X$_1$ is T or S;
X$_2$ is S, R or A;
X$_3$ is E, T or N;
X$_4$ is E or Q;
X$_5$ is V or S;
X$_6$ is R or T; and
X$_7$ is K or R.

Another embodiment is an isolated Protoxin-II variant comprising the amino acid sequence that is 90%, 91%, 92%, 93%, 94%, 95%, 96%, 97%, 98% or 99% identical to the amino acid sequence of SEQ ID NO: 78

(GPQCQKWMQTCDRERKCCEGFVCTLWCRKKLW-COOH);

wherein
the amino acid sequence has Q at position 1, Q at position 7 and F at position 19, when residue numbering is according to SEQ ID NO: 1;
the polypeptide inhibits human Nav1.7 activity with an IC$_{50}$ value of about 30×10$^{-9}$ M or less, wherein the IC$_{50}$ value is measured using a FLIPR® Tetra membrane depolarization assay using fluorescence resonance energy transfer (FRET) in the presence of 25×10$^{-6}$ M 3-veratroylveracevine in HEK293 cells stably expressing human Nav1.7; and
the polypeptide selectively inhibits Nav1.7.

In some embodiments, the isolated Protoxin-II variant has a free C-terminal carboxylic acid, amide, methylamide or butylamide group, which are generated via routine synthetic methods.

Another embodiment of the invention is an isolated fusion protein comprising the Protoxin-II variant of SEQ ID NOs: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 109, 110, 111, 112, 113, 114, 115, 116, 117, 118, 119, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 35, 357, 358, 359, 360, 361, 362, 363, 364, 365, 366, 367, 368 367, 370 or 371. Such second polypeptides may be well known leader or secretory signal sequences, or synthetic sequences resulting for example from cloning steps, or tags such as hexahistidine tag (SEQ ID NO: 108). Such second polypeptide may be a half-life extending moiety. In one embodiment, the isolated fusion protein comprises the Protoxin-II variant of the invention conjugated to a half-life extending moiety.

Exemplary half-life extending moieties that can be used include well known human serum albumin, transthyretin (TTR), a thyroxine-binding globulin (TGB), albumin-binding domains, or an Fc or fragments thereof. Biologically suitable polymers or copolymers may also be used, for example ethylene glycol or polyethylene glycol (PEG) molecules, such as PEG5000 or PEG20000, dextran, polylysine, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, octane, or carbohydrates (dextran, cellulose, oligo- or polysaccharides). These moieties may be direct fusions with the Protoxin-II variant polypeptides and may be generated by standard cloning and expression techniques. Alternatively, well known chemical coupling methods may be used to attach the moieties to recombinantly produced Protoxin-II variants of the invention.

In another embodiment, the half-life extending moiety of the fusion protein of the invention is human serum albumin, albumin binding domain (ABD), or polyethylene glycol (PEG).

In another embodiment, the half-life extending moiety of is conjugated to the Protoxin-II variant via a linker. Suitable linkers are well known and include linkers having the sequence shown in SEQ ID NOs: 80 or 81.

Exemplary fusion proteins incorporating Protoxin-II variants of the invention are those having the polypeptide sequence of SEQ ID NOs: 83, 85, 87, 89, 91, 93, 95, 97, 99, 101 or 103.

Protoxin-II variants of the invention incorporating additional moieties may be compared for functionality by several well-known assays. For example, pharmacokinetic properties of Protoxin-II variants coupled to PEG may be evaluated in well known in vivo models.

Additional Protoxin-II variants and Protoxin-II variant fusion proteins are within the scope of the invention. Additional substitutions to the Protoxin-II variants of the invention can be made as long as the resulting variant or the fusion protein retains similar characteristics when compared to the parent peptide. Exemplary modifications are for example conservative substitutions that will result in Protoxin-II variants with similar characteristics to those of the parent molecules. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. Alternatively, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally grouped separately as aliphatic-hydroxyl; (4) aromatic (phenylalanine, tyrosine, tryptophan); (5) amide (asparagine, glutamine); and (6) sulfur-containing (cysteine and methionine)

(Stryer (ed.), Biochemistry, 2nd ed, WH Freeman and Co., 1981). Non-conservative substitutions can be made to the Protoxin-II variants that involve substitutions of amino acid residues between different classes of amino acids to improve properties of the Protoxin-II variants and Protoxin-II variant fusion proteins. Whether a change in the amino acid sequence of a polypeptide or fragment thereof results in a functional homolog can be readily determined by assessing the ability of the modified polypeptide or fragment to produce a response in a fashion similar to the unmodified polypeptide or fragment using the assays described herein. Peptides, polypeptides or proteins in which more than one replacement takes place can readily be tested in the same manner.

Another embodiment of the invention is an isolated synthetic polynucleotide comprising a polynucleotide encoding the Protoxin-II variant of the invention.

Certain exemplary synthetic polynucleotides are disclosed herein, however, other synthetic polynucleotides which, given the degeneracy of the genetic code or codon preferences in a given expression system, encode the Protoxin-II variants and Protoxin-II variant fusion proteins of the invention are also within the scope of the invention. Exemplary synthetic polynucleotides are for example polynucleotide sequences shown in SEQ ID NOs: 84, 86, 88, 90, 92, 94, 96, 98, 100, 102 and 104, which encode the Protoxin-II variant fusion proteins of the invention. Those skilled in the art can readily identify the polynucleotide segments in the fusion proteins that encode the Protoxin-II variant itself. The synthetic polynucleotide sequences encoding the Protoxin-II variants or fusion proteins of the invention can be operably linked to one or more regulatory elements, such as a promoter and enhancer, that allow expression of the nucleotide sequence in the intended host cell. The synthetic polynucleotide may be a cDNA.

The polynucleotides of the invention may be produced by chemical synthesis such as solid phase polynucleotide synthesis on an automated polynucleotide synthesizer. Alternatively, the polynucleotides of the invention may be produced by other techniques such as PCR based duplication, vector based duplication, or restriction enzyme based DNA manipulation techniques. Techniques for producing or obtaining polynucleotides of known sequences are well known.

The polynucleotides of the invention may also comprise at least one non-coding sequence, such as transcribed but not translated sequences, termination signals, ribosome binding sites, mRNA stabilizing sequences, introns and polyadenylation signals. The polynucleotide sequences may also comprise additional sequences encoding additional amino acids. These additional polynucleotide sequences may, for example, encode a marker or well-known tag sequences such as a hexa-histidine (SEQ ID NO: 108) or a HA tag which facilitate the purification of fused polypeptides.

Another embodiment of the invention is a vector comprising the polynucleotide of the invention. Such vectors may be plasmid vectors, viral vectors, vectors for baculovirus expression, transposon based vectors or any other vector suitable for introduction of the polynucleotide of the invention into a given organism or genetic background by any means. For example, polynucleotides encoding the Protoxin-II variants or the Protoxin-II variant fusion proteins of the invention are inserted into an expression vector and may be operably linked to control sequences in the expression vector to ensure efficient expression, such as signal sequences, promoters (e.g. naturally associated or heterologous promoters), enhancer elements, and transcription termination sequences, and are chosen to be compatible with the host cell chosen to express the Protoxin-II variant or the Protoxin-II variant fusion protein of the invention. Once the vector has been incorporated into the appropriate host, the host is maintained under conditions suitable for high level expression of the proteins encoded by the incorporated polynucleotides.

Suitable expression vectors are typically replicable in the host organisms either as episomes or as an integral part of the host chromosomal DNA. Commonly, expression vectors contain selection markers such as ampicillin-resistance, hygromycin-resistance, tetracycline resistance, kanamycin resistance or neomycin resistance to permit detection of those cells transformed with the desired DNA sequences.

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters. For expression in a yeast cell, a suitable promoter is a constitutive promoter such as an ADH1 PGK1, ENO or PYK1 promoter and the like, or a regulatable promoter such as a GAL1 or GAL10 promoter. Selection of the appropriate vector and promoter is well within the level of ordinary skill in the art.

Large numbers of suitable vectors and promoters are known to those of skill in the art; many are commercially available for generating recombinant constructs. The following vectors are provided by way of example. Bacterial: pBs, phagescript, PsiX174, pBluescript SK, pBs KS, pNH8a, pNH16a, pNHl8a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

An exemplary vector for expression of the Protoxin-II variants or Protoxin-II variant fusion proteins is a vector having ampicillin-resistance selection marker, CMV promoter, CMV intron, signal peptide, neomycin resistance, f1 origin of replication, SV40 polyadenylation signal, and cDNA encoding the Protoxin-II variant or the Protoxin-II variant fusion protein of the invention.

Another embodiment of the invention is a host cell comprising the vector of the invention. The term "host cell" refers to a cell into which a vector has been introduced. It is understood that the term host cell is intended to refer not only to the particular subject cell but also to the progeny of such a cell. Because certain modifications may occur in succeeding generations due to either mutation or environmental influences, such progeny may not be identical to the parent cell, but are still included within the scope of the term "host cell" as used herein. Such host cells may be eukaryotic cells, prokaryotic cells, plant cells or archeal cells.

*Escherichia coli*, bacilli, such as *Bacillus subtilis*, and other enterobacteriaceae, such as *Salmonella, Serratia*, and various *Pseudomonas* species, are examples of prokaryotic host cells. Other microbes, such as yeast, are also useful for expression. *Saccharomyces* (e.g., *S. cerevisiae*) and *Pichia* are examples of suitable yeast host cells. Exemplary eukaryotic cells may be of mammalian, insect, avian or other animal origins. Mammalian eukaryotic cells include immortalized cell lines such as hybridomas or myeloma cell lines such as SP2/0 (American Type Culture Collection (ATCC), Manassas, Va., CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHO-K1SV (Lonza Biologics, Walkersville, Md.), CHO-K1 (ATCC CRL-61) or DG44.

Introduction of a polynucleotide, such as a vector, into a host cell can be effected by methods well known to those skilled in the art. Exemplary methods are calcium phosphate transfection, DEAE-Dextran mediated transfection, microinjection, cationic lipid-mediated transfection and electroporation.

Another embodiment of the invention is a method for producing the Protoxin-II variant of the invention comprising the steps of providing a host cell of the invention; and culturing the host cell under conditions sufficient for the expression of at least one Protoxin-II variant of the invention.

Host cells can be cultured under any conditions suitable for maintaining or propagating a given type of host cell and sufficient for expressing a polypeptide. Culture conditions, media, and related methods sufficient for the expression of polypeptides are well known in the art. For example, many mammalian cell types can be aerobically cultured at 37° C. using appropriately buffered DMEM media while bacterial, yeast and other cell types may be cultured at 37° C. under appropriate atmospheric conditions in LB media.

In the methods of the invention, the expression of the Protoxin-II variant can be confirmed using a variety of well-known methods. For example, expression of a polypeptide can be confirmed using detection reagents, such as using SDS-PAGE or HPLC.

Another aspect of the invention is a method of modulating the activity of Nav1.7 in a biological tissue, the method comprising contacting the biological tissue expressing Nav1.7 with a Nav1.7-modulating amount of the Protoxin-II variant of the invention.

Methods of Treatment

Protoxin-II variants of the invention may be utilized in any therapy where it is desired to treat, reduce or alleviate symptoms of pain or other disorders of sensory or sympathetic neuron dysfunction.

Pain treated with the Protoxin-II variants of the invention may be any type of pain, such as chronic pain, acute pain, neuropathic pain, nociceptive pain, visceral pain, back pain, pain associated with inflammatory conditions, post-operative pain, thermal pain or pain associated with disease and degeneration.

Pain treated with the Protoxin-II variants of the invention may be Nav1.7-mediated pain.

Nav1.7-mediated pain as used herein refers to pain resulting at least partially from increased Nav1.7 channel activity.

The methods of the invention may be used to treat an animal patient belonging to any classification. Examples of such animals include mammals such as humans, rodents, dogs, cats and farm animals.

The pain and/or Nav1.7-mediated pain may result from one or more causes, such as peripheral neuropathy, central neuropathy, nerve compression or entrapment syndromes such as carpal tunnel syndrome, tarsus tunnel syndrome, ulnar nerve entrapment, compression radiculopathy, lumbar spinal stenosis, sciatic nerve compression, spinal root compression, intercostal neuralgia, compression radiculopathy and radicular lower back pain, spinal root lesions, neuritis, autoimmune diseases, general inflammation, chronic inflammatory conditions, arthritis, rheumatic diseases, lupus, osteoarthritis, general gastrointestinal disorders, colitis, gastric ulceration, duodenal ulcers, inflammatory bowel disorders, irritable bowel syndrome, pain associated with diarrhea, inflammatory eye disorders, inflammatory or unstable bladder disorders, psoriasis, skin complaints with inflammatory components, sunburn, carditis, dermatitis, myositis, neuritis, collagen vascular diseases, inflammatory pain and associated hyperalgesia and allodynia, neuropathic pain and associated hyperalgesia and allodynia, multiple sclerosis, demyelinating diseases, diabetes, diabetic neuropathy pain, causalgia, pain resulting from amputation or abscess, phantom limb pain, fracture pain, bone injury, direct trauma, HIV infection, acquired immune deficiency syndrome ("AIDS"), small pox infection, herpes infection, exposure to toxins or other foreign particles or molecules, invasive cancer, cancer, chemotherapy, radiotherapy, hormonal therapy, burns, congenital defect, dental pain, gout pain, fibromyalgias, encephalitis, chronic alcoholism, hypothyroidism, uremia and vitamin deficiencies, trigeminal neuralgia, stroke, thalamic pain syndrome, general headache, migraine, cluster headache, tension headache, mixed-vascular and non-vascular syndromes, sympathetically maintained pain, deafferentation syndromes, asthma, epithelial tissue damage or dysfunction, disturbances of visceral motility at respiratory, genitourinary, gastrointestinal or vascular regions, wounds, burns, allergic skin reactions, pruritis, vasomotor or allergic rhinitis, or bronchial disorders, dysmenorrhoea, pain during labor and delivery, dyspepsia, gastroesophageal reflux, pancreatitis, and visceralgia.

Other disorders of sensory or sympathetic neuron dysfunction that may be alleviated by the Protoxin-II variants of the invention include itch, cough and asthma. In mice, global deletion of the SCN9A gene leads to complete insensitivity to histamine-induced itch (Gingras et al., American Pain Society Meeting Abstract 2013 and U.S. Pat. Publ. No. 2012/0185956). This finding suggests that peptide Nav1.7 blockers may have utility in the treatment of itch, which may arise from various sources, such as dermatological or inflammatory disorders; or inflammatory disorders such as renal or hepatobiliary disorders, immunological disorders, medication reactions and unknown/idiopathic conditions, including dermatitis, psoriasis, eczema, insect sting or bite. Nav1.7 is also expressed in sensory nerves innervating the airways (Muroi et al., J Physiol. 2011 Dec. 1; 589(Pt 23):5663-76; Muroi et al., Am J Physiol Regul Integr Comp Physiol. 2013 Apr. 10), suggesting that peptide Nav1.7 blockers may be beneficial in the treatment of cough e.g., acute or chronic cough, or cough caused by irritation from gastroesophageal reflux disease, and inflammatory diseases of the airways such as asthma and allergy-related immune responses, bronchospasm, chronic obstructive pulmonary disease, chronic bronchitis, emphysema, and hiccups (hiccoughs, singultus). Silencing Nav1.7 in vivo in nodose ganglia of guinea pigs using shRNA nearly abolished the cough reflex induced by mechanical probing (Muroi et al., Am J Physiol Regul Integr Comp Physiol. 2013 Apr. 10).

One aspect of the invention is a method of alleviating or treating itch, cough or asthma in a subject by administering a therapeutically effective amount of the Protoxin-II variant of the invention to a subject in need thereof for a time sufficient to alleviate the itch, cough or asthma.

Another aspect of the invention is a method of alleviating or treating Nav1.7-mediated itch, Nav1.7-mediated cough or Nav1.7-mediated asthma in a subject by administering a therapeutically effective amount of the Protoxin-II variant of the invention to a subject in need thereof for a time sufficient to alleviate the itch, cough or asthma.

Nav1.7-mediated itch as used herein refers to itch resulting at least partially from increased Nav1.7 channel activity.

Nav1.7-mediated cough as used herein refers to cough resulting at least partially from increased Nav1.7 channel activity.

Nav1.7-mediated asthma as used herein refers to asthma resulting at least partially from increased Nav1.7 channel activity.

Protoxin-II variants of the invention may be tested for their effect in reducing or alleviating pain and/or Nav1.7-mediated pain using animal models described herein, and models such as the rat spinal nerve ligation (SNL) model of neuropathic pain, carageenan induced allodynia model, the Freund's complete adjuvant (CFA)-induced allodynia model, the thermal injury model, the formalin model and the Bennett Model, and other models as described in U.S. Pat. Appl. No. 2011/0124711 and U.S. Pat. No. 7,998,980. Carageenan induced allodynia and CFA-induced allodynia are models of inflammatory pain. The Bennett model provides an animal model for chronic pain including post-operative pain, complex regional pain syndrome, and reflex sympathetic dystrophy.

Any of the foregoing animal models may be used to evaluate the efficacy of Protoxin-II variants of the invention inhibitor in treating pain and/or NAv1.7-mediated pain. The efficacy of the Protoxin-II variants of the invention may be compared to a no treatment or placebo control. Additionally or alternatively, efficacy may be evaluated in comparison to one or more known pain-relieving medicaments.

The present invention provides methods of treating Nav1.7-mediated pain using the Protoxin-II variants of the invention. It has been discovered in the pending application by the inventors (U.S. Patent Application No. 61/781,276) that administration of Nav1.7 blocking peptides are efficacious in treating and/or alleviating pain in various animal models of pain, contrary to what was disclosed and suggested in the literature. While peptide inhibitors of Nav1.7 have been shown to be potent and/or selective towards Nav1.7 in in vitro cell culture models using overexpressed Nav1.7 or on isolated neurons in which the blood-nerve barrier is subverted through desheathing or hypertonic saline injection, they have so far proven non-efficacious in in vivo animal models of pain, where the lack of efficacy has been reported to result from the inability of the peptides to pass the blood-nerve barrier. Several publications describe lack of efficacy of Nav1.7 blocking peptides in animal models of pain or in isolated nerves. For example Hackel et al., Proc Natl Acad Sci 109:E2018-27, 2012, describes the inability of ProTx-II to inhibit action potential firing in isolated nerves unless the perineural barrier, which provides a diffusion barrier in this model, is compromised. ProTx-II was found non-efficacious in rodent models of acute and inflammatory pain; a likely explanation stated the inability of ProTx-II to cross the blood-nerve barrier (Schmalhofer et al., Mol Pharmacol 74:1476-1484, 2008). It has been proposed that Nav1.7 peptide toxin blockers have poor oral bioavailability and they are difficult to deliver to nerve endings, implying that their use as therapeutic agents remain limited (Dib-Hajj et al., Nature Rev Neuroscience 14, 49-62, 2013).

Nav1.7 is expressed in the peripheral nervous system e.g., in nociceptive dorsal root ganglions (DRG), most notably in nociceptive small-diameter DRG neurons, in particular in peripheral terminals in the skin, with little representation in the brain. Nav1.7 distribution (e.g. sensory ending) and physiology predispose it to a major role in transmitting painful stimuli.

One embodiment of the invention is a method of treating Nav1.7-mediated pain by administering a therapeutically effective amount of the Protoxin-II variant of the invention to a subject in need thereof for a time sufficient to treat the Nav1.7-mediated pain.

The Protoxin-II variants of the invention Nav1.7 may be utilized in any therapy where it is desired to treat Nav1.7-mediated pain or other disorders of sensory or sympathetic neuron dysfunction. "Treat" or "treatment" of pain is meant to include partially or completely to prevent, stop, inhibit, reduce, or delay the perception of pain.

In some embodiments, the Nav1.7-mediated pain is chronic pain, acute pain, neuropathic pain, nociceptive pain, visceral pain, back pain, post-operative pain, thermal pain, phantom limb pain, or pain associated with inflammatory conditions, primary erythemalgia (PE), paraoxysmal extreme pain disorder (PEPD), osteoarthritis, rheumatoid arthritis, lumbar discectomy, pancreatitis, fibromyalgia, painful diabetic neuropathy (PDN), post-herpetic neuropathy (PHN), trigeminal neuralgia (TN), spinal cord injuries or multiple sclerosis, or pain associated with disease and degeneration.

Neuropathic pain includes for example painful diabetic neuropathy (PDN), post-herpetic neuropathy (PHN) or trigeminal neuralgia (TN). Other causes of neuropathic pain include spinal cord injuries, multiple sclerosis, phantom limb pain, post-stroke pain and HIV-associated pain. Conditions such as chronic back pain, osteoarthritis and cancer may also result in the generation of neuropathic-related pain and thus are potentially suitable for treatment with the Protoxin-II variants of the invention.

In another embodiment, the Nav1.7-mediated pain is associated with primary erythemalgia (PE), paraoxysmal extreme pain disorder (PEPD), osteoarthritis, rheumatoid arthritis, lumbar discectomy, pancreatitis or fibromyalgia.

In the methods of the invention, the Protoxin-II variants of the invention may be conjugated to a second polypeptide to form a fusion protein. Such fusion proteins are for example the well-known Fc fusions or fusions to human serum albumin to extend half-life of the peptide inhibitors. The conjugation may be a direct conjugation via a linker, such as a glycine-serine rich linker. Such linkers are well known in the art. The Protoxin-II variants of the invention incorporating additional moieties may be compared for their Nav1.7 blocking ability and efficacy in treatment or reducing pain using well known methods and those described herein.

Other disorders of sensory or sympathetic neuron dysfunction that can be treated with the Protoxin-II variants of the invention, including asthma, cough, heart-burn, itch, dermatitis, bladder instability, and Reynaud's disease.

Pharmaceutical Compositions

The Protoxin-II variants of the invention may be formulated in a pharmaceutically acceptable vehicle or carrier. One embodiment of the invention is a pharmaceutical composition comprising the isolated Protoxin-II variant of the invention and a pharmaceutically acceptable excipient.

A suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. These solutions are sterile and generally free of particulate matter, and may be sterilized by conventional, well-known sterilization techniques (e.g., filtration).

The compositions may contain pharmaceutically acceptable excipients as required to approximate physiological conditions, such as pH adjusting and buffering agents, stabilizing, thickening, lubricating and coloring agents, etc. Suitable vehicles and their formulation and packaging are described, for example, in Remington: The Science and Practice of Pharmacy (21st ed., Troy, D. ed., Lippincott Williams & Wilkins, Baltimore, Md. (2005) Chapters 40 and 41).

In the methods of the invention, the Protoxin-II variants of the invention may be administered by peripheral administration. "Peripheral administration" or "administered peripherally" means introducing an agent into a subject outside of the central nervous system. Peripheral administration encompasses any route of administration other than direct administration to the spine or brain.

Peripheral administration can be local or systemic. Local administration may be used to concentrate the therapeutic to the site of action, such as local administration to joints, spinal cord, surgical wounds, sites of injury/trauma, peripheral nerve fibers, various organs (GI, urogenital, etc) or inflamed tissues. Systemic administration results in delivery of a pharmaceutical composition to essentially the entire peripheral nervous system of the subject and may also result in delivery to the central nervous system depending on the properties of the composition.

Routes of peripheral administration encompass, without limitation, topical administration, intravenous or other injection, and implanted mini-pumps or other extended release devices or formulations.

Pharmaceutical compositions of the invention include formulations involving the Protoxin-II variants of the invention in sustained- or controlled-delivery formulations. These formulations may be achieved through use of for example injectable microspheres, bio-erodible particles, microemulsions, nanoparticles, nanocapsules, macroemulsions, polymeric compounds (such as polyesters, polyamino acids, hydrogels, poly(lactic acid), polyglycolic acid or ethylene vinylacetate copolymers), beads or liposomes, hyaluronic acid or implantable drug delivery devices.

The Protoxin-II variants of the invention may be prepared for use for parenteral (subcutaneous, intramuscular or intravenous), intracerebral (intra-parenchymal), intracerebroventricular, intramuscular, intra-ocular, intra-arterial, intraportal, or intralesional routes; by sustained release systems or by implantation devices, or any other administration, particularly in the form of liquid solutions or suspensions; for buccal or sublingual administration such as in the form of tablets or capsules; or intranasally such as in form of powders, nasal drops or aerosols or certain agents; transdermally in a form of a gel, ointment, lotion, cream or dusting powder, suspension or patch delivery system with chemical enhancers to either modify the skin structure or to increase the drug concentration in the transdermal patch, or with agents that enable the application of formulations containing proteins and peptides onto the skin (Int. Pat. Publ. No. WO98/53847), or applications of electric fields to create transient transport pathways such as electroporation, or to increase the mobility of charged drugs through the skin such as iontophoresis, or application of ultrasound such as sonophoresis (U.S. Pat. Nos. 4,309,989 and 4,767,402). The composition also may be administered locally via implantation of a membrane, sponge or another appropriate material onto which the desired molecule has been absorbed or encapsulated.

In certain embodiments, where an implantation device is used, the device may be implanted into any suitable tissue or organ, and delivery of the desired molecule may be via diffusion, timed-release bolus, or continuous administration.

The concentration of the Protoxin-II variants of the invention or other peptide inhibitors of Nav1.7 in such pharmaceutical formulation can vary widely, for example from about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2%, or between 2% to 5%, up to as much as 15%, 20%, 30%, 40%, 50%, 60% or 70% by weight and will be selected primarily based on fluid volumes, viscosities and other factors, according to the particular mode of administration selected. The Protoxin-II variants of the invention can be lyophilized for storage and reconstituted in a suitable vehicle prior to use. This technique has been shown to be effective with conventional protein preparations. Lyophilization and reconstitution techniques are well known in the art.

An exemplary pharmaceutical compositions of the present invention may comprise Tris buffer of about pH 7.0-8.5, or acetate buffer of about pH 4.0-5.5, and may further include sorbitol, sucrose, Tween-20 and/or a suitable substitute thereof.

The appropriate therapeutically effective dose may be determined readily by those skilled in the art. An effective dose refers to an amount or dosage sufficient to produce a desired result, i.e. to partially or completely prevent, stop, inhibit, reduce, or delay the perception of pain associated with any painful medical condition. The effective amount may vary depending on the specific vehicle and the Protoxin-II variants of the invention selected, and is also dependent on a variety of factors and conditions related to the subject to be treated and the severity of the pain. For example, factors such as age, weight and health of the subject to be administered with the pharmaceutical compositions of the invention as well as dose response curves and toxicity data obtained in preclinical animal work could be among those considered. A determined dose may, if necessary, be repeated at appropriate time intervals selected as appropriate by a physician or other person skilled in the relevant art (e.g. nurse, veterinarian, or veterinary technician) during the treatment period. The determination of an effective amount or a therapeutically effective amount for a given agent is well within the ability of those skilled in the art.

Thus, a pharmaceutical composition of the invention for intramuscular injection could be prepared to contain 1 ml sterile buffered water, and between about 1 ng to about 100 mg, about 50 ng to about 30 mg or about 5 mg to about 25 mg of a Protoxin-II variant of the invention. Similarly, a pharmaceutical composition of the invention for intravenous infusion could be made up to contain about 250 ml of sterile Ringer's solution, and about 1 mg to about 30 mg or about 5 mg to about 25 mg of the Protoxin-II variants of the invention. Actual methods for preparing parenterally administrable compositions are well known and are described in more detail in, for example, "Remington's Pharmaceutical Science", 15th ed., Mack Publishing Company, Easton, Pa.

The present invention will now be described with reference to the following specific, non-limiting examples.

Example 1: Design and Generation of Protoxin-II Variants

Protoxin-II single position limited amino acid scanning library substitution was designed to assess to what degree selectivity, peptide yield, and homogeneity can be improved.

Protoxin-II variants were designed as HRV3C protease cleavable HSA fusion proteins in the following format from N- to C-terminus: 6×His-HSA-linker-HRV3C cleavable peptide-Protoxin-II variant ("6×His" disclosed as SEQ ID NO: 108); linker being (GGGGSGGGGSGGGGSGGGGS; SEQ ID NO: 80, HSA having the sequence of SEQ ID NO: 106, HRV3C cleavable peptide having the sequence of SEQ ID NO: 82). Each Protoxin-II variant, after cleavage from HSA had a residual N-terminal GP from the cleavage site.

The variants were characterized in membrane depolarization assays using FLIPR® Tetra as described in Example 3 FLIPR® Tetra membrane depolarization assay, and in whole cell patch clamp experiments using the QPatch assay as described in Example 3.

Combinatorial libraries were designed to test for additive effects of select single position hits in an attempt to generate Nav1.7 antagonists with further improved potency and selectivity profile compared to the native peptide.

Construction of the Expression Vectors

The designed Protoxin-II variant genes were generated using synthetic gene assembly technology as described in U.S. Pat. No. 6,521,427. The amino acid sequences of the designed peptide variants were back-translated to DNA sequences using human high-frequency codons. The DNA sequence of each variant gene, together with a portion of vector DNA including the DNA cloning sites, was synthesized as multiple oligonucleotides, some of which contained degenerate codons, and assembled into full-length DNA fragments. The assembled DNA fragments were amplified by PCR and PCR products were subsequently cloned as a pool. Pooled PCR products were digested with the appropriate restriction enzymes and cloned into the designed expression vector in such a manner as to fuse each toxin variant gene to the signal peptide and the fusion partner (6×His-HSA-linker-HRV3C cleavable peptide ("6×His" disclosed as SEQ ID NO: 108) contained in the vector. Standard molecular biology techniques were used to identify a positive clone for each designed variant. The plasmid DNA from these positive clones was purified and sequence confirmed before expressing the Protoxin-II peptide variant fusion proteins using standard methods.

Protein Expression

HEK 293-F cells were maintained in 293 Freestyle™ media (Invitrogen Cat #12338) and split when the cell concentration was between 1.5 and $2.0\times10^6$ cells per ml. The cells were grown in suspension, shaking at 125 RPM in a humidified incubator set at 37° C. and 8% $CO_2$. HEK 293F cells were transiently transfected using a DNA/lipid complex after they were diluted to $1.0\times10^6$ cells per ml. To generate the complex, 1.25 μg DNA per ml of transfection was diluted in 1.0 ml of OptiPro media (Invitrogen Cat #12309) and 1.25 ml of Freestyle™ Max transfection reagent (Invitrogen Cat #16447) was diluted in 1.0 ml of OptiPro media. The DNA and Max transfection reagent were mixed together and incubated for 10 minutes at room temperature before adding to the cells. Transfected cells were placed in a humidified incubator set at 37° C. and 8% $CO_2$ for 4 days shaking at 125 RPM. The supernatant was separated from the cells by centrifugation at 5,000×g for 10 minutes and filtered through a 0.2 μm filter (Corning; Cat #431153), then concentrated 10 and 50 fold using an Amicon Ultra Concentrator 10K (Cat #UFC901096), and centrifuging for approximately 10 minutes at 3,750×g.

Example 2: Purification of Protoxin-II Variants

Protoxin-II variants were expressed as HSA fusion proteins as indicated in Example 1 and the Protoxin-II variant peptides were cleaved with HRV3C protease prior to purification. Two methodologies were tested for efficient purification of the Protoxin-II variants.

Protein Purification

Purification of Protoxin-II Variants by RP-HPLC

The secreted proteins were purified from the expression supernatants via IMAC using 1 ml HisTrap HP columns (GE Healthcare Cat #17-5247-01). The chromatography method was run using an AKTA Xpress and protein was eluted from the column using a step gradient of Imidazole. Peak fractions were pooled and digested overnight with HRV 3C protease (1 μg protease/150 μg fusion).

Cleaved peptide-fusion pools were further purified using a Dionex HPLC system with a reverse phase Phenomenex Luna 5 μm C18(2) column (Cat #00B-4252-PO-AX). Samples were eluted from the column with a 0-68% Acetonitrile (0.05% TFA) linear gradient. Elution fractions were pooled, lyophilized overnight and reconstituted in HEPES buffered saline, pH 7.4 (10 mM HEPES, 137 mM NaCl, 5.4 mM KCl, 5 mM glucose, 2 mM $CaCl_2$, 1 mM $MgCl_2$).

Table 4 shows yields of Protoxin-II variants purified by RP-HPLC. The average mg yield/L was 0.01615.

TABLE 4

| Protoxin-II Variant Peptide ID | yield (mg) | Protoxin-II Variant Peptide ID | yield (mg) |
|---|---|---|---|
| NV1D816 | 0.0008 | NV1D2496 | 0.0006 |
| NV1D2511 | 0.0009 | NV1D2503 | 0.0030 |
| NV1D2513 | 0.0034 | NV1D766 | 0.0054 |
| NV1D2504 | 0.0071 | NV1D770 | 0.0040 |
| NV1D2260 | 0.0129 | NV1D772 | 0.0015 |
| NV1D2498 | 0.0079 | NV1D792 | 0.0016 |
| NV1D2499 | 0.0076 | NV1D815 | 0.0008 |
| NV1D2512 | 0.0061 | NV1D768 | 0.0060 |
| NV1D2267 | 0.0095 | NV1D2508 | 0.0017 |
| NV1D2507 | 0.0000 | NV1D2501 | 0.0008 |
| NV1D2509 | 0.0000 | NV1D2296 | 0.0018 |
| NV1D2305 | 0.0001 | NV1D2292 | 0.0059 |
| NV1D815 | 0.0021 | NV1D750 | 0.0023 |
| NV1D2506 | 0.0001 | NV1D748 | 0.0036 |
| NV1D2505 | 0.0006 | NV1D774 | 0.0050 |
| NV1D812 | 0.0001 | NV1D786 | 0.0036 |
| NV1D2510 | 0.0009 | NV1D855 | 0.0008 |
| NV1D769 | 0.0031 | NV1D2312 | 0.0011 |
| NV1D2497 | 0.0038 | NV1D1410 | 0.0074 |
| NV1D2500 | 0.0004 | NV1D1415 | 0.0128 |
| NV1D767 | 0.0004 | NV1D751 | 0.0033 |
| NV1D2502 | 0.0002 | | |

Purification of Protoxin-II Variants by Solid Phase Extraction (SPE)

The secreted proteins were purified from the expression supernatants via IMAC using 1 ml HisTrap HP columns (GE Healthcare Cat #17-5247-01). The chromatography method was run using an AKTA Xpress and protein was eluted from the column using a step gradient of Imidazole. Peak fractions were pooled and digested overnight with HRV3C protease (1 μg protease/150 μg fusion). The cleaved sample was loaded into a 50 kDa molecular weight cut off centrifugal filter unit (Millipore UFC805096) and cleaved peptide collected in the filtrate fraction.

Peptide pools were loaded onto a 96-well solid phase extraction block (Agilent Bond Elut Plexa A3969030) for further purification, desalting, and concentration. Blocks were used in conjunction with a vacuum manifold (Whatman). Peptide samples were loaded and washed in 0.05% TFA in water and eluted with a step gradient of acetonitrile with 0.05% TFA in water. Elution fractions were then lyophilized overnight and reconstituted in HEPES buffered saline, pH 7.4 (10 mM HEPES, 137 mM NaCl, 5.4 mM KCl, 5 mM glucose, 2 mM $CaCl_2$, 1 mM $MgCl_2$).

Peptides were reconstituted in supplemented HEPES buffered saline, pH 7.4 (10 mM HEPES, 137 mM NaCl, 5.4 mM KCl, 5 mM glucose, 2 mM $CaCl_2$, 1 mM $MgCl_2$) and absorbance was measured at 280 nm. Concentration values were then calculated using each sample's extinction coefficient. 2 µg of each peptide were loaded onto an Invitrogen NuPAGE® Novex® Bis-Tris Gel 15 well gel and run in MES buffer non-reduced.

Samples were analyzed on Agilent 1100 HPLC using 4-80% acetonitrile in 0.05% TFA linear gradient with a Phenomenex Luna C18(2) analytical column (Cat #00A-4041-B0). Concentrations of all peptides were normalized and 10 µl of each were injected for a total of 1.3 µg per sample. Absorbance at 220 nm was monitored and chromatograms analyzed were using Chromeleon software.

Table 5 shows yields (mg) of Protoxin-II variants purified by SPE. The average mg yield/L was 0.05353.

The benefits of the SPE purification process are ease and throughput of purification since samples are processed in parallel in a 96-well block rather than serially on RP-HPLC, and improvement in yield. There was, on average, more than 3-fold higher yield (mg/L) for variants purified by SPE versus RP-HPLC.

TABLE 5

| Protoxin-II Variant Peptide ID | yield (mg) | Protoxin-II Variant Peptide ID | yield (mg) |
|---|---|---|---|
| NV1D12 | 0.0054 | NV1D2734 | 0.0602 |
| NV1D2659 | 0.0234 | NV1D2772 | 0.2050 |
| NV1D2664 | 0.0060 | NV1D2775 | 0.2225 |
| NV1D2666 | 0.0225 | NV1D2738 | 0.0512 |
| NV1D2708 | 0.0721 | NV1D2740 | 0.0373 |
| NV1D2725 | 0.0144 | NV1D2733 | 0.1913 |
| NV1D2739 | 0.0053 | NV1D788 | 0.0000 |
| NV1D2765 | 0.0097 | NV1D757 | 0.0021 |
| NV1D2748 | 0.0995 | NV1D791 | 0.0007 |
| NV1D2771 | 0.0103 | NV1D2310 | 0.0011 |
| NV1D2770 | 0.0121 | NV1D2308 | 0.0014 |
| NV1D2778 | 0.0644 | NV1D778 | 0.0019 |
| NV1D2782 | 0.0202 | NV1D2294 | 0.0000 |
| NV1D2756 | 0.0466 | NV1D856 | 0.0047 |
| NV1D2759 | 0.0218 | NV1D2309 | 0.0023 |
| NV1D2712 | 0.0558 | NV1D846 | 0.0020 |
| NV1D12 | 0.0127 | NV1D2896 | 0.0504 |
| NV1D2673 | 0.0625 | NV1D2913 | 0.0203 |
| NV1D2662 | 0.0433 | NV1D2910 | 0.0253 |
| NV1D2669 | 0.2661 | NV1D2893 | 0.0569 |
| NV1D2665 | 0.0389 | NV1D2909 | 0.0195 |
| NV1D2731 | 0.2547 | NV1D2917 | 0.0339 |
| NV1D2767 | 0.0238 | NV1D2914 | 0.0201 |
| NV1D2730 | 0.2566 | NV1D2922 | 0.0554 |
| NV1D2766 | 0.0198 | NV1D2902 | 0.0061 |
| NV1D2667 | 0.0050 | NV1D2889 | 0.0022 |
| NV1D2769 | 0.0142 | NV1D2887 | 0.0025 |
| NV1D2719 | 0.0675 | NV1D2878 | 0.0272 |
| NV1D2776 | 0.0633 | NV1D2877 | 0.0129 |
| NV1D2663 | 0.0344 | NV1D2851 | 0.0029 |
| NV1D2709 | 0.1841 | NV1D2850 | 0.0026 |
| NV1D2720 | 0.0538 | NV1D2820 | 0.0020 |
| NV1D12 | 0.0095 | NV1D2819 | 0.0015 |
| NV1D2773 | 0.1921 | NV1D2814 | 0.0163 |
| NV1D2810 | 0.0086 | NV1D2918 | 0.0256 |
| NV1D2732 | 0.0262 | NV1D2921 | 0.0533 |
| NV1D757 | 0.0026 | NV1D2905 | 0.0126 |
| NV1D791 | 0.0206 | NV1D2906 | 0.0189 |
| NV1D2310 | 0.0085 | NV1D2881 | 0.0207 |
| NV1D2308 | 0.0179 | NV1D2882 | 0.0223 |
| NV1D778 | 0.0094 | NV1D2869 | 0.0038 |
| NV1D856 | 0.0247 | NV1D2870 | 0.0187 |

TABLE 5-continued

| Protoxin-II Variant Peptide ID | yield (mg) | Protoxin-II Variant Peptide ID | yield (mg) |
|---|---|---|---|
| NV1D2309 | 0.0035 | NV1D2867 | 0.0147 |
| NV1D846 | 0.0043 | NV1D2888 | 0.0045 |
| NV1D2889 | 0.0107 | NV1D2816 | 0.0133 |
| NV1D2887 | 0.0061 | NV1D2885 | 0.0025 |
| NV1D2861 | 0.0469 | NV1D2974 | 0.0418 |
| NV1D2729 | 0.1101 | NV1D2972 | 0.1089 |
| NV1D2890 | 0.0088 | NV1D2971 | 0.0407 |
| NV1D2899 | 0.0402 | NV1D2970 | 0.0557 |
| NV1D2804 | 0.0044 | NV1D2969 | 0.0799 |

Example 3: Characterization of Protoxin-II Variants

Select Protoxin-II variants were characterized in membrane depolarization and whole cell patch clamp assays to assess their potency and selectivity towards Nav1.7.

FLIPR® Tetra Membrane Depolarization Assay

The ability of the generated peptides to inhibit membrane depolarization induced by Nav1.7 agonist veratridine (3-Veratroylveracevine; Biomol, Catalog #NA125) was measured with a FRET (fluorescence resonance energy transfer) assay on FLIPR® Tetra using DISBAC2(3) (Invitrogen, K1018) as an electron acceptor and PTS18 (Trisodium 8-octadecyloxypyrene-1,3,6-trisulfonate) (Sigma) as a donor by exciting the donor at 390-420 nm and measuring FRET at 515-575 nm.

HEK293 cells stably expressing human Nav1.7 were cultured in DMEM/F-12 media (1:1), supplemented with 10% fetal bovine serum, 1% penicillin/streptomycin, 400 μg/mL geneticin and 100 μM NEAAs (all reagents from Invitrogen). 50 μL of harvested cells were plated at 25,000 cells/well into poly-lysine coated 384-well black clear bottom plates. The plates were incubated at room temperature (RT) for 15 min followed by an overnight incubation at 37° C. All incubations were done in the dark unless otherwise stated. The next day, the wells were washed 4 times with assay buffer (137 mM NaCl, 4 mM KCl, 2 mM $MgCl_2$, 2 mM $CaCl_2$, 5 mM Glucose, 10 mM HEPES, pH 7.4), and resuspended in 25 μL of assay buffer. 2× stock (6 μM) of the PTS18 dye was prepared by suspending the dye in 10% pluronic F127 in DMSO at 1:1 (v/v ratio). 25 μL of the 2×PTS18 stock was added into the wells and the cells were stained for 30 min at RT, after which the dye was washed off with the assay buffer. Peptides were suspended at 3× their final concentration in the assay buffer containing 10 μM DISBAC2(3) and 400 μM VABSC-1 to suppress background fluorescence (Sigma, cat #201987). 25 μL/well of the suspended peptides were added into each well, and incubated for 60 minutes at RT. Depolarization was induced by 25 μM final concentration of veratridine (by adding 25 μL/well of 75 μM (3×) stock solution), and the reduction in the mean intensity of FRET dye fluorescence was measured 30-100 seconds after adding the agonist. A 1.3× dilution of each measured peptide occurred after adding veratridine by convention, the concentration at the beginning of the FLIPR® Tetra assay is reported.

Concentration-response curves of synthetic Protoxin-II (Peptide International) were constructed in each experimental series and were used as controls. Fluorescence counts for each well were converted to % response by normalizing the signal to the difference between negative control (response to agonist veratridine alone) and positive control (response to veratridine in the presence of 10 μM tetracaine) values.

For measurements, "spatial uniformity correction" (all fluorescence traces are normalized to the average initial starting intensity) and "subtract bias value" (subtract the initial starting intensity from each trace) were turned on in FLIPR® Tetra. Each data point represented the response in an individual well. All individual data points were used in a non-linear least-squares fitting procedure to find the best fit to a Hill function using Origin (Microcal). $IC_{50}$ values were extracted from the resultant fitted curve. The mean responses of the positive (P) and negative (N) controls were used to calculate the % response in a well as follows: % response=100*(N−R)/(N−P).

Assay plates were accepted if the potency of control antagonists for that day were within ±0.5 log units of their historical mean.

QPatch Assay

HEK293 cells stably expressing human Nav1.5 (SEQ ID NO: 105), Nav1.7 (SEQ ID NO: 79) or Nav1.6 (SEQ ID NO: 407) were cultured in DMEM/F-12 media (1:1), supplemented with 10% fetal bovine serum, 1% penicillin/streptomycin, 400 μg/mL Geneticin and 100 μM NEAAs (all reagents from Invitrogen). Cells were maintained at 37° C. and in 5% CO2 and assayed upon reaching 50-90% confluency. CHO cells stably expressing human Nav1.6 in a tetracycline-inducible manner (SEQ ID NO: 407) were cultured in HAMs F12, supplemented with 10% fetal bovine serum, 1% penicillin/streptomycin, 10 μg/mL Blasticidin and 400 μg/mL Zeocin. Cells were maintained at 37° C. and in 5% CO2, and assayed upon reaching 50-90% confluency. Nav1.6 expression was induced with 1 μg/ml of tetracycline, 24-48 h prior to an experiment.

Before testing in QPatch HT (Sophion), cells were first dissociated using 0.05% trypsin (5 min at 37° C.), resuspended in CHO-S-SFM media (Life Technologies) and gently triturated to break up cell clumps. Cell density was adjusted to $1\text{-}2\times10^6$/mL with the same media and cells were the transferred to a cell "hotel" in QPatch HT and used in experiments for several hours. For giga-ohm seal formation and whole-cell patch clamp recording, the extracellular solution contained 137 mM NaCl, 5.4 mM KCl, 1 mM $MgCl_2$, 2 mM $CaCl_2$, 5 mM glucose, and 10 mM HEPES, pH=7.4 and osmolarity=315 mOsm. The intracellular solution contained 135 mM CsF, 10 mM CsCl, 5 mM EGTA, 5 mM NaCl and 10 mM HEPES, pH=7.3 and osmolarity=290 mOsm. The voltage protocol used in the assay was as follows. From a holding potential of −75 mV (Nav1.7), −60 mV (Nav1.6), or −105 mV (Nav1.5) cells were first hyperpolarized to −120 mV for 2 sec and then depolarized to 0 mV for 5 ms before returning to the holding potential. This protocol was repeated once every 60 sec during liquid applications (see below). Cells were otherwise held at the holding potential when the above voltage protocol was not executed. Upon establishment of the whole-cell recording configuration, a total of five applications of the extracellular solution (all containing 0.1% bovine serum albumin (BSA) with or without test compound, except for the last application, which contained 1 μM TTX or 10 mM lidocaine as a positive control) were made on to cells being recorded. The first liquid application contained only the control buffer (5 μl). The voltage protocol was executed 10 times (for a total duration of 10 min) five sec after the application. The next three liquid applications (5 μl each) contained a test compound (same compound at the same concentration for all three applications) or control buffer (for control cells only). Five seconds after each of these applications, the voltage protocol was again executed 10 times (also once per min). The last application contained positive (composed of three 10 μl sub-applications, each separated by 2 sec), five seconds after which the same voltage protocol was executed twice to obtain the baseline current. Currents were sampled at 25 kHz and filtered at 5 kHz with an 8-pole Bessel filter. The series resistance compensation level was set at 80%. For each cell, the peak current amplitude at 0 mV for each current trace in the first four liquid applications was first subtracted from that of the last trace in the presence of positive control and then normalized to that of the last trace in the first (control buffer) application as % inhibition. To control for current rundown, this (% inhibition) value for each cell in the presence of a test compound was further normalized to the average % inhibition value for control (typically 5-6) cells in the same experiment. The mean of the last two such values in the last compound application (i.e., the corrected % inhibition value for each concentration of a test compound) were taken as the % inhibition value for each cell at the particular compound concentration tested. The % inhibition values for all cells tested at each compound concentration were averaged and used in concentration response calculations. All experiments were performed at room temperature (22° C.). Data are expressed as mean±se. Wild type Protoxin-II was included in each experiment as a positive control. Data were accepted only if the potency of Protoxin-II was within ±0.5 log units of its historical mean.

$IC_{50}$ values for Nav1.7 for select Protoxin-II variants obtained using the FLIPR® Tetra are shown in Table 6.

TABLE 6

| Protein ID | Protoxin-II Variant Peptide ID | Protoxin-II variant Peptide SEQ ID NO: | hNav1.7 TETRA $IC_{50}$ (nM) |
|---|---|---|---|
| NV1D12_5 | NV1D12 | 2 | 4.1 ± 3.6 |
| NV1G1045 | NV1D791 | 11 | 4.8 ± 0.4 |
| NV1D1332_1 | NV1D1332 | 12 | 6.7 ± 0.5 |
| NV1D1336_1 | NV1D1336 | 14 | 10.5 ± 1.2 |
| NV1D1337_1 | NV1D1337 | 15 | 10.3 ± 1.0 |
| NV1G1049 | NV1D2308 | 16 | 4.5 ± 0.4 |
| NV1G953 | NV1D2670 | 17 | 22.2 ± 3.3 |
| NV1G951 | NV1D2674 | 18 | 4.0 ± 0.2 |
| NV1G963 | NV1D2671 | 20 | 31.5 ± 6.4 |
| NV1G949 | NV1D2675 | 21 | 4.3 ± 0.3 |
| NV1G977 | NV1D2665 | 22 | 4.9 ± 0.4 |
| NV1G957 | NV1D2668 | 23 | 17.5 ± 2.6 |
| NV1G965 | NV1D2672 | 24 | 4.5 ± 0.3 |
| NV1G973 | NV1D2662 | 25 | 4.0 ± 0.4 |
| NV1G975 | NV1D2669 | 26 | 18.4 ± 5.7 |
| NV1G971 | NV1D2673 | 27 | 4.3 ± 0.5 |
| NV1G995 | NV1D2663 | 28 | 4.2 ± 0.4 |
| NV1G961 | NV1D2676 | 29 | 26.5 ± 2.9 |
| NV1G911 | NV1D2666 | 30 | 66.5 ± 36.7 |
| NV1G1133 | NV1D2816 | 31 | 667 ± 93.6 |
| NV1G905 | NV1D2735 | 32 | 60.0 ± 16.2 |
| NV1G979 | NV1D2731 | 34 | 20.7 ± 7.2 |
| NV1G1097 | NV1D2810 | 35 | 339 ± 5750 |
| NV1G1099 | NV1D2732 | 36 | 126 ± 26.9 |
| NV1G1011 | NV1D2740 | 37 | 3.6 ± 9.9 |
| NV1G1105 | NV1D2729 | 39 | 8.0 ± 0.9 |
| NV1G1013 | NV1D2733 | 40 | 7.5 ± 2.9 |
| NV1G1095 | NV1D2814 | 41 | 754 ± 51.3 |
| NV1G983 | NV1D2730 | 43 | 25.5 ± 4.3 |
| NV1G1003 | NV1D2734 | 44 | 13.4 ± 0.8 |
| NV1G1009 | NV1D2738 | 45 | 2.6 ± 0.2 |
| NV1G1129 | NV1D2867 | 49 | >1000 |
| NV1G1121 | NV1D2881 | 50 | 488 ± 72.2 |
| NV1G1123 | NV1D2882 | 51 | 857 ± 65.7 |
| NV1G899 | NV1D2774 | 52 | 50.5 ± 15.2 |
| NV1G1103 | NV1D2861 | 54 | >1000 |
| NV1G1127 | NV1D2870 | 55 | 784 ± 84.8 |
| NV1G1007 | NV1D2775 | 56 | 25.4 ± 2.0 |
| NV1G1067 | NV1D2893 | 57 | 75.5 ± 10.5 |

TABLE 6-continued

| Protein ID | Protoxin-II Variant Peptide ID | Protoxin-II variant Peptide SEQ ID NO: | hNav1.7 TETRA IC$_{50}$ (nM) |
|---|---|---|---|
| NV1G1005 | NV1D2772 | 59 | 15.6 ± 1.8 |
| NV1G1061 | NV1D2896 | 60 | 80.3 ± 7.1 |
| NV1G1085 | NV1D2877 | 61 | 441 ± 73.3 |
| NV1G1083 | NV1D2878 | 62 | 680 ± 40.7 |
| NV1G1079 | NV1D2889 | 64 | 12.1 ± 1.5 |
| NV1G1001 | NV1D2773 | 65 | 18.8 ± 1.5 |
| NV1G1107 | NV1D2890 | 66 | 25.8 ± 4.2 |
| NV1G1109 | NV1D2899 | 67 | 33.3 ± 6.7 |
| NV1G1117 | NV1D2905 | 68 | 713 ± 87.3 |
| NV1G1119 | NV1D2906 | 69 | 940 ± 86.7 |
| NV1G1115 | NV1D2921 | 70 | 586 ± 71.7 |
| NV1G1075 | NV1D2922 | 71 | 204 ± 45.7 |
| NV1G1069 | NV1D2909 | 72 | 97.1 ± 10.1 |
| NV1G1065 | NV1D2910 | 73 | 441 ± 41.7 |
| NV1G1063 | NV1D2913 | 74 | 79.7 ± 9.3 |
| NV1G1073 | NV1D2914 | 75 | 135 ± 7.8 |
| NV1G1071 | NV1D2917 | 76 | 197 ± 48.3 |
| NV1G1113 | NV1D2918 | 77 | 983 ± 98.7 |
| NV1G1153 | NV1D3034 | 78 | 10.3 ± 2.1 |

Select Protoxin-II variants were tested for selectivity against human Nav1.5 using QPatch. IC$_5$, values for both Nav1.7 and Nav1.5 for select peptides obtained using QPatch are shown in Table 7.
Table 7.

TABLE 7

| Protoxin-II Variant Protein ID | Protoxin-II variant Peptide ID | Protoxin-II variant Peptide SEQ ID NO: | hNav1.7 QPatch IC$_{50}$ (nM) | hNav1.5 QPatch IC$_{50}$ (nM) |
|---|---|---|---|---|
| NV1D12_5 | NV1D12 | 2 | 2.2 ± 1.3 | >1000 |
| NV1G899 | NV1D2774 | 52 | 18.7 ± 13.6 | >3000 |
| NV1G1007 | NV1D2775 | 56 | 4.0 ± 8.9 | >3000 |
| NV1G1005 | NV1D2772 | 59 | 6.2 ± 3.2 | >3000 |
| NV1G1001 | NV1D2773 | 65 | 4.3 ± 3.3 | >3000 |
| NV1G1153 | NV1D3034 | 78 | 4.3 ± 4.3 | >1000 |

Example 4. Generation and Characterization of Combinatorial Protoxin-II Variants Combinatorial libraries were designed to test for additive effects of select single position hits in an attempt to generate Nav1.7 antagonists with further improved potency and selectivity profile compared to the native peptide using several approaches.

A limited amino acid scan was conducted at all non-cysteine Protoxin-II positions using A, D, Q, R, K and S for diversification. In these experiments, Protoxin-II was expressed and tested as monovalent Fc fusion protein as described in Example 1. From this scan, substitutions Y1Q, W7Q, S11A, were identified that improved potency and/or selectivity of the resulting variants.

A full amino acid scan (excluding cys and trp) at positions M6 and M19 was also conducted. M19F substitution was identified from this scan that improved potency and/or selectivity of the resulting variants.

Protoxin-II/Huwentoxin-IV single position chimeras were designed bidirectionally. The purpose of this library was to obtain Protoxin-II variants that retained potency and selectivity profile of the wild type Protoxin-II and would achieve beneficial refolding properties associated with Huwentoxin-IV. Substitutions R22T and E12N were identified from this scan.

Peptide NV1G1153 was further engineered by diversifying position Y1 by a limited amino acid scan using R, K, T, A, D, E, Q and S, and by charge cluster engineering, where all sets of charged residues in the three-dimensional structure of the peptide (D10/E12, K4/E17, D10/E12/R13) were mutated.

N- and C-terminal extensions were introduced to select peptides, including NV1G1153 with the purpose of improving peptide distribution to the site of action and of improving half-life of the peptides without significantly increasing the molecular weight of the resulting peptide. The N- and C-terminal extensions that were used are shown in Table 8 and 9, respectively, and are described in Oi et. al., Neuroscience Letters 434, 266-272, 2008; Whitney et. al., Nature Biotechnology 2011 29:4, 352-356; Sockolosky et. al., (2012) 109:40, 16095-16100. Cell penetrating peptides HIV Tat and polyarginine were also used. Various linkers were used to couple the Protoxin-II variant to the N- and/or C-terminal extensions. The linkers used are shown in Table 10.

Protoxin-II variants from each campaign were tested for their potency and selectivity for Nav1.7 using methods described in Example 3. The amino acid sequences of the variants that inhibited Nav1.7 with an IC$_{50}$ value of 200 nM or less are shown in Table 3. Table 11 shows the amino acid substitutions in select variant when compared to the wild type Protoxin-II, and the IC$_{50}$ values for Nav1.7 inhibition in the FLIPR Tetra assay.

TABLE 8

| N-terminal extension | |
|---|---|
| Amino acid sequence | SEQ ID NO: |
| GPAAAAA | 372 |
| GPAPAPA | 373 |
| GGGGGG | 374 |
| GPCCNCSSKWCRDHSRCC | 375 |
| GPSPGARAF | 376 |
| GPDGPWRKM | 377 |
| GPFGQKASS | 378 |
| GPCRTIGPSVC | 379 |
| GPSHSNTQTLAKAPEHTG | 380 |
| GPQRFVTGHFGGLYPANG | 381 |
| GPGWCGDPGATCGKLRLYCCSGFCDSYTKTCKDKSSA | 382 |
| APAPAPAPAP | 383 |
| GPYGRKKRRQRRR | 384 |
| GPRRRRRRRRRRR | 385 |

TABLE 9

| C-terminal extensions | |
|---|---|
| Amino acid sequence | SEQ ID NO: |
| CRTIGPSVC | 386 |
| YGRKKRRQRRR | 387 |
| GGGGG | 374 |
| DGPWRKM | 388 |
| CCNCSSKWCRDHSRCC | 389 |
| RRRRRRRRRRR | 390 |
| SHSNTQTLAKAPEHTG | 391 |
| APAPA | 392 |
| AAAAA | 393 |
| FGQKASS | 394 |
| QRFVTGHFGGLYPANG | 395 |
| SPGARAF | 396 |
| GPGWCGDPGATCGKLRLYCCSGFCDAYTKTCKDKSSA | 397 |

TABLE 10

| Linkers | |
|---|---|
| Amino acid sequence | SEQ ID NO: |
| GSAPAPAPAPAPGS | 398 |
| GSAPAPAPAPAPAPAPAPAPAPGS | 399 |
| GGGGSAPAPAPAPAPAPAPAPAPAPAPAPAPAPAPGGGGS | 400 |
| APAPA | 392 |
| GSGGGGSAPAPAPAPAPAPAPAPAPGGGGSGS | 401 |
| APAPAPAPAP | 383 |
| APAPAPAPAPAPAPAPAPAP | 402 |

TABLE 11

| Protein name | Protoxin-II variant peptide name | Protein SEQ ID NO: | Substitutions | Nav1.7 $IC_{50}$ (nM) | SE |
|---|---|---|---|---|---|
| NV1G1728 | NV1D3541 | 281 | Y1A, W7Q, S11R, E12N, M19F, R22T, K26R | 9.4 | 1.2 |
| NV1G1870 | NV1D3583 | 321 | Y1A, W7Q, S11A, E12R, M19F, V20S | 13.1 | 1.57 |
| NV1G1752 | NV1D3532 | 272 | Y1A, W7Q, S11A, E12K, M19F, R22T, K26R | 17.3 | 2 |
| NV1G1749 | NV1D3587 | 326 | Y1A, W7Q, S11A, E12N, M19F, V20S | 18.3 | 2.6 |
| NV1G1725 | NV1D3572 | 310 | Y1A, W7Q, S11A, E12R, M19F, R22T | 19.8 | 2.2 |
| NV1G1745 | NV1D3537 | 277 | Y1A, W7Q, S11A, E12K, M19F, V20S, R22T, K26R | 21.4 | 4.1 |
| NV1G1720 | NV1D3565 | 304 | Y1A, W7Q, S11A, E12R, M19F, V20S, R22T | 23 | 2.8 |
| NV1G1761 | NV1D3550 | 290 | Y1A, W7Q, S11R, M19F, R22T, K26R | 25.8 | 2.7 |
| NV1G1746 | NV1D3576 | 314 | Y1A, W7Q, S11A, E12N, M19F, R22T | 26.7 | 5.2 |
| NV1G979 | NV1D2731 | 34 | Y1A, W7Q, S11A | 20.7 | 7.2 |
| NV1G953 | NV1D2670 | 17 | Y1A, W7Q | 22.2 | 3.3 |
| NV1G1519 | NV1D3006 | 133 | Y1Q, W7Q, S11A, E12R, M19F | 4.03 | 1.05 |
| NV1G1007-NH2 | NV1D2775-NH2 | 111 | Y1Q, W7Q, S11A, M19F | 5.06 | 0.473 |
| NV1G1517 | NV1D3004 | 131 | Y1Q, W7Q, S11R, M19F | 6.23 | 1.56 |
| (-GP) N-Ac-NV1G1137-NH2 | (-GP) N-Ac-NV1D2974-NH2 | 114 | Y1Q, W7Q, S11A, M19F, V20S, R22T | 6.43 | 1.06 |
| NV1G1776 | NV1D3339 | 172 | Y1Q, Q3R, W7Q, S11R, M19F, R22T, K26R | 6.57 | 0.675 |
| NV1G1153-NH-methyl | NV1D3034-NH-methyl | 119 | Y1Q, W7Q, S11R, M19F, R22T, K26R | 7.1 | 0.9 |
| (-GP) N-Ac-NV1G1153-NH2 | (-GP) N-Ac-NV1D3034-NH2 | 121 | Y1Q, W7Q, S11R, M19F, R22T, K26R | 7.63 | 1.04 |
| NV1G1523 | NV1D3012 | 135 | Y1Q, W7Q, S11R, E12N, M19F | 7.74 | 0.904 |
| NV1G1515 | NV1D3005 | 132 | Y1Q, W7Q, S11A, E12N, M19F | 7.83 | 1.38 |

TABLE 11-continued

| Protein name | Protoxin-II variant peptide name | Protein SEQ ID NO: | Substitutions | Nav1.7 IC$_{50}$ (nM) | SE |
|---|---|---|---|---|---|
| NV1G1187 | NV1D3015 | 138 | Y1Q, W7Q, S11R, M19F, K26R | 8.86 | 2.28 |
| NV1G1521 | NV1D3018 | 141 | Y1Q, W7Q, S11A, E12N, M19F, K26R | 9.79 | 2.91 |
| NV1G1267 | NV1D3044 | 150 | Y1Q, W7Q, S11R, E12N, M19F, R22T, K26R | 9.8 | 0.849 |
| NV1G1153 | NV1D3034 | 78 | Y1Q, W7Q, S11R, M19F, R22T, K26R | 10.3 | 2.14 |
| NV1G1836 | NV1D3359 | 190 | Y1Q, W7Q, T8S, S11R, M19F, R22T, K26R | 10.5 | 0.739 |
| NV1G1593 | NV1D3050 | 153 | Y1Q, W7Q, S11R, E12K, M19F | 10.8 | 1.3 |
| NV1G1215 | NV1D3048 | 152 | Y1Q, W7Q, S11A, E12K, M19F | 11.1 | 1.05 |
| NV1G1868 | NV1D3353 | 185 | Y1Q, W7Q, T8R, S11R, M19F, R22T, K26R | 11.2 | 1.25 |
| NV1G1525 | NV1D3013 | 136 | Y1Q, W7Q, S11R, E12R, M19F | 11.3 | 1.83 |
| NV1G1775 | NV1D3340 | 173 | Y1Q, Q3K, W7Q, S11R, M19F, R22T, K26R | 11.5 | 0.798 |
| NV1G1833 | NV1D3381 | 210 | Y1Q, W7Q, S11RK14Q, M19F, R22T, K26R | 12.2 | 1.56 |
| NV1G1153-NH2 | NV1D3034-NH2 | 117 | Y1Q, W7Q, S11R, M19F, R22T, K26R | 12.2 | 1 |
| NV1G1777 | NV1D3342 | 175 | Y1Q, Q3A, W7Q, S11R, M19F, R22T, K26R | 12.8 | 2.67 |
| NV1G1259 | NV1D3058 | 158 | Y1Q, W7Q, S11A, E12K, M19F, R22T, K26R | 12.9 | 1.29 |
| NV1G1511 | NV1D3032 | 146 | Y1Q, W7Q, S11R, E12N, M19F, K26R | 13 | 203 |
| NV1G1527 | NV1D3031 | 145 | Y1Q, W7Q, S11R, E12R, M19F, R22T | 13 | 1.36 |
| NV1G1265 | NV1D3062 | 159 | Y1Q, W7Q, S11R, E12K, M19F, R22T, K26R | 13.2 | 1.43 |
| NV1G1781 | NV1D3388 | 217 | Y1Q, W7Q, S11RE17Q, M19F, R22T, K26R | 13.5 | 1.14 |
| NV1G1824 | NV1D3354 | 186 | Y1Q, W7Q, T8K, S11R, M19F, R22T, K26R | 13.9 | 1.12 |
| NV1G1772 | NV1D3352 | 184 | Y1Q, K4S, W7Q, S11R, M19F, R22T, K26R | 14.2 | 2.01 |
| NV1G1509 | NV1D3033 | 147 | Y1Q, W7Q, S11R, E12R, M19F, K26R | 14.5 | 2.18 |
| NV1G1779 | NV1D3351 | 183 | Y1Q, K4Q, W7Q, S11R, M19F, R22T, K26R | 15.3 | 2.39 |
| NV1G1687 | NV1D3526 | 266 | Y1Q, W7Q, S11R, M19F, R22T, K26R | 15.4 | |
| NV1G1269 | NV1D3045 | 151 | Y1Q, W7Q, S11R, E12R, M19F, R22T, K26R | 15.6 | 1.39 |
| NV1G1623 | NV1D3056 | 156 | Y1Q, W7Q, S11R, E12K, M19F, R22T | 16.2 | 2.99 |
| NV1G1859 | NV1D3376 | 205 | Y1Q, W7Q, S11R, K14R, M19F, R22T, K26R | 16.3 | 2.53 |
| NV1G1153-NH-butyl | NV1D3034-NH-butyl | 118 | Y1Q, W7Q, S11R, M19F, R22T, K26R | 16.6 | 1.4 |
| NV1G1211 | NV1D3036 | 149 | Y1Q, W7Q, S11A, E12R, M19F, R22T, K26R | 17.2 | 1.55 |
| NV1G1885 | NV1D3254 | 165 | Y1Q, W7Q, S11A, M19F | 17.5 | 2.45 |
| NV1G1730 | NV1D3542 | 282 | Y1Q, W7Q, S11R, E12N, M19F, V20S, R22T, K26R | 17.7 | 2.5 |
| NV1G1263 | NV1D3051 | 154 | Y1Q, W7Q, S11A, E12K, M19F, R22T | 17.9 | 1.78 |
| NV1G1818 | NV1D3368 | 122 | Y1Q, W7Q, S11R, E12T, M19F, R22T, K26R | 17.9 | 1.89 |
| NV1G1153 (synthetic) | NV1D3034 | 116 | Y1Q, W7Q, S11R, M19F, R22T, K26R | 18 | 2.5 |
| NV1G1823 | NV1D3367 | 197 | Y1Q, W7Q, S11R, E12Q, M19F, R22T, K26R | 18.6 | 2.17 |
| NV1G1820 | NV1D3362 | 193 | Y1Q, W7Q, D10T, S11R, M19F, R22T, K26R | 20.1 | 2.32 |
| NV1G1811 | NV1D3369 | 199 | Y1Q, W7Q, S11R, R13K, M19F, R22T, K26R | 20.4 | 2.44 |
| NV1G1810 | NV1D3358 | 189 | Y1Q, W7Q, T8Q, S11R, M19F, R22T, K26R | 20.5 | 2.11 |
| NV1G1818-NH2 | NV1D3368-NH2 | 123 | Y1Q, W7Q, S11R, E12T, M19F, R22T, K26R | 20.5 | 2.8 |
| NV1G1137 (synthetic) | NV1D2974 | 129 | Y1Q, W7Q, S11A, M19F, V20S, R22T | 21.6 | 1.34 |
| NV1G1221 | NV1D3017 | 140 | Y1Q, W7Q, S11A, E12R, M19F, R22T | 21.9 | 2.48 |

TABLE 11-continued

| Protein name | Protoxin-II variant peptide name | Protein SEQ ID NO: | Substitutions | Nav1.7 IC$_{50}$ (nM) | SE |
|---|---|---|---|---|---|
| NV1G1722 | NV1D3533 | 273 | Y1Q, W7Q, S11A, E12K, M19F, V20S, R22T, K26R | 22.4 | 3.5 |
| NV1G1767 | NV1D3345 | 177 | Y1Q, Q3S, W7Q, S11R, M19F, R22T, K26R | 22.4 | 2.52 |
| NV1G1769 | NV1D3346 | 178 | Y1Q, K4R, W7Q, S11R, M19F, R22T, K26R | 23.2 | 3.39 |
| NV1G1780 | NV1D3387 | 216 | Y1Q, W7Q, S11R, E17D, M19F, R22T, K26R | 23.7 | 2.85 |
| NV1G1886 | NV1D3249 | 162 | Y1Q, W7Q, S11A, M19F | 24.1 | 11.5 |
| NV1G1812 | NV1D3382 | 211 | Y1Q, W7Q, S11R, K14S, M19F, R22T, K26R | 24.3 | 2.14 |
| NV1G1857 | NV1D3366 | 196 | Y1Q, W7Q, D10S, S11R, M19F, R22T, K26R | 24.6 | 3.8 |
| NV1G1821 | NV1D3378 | 207 | Y1Q, W7Q, S11R, K14A, M19F, R22T, K26R | 24.8 | 2.66 |
| NV1G1993 | NV1D3792 | 335 | Y1Q, W7Q, S11R, M19F, R22T, K26R | 25.3 | 2.8 |
| NV1G1007 | NV1D2775 | 56 | Y1Q, W7Q, S11A, M19F | 25.4 | 2 |
| NV1G1787 | NV1D3396 | 224 | Y1Q, W7Q, S11R, G18Q, M19F, R22T, K26R | 26.4 | 3.17 |
| NV1G1257 | NV1D3016 | 139 | Y1Q, W7Q, S11A, E12N, M19F, R22T | 26.6 | 3.1 |
| NV1G1153 (synthetic) | NV1D3034 | 116 | Y1Q, W7Q, S11R, M19F, R22T, K26R | 27.3 | 2.02 |
| NV1G1803 | NV1D3403 | 230 | Y1Q, W7Q, S11R, M19F, R22T, K26R, K27A | 28.3 | 1.97 |
| (-GP)N-Ac-NV1G1137 | N-Ac-NV1D2974 | 115 | Y1Q, W7Q, S11A, M19F, V20S, R22T | 28.6 | 2.23 |
| NV1G1531 | NV1D3019 | 142 | Y1Q, W7Q, S11A, E12R, M19F, K26R | 28.7 | 4.78 |
| NV1G1513 | NV1D3007 | 134 | Y1Q, W7Q, S11A, M19F, K26R | 29.6 | 9.17 |
| NV1G1991 | NV1D3789 | 333 | Y1Q, W7Q, S11R, M19F, R22T, K26R | 29.9 | 5.19 |
| NV1G1013 | NV1D2733 | 40 | Y1R, W7Q, M19F | 7.54 | 2.9 |
| NV1G1740 | NV1D3580 | 318 | Y1R, W7Q, S11A, E12R, M19F, V20S | 8.4 | 1.5 |
| NV1G1757 | NV1D3538 | 278 | Y1R, W7Q, S11R, E12N, M19F, R22T, K26R | 11.6 | 1.4 |
| NV1G1741 | NV1D3569 | 307 | Y1R, W7Q, S11A, E12R, M19F, R22T | 11.9 | 0.8 |
| NV1G1715 | NV1D3584 | 322 | Y1R, W7Q, S11A, E12N, M19F, V20S | 13.9 | 1.4 |
| NV1G1754 | NV1D3529 | 269 | Y1R, W7Q, S11A, E12K, M19F, R22T, K26R | 14.6 | 1.7 |
| NV1G1005 | NV1D2772 | 59 | Y1R, W7Q, S11A, M19F | 15.6 | 1.8 |
| NV1G1733 | NV1D3577 | 315 | Y1R, W7Q, S11A, M19F, V20S | 18.8 | 2.2 |
| NV1G1744 | NV1D3534 | 274 | Y1R, W7Q, S11A, E12K, M19F, V20S, R22T, K26R | 20.6 | 2.2 |
| NV1G1724 | NV1D3562 | 301 | Y1R, W7Q, S11A, E12R, M19F, V20S, R22T | 23.6 | 2.7 |
| NV1G1735 | NV1D3566 | 305 | Y1R, W7Q, S11A, M19F, R22T | 23.7 | 2.5 |
| NV1G1760 | NV1D3543 | 283 | Y1R, W7Q, S11R, E12N, M19F, V20S, R22T, K26R | 23.8 | 1.9 |
| NV1G1759 | NV1D3547 | 287 | Y1R, W7Q, S11R, M19F, R22T, K26R | 26.5 | 2.1 |
| NV1G1751 | NV1D3558 | 297 | Y1R, W7Q, S11A, E12N, M19F, V20S, R22T | 26.7 | 3.4 |
| NV1G1726 | NV1D3551 | 291 | Y1R, W7Q, S11R, M19F, V20S, R22T, K26R | 29.3 | 3.8 |
| NV1G1105 | NV1D2729 | 39 | Y1R, W7Q, S11A | 8 | 8.85E−01 |
| NV1G957 | NV1D2668 | 23 | Y1R, W7Q | 17.5 | 2.6 |
| (-GP)NV1G1001 | (-GP)NV1D2773 | 109 | Y1S, W7Q, S11A, M19F | 9.47 | 1.28 |
| (-GP)NV1G1001-NH-methyl | (-GP)NV1D2773-NH-methyl | 110 | Y1S, W7Q, S11A, M19F | 11.5 | 0.61 |
| NV1G1003 | NV1D2734 | 44 | Y1S, W7Q, M19F | 13.4 | 0.8 |
| NV1G1864 | NV1D3581 | 319 | Y1S, W7Q, S11A, E12R, M19F, V20S | 14.6 | 1.7 |
| NV1G1748 | NV1D3530 | 270 | Y1S, W7Q, S11A, E12K, M19F, R22T, K26R | 15.6 | 2.2 |
| NV1G1758 | NV1D3548 | 288 | Y1S, W7Q, S11R, M19F, R22T, K26R | 17.6 | 1.9 |
| NV1G1727 | NV1D3544 | 284 | Y1S, W7Q, S11R, E12N, M19F, V20S, R22T, K26R | 17.8 | 2.2 |

TABLE 11-continued

| Protein name | Protoxin-II variant peptide name | Protein SEQ ID NO: | Substitutions | Nav1.7 IC$_{50}$ (nM) | SE |
|---|---|---|---|---|---|
| NV1G1719 | NV1D3570 | 308 | Y1S, W7Q, S11A, E12R, M19F, R22T | 18.1 | 1.5 |
| NV1G1742 | NV1D3535 | 275 | Y1S, W7Q, S11A, E12K, M19F, V20S, R22T, K26R | 18.7 | 2.8 |
| NV1G1001 | NV1D2773 | 65 | Y1S, W7Q, S11A, M19F | 18.8 | 1.5 |
| NV1G1753 | NV1D3585 | 323 | Y1S, W7Q, S11A, E12N, M19F, V20S | 19.4 | 2.1 |
| NV1G1762 | NV1D3539 | 279 | Y1S, W7Q, S11A, E12N, M19F, R22T, K26R | 19.4 | 1.8 |
| NV1G1755 | NV1D3574 | 312 | Y1S, W7Q, S11A, E12N, M19F, R22T | 22.3 | 2.7 |
| NV1G1717 | NV1D3563 | 302 | Y1S, W7Q, S11A, E12R, M19F, V20S, R22T | 22.4 | 2.4 |
| NV1G1866 | NV1D3559 | 298 | Y1S, W7Q, S11A, E12N, M19F, V20S, R22T | 26.5 | 5.02 |
| NV1G1721 | NV1D3552 | 292 | Y1S, W7Q, S11R, M19F, V20S, R22T, K26R | 28.1 | 3.7 |
| NV1G975 | NV1D2669 | 26 | Y1S, W7Q | 18.4 | 5.7 |
| NV1G983 | NV1D2730 | 43 | Y1S, W7Q, S11A | 25.5 | 4.3 |
| NV1G1750-NH2 | NV1D3586-NH2 | 325 | W7Q, S11A, E12N, M19F, V20S | 4.23 | 0.33 |
| NV1G1747 | NV1D3531 | 271 | W7Q, S11A, E12K, M19F, R22T, K26R | 13 | 2.1 |
| NV1G1763 | NV1D3540 | 280 | W7Q, S11R, E12N, M19F, R22T, K26R | 16 | 1.5 |
| NV1G1739 | NV1D3582 | 320 | W7Q, S11A, E12R, M19F, V20S | 17.8 | 2.2 |
| NV1G1750 | NV1D3586 | 324 | W7Q, S11A, E12N, M19F, V20S | 20.5 | 2.2 |
| NV1G1718 | NV1D3571 | 309 | W7Q, S11A, E12R, M19F, R22T | 21 | 2.3 |
| NV1G1865 | NV1D3560 | 299 | W7Q, S11A, E12N, M19F, V20S, R22T | 27.2 | 3.42 |
| NV1G1766 | NV1D3549 | 289 | W7Q, S11R, M19F, R22T, K26R | 27.5 | 3.2 |
| NV1G961 | NV1D2676 | 29 | W7Q, S11A | 26.5 | 2.9 |
| NV1G951 | NV1D2674 | 18 | Y1A, S11A | 4.03 | 0.2 |
| NV1G1011 | NV1D2740 | 37 | Y1Q, S11A, M19F | 3.62 | 9.9 |
| NV1G977 | NV1D2665 | 22 | Y1Q, M19F | 4.9 | 0.4 |
| NV1G949 | NV1D2675 | 21 | Y1Q, S11A | 4.33 | 0.3 |
| NV1G973 | NV1D2662 | 25 | Y1R, M19F | 4.03 | 0.4 |
| NV1G965 | NV1D2672 | 24 | Y1R, S11A | 4.5 | 0.3 |
| NV1G1009 | NV1D2738 | 45 | Y1S, S11A, M19F | 2.57 | 0.2 |
| NV1G995 | NV1D2663 | 28 | Y1S, M19F | 4.19 | 0.4 |
| NV1G1107-NH2 | NV1D2890-NH2 | 112 | Y1S, M6F, S11A, M19L | 9.12 | 1.17 |
| NV1G971 | NV1D2673 | 27 | Y1S, S11A | 4.31 | 0.5 |
| NV1G1782 | NV1D3383 | 212 | Y1Q, W7Q, S11R, E17R, M19F, R22T, K26R, | 30.3 | 4.06 |
| NV1G1990 | NV1D3788 | 332 | Y1Q, W7Q, S11R, M19F, R22T, K26R, | 30.3 | 4.78 |
| (-GP)N-Ac-NV1G1153- | (-GP)N-Ac-NV1D3034 | 120 | Y1Q, W7Q, S11R, M19F, R22T, K26R | 30.4 | 2.96 |
| NV1G1786 | NV1D3389 | 218 | Y1Q, W7Q, S11R, E17S, M19F, R22T, K26R, | 30.8 | 4.48 |
| NV1G1147 | NV1D2969 | 124 | Y1S, W7Q, S11A, M19F, V20S | 31 | 6.15 |
| NV1G1764 | NV1D3554 | 294 | Y1A, W7Q, S11R, M19F, V20S, R22T, K26R | 31.4 | 3.3 |
| NV1G963 | NV1D2671 | 20 | Y1Q, W7Q | 31.5 | 6.4 |
| NV1G1835 | NV1D3379 | 208 | Y1Q, K4D, W7Q, S11R, M19F, R22T, K26R | 31.6 | 2.88 |
| NV1G1231 | NV1D3035 | 148 | Y1Q, W7Q, S11A, E12N, M19F, R22T, K26R | 32 | 4.9 |
| NV1G1743 | NV1D3564 | 303 | W7Q, S11A, E12R, M19F, V20S, R22T | 32.3 | 3.1 |
| NV1G1960 | NV1D3803 | 345 | Y1Q, W7Q, S11R, M19F, R22T, K26R | 32.3 | 5.33 |
| NV1G1924 | NV1D3470 | 250 | Y1Q, W7Q, S11R, M19L, R22T, K26R | 32.5 | 403 |
| NV1G1756 | NV1D3575 | 313 | W7Q, S11A, E12N, M19F, R22T | 33.2 | 3.9 |
| NV1G1109 | NV1D2899 | 67 | Y1S, W7Q, S11A, M19L | 33.3 | 6.7 |
| NV1G1818 | NV1D3368 | 122 | Y1Q, W7Q, S11R, E12T, M19F, R22T, K26R | 33.5 | 10.7 |
| NV1G1784 | NV1D3386 | 215 | Y1Q, W7Q, S11R, E17A, M19F, R22T, K26R | 33.6 | 4.71 |
| NV1G1141 | NV1D2972 | 127 | Y1Q, W7Q, S11A, M19F, V20S | 34.1 | 6.2 |
| NV1G1774 | NV1D3347 | 179 | Y1Q, K4T, W7Q, S11R, M19F, R22T, K26R | 34.2 | 5.99 |
| NV1G1881 | NV1D3257 | 167 | Y1Q, W7Q, S11A, M19F | 34.2 | 2.81 |

TABLE 11-continued

| Protein name | Protoxin-II variant peptide name | Protein SEQ ID NO: | Substitutions | Nav1.7 IC$_{50}$ (nM) | SE |
|---|---|---|---|---|---|
| NV1G1915 | NV1D3467 | 249 | Y1Q, W7Q, S11R, E17G, M19F, R22T, K26R | 34.5 | 4 |
| NV1G1984 | NV1D3806 | 348 | Y1Q, W7Q, S11R, M19F, R22T, K26R | 35.1 | 4.56 |
| NV1G1716 | NV1D3561 | 300 | Y1A, W7Q, S11A, E12N, M19F, V20S, R22T, | 35.6 | 5 |
| NV1G1255 | NV1D3014 | 137 | Y1Q, W7Q, S11R, M19F, R22T | 36.1 | 5.37 |
| NV1G1959 | NV1D3818 | 357 | Y1Q, W7Q, S11R, M19F, R22T, K26R | 36.3 | 204 |
| NV1G1825 | NV1D3377 | 206 | Y1Q, W7Q, S11R, K14T, M19F, R22T, K26R | 36.4 | 4.83 |
| NV1G1723 | NV1D3536 | 276 | W7Q, S11A, E12K, M19F, V20S, R22T, K26R | 37 | 5.4 |
| NV1G1732 | NV1D3555 | 295 | Y1R, W7Q, S11A, M19F, V20S, R22T, | 37.4 | 4.3 |
| NV1G1983 | NV1D3809 | 350 | Y1Q, W7Q, S11R, M19F, R22T, K26R | 38.9 | 4.81 |
| NV1G1982 | NV1D3805 | 347 | Y1Q, W7Q, S11R, M19F, R22T, K26R | 41.2 | 5.44 |
| NV1G1785 | NV1D3385 | 214 | Y1Q, W7Q, S11R, E17T, M19F, R22T, K26R | 41.5 | 6.5 |
| NV1G1583 | NV1D3030 | 144 | Y1Q, W7Q, S11R, E12N, M19F, R22T | 41.9 | 5.15 |
| NV1G1729 | NV1D3545 | 285 | W7Q, S11R, E12N, M19F, V20S, R22T, K26R | 42.8 | 4.6 |
| NV1G1007 | NV1D2775 | 56 | Y1Q, W7Q, S11A, M19F | 42.9 | 6.7 |
| NV1G1734 | NV1D3568 | 306 | Q1A, W7Q, S11A, M19F, R22T | 44 | 8.3 |
| NV1G1683 | NV1D3523 | 263 | Y1Q, W7Q, S11R, M19F, R22T, K26R | 44.7 | |
| NV1G1834 | NV1D3360 | 191 | Y1Q, W7Q, D10R, S11R, M19F, R22T, K26R | 45.2 | 3.79 |
| NV1G1795 | NV1D3401 | 229 | Y1Q, W7Q, S11R, M19F, R22T, K26R, K27R | 45.5 | 6.58 |
| NV1G1689 | NV1D3514 | 255 | Y1Q, W7Q, S11R, M19F, R22T, K26R | 46.4 | |
| NV1G2043 | NV1D3835 | 370 | Y1Q, W7Q, S11R, M19F, R22T, K26R | 46.4 | 4.09 |
| NV1G1783 | NV1D3384 | 213 | Y1Q, W7Q, S11R, E17K, M19F, R22T, K26R | 46.8 | 7.39 |
| NV1G1239 | NV1D3020 | 143 | Y1Q, W7Q, S11A, M19F, R22T, K26R | 47.2 | 7.84 |
| NV1G1788 | NV1D3399 | 227 | Y1Q, W7Q, S11R, M19F, V20T, R22T, K26R | 47.3 | 6.36 |
| NV1G899 | NV1D2774 | 52 | Y1A, W7Q, S11A, M19F | 50.5 | 15.2 |
| NV1G2057 | NV1D3799 | 341 | Y1Q, W7Q, S11R, M19F, R22T, K26R | 50.6 | 6.33 |
| NV1G1738 | NV1D3578 | 316 | W7Q, S11A, M19F, V20S, | 50.7 | 5.7 |
| NV1G1713 | NV1D3525 | 265 | Y1Q, W7Q, S11R, M19F, R22T, K26R | 52.3 | |
| NV1G1765 | NV1D3553 | 293 | W7Q, S11R, M19F, V20S, R22T, K26R | 52.4 | 10 |
| NV1G1916 | NV1D3465 | 247 | Y1Q, W5F, W7Q, S11R, M19F, R22T, K26R | 52.8 | 10.3 |
| NV1G1977 | NV1D3804 | 346 | Y1Q, W7Q, S11R, M19F, R22T, K26R | 53.6 | 6.27 |
| NV1G1879 | NV1D3259 | 168 | Y1Q, W7Q, S11A, M19F | 54.9 | 7.62 |
| NV1G1884 | NV1D3256 | 166 | Y1Q, W7Q, S11A, M19F | 55.7 | 10.5 |
| NV1G1986 | NV1D3819 | 358 | Y1Q, W7Q, S11R, M19F, R22T, K26R | 56 | 6.57 |
| NV1G1633 | NV1D3251 | 163 | Y1Q, W7Q, S11A, M19F | 56.1 | 13.9 |
| NV1G1880 | NV1D3261 | 170 | Y1Q, W7Q, S11A, M19F | 57 | 6.25 |
| NV1G1985 | NV1D3808 | 349 | Y1Q, W7Q, S11R, M19F, R22T, K26R | 57 | 6.74 |
| NV1G1849 | NV1D3400 | 228 | Y1Q, W7Q, S11R, M19F, V20Q, R22T, K26R | 57.3 | 9.52 |
| NV1G1883 | NV1D3260 | 169 | Y1Q, W7Q, S11A, M19F | 57.6 | 6.91 |
| NV1G1145 | NV1D2970 | 125 | Y1S, W7Q, S11A, M19F, R22T | 58 | 18.8 |
| NV1G1697 | NV1D3517 | 258 | Y1Q, W7Q, S11R, M19F, R22T, K26R | 58.5 | |
| NV1G1737 | NV1D3579 | 317 | Y1A, W7Q, S11A, M19F, V20S | 59.9 | 9.6 |
| NV1G1978 | NV1D3833 | 368 | Y1Q, W7Q, S11R, M19F, R22T, K26R | 60.3 | 9.57 |
| NV1G1954 | NV1D3800 | 342 | Y1Q, W7Q, S11R, M19F, R22T, K26R | 60.9 | 6.43 |

TABLE 11-continued

| Protein name | Protoxin-II variant peptide name | Protein SEQ ID NO: | Substitutions | Nav1.7 $IC_{50}$ (nM) | SE |
|---|---|---|---|---|---|
| NV1G1989 | NV1D3791 | 334 | Y1Q, W7Q, S11R, M19F, R22T, K26R | 61.8 | 8.66 |
| NV1G1815 | NV1D3380 | 209 | Y1Q, K4E, W7Q, S11R, M19F, R22T, K26R | 64 | 10.5 |
| NV1G1967 | NV1D3793 | 336 | Y1Q, W7Q, S11R, M19F, R22T, K26R | 64.6 | 8.19 |
| NV1G1869 | NV1D3573 | 311 | Y1R, W7Q, S11A, E12N, M19F, R22T | 64.7 | 50.7 |
| NV1G1872 | NV1D3777 | 330 | Y1Q, W7Q, S11R, M19F, R22T, K26R | 64.9 | 15.3 |
| NV1G1979 | NV1D3834 | 369 | Y1Q, W7Q, S11R, M19F, R22T, K26R | 65.5 | 7.59 |
| NV1G1827 | NV1D3365 | 195 | Y1Q, W7Q, D10Q, S11R, M19F, R22T, K26R | 66.1 | 10.1 |
| NV1G1768 | NV1D3341 | 174 | Y1Q, Q3T, W7Q, S11R, M19F, R22T, K26R | 66.2 | 9.32 |
| NV1G911 | NV1D2666 | 30 | W7Q, M19F | 66.5 | 36.7 |
| NV1G1856 | NV1D3397 | 225 | Y1Q, W7Q, S11R, G18S, M19F, R22T, K26R | 66.7 | 7.31 |
| NV1G1973 | NV1D3810 | 351 | Y1Q, W7Q, S11R, M19F, R22T, K26R | 66.9 | 7.04 |
| NV1G1855 | NV1D3398 | 226 | Y1Q, W7Q, S11R, M19F, V20S, R22T, K26R | 67.3 | 11 |
| NV1G1961 | NV1D3802 | 344 | Y1Q, W7Q, S11R, M19F, R22T, K26R | 68 | 8.23 |
| NV1G1846 | NV1D3431 | 244 | Y1Q, K4E, W7Q, S11R, E17K, M19F, R22T, K26R | 68.6 | 13.9 |
| NV1G1771 | NV1D3348 | 180 | Y1Q, K4A, W7Q, S11R, M19F, R22T, K26R | 70.6 | 15.9 |
| NV1G1691 | NV1D3520 | 261 | Y1Q, W7Q, S11R, M19F, R22T, K26R | 71.4 | |
| NV1G1681 | NV1D3511 | 252 | Y1Q, W7Q, S11R, M19F, R22T, K26R | 71.5 | |
| NV1G1968 | NV1D3822 | 359 | Y1Q, W7Q, S11R, M19F, R22T, K26R | 74.2 | 11.1 |
| NV1G1813 | NV1D3424 | 238 | Y1Q, W7Q, D10K, S11R, E12K, M19F, R22T, K26R | 75.2 | 12.2 |
| NV1G1067 | NV1D2893 | 57 | Y1Q, W7Q, S11A, M19L | 75.5 | 10.5 |
| NV1G1867 | NV1D3546 | 286 | Y1A, W7Q, S11R, E12N, M19F, V20S, R22T, K26R | 76 | 17.6 |
| NV1G1143 | NV1D2971 | 126 | Y1S, W7Q, S11A, M19F, V20S, R22T | 77.5 | 22.1 |
| NV1G1806 | NV1D3409 | 232 | Y1Q, W7Q, S11R, M19F, R22T, K26R, K28T | 79.1 | 11.3 |
| NV1G1061 | NV1D2896 | 60 | Y1R, W7Q, S11A, M19L | 80.3 | 7.13 |
| NV1G1793 | NV1D3419 | 236 | Y1Q, W7Q, S11R, M19F, R22T, K26R, W30D | 80.9 | 11.9 |
| NV1G1613 | NV1D3057 | 157 | Y1Q, W7Q, S11R, E12K, M19F, K26R | 83.4 | 16.6 |
| NV1G1585 | NV1D3052 | 155 | Y1Q, W7Q, S11A, E12K, M19F, K26R | 84.8 | 28.8 |
| NV1G1707 | NV1D3524 | 264 | Y1Q, W7Q, S11R, M19F, R22T, K26R | 84.9 | |
| NV1G1773 | NV1D3350 | 182 | Y1Q, K4E, W7Q, S11R, M19F, R22T, K26R | 85.6 | 14.4 |
| NV1G1949 | NV1D3828 | 364 | Y1Q, W7Q, S11R, M19F, R22T, K26R | 87.5 | 11 |
| NV1G1976 | NV1D3811 | 352 | Y1Q, W7Q, S11R, M19F, R22T, K26R | 87.7 | 15.7 |
| NV1G1956 | NV1D3801 | 343 | Y1Q, W7Q, S11R, M19F, R22T, K26R | 88.1 | 11.4 |
| NV1G1975 | NV1D3832 | 367 | Y1Q, W7Q, S11R, M19F, R22T, K26R | 88.4 | 12.3 |
| NV1G1839 | NV1D3774 | 328 | Y1Q, W7Q, S11R, M19F, R22T, K26R | 88.6 | 19.6 |
| NV1G1971 | NV1D3830 | 366 | Y1Q, W7Q, S11R, M19F, R22T, K26R | 88.6 | 9.88 |
| NV1G1882 | NV1D3262 | 171 | Y1Q, W7Q, S11A, M19F | 89.2 | 8.32 |
| NV1G1950 | NV1D3797 | 339 | Y1Q, W7Q, S11R, M19F, R22T, K26R | 91.1 | 13.5 |
| NV1G1828 | NV1D3363 | 194 | Y1Q, W7Q, D10A, S11R, M19F, R22T, K26R | 93.1 | 15.3 |
| NV1G1139 | NV1D2973 | 128 | Y1Q, W7Q, S11A, M19F, R22T | 93.9 | 19.5 |
| NV1G1842 | NV1D3430 | 243 | Y1Q, K4D, W7Q, S11R, E17K, M19F, R22T, K26R | 93.9 | 14.1 |

TABLE 11-continued

| Protein name | Protoxin-II variant peptide name | Protein SEQ ID NO: | Substitutions | Nav1.7 IC$_{50}$ (nM) | SE |
|---|---|---|---|---|---|
| NV1G1948 | NV1D3798 | 340 | Y1Q, W7Q, S11R, M19F, R22T, K26R | 94.5 | 17.8 |
| NV1G1807 | NV1D3408 | 231 | Y1Q, W7Q, S11R, M19F, R22T, K26R, K28R | 94.8 | 17.8 |
| NV1G1137 | NV1D2974 | 129 | Y1Q, W7Q, S11A, M19F, V20S, R22T | 95.7 | 16.2 |
| NV1G1843 | NV1D3432 | 245 | Y1Q, K4E, W7Q, S11R, E17R, M19F, R22T, K26R | 95.9 | 10.4 |
| NV1G1822 | NV1D3423 | 237 | Y1Q, W7Q, D10R, S11R, E12R, M19F, R22T, K26R | 99.5 | 9.45 |
| NV1G1862 | NV1D3556 | 296 | W7Q, S11A, M19F, V20S, R22T | 100 | 18.5 |
| NV1G1969 | NV1D3795 | 337 | Y1Q, W7Q, S11R, M19F, R22T, K26R | 100 | 14.5 |
| NV1G1980 | NV1D3812 | 353 | Y1Q, W7Q, S11R, M19F, R22T, K26R | 101 | 23.6 |
| NV1G1850 | NV1D3414 | 235 | Y1Q, W7Q, S11R, M19F, R22T, K26R, K28S | 102 | 19.4 |
| NV1G1981 | NV1D3815 | 356 | Y1Q, W7Q, S11R, M19F, R22T, K26R | 102 | 13.5 |
| NV1G1851 | NV1D3390 | 219 | Y1Q, W7Q, S11R, G18R, M19F, R22T, K26R | 108 | 15.5 |
| NV1G1922 | NV1D3466 | 248 | Y1Q, W7Q, S11E, M19F, R22T, K26R | 108 | 922 |
| NV1G1778 | NV1D3349 | 181 | Y1Q, K4D, W7Q, S11R, M19F, R22T, K26R | 109 | 16 |
| NV1G1972 | NV1D3824 | 361 | Y1Q, W7Q, S11R, M19F, R22T, K26R | 110 | 16.1 |
| NV1G1974 | NV1D3796 | 338 | Y1Q, W7Q, S11R, M19F, R22T, K26R | 110 | 19.6 |
| NV1G1826 | NV1D3357 | 188 | Y1Q, W7Q, T8E, S11R, M19F, R22T, K26R | 111 | 15.1 |
| NV1G1892 | NV1D3439 | 246 | Y1Q, W7Q, S11R, M19F, R22T, K26R, W30G | 112 | 13.2 |
| NV1G1819 | NV1D3375 | 204 | Y1Q, W7Q, S11R, R13S, M19F, R22T, K26R | 113 | 1270 |
| NV1G1805 | NV1D3410 | 233 | Y1Q, W7Q, S11R, M19F, R22T, K26R, K28A | 114 | 21.5 |
| NV1G1831 | NV1D3374 | 203 | Y1Q, W7Q, S11R, R13Q, M19F, R22T, K26R | 114 | 1600 |
| NV1G1693 | NV1D3512 | 253 | Y1Q, W7Q, S11R, M19F, R22T, K26R | 115.6 | |
| NV1G1854 | NV1D3392 | 221 | Y1Q, W7Q, S11R, G18T, M19F, R22T, K26R | 117 | 21.8 |
| NV1G1951 | NV1D3829 | 365 | Y1Q, W7Q, S11R, M19F, R22T, K26R | 122 | 13.3 |
| NV1G1860 | NV1D3393 | 222 | Y1Q, W7Q, S11R, G18A, M19F, R22T, K26R | 125 | 24.8 |
| NV1G1099 | NV1D2732 | 36 | Y1Q, W7Q, S11A | 126 | 26.9 |
| NV1G1705 | NV1D3513 | 254 | Y1Q, W7Q, S11R, M19F, R22T, K26R | 131.2 | |
| NV1G1848 | NV1D3426 | 240 | Y1Q, W7Q, D10K, S11R, E12K, R13D, M19F, R22T, K26R | 135 | 39.9 |
| NV1G1952 | NV1D3813 | 354 | Y1Q, W7Q, S11R, M19F, R22T, K26R | 139 | 30.1 |
| NV1G1631 | NV1D3252 | 164 | Y1Q, W7Q, S11A, M19F | 145 | 53 |
| NV1G1817 | NV1D3371 | 201 | Y1Q, W7Q, S11R, R13A, M19F, R22T, K26R | 151 | 33.7 |
| NV1G1789 | NV1D3394 | 223 | Y1Q, W7Q, S11R, G18D, M19F, R22T, K26R | 155 | 41.4 |
| NV1G1852 | NV1D3391 | 220 | Y1Q, W7Q, S11R, G18K, M19F, R22T, K26R | 157 | 23.1 |
| NV1G1709 | NV1D3510 | 251 | Y1Q, W7Q, S11R, M19F, R22T, K26R | 159 | |
| NV1G1840 | NV1D3425 | 239 | Y1Q, W7Q, D10R, S11R, E12R, R13D, M19F, R22T, K26R | 161 | 27.9 |
| NV1G1809 | NV1D3413 | 234 | Y1Q, W7Q, S11R, M19F, R22T, K26R, K28Q | 164 | 43.7 |
| NV1G1863 | NV1D3356 | 187 | Y1Q, W7Q, T8D, S11R, M19F, R22T, K26R | 167 | 32.2 |
| NV1G1699 | NV1D3527 | 267 | Y1Q, W7Q, S11R, M19F, R22T, K26R | 169.1 | |
| NV1G1844 | NV1D3428 | 242 | Y1Q, W7Q, D10K, S11R, E12K, R13E, M19F, R22T, K26R | 180 | 52.4 |
| NV1G1853 | NV1D3370 | 200 | Y1Q, W7Q, S11R, R13T, M19F, R22T, K26R | 181 | 25.1 |

TABLE 11-continued

| Protein name | Protoxin-II variant peptide name | Protein SEQ ID NO: | Substitutions | Nav1.7 IC$_{50}$ (nM) | SE |
|---|---|---|---|---|---|
| NV1G1946 | NV1D3825 | 362 | Y1Q, W7Q, S11R, M19F, R22T, K26R | 194 | 28.4 |

The wild-type Protoxin-II inhibits Nav1.7 with an IC$_{50}$ value of about 4 nM in FLIPR assay as described in Example 3. Variants retaining significant Nav1.7 potency were characterized further. FIG. 1 shows the sequence genus of generated Protoxin-II variants that inhibit Nav1.7 with an IC$_{50}$ value of 30 nM or less.

Select Protoxin-II variants were tested for their inhibition of Nav1.7 and for their selectivity against human Nav1.6 using QPatch. IC$_{50}$ values for both Nav1.7 and Nav1.6 for select peptides obtained using QPatch are shown in FIG. 2. These peptides inhibited Nav1.7 with an IC$_{50}$ of 30 nM or less, and were at least 30-fold selective over Nav1.7 when compared to Nav1.6.

The amino acid sequences of the peptides shown in FIG. 2 are shown in FIG. 3. All these peptides had W7Q and M19F substitutions when compared to the wild type Protoxin-II.

The protoxin-II variants were expressed and purified as described in Example 1, or synthesized by standard solid phase synthesis methods. The yields of the recombinant or synthetic peptides were compared to the yields of the wild-type protoxin. Table 12 shows that the yields of the select protoxin-II variants were significantly higher than that of protoxin-II, indicating improved folding properties of the variants. The scale of the solid-phase synthesis was 0.5 mmol.

TABLE 12

| | Solid phase synthesis | | | Recombinant |
|---|---|---|---|---|
| Peptide | Total yield | Yield from Crude | Yield From Linear | expression % active isomer |
| Protoxin-II | 52 mg | 2.7% | 7.3% | 54.0% |
| NV1D2775 | 84 mg | 4.5% | 18.7% | 89.1% |
| NV1D3034 | 149 mg | 8.0% | 21.0% | 85.2% |
| NV1D3368 | 83 mg | 4.0% | 24.0% | 93.8% |

Example 5. Protoxin-II Variants are Efficient in In Vivo Models of Pain

Materials and Methods
Animals Male C57Bl/6 mice (24-26 g), ordered from Charles River and housed individually, were used for this study.
Behavioral Tests
Von Frey Test: Mechanical (tactile) threshold was assessed by Von Frey Hairs following the Up-Down method (Dixon, 1980, Chaplan et al., 1994). 7 graded stimuli (von Frey filaments: 0.03, 0.07, 0.16, 0.4, 0.6, 1, 2 g; Stoelting, Wood Dale, Ill.) were used. Von Frey hairs were presented perpendicularly against the center plantar area (between toris) on a hindpaw. Sufficient force was applied to bend the filament slightly and held for 3 seconds. Per the Chaplan paper, a positive response can be either 1) a sharp withdrawal or 2) immediate flinching upon removal of the filament. See Chaplan et al for more details. Mice were acclimated to the wire mesh in the testing chamber for 30-60 minutes prior to testing.

Hargreaves Test: A modified Hargreaves box was used to measure thermal paw withdrawal latency (PWL) (Hargreaves et al., 1988, Pain, 32:77-88; Dirig et al., 1997, J Neurosci. Methods, 76:183-191). This box consists of a chamber with a raised glass floor maintained at a constant temperature (27° C.). The thermal nociceptive stimulus originates from a projection bulb light beam below the glass surface. The light beam is aimed at the area between toris (center plantar). The "start" button will turn on the light and start the timer. Movements (such as a sudden withdrawal) of the stimulated paw will trigger the switch to turn off the light and stop the timer. The latency in seconds is displayed. If no movement occurs, the bulb will be turned off after 20 seconds (cutoff) to prevent tissue injury. The animals were allowed to habituate on the glass surface for 30-60 minutes before PWL measurement. Constant amperage was used throughout the study, which resulted in Pre-test paw withdrawal latencies between 8-12 seconds when averaged over 3 to 6 read-outs taken at least 5 minutes apart.

MPE % Calculation: Percent maximum possible effect (MPE %)=$(T_1-T_0)/(Tc-T_0) \times 100\%$. $T_0$: threshold on day0 (post-CFA, pre-pump); $T_1$: threshold on day1 post pump implantation; Tc: cut-off of the test (20 s for the Hargreaves test and 2 g for the Von Frey test)

Hotplate Test: Animals were placed on a 10"×10" metal plate surrounded by 4 Plexiglas walls (15 inches high). The plate was maintained at a temperature of either 50 or 55° C. The response latency (time when the animal first flinches or licks its hind paw, jumps, or vocalizes) was measured and the animal removed from the plate. Animals showing no response were removed from the plate after 40 s (50° C.) or 20 s (55° C.) to prevent any possible tissue damage. This trial was repeated 2-5 times every 15-60 minutes in a day.
Inflammatory Pain Models
CFA Model: Animals were anesthetized with isoflurane (4% induction and 2% maintenance) and 20 μL of 100% Complete Freund's Adjuvant (CFA; Sigma-Aldrich; Saint Louis, Mo.) was injected into the center plantar area on one hind paw using a 27 gauge needle attached to a 50 μL Hamilton syringe.

Carrageenan model: Animals were anesthetized with isoflurane (4% induction and 2% maintenance) and 25 μL of 2% A-carrageenan (Sigma-Aldrich; Saint Louis, Mo.) dissolved in normal saline was injected into the center plantar area on hind paws using an insulin syringe (BD; Franklin Lakes, N.J.).
Implantation of Mini Pumps
Alzet micro-osmotic mini pumps (Durect Corporation Model 1003D and 2001D) were filled and primed per manufacturer's guide. Mice were anesthetized with isoflurane (5% induction; 2% maintenance). Their backs were shaved, wiped down with isopropyl alcohol and povidone iodine, and a small incision was made between the scapulae. Using a pair of forceps or hemostat, a small pocket was formed by spreading the subcutaneous connective tissues apart. The pump was inserted into the pocket with the flow moderator pointing away from the incision. The skin incision was then closed using 7 mm staples and the animals were allowed to recover in their home cages.

Data Analysis

Data are represented as mean±s.e.m. Prism (Graphpad Software Inc., La Jolla, Calif.) was used for graphing and statistical analysis. For comparison of threshold values over time, a two-way ANOVA followed by Bonferroni's multiple comparison test was used with a significance level of $p<0.05$. Hotplate and MPE % data were analyzed by one-way ANOVA followed by Bonferroni's multiple comparison test.

Results

Figure 4B:
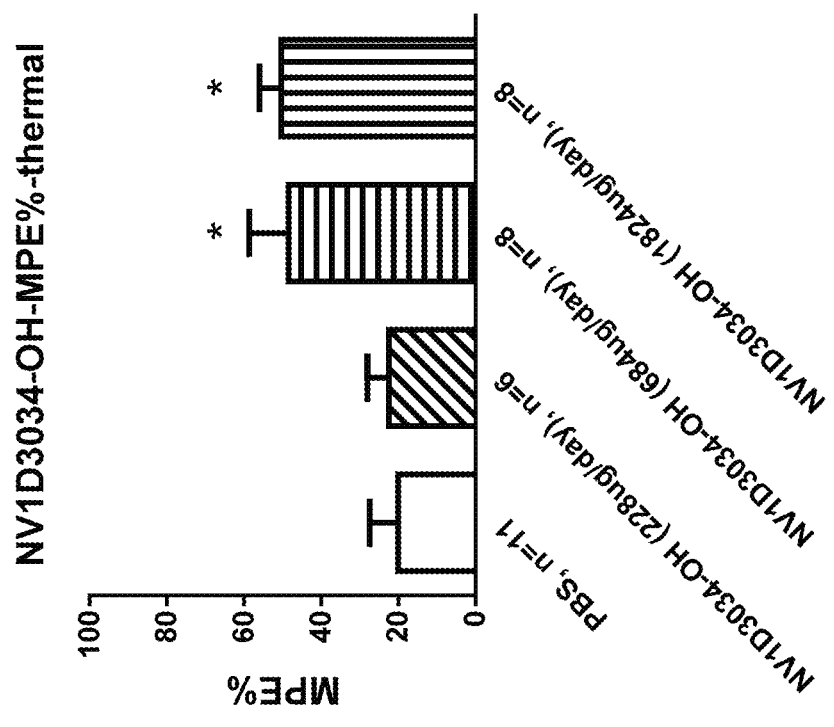
FIG. 4B shows efficacy of NV1D3034 (NV1D3034-OH) (SEQ ID NO: 78) in CFA-induced thermal hyperalgesia expressed as percent MPE (maximum possible effect) (MPE %) at each dose on day1 following peptide administration. *$P<0.05$ vs PBS, one-way ANOVA followed by Bonferroni's multiple comparison.
Figure 6A:
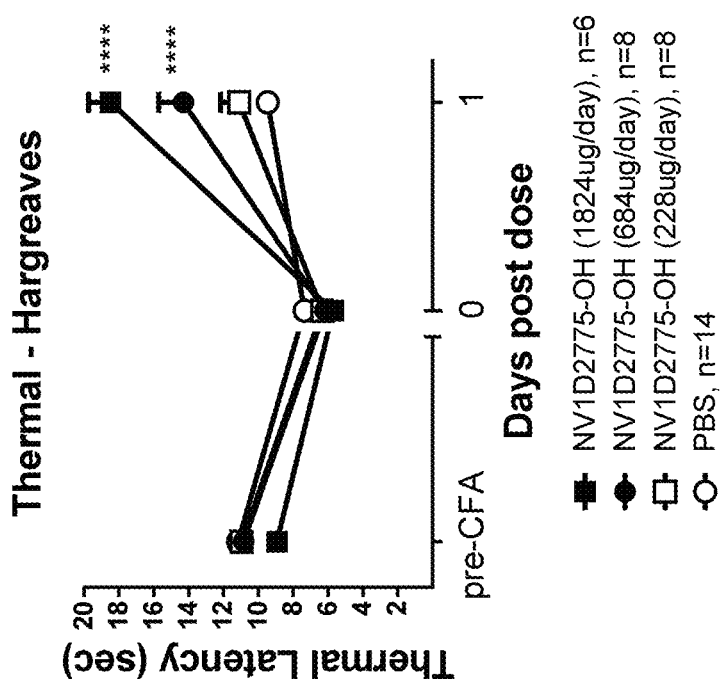
FIG. 6A shows efficacy of NV1D2775-OH (SEQ ID NO: 56) against CFA-induced thermal hyperalgesia assessed by measurement of paw withdrawal latency in the Hargreaves test before (pre-CFA) and after CFA injection (0) and 1-day after peptide administration (1). ****$P<0.0001$ vs. PBS, two-way ANOVA followed by Bonferroni's multiple comparison.

Efficacy of variants NV1D3034-OH (NV1D3034-COOH), NV1D3368-OH (NV1D3368-COOH) and NV1D2775-OH (NV1D2775-COOH) was studied in the CFA model, a commonly used model of inflammatory pain. The injection of CFA in the hindpaw induced paw edema (not shown) and hypersensitivity to thermal stimuli (thermal hyperalgesia), as indicated by the lowered thermal latency in the injected paw on day0 (FIG. 6A). Thermal hyperalgesia was completely reversed by NV1D3034-OH at 684 and 1824 µg/day, when administered by a subcutaneous osmotic mini-pump (FIGS. 4A and 4B).

Figure 5A:
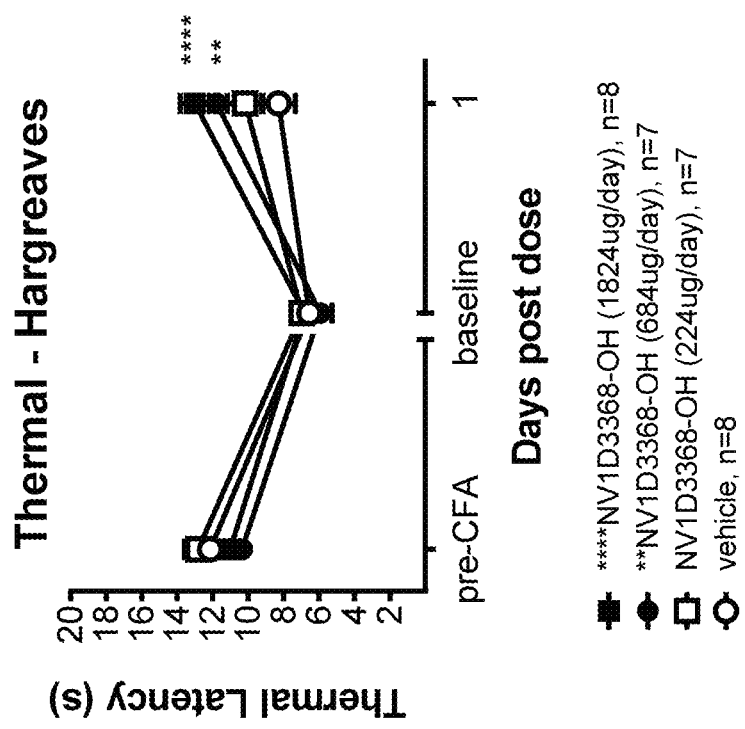
FIG. 5A shows efficacy of NV1D3368 (NV1D3368-OH) (SEQ ID NO: 198) against CFA-induced thermal hyperalgesia assessed by measurement of paw withdrawal latency in the Hargreaves test before (pre-CFA) and after CFA injection (0) and 1-day after peptide administration (1). $P<0.01$ and **$P<0.0001$ vs. PBS, two-way ANOVA followed by Bonferroni's multiple comparison
Figure 5B:
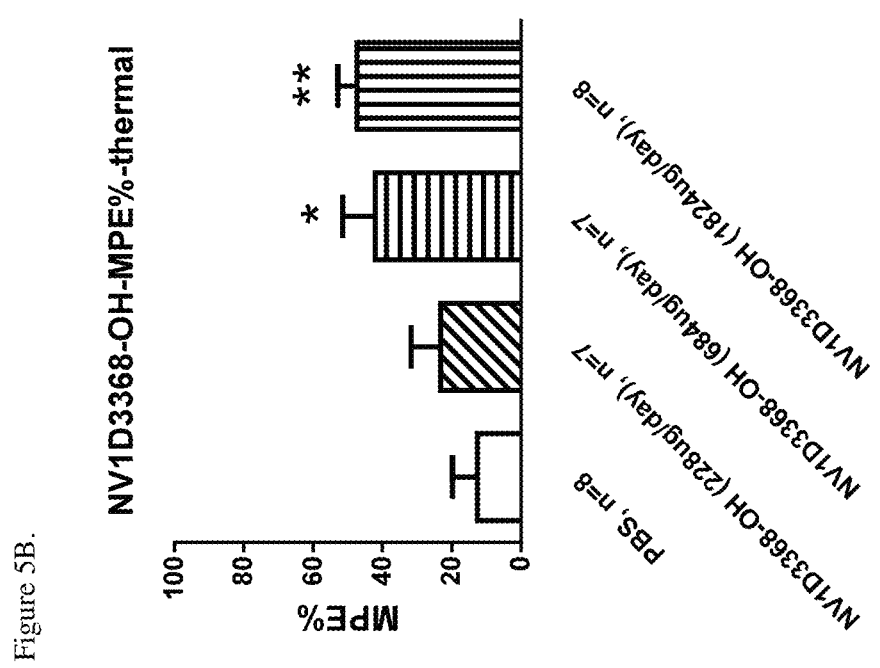
FIG. 5B shows efficacy of NV1D3368 (NV1D3368-OH) (SEQ ID NO: 198) in CFA-induced thermal hyperalgesia expressed as percent MPE (MPE %) at each dose on day1 following peptide administration. *$P<0.05$ and **$P<0.01$ vs PBS, one-way ANOVA followed by Bonferroni's multiple comparison.
Figure 6B:
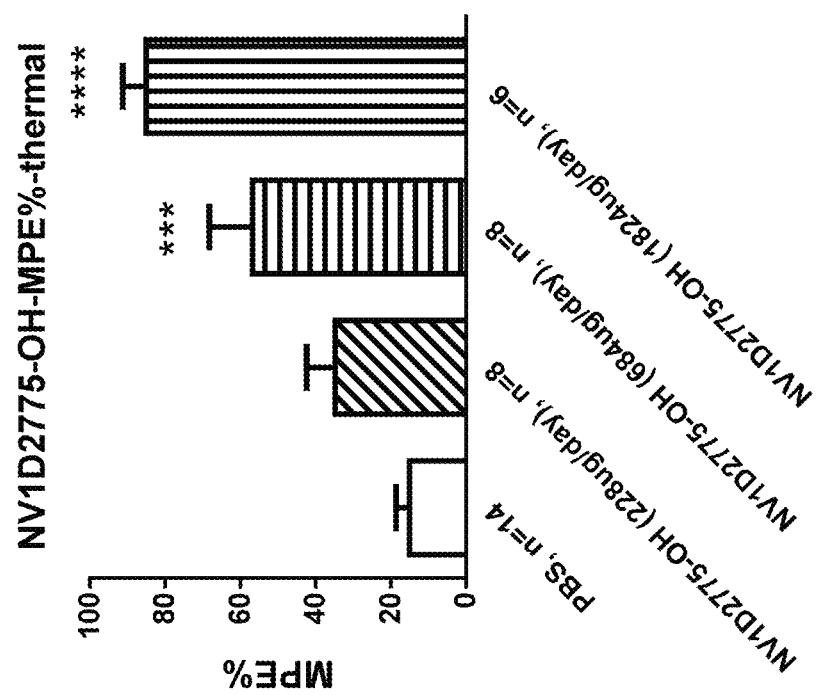
FIG. 6B shows efficacy of NV1D2775-OH (SEQ ID NO: 56) in CFA-induced thermal hyperalgesia expressed as percent MPE (MPE %) at each dose on day1 following peptide administration. *$P<0.001$ and **$P<0.0001$ vs PBS, one-way ANOVA followed by Bonferroni's multiple comparison.
Figure 6C:
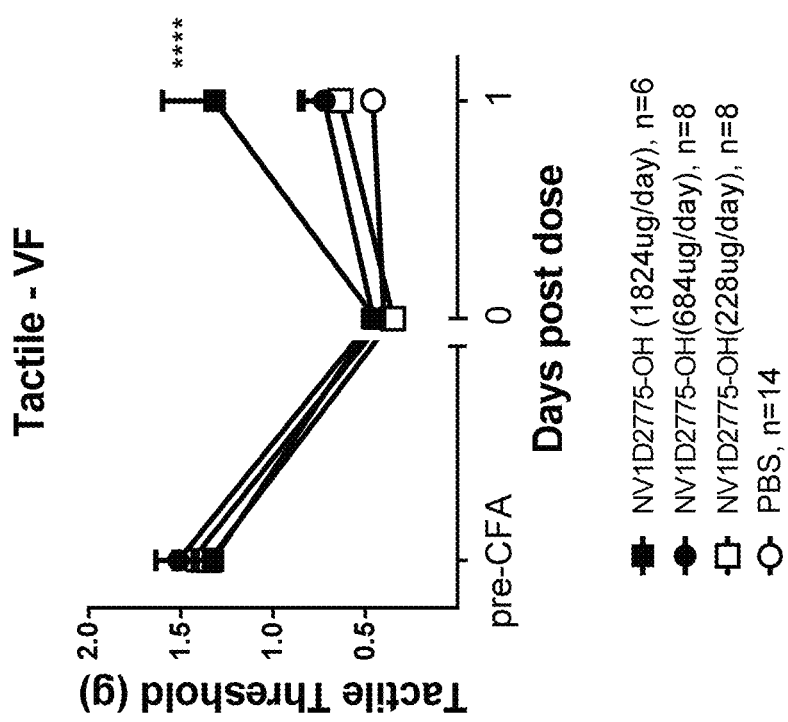
FIG. 6C shows efficacy of NV1D2775-OH (SEQ ID NO: 56) against CFA-induced tactile allodynia. Tactile thresholds of hind paw before (pre-CFA) and after CFA (0) and 1-day after peptide administration (1). ****$P<0.0001$ vs. PBS, two-way ANOVA followed by Bonferroni's multiple comparison.
Figure 6D:
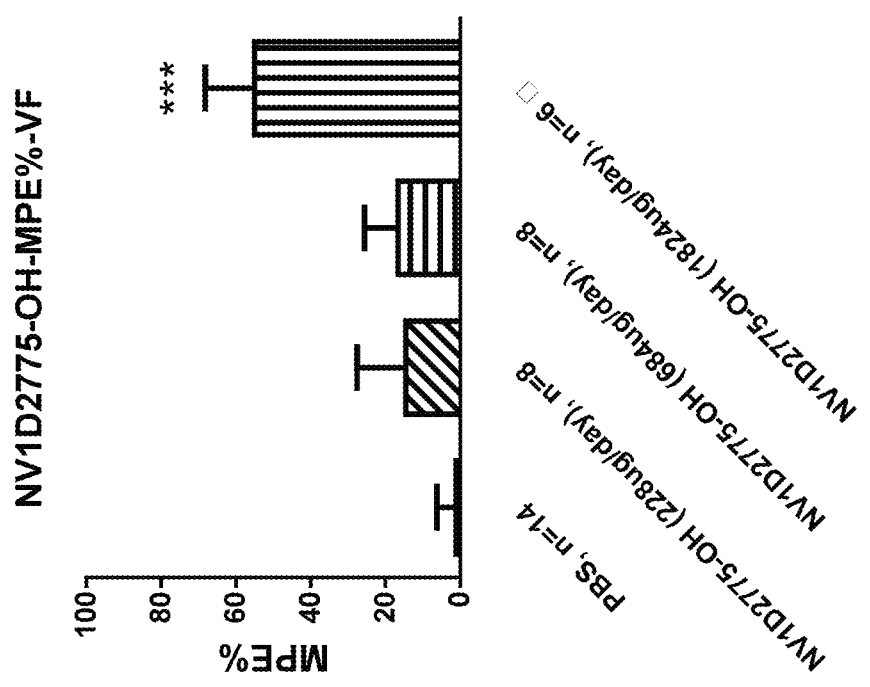
FIG. 6D shows efficacy of NV1D2775-OH (SEQ ID NO: 56) against CFA-induced tactile allodynia expressed as percent MPE (MPE %) on day1 following peptide. ***$P<0.001$ vs PBS, one-way ANOVA followed by Bonferroni's multiple comparison.
Figure 7A:
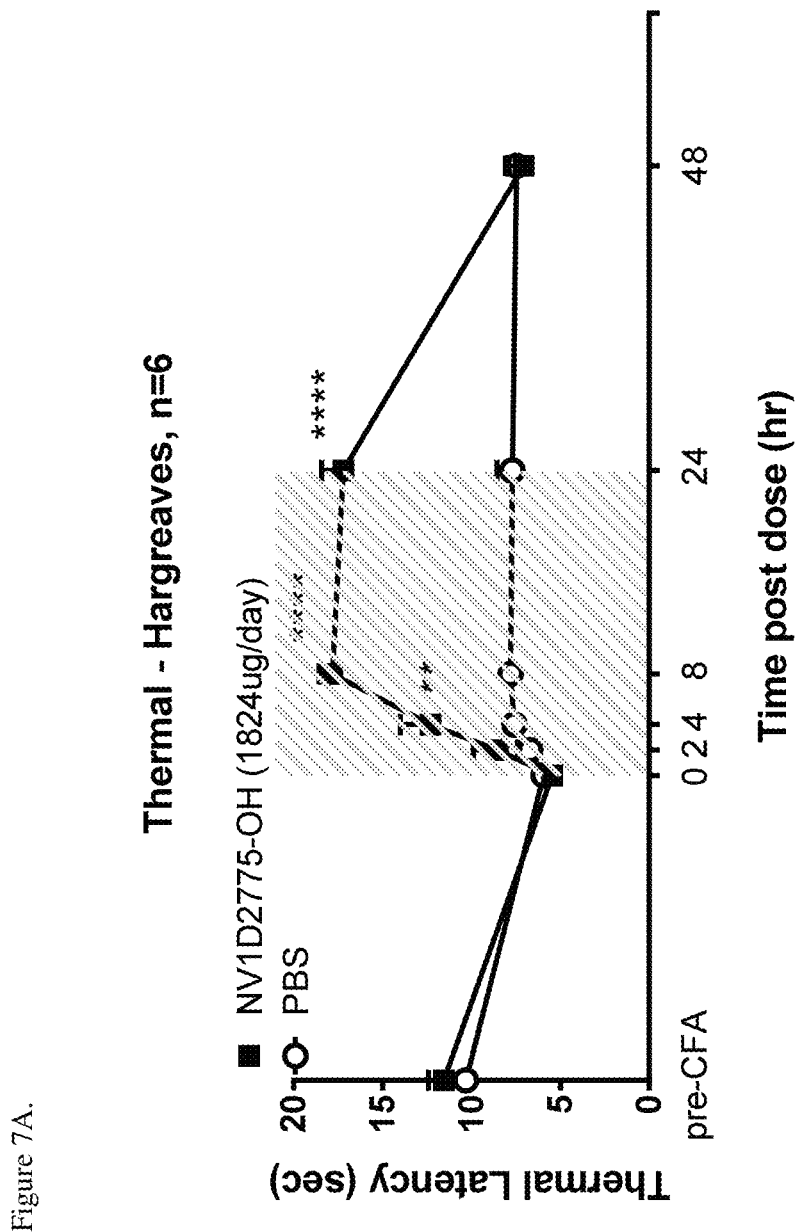
FIG. 7A shows time course of NV1D2775-OH mediated reversal of thermal hyperalgesia in the CFA model as assessed by measurement of paw withdrawal latency in the Hargreaves test before and after CFA and at various time points post-peptide administration. **$P<0.01$ vs. PBS, two-way ANOVA followed by Bonferroni's multiple comparison. Shaded areas indicate compound delivery period (0-24 hr).
Figure 7B:
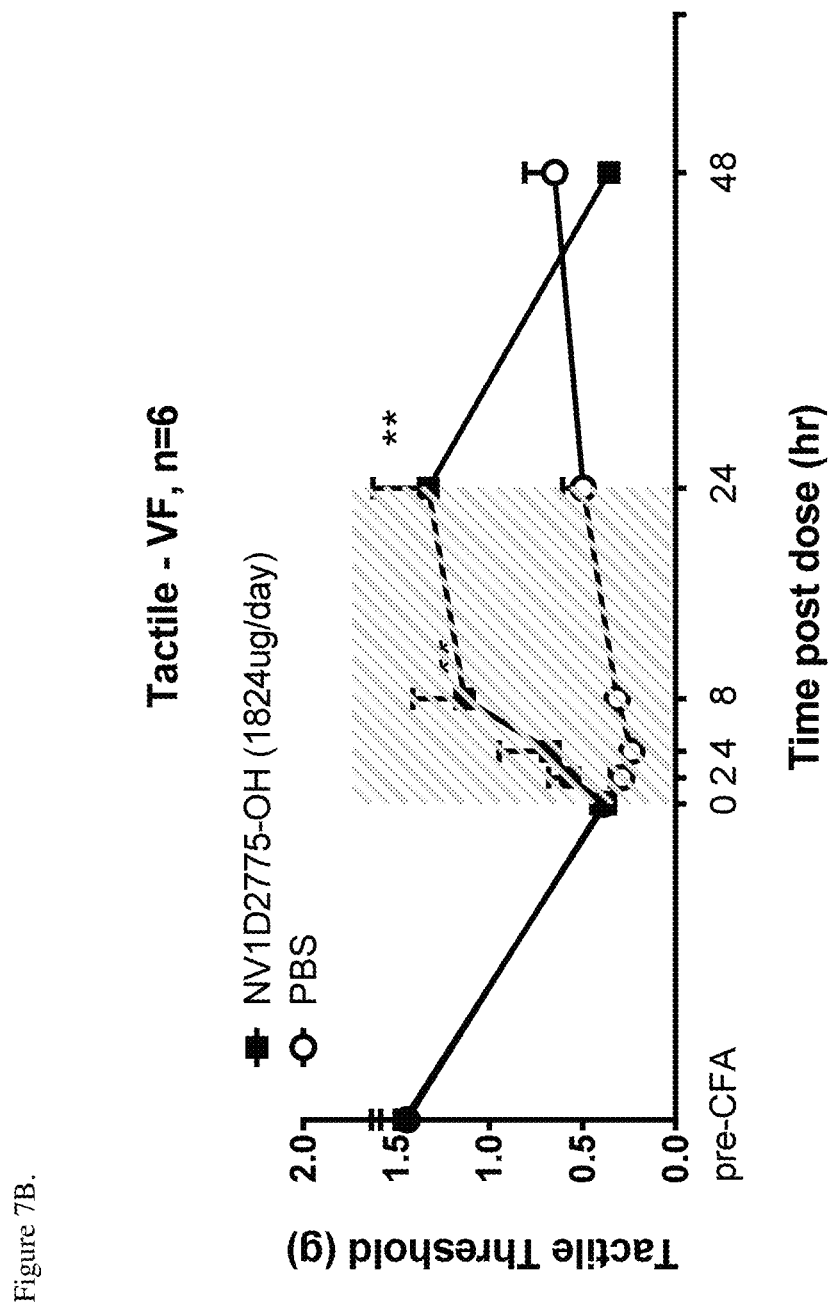
FIG. 7B shows time course of NV1D2775-OH mediated reversal of tactile allodynia in the CFA model as assessed by measurement of tactile threshold before and after CFA and at various time points post-peptide administration. **$P<0.01$ vs. PBS, two-way ANOVA followed by Bonferroni's multiple comparison. Shaded areas indicate compound delivery period (0-24 hr).

NV1D3368-OH fully reversed CFA-induced thermal hyperalgesia at 684 and 1824 µg/day (FIGS. 5A and 5B). NV1D2775-OH demonstrated strong efficacy in the CFA model. Thermal latencies reached values close to the cut-off following NV1D2775 administration (FIGS. 6A and 6B, 1824 µg/day), suggesting a strong analgesia effect on top of the anti-hyperalgesia effect. In addition, NV1D2775-OH reversed CFA-induced tactile allodynia (FIGS. 6C and 6D, 1824 µg/day). The anti-hyperalgesic effect of NV1D2775-OH was seen as early as 4 hr post-pump implantation (FIG. 7A). The effect reached the maximum at 8 hr in both the thermal and tactile tests (FIGS. 7A and 7B), which was maintained at 24 hr. Thermal latency and tactile threshold returned the control level by 48 h post pump implantation (approximately 24 h after the pumps were predicted to be empty) (FIGS. 7A and 7B).

CFA-induced thermal hyperalgesia was readily reversed by two additional peptides, NV1D3368-amide (NV1D3368-NH$_2$) and NV1D3034-N-methylamide (NV1D3034-NHMe). Thermal MPE % from the experiments is summarized in Table 13.

TABLE 13

| Peptide | Vehicle (PBS) | | 228 | | 684 | | 1824 | |
|---|---|---|---|---|---|---|---|---|
| NV1D3034-OH | 20 ± 7 | (11) | 22 ± 6 | (6) | 48 ± 10* | (8) | 50 ± 6* | (8) |
| NV1D3368-OH | 13 ± 7 | (8) | 23 ± 8 | (7) | 42 ± 9* | (7) | 47 ± 6** | (8) |
| NV1D2775-OH | 15 ± 4 | (20) | 35 ± 8 | (8) | 57 ± 12*** | (8) | 85 ± 6**** | (12) |
| NV1D3368-NH$_2$ | 15 ± 13 | (6) | 27 ± 4 | (4) | 46 ± 9 | (4) | 55 ± 15 | (6) |
| NV1D3034-NHMe | 5 ± 25 | (3) | | | | | 49 ± 17 | (6) |

*P < 0.05, P < 0.01, *P < 0.001 and ****P < 0.0001 vs. PBS, one-way ANOVA followed by Bonferroni's multiple comparison.

Figure 8:
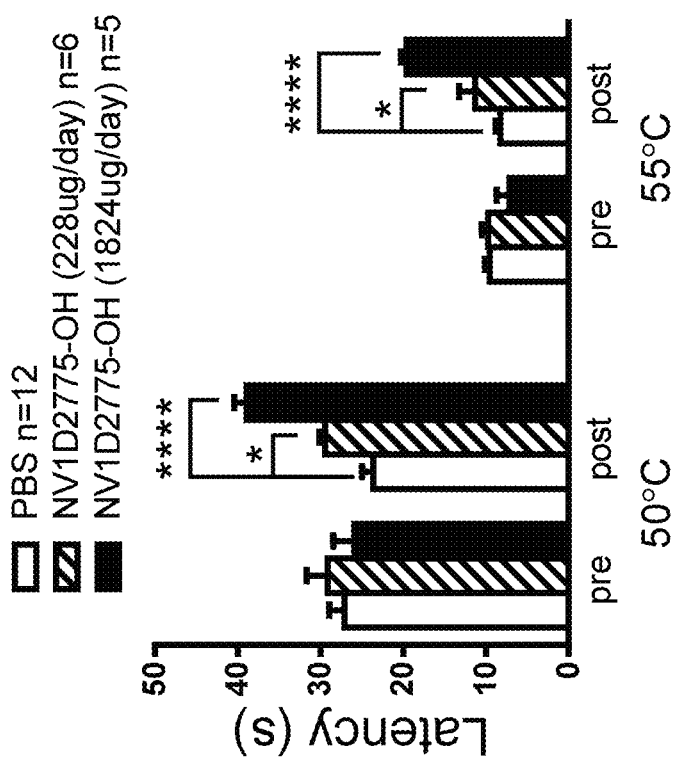
FIG. 8 shows that NV1D2775-OH produced significant analgesia in the hotplate test. Thermal withdrawal latency was evaluated at 50 and 55° C. pre- and post-pump implantation. Pump implantation had no impact on the latency in the control PBS group. One day after pump, NV1D2775-OH treated-mice exhibited prolonged latency compared to the PBS group. *$P<0.05$ and ****$P<0.0001$ vs. PBS, one-way ANOVA followed by Bonferroni's multiple comparison.

NV1D2775-OH also exhibited strong, dose-dependent efficacy in the hotplate test (FIG. 8). Latencies at 50 and 55° C. reached values near cut-off following the administration of 1824 µg/day. At 228 µg/day, NV1D2775-OH produced a modest yet significant increase in the thermal latency, compared to the PBS control.

Figure 9:
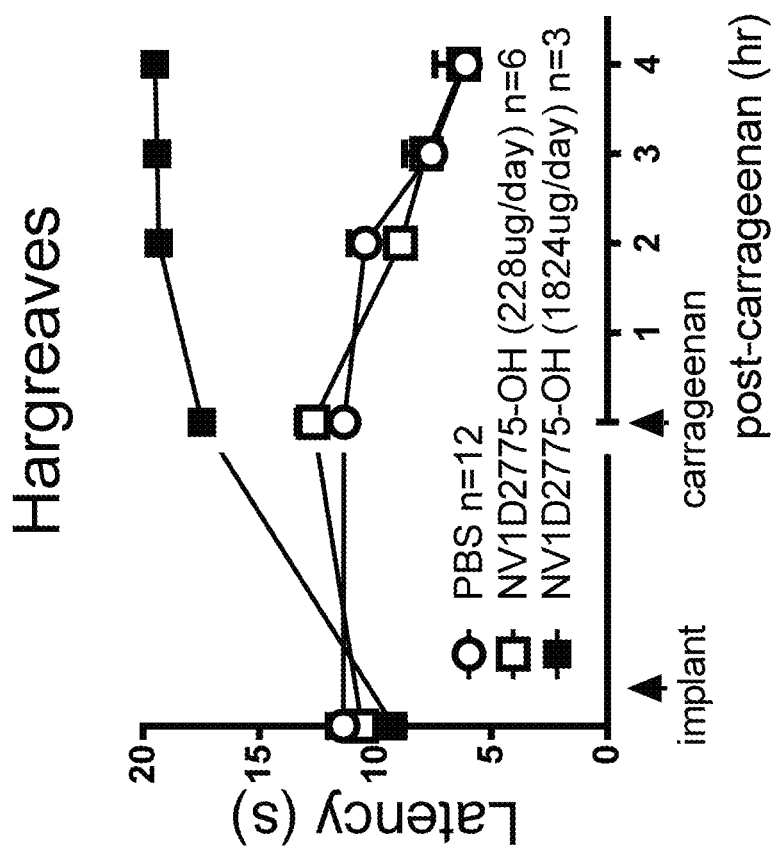
FIG. 9 shows that NV1D2775-OH pretreatment protected animals from carrageenan-induced thermal hyperalgesia. Paw withdrawal latencies were measured pre- and on day1 post-pump before intraplantar carrageenan injection. Latencies were measured again at 2, 3 and 4 hr following carrageenan.

The efficacy of NV1D2775-OH was evaluated in another model of inflammatory pain, the carrageenan model. Animals were implanted with NV1D2775-OH or PBS pumps. Thermal withdrawal latencies were measured pre- and on day1 post-pump. A-carrageenan was injected into the hindpaws and thermal latencies were measured again on 2, 3 and 4 hr following carrageenan. NV1D2775-OH at 1824 µg/day produced significant analgesia (FIG. 9). Injection of A-carrageenan in the hindpaws induced inflammation (not shown) and lowered thermal paw withdrawal latency in the Hargreaves test over the 4 hr test-period (FIG. 9, PBS group). Animals pretreated with NV1D2775-OH at 1824 µg/day were fully protected from carrageenan-induced hyperalgesia.

We claim:

1. An isolated Protoxin-II variant comprising the sequence of SEQ ID NO: 56 or SEQ ID NO: 78.

2. The Protoxin-II variant of claim 1, further comprising an N-terminal and/or C-terminal extension that is conjugated to the Protoxin-II variant via a linker.

3. The Protoxin-II variant of claim 2, wherein the linker comprises the amino acid sequence of SEQ ID NOs: 383, 392, 398, 399, 400, 401 or 402.

4. The isolated Protoxin-II variant of claim 3, having a free C-terminal carboxylic acid, amide, methylamide or butylamide group.

5. A pharmaceutical composition comprising the isolated Protoxin-II variant of claim 4 and a pharmaceutically acceptable excipient.

6. An isolated polynucleotide encoding the Protoxin-II variant of claim 3.

7. A vector comprising the isolated polynucleotide of claim 6.

8. A host cell comprising the vector of claim 7.

9. A method of producing an isolated Protoxin-II variant, comprising culturing the host cell of claim 8 and recovering the Protoxin-II variant produced by the host cell.

10. A pharmaceutical composition comprising the isolated Protoxin-II variant of claim 3 and a pharmaceutically acceptable excipient.

11. The isolated Protoxin-II variant of claim 2, having a free C-terminal carboxylic acid, amide, methylamide or butylamide group.

12. A pharmaceutical composition comprising the isolated Protoxin-II variant of claim 11 and a pharmaceutically acceptable excipient.

13. A pharmaceutical composition comprising the isolated Protoxin-II variant of claim 2 and a pharmaceutically acceptable excipient.

14. The isolated Protoxin-II variant of claim 1, having a free C-terminal carboxylic acid, amide, methylamide or butylamide group.

15. A pharmaceutical composition comprising the isolated Protoxin-II variant of claim 14 and a pharmaceutically acceptable excipient.

16. An isolated fusion protein comprising the Protoxin-II variant of claim 1 that is conjugated to a half-life extending moiety.

17. The isolated fusion protein of claim 16, wherein the half-life extending moiety is human serum albumin (HSA), albumin binding domain (ABD), Fc or polyethylene glycol (PEG).

18. A pharmaceutical composition comprising the isolated fusion protein of claim 17 and a pharmaceutically acceptable excipient.

19. A pharmaceutical composition comprising the isolated fusion protein of claim 16 and a pharmaceutically acceptable excipient.

20. A method of reducing the perception of pain in a subject, comprising administering to a subject in need thereof an effective amount of the fusion protein of claim 16 to treat the pain.

21. The method of claim 20, wherein the pain is chronic pain, acute pain, neuropathic pain, nociceptive pain, visceral pain, back pain, post-operative pain, thermal pain, phantom limb pain, or pain associated with inflammatory conditions, primary erythemalgia (PE), paroxysmal extreme pain disorder (PEPD), osteoarthritis, rheumatoid arthritis, lumbar discectomy, pancreatitis, fibromyalgia, painful diabetic neuropathy (PDN), post-herpetic neuropathy (PHN), trigeminal neuralgia (TN), spinal cord injuries or multiple sclerosis.

22. The method of claim 20, wherein the fusion protein is administered peripherally.

23. The method of claim 20, wherein the fusion protein is administered locally to a joint, spinal cord, surgical wound, sites of injury or trauma, peripheral nerve fibers, urogenital organs, or inflamed tissues.

24. The method of claim 20, wherein the subject is a human.

25. An isolated polynucleotide encoding the Protoxin-II variant of claim 1.

26. A vector comprising the isolated polynucleotide of claim 25.

27. A host cell comprising the vector of claim 26.

28. A method of producing an isolated Protoxin-II variant, comprising culturing the host cell of claim 27 and recovering the Protoxin-II variant produced by the host cell.

29. A pharmaceutical composition comprising the isolated Protoxin-II variant of claim 1 and a pharmaceutically acceptable excipient.

30. A method of reducing the perception of pain in a subject, comprising administering to a subject in need thereof an effective amount of the Protoxin-II variant of claim 1 to treat the pain.

31. The method of claim 30, wherein the pain is chronic pain, acute pain, neuropathic pain, nociceptive pain, visceral pain, back pain, post-operative pain, thermal pain, phantom limb pain, or pain associated with inflammatory conditions, primary erythemalgia (PE), paroxysmal extreme pain disorder (PEPD), osteoarthritis, rheumatoid arthritis, lumbar discectomy, pancreatitis, fibromyalgia, painful diabetic neuropathy (PDN), post-herpetic neuropathy (PHN), trigeminal neuralgia (TN), spinal cord injuries or multiple sclerosis.

32. The method of claim 30, wherein the Protoxin-II variant is administered peripherally.

33. The method of claim 30, wherein the Protoxin-II variant is administered locally to a joint, spinal cord, surgical wound, sites of injury or trauma, peripheral nerve fibers, urogenital organs, or inflamed tissues.

* * * * *